US012728175B2

(12) United States Patent
Wanner et al.

(10) Patent No.: US 12,728,175 B2
(45) Date of Patent: Sep. 8, 2026

(54) GASTRIN-RELEASING PEPTIDE RECEPTOR (GRPR)-TARGETED COMPOUNDS AND USES THEREOF

(71) Applicant: Alpha-9 Oncology Inc., Vancouver (CA)

(72) Inventors: Jutta Wanner, Vancouver (CA); Chengcheng Zhang, Vancouver (CA); Kaveh Matinkhoo, Vancouver (CA); Stephen Barigye, Vancouver (CA); Hsiou-Ting Kuo, Vancouver (CA)

(73) Assignee: Alpha-9 Oncology Inc., Vancouver (CA)

(*) Notice: Subject to any disclaimer, the term of this patent is extended or adjusted under 35 U.S.C. 154(b) by 0 days.

(21) Appl. No.: 19/334,526

(22) Filed: Sep. 19, 2025

(65) Prior Publication Data

US 2026/0077073 A1 Mar. 19, 2026

Related U.S. Application Data

(63) Continuation of application No. PCT/CA2025/051213, filed on Sep. 12, 2025.

(60) Provisional application No. 63/694,257, filed on Sep. 13, 2024.

(51) Int. Cl.

| | |
|---|---|
| ***A61K 51/08*** | (2006.01) |
| ***A61K 51/04*** | (2006.01) |
| ***A61P 35/00*** | (2006.01) |
| ***C07K 1/107*** | (2006.01) |

(52) U.S. Cl.

CPC ........ *A61K 51/088* (2013.01); *A61K 51/0482* (2013.01); *A61P 35/00* (2018.01); *C07K 1/1077* (2013.01); *A61K 2121/00* (2013.01); *A61K 2123/00* (2013.01)

(58) Field of Classification Search

None

See application file for complete search history.

(56) References Cited

U.S. PATENT DOCUMENTS

| | | | |
|---|---|---|---|
| 9,035,023 | B2 | 5/2015 | Maecke et al. |
| 9,839,703 | B2 | 12/2017 | Maina-Nock et al. |
| 12,246,076 | B2 | 3/2025 | Lin et al. |
| 2011/0052491 | A1 | 3/2011 | Cappelletti et al. |
| 2014/0023585 | A1 | 1/2014 | Borkowski et al. |
| 2016/0318987 | A1 | 11/2016 | Revell et al. |
| 2017/0107255 | A1 | 4/2017 | Holder et al. |
| 2021/0402016 | A1 | 12/2021 | Benard et al. |
| 2024/0123099 | A1 | 4/2024 | Lin et al. |
| 2025/0195702 | A1 | 6/2025 | Lin et al. |
| 2025/0339567 | A1 | 11/2025 | Wester |

FOREIGN PATENT DOCUMENTS

| | | | |
|---|---|---|---|
| EP | 2198878 | A1 | 6/2010 |
| EP | 2900279 | B1 | 8/2019 |
| JP | 2000502055 | A | 2/2000 |
| JP | 2010150253 | A | 7/2010 |
| JP | 2011515338 | A | 5/2011 |
| JP | 2015533119 | A | 11/2015 |
| WO | WO-9719954 | A1 | 6/1997 |
| WO | WO-2009109332 | A1 | 9/2009 |
| WO | WO-2014052471 | A1 | 4/2014 |
| WO | WO-2021053040 | A1 | 3/2021 |
| WO | WO-2021068051 | A1 | 4/2021 |
| WO | WO-2021121734 | A1 | 6/2021 |
| WO | WO-2023178449 | A1 | 9/2023 |
| WO | WO-2025054727 | A1 | 3/2025 |
| WO | WO-2025111712 | A1 | 6/2025 |

OTHER PUBLICATIONS

Lau (Positron Emission Tomography Imaging of the Gastrin-Releasing Peptide Receptor with a Novel Bombesin Analogue. ACS Omega. 2019.) (Year: 2019) (Year: 2019) (Year: 2019) (Year: 2019).*

Abd-Elgaliel, W.R. et al., Design, synthesis, and biological evaluation of an antagonist-bombesin analogue as targeting vector. Bioconjug Chem. Oct. 2008;19(10):2040-8. doi: 10.1021/bc800290c. Epub Sep. 23, 2008.

Accardo et al. "Pre-clinical evaluation of eight DOTA coupled gastrin-releasing peptide receptor (GRP-R) ligands for in vivo targeting of receptor-expressing tumors," EJNMMI Research, Dec. 2016; 6:17, 10 pages.

Amouroux, G. et al, Imaging Bradykinin B1 Receptor with 68Ga-Labeled [des-Arg10]Kallidin Derivatives: Effect of the Linker on Biodistribution and Tumor Uptake. Mol Pharm. Aug. 3, 2015;12(8):2879-88. doi: 10.1021/acs.molpharmaceut.5b00070. Epub Jul. 2, 2015.

Bajo, A.M. et al., Bombesin antagonists inhibit growth of MDA-MB-435 estrogen-independent breast cancers and decrease the expression of the ErbB-2/HER-2 oncoprotein and c-jun and c-fos oncogenes. Proc Natl Acad Sci USA. Mar. 19, 2002;99(6):3836-3841.

Bakker, I.L. et al. In Vivo Stabilized SB3, an Attractive GRPR Antagonist, for Pre- and Intra-Operative Imaging for Prostate Cancer. Mol Imaging Biol. Dec. 2018;20(6):973-983. doi: 10.1007/s11307-018-1185-z.

Baratto, L. et al., Prostate Cancer Theranostics Targeting Gastrin-Releasing Peptide Receptors. Molecular Imaging & Biology, Dec. 18, 2017; 20(4):501-509.

(Continued)

*Primary Examiner* — Michael G. Hartley
*Assistant Examiner* — Samantha L Mejias
(74) *Attorney, Agent, or Firm* — COOLEY LLP

(57) ABSTRACT

The present invention relates to gastrin-releasing peptide receptor (GRPR)-targeted compounds and their use for imaging and treatment of diseases or conditions characterized by expression of the gastrin-releasing peptide receptor.

34 Claims, No Drawings

Specification includes a Sequence Listing.

(56) References Cited

OTHER PUBLICATIONS

Baratto, L. et al. PSMA- and GRPR-targeted PET: Results from 50 Patients with Biochemically Recurrent Prostate Cancer. Journal of Nuclear Medicine, Mar. 2021;65(8). doi:10.2967/jnumed.120.259630; 23 pages.
Baum, R. et al. Molecular imaging of bombesin receptors in various tumors by Ga-68 AMBA PET/CT: First results. Journal of Nuclear Medicine. May 2007;48(supplement 2):79P, Abstract 265 [online]. Retrieved from: https://jnm.snmjournals.org/content/48/supplement_2/79P.2, 2 pages.
Berge et al. "Pharmaceutical salts." J Pharm Sci. Jan. 1977; 6(1):1-19.
Bitar, K.N. et al., "Expression of bombesin-receptor subtypes and their differential regulation of colonic smooth muscle contraction," Gastroenterology, Dec. 1993;105:1672-1680.
Bodei, Lisa et al. Lu-177-AMBA Bombesin Analogue in Hormone Refractory Prostate Cancer Patients: A Phase I Escalation Study with Single-Cycle Administrations. Eur. J. Nucl. Med. Mol. Imaging; Sep. 18, 2007; 34(Suppl. 2). p. S221, #463, 1 page.
Bratanovic et al., "A Radiotracer for Molecular Imaging and Therapy of Gastrin-releasing Peptide Receptor-positive Prostate Cancer," The Journal of Nuclear Medicine, Mar. 2022; vol. 63(3), pp. 424-430.
Bratanovic, I.J. et al. The Effect of a Cationic Linker on the Pharmacokinetics of ProBOMB2, a Novel Bombesin Derivative. Annual Congress of the European Association of Nuclear Medicine, Oct. 12-16, 2019, Barcelona, Spain. Eur J Nucl Med Mol Imaging, Sep. 18, 2019;46(Suppl 1):271, Abstract OP-709, 1 page.
Bratanovic, I.J. "Optimized bombesin analogues as nuclear imaging and therapy agents for gastrin-releasing peptide receptor positive neoplasms", [Thesis]. Master of Science, Interdisciplinary Oncology. The University of British Columbia, Vancouver; Jul. 2020 [online]. Retrieved from: http://hdl.handle.net/2429/75181; 100 pages.
Cai, P. et al., "Potent bombesin antagonists with C-terminal Leu-psi(CH2-N)-Tac-NH2 or its derivatives," Proc. Natl. Acad. Sci. USA, 91:12664-12668 (Dec. 1994).
Cai, R-Z. et al., New pseudononapeptide bombesin antagonists with C-terminal Leu-psi(CH2N)Tac-NH2 show high binding affinity to bombesin/GRP receptors on CFP AC-1 human pancreatic cancer cells. Int J Oncol., Jun. 1995; 6:1165-1172.
Chansaenpak, K. et al., [18 F]-NHC-BF3 adducts as water stable radio-prosthetic groups for PET imaging. Chemical Communications, Jun. 2015;51(62):12439-12442.
Conklin, B.R and Bourne, H.R. "Structural elements of Gα subunits that interact with Gβγ, receptors, and effectors", Cell. May 1993;73(4):631-641.
U.S. Appl. No. 18/787,207, inventors Bénard; François et al., filed Jul. 29, 2024.
U.S. Appl. No. 19/190,091, inventors Wanner; Jutta et al., filed Apr. 25, 2025.
Cornelio, D.B. et al., Gastrin-releasing peptide receptor as a molecular target in experimental anticancer therapy. Ann Oncol. Sep. 2007;18:1457-1466.
Coy, D.H. et al., Probing peptide backbone function in bombesin. A reduced peptide bond analogue with potent and specific receptor antagonist activity. J Biol Chem. Apr. 15, 1988;263(11):5056-5060.
Dalm, S.U. et al., "68Ga/177Lu-NeoBOMB1, a Novel Radiolabeled GRPR Antagonist for Theranostic Use in Oncology", J Nucl Med. Feb. 2017;58(2):293-299. doi: 10.2967/jnumed.116.176636. Epub Sep. 8, 2016. Erratum in: J Nucl Med. Jul. 2018;59(7):1164, 1 page.
Dalm, S.U. et al., Prospects of Targeting the Gastrin Releasing Peptide Receptor and Somatostatin Receptor 2 for Nuclear Imaging and Therapy in Metastatic Breast Cancer, PLoS One. Jan. 20, 2017;12(1):e0170536, 12 pages.
De Visser, M. et al., Novel 111In-labelled bombesin analogues for molecular imaging of prostate tumours. Eur J Nucl Med Mol Imaging, Aug. 2007; 34:1228-1238.
Eder, M. et al., Preclinical Evaluation of a Bispecific Low-Molecular Heterodimer Targeting Both PSMA and GRPR for Improved PET Imaging and Therapy of Prostate Cancer. The Prostate, May 2014; 74:659-668.
European Application No. 19948391.8: Extended European Search Report, dated Aug. 22, 2022, 10 pages.
Fani, M. et al., Radiolabeled peptides: Valuable tools for the detection and treatment of cancer. Theranostics. May 2012; 2(5):481-501.
Giglio, B.C. et al., "Synthesis of 5-[18F]Fluoro-α-methyl Tryptophan: New Trp Based PET Agents", Theranostics. Apr. 7, 2017;7(6):1524-1530.
Ginj, M. et al. "Radiolabeled somatostatin receptor antagonists are preferable to agonists for in vivo peptide receptor targeting of tumors", Proc. Natl. Acad. Sci. U.S.A. Oct. 2006;103(44):16436-16441.
Gonzalez, N. et al., "Molecular basis for the selectivity of the mammalian bombesin peptide, neuromedin B, for its receptor," J Pharmacol Exp Ther.; Oct. 2009;331(1):265-276.
Gugger, M. and Reubi, J.C. "Gastrin-releasing peptide receptors in non-neoplastic and neoplastic human breast", The American Journal of Pathology, Dec. 1999;155(6):2067-2076.
Gunther, T. et al. Optimization of the pharmacokinetic profile of 99mTc-N4-Bombesin derivatives by modification of the pharmacophoric Gln-Trp sequence. Journal of Nuclear Medicine. May 2021;62(supplement 1), Abstract 1474 [online]. Retrieved from: https://jnm.snmjournals.org/content/62/supplement_1/1474, 2 pages.
Gunther, T. et al. Substitution of L-Tryptophan by α-Methyl-L-Tryptophan in 177Lu-RM2 Results in 177Lu-AMTG, a High-Affinity Gastrin-Releasing Peptide Receptor Ligand with Improved In Vivo Stability. J Nucl Med. Sep. 2022;63(9):1364-1370, DOI: https://doi.org/10.2967/jnumed.121.263323.
Guo, M. et al., Bombesin-like peptides and their receptors: recent findings in pharmacology and physiology. Curr Opin Endocrinol Diabetes Obes. Feb. 2015;22(1):3-8.
Hajri, A. et al. "Expression and characterization of gastrin-releasing peptide receptor in normal and cancerous pancreas", Pancreas. Jan. 1996;12:25-35.
Heimbrook, D.C. et al., "Gastrin releasing peptide antagonists with improved potency and stability," J. Med. Chem. Jul. 1991;34:2102-2107.
Hofstetter, M. et al. "Effect of the versatile bifunctional chelator AAZTA5 on the radiometal labelling properties and the in vitro performance of a gastrin releasing peptide receptor antagonist," EJNMMI Radiopharm. Chem., Nov. 2020; 5:29, 19 pages.
Horwell, D.C. et al., "Alanine scan and N-methyl amide derivatives of Ac-bombesin[7-14]. Development of a proposed binding conformation at the neuromedin B (NMB) and gastrin releasing peptide (GRP) receptors," Int. J. Peptide Protein Res., Dec. 1996;48:522-531.
Inkster, J. et al., "2-Fluoropyridine prosthetic compounds for the 18F labeling of bombesin analogues," Bioorganic Med Chem Lett., Jul. 2013;23:3920-3926.
Ischia, J. et al., "Expression and function of gastrin-releasing peptide (GRP) in normal and cancerous urological tissues," BJU Int. Mar. 2014;113 Suppl 2:40-47.
Jensen, R.T and Coy, D.H. "Progress in the development of potent bombesin receptor antagonists", Trends Pharmacol. Sci. Jan. 1991;12:13-19.
Jensen, R.T. et al., "International Union of Pharmacology. LXVIII. Mammalian Bombesin Receptors: Nomenclature, Distribution, Pharmacology, Signaling, and Functions in Normal and Disease States," Pharmacol Rev. Mar. 2008;60(1):1-42. doi: 10.1124/pr.107.07108. Epub Nov. 30, 2007. NIH Public Access Author Manuscript [online]. Retrieved from: https://www.ncbi.nlm.nih.gov/pmc/articles/PMC2517428/pdf/nihms-45053.pdf, 74 printed pages.
Jungwirth, A. et al, "Inhibition of growth of androgen-independent DU-145 prostate cancer in vivo by luteinising hormone-releasing hormone antagonist cetrorelix and bombesin antagonists RC-3940-II and RC-3950-II," Eur J Cancer Part A., Jun. 1997;33(7):1141-1148.
Kaloudi, A. et al., NeoBOMB1, a GRPR-Antagonist for Breast Cancer Theragnostics: First Results of a Preclinical Study with

(56) References Cited

OTHER PUBLICATIONS

[67Ga]NeoBOMB1 in T-47D Cells and Tumor-Bearing Mice. Molecules, Nov. 1, 20171;22(11):1950, 13 pages.
Keenan, M.A. et al., "RADAR Realistic Animal Model Series for Dose Assessment," J Nucl Med, Mar. 2010; vol. 51, No. 3, pp. 471-476.
Kähkönen, E. et al., In vivo imaging of prostate cancer using [68Ga]-labeled bombesin analog BAY86-7548. Clin Cancer Res. Oct. 1, 2013;19(19):5434-43. doi: 10.1158/1078-0432.CCR-12-3490. Epub Aug. 9, 2013.
Koppan, M. et al., "Bombesin/gastrin-releasing peptide antagonists RC-3095 and RC-3940-II inhibit tumor growth and decrease the levels and mRNA expression of epidermal growth factor receptors in H-69 small cell lung carcinoma," Cancer; 83:1335-1343 (Oct. 1998).
Kuo, H-T. et al., "One-Step $^{18}$F-Labeling and Preclinical Evaluation of Prostate-Specific Membrane Antigen Trifluoroborate Probes for Cancer Imaging," J Nucl Med, Aug. 2019; 60:1160-1166.
Kurth, J. et al. First-in-human dosimetry of gastrin-releasing peptide receptor antagonist [177Lu]Lu-RM2: a radiopharmaceutical for the treatment of metastatic castration-resistant prostate cancer. Eur J Nucl Med Mol Imaging. Jan. 2020;47(1):123-135. doi: 10.1007/s00259-019-04504-3. Epub Sep. 3, 2019.
Lau, J. et al., Positron Emission Tomography Imaging of the Gastrin-Releasing Peptide Receptor with a Novel Bombesin Analogue. ACS Omega. Jan. 31, 2019;4(1):1470-1478. doi: 10.1021/acsomega.8b03293. Epub Jan. 16, 2019.
Leban, J.J. et al., Development of potent gastrin-releasing peptide antagonists having a D-Pro-psi(CH2NH)-Phe-NH2 C terminus. Proc Natl Acad Sci U S A. Mar. 1, 1993;90(5):1922-6. doi: 10.1073/pnas.90.5.1922.
Leban, J.J. et al. Potent gastrin-releasing peptide (GRP) antagonists derived from GRP(19-27) with a C-terminal DPro psi[CH2NH]Phe-NH2 and N-terminal aromatic residues. J Med Chem. Feb. 18, 1994;37(4):439-445. doi: 10.1021/jm00030a002.
Li, L. et al. Functionally Versatile and Highly Stable Chelator for 111In and 177Lu: Proof-of-Principle Prostate-Specific Membrane Antigen Targeting. Bioconjug Chem. May 15, 2019;30(5):1539-1553. doi: 10.1021/acs.bioconjchem.9b00225. Epub May 5, 2019.
Li, Y. et al., "Evaluation of 227Th chelation of hydroxypyridinone- and picolinic acid containing ligands to simulate 226Th chelation", Poster #102, University of Washington, 2018. Nuclear Medicine and Biology, May 2019;72-73(Supplement 1):S38, 1 page.
Lin, J.T. et al., Comparison of the peptide structural requirements for high affinity interaction with bombesin receptors. Eur J Pharmacol. Dec. 27, 1995;294(1):55-69.
Lin, K-S. et al. A new high affinity technetium analogue of bombesin containing DTPA as a pharmacokinetic modifier. Bioconjug Chem. Nov.-Dec. 2004;15(6):1416-23.
Lin, K-S. et al., "In vivo radioimaging of bradykinin receptor b1, a widely overexpressed molecule in human cancer," Cancer Res. Jan. 2015;75(2):387-393.
Linder, K.E. et al. In vitro and in vivo metabolism of Lu-AMBA, a GRP-receptor binding compound, and the synthesis and characterization of its metabolites. Bioconjug Chem. Jun. 2009;20(6):1171-8.
Liu, Z. et al., "An Organotrifluoroborate for Broadly Applicable One-Step$^{18}$F-Labeling," Angewandte Chemie International Edition, Sep. 2014, vol. 53, No. 44, pp. 11876-11880.
Liu, Z. et al., "One-step 18F labeling of biomolecules using organotrifluoroborates," Nat Protoc, Sep. 2015, vol. 10, No. 9, pp. 1423-1432.
Liu, Z. et al. "Preclinical Evaluation of a High-Affinity $^{18}$F-Trifluoroborate Octreotate Derivative for Somatostatin Receptor Imaging", Journal of Nuclear Medicine. Sep. 2014;55(9):1499-1505.
Lui, Y. et al. "G protein-coupled receptors as promising cancer targets", Cancer Lett. Jul. 2016;376(2):226-239.
Maina, T. et al., Preclinical and first clinical experience with the gastrin-releasing peptide receptor antagonist [68Ga]SB3 and PET/CT. Eur J Nucl Med Mol Imaging; 43(Suppl 1):964-973 (Oct. 2016).
Maina, T. et al., "Theranostic Prospects of Gastrin-Releasing Peptide Receptor-Radioantagonists in Oncology," PET Clin.; 12:297-309 (Jul. 2017).
Mansi et al. "Evaluation of Three Different Families of Bombesin Receptor Radioantagonists for Targeted Imaging and Therapy of Gastrin Releasing Peptide Receptor GRP-R) Positive Tumors," Journal of Medicinal Chemistry, Jan. 2015; 58:682-691.
Mansi, R. et al., "Bombesin-Targeted PET of Prostate Cancer," J Nucl Med.; 57(Suppl. 3):67S-72S (Oct. 2016).
Mansi, R. et al. "Targeting GRPR in urological cancers-from basic research to clinical application", Nat. Rev. Urol. Apr. 2013;10(4):235-244.
Markwalder, R. and Reubi, J.C. "Gastrin-releasing peptide receptors in the human prostate: relation to neoplastic transformation", Cancer Research. Mar. 1999;59:1152-1159.
Minamimoto, R. et al., "Pilot Comparison of 68Ga-RM2 PET and 68Ga-PSMA-11 PET in Patients with Biochemically Recurrent Prostate Cancer," J Nucl Med. Apr. 2016;57:557-562.
Moody, T. et al. "GRP receptors are present in non small cell lung cancer cells", Journal of Cellular Biochemistry Supplement. 1996;24:247-256.
Moreno, P. et al. "Bombesin related peptides/receptors and their promising therapeutic roles in cancer imaging, targeting and treatment", Expert Opin. Ther. Targets. Sep. 2016;20(9):1055-1073. HHS Public Access Author Manuscript, 37 pages.
Morgat, C. et al., "Expression of Gastrin-Releasing Peptide Receptor in Breast Cancer and Its Association with Pathologic, Biologic, and Clinical Parameters: A Study of 1,432 Primary Tumors," J Nucl Med.;58:1401-1407 (Sep. 2017).
Nock, B.A. et al., Theranostic Perspectives in Prostate Cancer with the Gastrin-Releasing Peptide Receptor Antagonist NeoBOMB1: Preclinical and First Clinical Results. J Nucl Med. Jan. 2017;58(1):75-80. doi: 10.2967/jnumed.116.178889. Epub Aug. 4, 2016.
Nock, B.A. et al., "To Serve and Protect: Enzyme Inhibitors as Radiopeptide Escorts Promote Tumor Targeting," J Nucl Med.; 55:121-127 (Jan. 2014).
Pan D. et al. A new (68)Ga-labeled BBN peptide with a hydrophilic linker for GRPR-targeted tumor imaging. Amino Acids. Jun. 2014;46(6):1481-9. doi: 10.1007/s00726-014-1718-y. Epub Mar. 17, 2014.
Popp et al., "Approaches to improve metabolic stability of a statine-based GRP receptor antagonist," Nucl. Med. Biol. Feb. 2017; 45:22-29.
Pourghisian, M. et al., "$^{18}$F-AmBF$_3$-MJ9: a novel radiofluorinated bombesin derivative for prostate cancer imaging," Bioorganic & Medicinal Chemistry, Apr. 2015; vol. 23, No. 7, pp. 1500-1506.
Preston, S.R. et al. "Characterization of a bombesin/gastrin-releasing peptide receptor on a human gastric-cancer cell line", International Journal of Cancer. Jun. 1994;57:734-741.
Preston, S.R. et al. "High-affinity binding sites for gastrin-releasing peptide on human colorectal cancer tissue but not uninvolved mucosa," British Journal of Cancer. May 1995; 71:1087-1089.
Price et al. "Matching chelators to radiometals for radiopharmaceuticals" Chemical Society Reviews Jan. 2014; 43(1):260-290.
Ramos-Alvarez, I. et al. Insights into bombesin receptors and ligands: Highlighting recent advances. Peptides. Oct. 2015;72:128-44. doi: 10.1016/j.peptides.2015.04.026. Epub May 11, 2015.
Reile, H. et al. New antagonists of bombesin gastrin-releasing peptide with C-terminal Leu-psi-(CH2N)Tac-NH2. Int J Oncol. Oct. 1995;7(4):749-54. doi: 10.3892/ijo.7.4.749.
Richter, S. et al., Metabolically Stabilized 68Ga-NOTA-Bombesin for PET Imaging of Prostate Cancer and Influence of Protease Inhibitor Phosphoramidon. Mol Pharm.;13:1347-1357 (Apr. 2016).
Roesler, R. et al., Gastrin-releasing peptide receptors in the central nervous system: Role in brain function and as a drug target. Front Endocrinol;3:159, 12 pages (Dec. 2012).
Rousseau, E. et al. Comparison of biological properties of [177 Lu]Lu-ProBOMB1 and [177 Lu]Lu-NeoBOMB1 for GRPR targeting. J Labelled Comp Radiopharm. Feb. 2020;63(2):56-64. doi: 10.1002/jlcr.3815. Epub Jan. 11, 2020.

(56) References Cited

OTHER PUBLICATIONS

Sah, B-R. et al., Dosimetry and First Clinical Evaluation of the New 18F-Radiolabeled Bombesin Analogue BAY 864367 in Patients with Prostate Cancer. J Nucl Med.; 56:372-378 (Mar. 2015).
Shirahige, Y. et al, Inhibitory effect of bombesin/Gastrin-releasing peptide (GRP) antagonists RC-3950-II and RC-3095 onMCF-7 MIII human breast cancer xenografts in nude mice. Biomed Pharmacother.;48:465-472 (Apr. 1994).
Sonni, I. et al., Imaging of Prostate Cancer Using Gallium-68-Labeled Bombesin. PET Clin.; 12:159-171 (Apr. 2017).
Stabin, M.G. et al., "OLINDA/EXM: the second-generation personal computer software for internal dose assessment in nuclear medicine," J Nucl Med.;46:1023-1027 (Jun. 2005).
Stoykow et al., "Gastrin-releasing Peptide Receptor Imaging in Breast Cancer Using the Receptor Antagonist$^{68}$Ga-RM2 and PET," Theranostics, Jun. 2016; 6:1641-1650.
Wang, L. et al. 68Ga-Labeled [Leu13ψThz14]Bombesin(7-14) Derivatives: Promising GRPR-Targeting PET Tracers with Low Pancreas Uptake. Molecules, Jun. 2022;27(12):3777, 14 pages.
Wang, L. et al. "$^{68}$Ga-Labeled [Thz$^{14}$]Bombesin(7-14) Analogs: Promising GRPR-Targeting Agonist PET Tracers with Low Pancreas Uptake", Molecules, Feb. 2023; 28:1977, 15 pages.
Wang, L. et al. "Synthesis and Evaluation of Novel 68Ga-Labeled [D-Phe6,Leu13ψThz14]bombesin(6-14) Analogs for Cancer Imaging with Positron Emission Tomography", Pharmaceuticals, May 2024; 17:621, 15 pages.
Weber, H.C., Regulation and signaling of human bombesin receptors and their biological effects. Curr Opin Endocrinol Diabetes Obes, 16:66-71 (Feb. 2009).
Wieser, G. et al., "Positron emission tomography (PET) imaging of prostate cancer with a gastrin releasing peptide receptor antagonist—from mice to men," Theranostics, 4(4):412-419 (Feb. 2014).
Zang, J. et al., "68Ga-NOTA-RM26 PET/CT in the Evaluation of Breast Cancer: A Pilot Prospective Study," Clin Nucl Med;43:663-669 (Sep. 2018); HHS Public Access Author Manuscript [online]. Retrieved from: https://www.ncbi.nlm.nih.gov/pmc/articles/PMC6076351/pdf/nihms974578.pdf, (retrieval date unknown), 16 printed pages.
U.S. Appl. No. 19/363,051, inventors Bénard; François et al., filed Oct. 20, 2025.
Wang et al., "Novel 177Lu-Labeled [Thz14]Bombesin(6-14) Derivatives with Low Pancreas Accumulation for Targeting Gastrin-Releasing Peptide Receptor-Expressing Cancer," Pharmaceuticals (Basel), (Mar. 23, 2025), 18(4):449. doi: 10.3390/ph18040449; 18 pages.
Wang et al., "Unnatural amino acid substitutions to improve in vivo stability and tumor uptake of 68Ga-labeled GRPR-targeted TacBOMB2 derivatives for cancer imaging with positron emission tomography," EJNMMI Radiopharm Chem, (Feb. 2, 2024), 9(1):8. doi: 10.1186/s41181-024-00241-7; 15 pages.
Wang et al., "Synthesis and Evaluation of 68Ga- and 177Lu-Labeled [diF-Pro14]Bombesin(6-14) Analogs for Detection and Radioligand Therapy of Gastrin-Releasing Peptide Receptor-Expressing Cancer," Pharmaceuticals (Basel), (Feb. 8, 2025), 18(2):234. doi: 10.3390/ph18020234; 22 pages.
Azay et al., "Comparative study of in vitro and in vivo activities of bombesin pseudopeptide analogs modified on the C-terminal dipeptide fragment," Peptides, (Jan. 1998), 19(1):57-63.
Hoppenz et al., "Identification and stabilization of a highly selective gastrin-releasing peptide receptor agonist," J Pep Sci, (Dec. 2019), 25(12):e3224, 12 pages; doi: 10.1002/psc.3224. Epub Nov. 19, 2019.
Lau et al., "Effect of Radiometal on Binding Affinity and Biodistribution of ProBOMB1, a Novel Bombesin Derivative," J Nucl Med, (May 2019), 60(Suppl. 1), 1013 [Abstract]; 4 pages.
Mansi et al., "Development of a potent DOTA-conjugated bombesin antagonist for targeting GRPr-positive tumours," Eur J Nucl Med Mol Imaging, (Jan. 2011), 38(1):97-107.
PCT Application No. PCT/CA2025/051213, International Search Report and Written Opinion mailed Nov. 28, 2025, Applicant Alpha-9 Oncology Inc.; 13 pages.
Wang, L. et al., "Synthesis and Evaluation of 68Ga- and 177Lu-Labeled [Pro14]bombesin(8-14) Derivatives for Detection and Radioligand Therapy of Gastrin-Releasing Peptide Receptor-Expressing Cancer," Mol Pharm. Dec. 2, 2024; 21(12):6385-6397. Epub Oct. 26, 2024.

* cited by examiner

GASTRIN-RELEASING PEPTIDE RECEPTOR (GRPR)-TARGETED COMPOUNDS AND USES THEREOF

CROSS-REFERENCE TO RELATED APPLICATIONS

This application is a continuation of International Patent Application No. PCT/CA2025/051213, filed on Sep. 12, 2025, which claims priority to U.S. Provisional Patent Application No. 63/694,257, filed on Sep. 13, 2024, the contents of each of which is hereby incorporated by reference in its entirety for all purposes.

REFERENCE TO AN ELECTRONIC SEQUENCE LISTING

The contents of the electronic sequence listing (A9TH_025_01US_SeqList_ST26.xml; Size: 218,087 bytes; and Date of Creation: Sep. 18, 2025) are herein incorporated by reference in its entirety.

FIELD

The present invention relates to gastrin-releasing peptide receptor (GRPR)-targeted compounds and their use for imaging and treatment of diseases or conditions characterized by expression of the gastrin-releasing peptide receptor.

BACKGROUND

Gastrin-releasing peptide receptor (GRPR) is a G protein-coupled receptor of the bombesin (BBN) receptor family (Roesler & Schwartsmann. 2012. *Front Endocrinol* (*Lausanne*) 3:159; Bitar & Zhu. 1993. *Gastroenterology.* 105: 1672-1680; Weber. 2009. *Curr Opin Endocrinol Diabetes Obes.* 16:66-71). Together with its endogenous ligand, gastrin-releasing peptide (GRP), GRPR is involved in synaptic plasticity, emotional and feeding behavior, hormone secretion, smooth muscle contraction, and cell proliferation (ibid.). In normal conditions, the expression of GRPR is restricted to the central nervous system, pancreas, adrenal cortex and gastrointestinal tract (Jensen, et al. 2008. *Pharmacol Rev.* 60:1-42). GRPR is also implicated in neoplastic progression, with overexpression of GRPR having been reported in many cancer subtypes including lung, head and neck, colon, kidney, ovarian, breast and prostate cancers (Cornelio, et al. *Ann Oncol.* 2007, 18:1457-1466). This ectopic expression in cancers makes it an attractive target for personalized therapies.

BBN is a 14 amino acid GRPR binding peptide (Lin, et al. 2004. Bioconjugate Chemistry. Vol 15. American Chemical Society pages 1416-1423; Inkster, et al. 2013 *Bioorganic Med Chem Lett.* 23:3920-3926; Mansi, et al. 2016 *J Nucl Med.* 57:67S-72S; Bodei, et al. 2007. $^{177}$Lu-AMBA Bombesin analogue in hormone refractory prostate cancer patients: a phase I escalation study with single-cycle administrations. In: JOINT EANM-EORTC Symposium; Sah, et al. 2015 *J Nucl Med.* 56:372-378; Zang, et al. 2018 *Clin Nucl Med.* 43:663-669; Nock, et al. 2017 *J Nucl Med.* 58:75-80; Maina, et al. 2016 *Eur J Nucl Med Mol Imaging* 43:964-973). BBN derivatives have been radiolabeled for imaging with single photon emission computed tomography (SPECT), positron emission tomography (PET), and have also been radiolabeled for therapy with beta and alpha emitters (Maina, et al. PET Clin. 2017; 12:297-309; Lin, et al. 2004. Bioconjugate Chemistry. Vol 15. American Chemical Society pages 1416-1423; Inkster, et al. 2013 *Bioorganic Med Chem Lett.* 23:3920-3926). Often, a radiolabelled group is appended directly onto the structure or via a linker at the N-terminus, while modifications at the C-terminus dictate agonist/antagonist properties. For targeting GRPR, antagonists are preferred since agonists have been shown to induce gastrointestinal adverse events (Bodei, et al. 2007. $^{177}$Lu-AMBA Bombesin analogue in hormone refractory prostate cancer patients: a phase I escalation study with single-cycle administrations. In: JOINT EANM-EORTC Symposium). Examples of GRPR antagonists evaluated in the clinic include: $^{68}$Ga-RM2, $^{68}$Ga-SB3, $^{68}$Ga-NeoBOMB1, $^{68}$Ga-RM26, $^{18}$F-BAY-864367, and $^{64}$Cu-CB-TE2A-AR06 (Mansi, et al. 2016 *J Nucl Med.* 57:67S-72S; Sah, et al. 2015 *J Nucl Med.* 56:372-378; Zang, et al. 2018 *Clin Nucl Med.* 43:663-669; Nock, et al. 2017 *J Nucl Med.* 58:75-80; Maina, et al. 2016 *Eur J Nucl Med Mol Imaging* 43:964-973; Kahkonen, et al. Clin Cancer Res. 2013; 19:5434-5443, Kahkonen, et al. Clin Cancer Res. 2013; 19:5434-5443; Baum, et al. 2007 *Journal of Nuclear Medicine* 48, 79P-79P). However, high pancreas uptake remains the major limitation of currently reported GRPR-targeting radioligands.

In a study, the high pancreas uptake of $^{68}$Ga-labeled AMBA was up to 54.9 SUV (SUV: standard uptake value) (Baum, et al. 2007 *Journal of Nuclear Medicine* 48, 79P-79P). In addition, $^{68}$Ga-labeled RM2 was also reported to show high uptake in pancreas (Kurth, et al. 2020. *European journal of nuclear medicine and molecular imaging* 47, 123-135; Minamimoto, et al. 2016 *J Nucl Med.* 57:557-562). It has also been reported that radiolabeled NeoBOMB1 showed high pancreas uptake in both PC-3 tumor-bearing mice and prostate cancer patients (Nock, et al. 2017 *J Nucl Med.* 58:75-80).

Another limitation for most of the reported GRPR-targeting ligands is their in vivo metabolic instability (Bakker, et al. 2018 *Molecular imaging and biology* 20, 973-983; Rousseau, et al. 2020 *Journal of Labelled Compounds and Radiopharmaceuticals* 63, 56-64) due to enzymatic degradation by neutral endopeptidase (NEP) (Nock, et al. 2014 *J Nucl Med.* 55:121-127). His$^{12}$-Leu$^{13}$, Trp$^{8}$-Ala$^{9}$ and Gln$^{7}$-Trp$^{8}$ were reported to be the main cleavage sites within the AMBA's sequence, and Trp$^{8}$-Ala$^{9}$, Ala$^{9}$-Val$^{10}$ and Gln$^{7}$-Trp$^{8}$ were considered to be the cleavage sites of RM2 (Kahkonen, et al. 2013 *Clin Cancer Res.* 19:5434-5443; Linder et al. 2009 *Bioconjugate chemistry* 20, 1171-1178).

A series of bombesin analogs modifying its C-terminal Leu$^{13}$-Met$^{14}$ have been developed. See, Rousseau, E. et al. *Journal of Labelled Compounds and Radiopharmaceuticals* 63, 56-64 (2020), Lau, J. et al. *ACS omega* 4, 1470-1478 (2019), and Bratanovic, I. J. et al. *J. of Nuclear Medicine* July 2021, jnumed.120.257758, each of which is hereby incorporated by reference in its entirety for all purposes. However, there still remain a need in the field for improved tracers for the non-invasive in-vivo imaging of the GRPR. Such tracers are useful for the diagnosis of disorders related to aberrant/ectopic expression of GRPR, including but not limited to cancer (e.g., prostate cancer). There also remains an unmet need for improved radiotherapeutic agents for treatment of diseases/disorders related to aberrant/ectopic expression of GRPR, including but not limited to cancer (e.g., prostate cancer). In particular, there is a need for GRPR-targeting radioligands (for imaging and/or therapy) with lower pancreas uptake, and useful stability in vivo.

No admission is necessarily intended, nor should it be construed, that any of the preceding information constitutes prior art against the present invention.

SUMMARY

In one aspect, this disclosure provides a peptidic compound of Formula (A), or a salt or solvate thereof:

$$R^{rad}_{n6}—R^L\text{-[linker]-}R^L—Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (A)$$

wherein:

- $Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;
- $Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;
- $Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;
- $Xaa^4$ is Ala, D-Ala, or Ser;
- $Xaa^5$ is Val, 2,3-dehydro-Val, cyclopentylglycine (Cpg), L-cyclopropylglycine, L-cyclobutylglycine, or tert-leucine (Tle);
- $Xaa^6$ is Gly or D-Ala;
- $Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;
- $Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;
- R is $—NH_2$ or —NHOH;
- m1 is 0 or 1;
- m2 is 0 or 1;
  - when m1 is 1 and m2 is 0, $Xaa^9$-R is a C-terminally amidated (R is $—NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;
  - when m1 is 1 and m2 is 1, $Xaa^9$ is Pro, Phe, oxazolidine-4-carboxylic acid (4-oxa-L-Pro), 4,4-difluoroproline (difluoroPro), Leu, $Me_2$Thz (5,5-dimethyl-1,3-thiazolidine-4-carboxylic acid), or thiazoline-4-carboxylic acid (Thz); and $Xaa^{10}$-R is a C-terminally amidated (R is $—NH_2$) or a C-terminally hydroxylamidated (R is —NHOH) amino acid residue selected from Val, Leu, Tle, lie, Nle, Ala, Gly, or Met;
- ψ represents a peptide bond or reduced peptide bond joining $Xaa^8$ to $Xaa^9$;
- each $R^L$ is independently absent, $—(C_{1-6}$ alkyl)-, $—(C_{1-6}$ alkyl)-C(O)—, —C(O)—, —NH—C(O)—, or —NH—C(S)—;
- the linker is a linear or branched chain of n1 units of -$Xaa^{11}$-, and/or -$L^1R^1$— and/or -$(L^1)_2R^1$—, wherein:
  - n1 is 1-20;
  - each $Xaa^{11}$ is independently an amino acid;
  - each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;
  - $L^1$ bonds to carbon, wherein each $L^1$ is independently —S—, $—N(R^2)C(O)—$, $—C(O)N(R^2)—$, —NH—C(O)—NH—, —NH—C(S)—NH—,

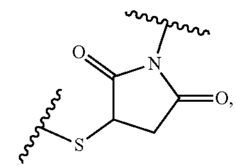
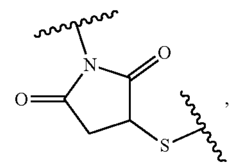
,
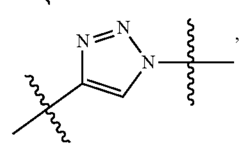
, or
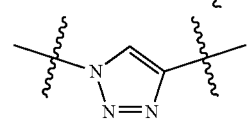
;

and

- $R^2$ is H, methyl or ethyl;
- optionally, the linker comprises an albumin binder ($R^{alb}$), wherein the albumin binder is:
  - $—(CH_2)_{n3}—CH_3$ wherein n3 is 8-20;
  - $—(CH_2)_{n4}—C(O)OH$ wherein n4 is 8-20;

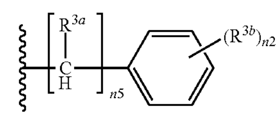

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

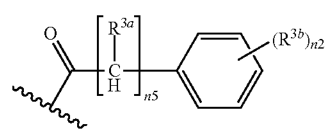

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

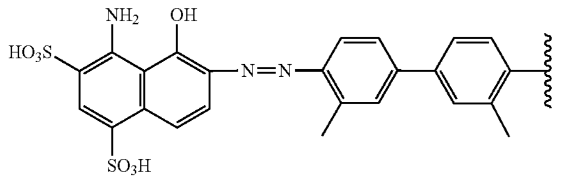

;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; wherein:

(i) $Xaa^3$ is αMe-Trp, provided that the compound is not AMTG, AMTG2, and/or LW01186 (DOTA-Pip-D-Phe-Gln-αMe-Trp-Ala-Tle-Gly-His-Leu-ψ-Thz-$NH_2$ (SEQ ID NO: 1));

(ii) $Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

(iii) $Xaa^2$ is Gly, Arg, Asp, Glu, citrulline (Cit), 2-amino-4-ureidobutanoic acid (Aub), or 2-amino-4-guanidinobutyric acid (Agb);

(iv) m2 is 1;

(v) at least one $R^{rad}$ is CROWN, CROWNGA, TCMC, PSC, a prosthetic group containing a trifluoroborate, an aryl or heteroaryl substituted with at least one radiohalogen, or an aryl or heteroaryl substituted with at least one fluorine precursor leaving group;

(vi) m1 is 0; or (vii) any combinations of (i)-(vi); and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In another aspect, this disclosure provides a peptidic compound of Formula (B-1), or a salt or solvate thereof:

$$R^{rad}\text{-[linker]-}Xaa^{13}\text{—}[Xaa^{12}\text{—}Xaa^1\text{—}Xaa^2\text{—}Xaa^3\text{—}Xaa^4\text{—}Xaa^5\text{—}Xaa^6\text{—}Xaa^7\text{—}Xaa^8\text{-}\psi\text{-}Xaa^9\text{—}(Xaa^{10})_{m2}\text{—}R]_2 \quad \text{(B-1)}$$

wherein:

$Xaa^{12}$ is an N-terminal amino acid residue selected from p-aminomethylaniline-diglycolic acid (pABzA-DIG), 4-amino-(1-carboxymethyl)piperidine (Pip), 9-amino-4,7-dioxanonanoic acid (dPEG2), or 4-(2-aminoethyl)-1-carboxymethyl-piperazine (Acp);

$Xaa^1$ is D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe;

R is —$NH_2$ or —NHOH;

m2 is 0 or 1;

when m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;

when m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

$Xaa^{13}$ is an amino acid with a sidechain comprising a carboxylic acid, wherein one $Xaa^{12}$ is bonded to the C-terminus of $Xaa^{13}$ and the other $Xaa^{12}$ is bonded to the sidechain of $Xaa^{13}$;

ψ represents a peptide bond or reduced peptide bond joining $Xaa^8$ to $Xaa^9$;

the linker absent or is a linear or branched chain of n1 units of -$Xaa^{11}$-, wherein:

n1 is 1-6;

each $Xaa^{11}$ is independently an amino acid;

$R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In still another aspect, the disclosure provides a composition comprising any one of the peptidic compounds as described herein and a pharmaceutically acceptable carrier or excipient.

In a further aspect, the disclosure provides a method of imaging gastrin-releasing peptide receptor (GRPR)-expressing tissue in a subject, the method comprising administering to the subject any one of the peptidic compounds described herein or compositions thereof, and imaging tissue of the subject.

In an additional aspect, the disclosure provides a method of treating cancer in a subject comprising, administering to the subject in need thereof a therapeutically effective amount of any one of the peptidic compounds described herein or compositions thereof.

DETAILED DESCRIPTION

As used herein, the terms "comprising," "having", "including" and "containing," and grammatical variations thereof, are inclusive or open-ended and do not exclude additional, unrecited elements and/or method steps, even if a feature/component defined as a part thereof consists or consists essentially of specified feature(s)/component(s). The term "consisting essentially of" if used herein in connection with a compound, composition, use or method, denotes that additional elements and/or method steps may be present, but that these additions do not materially affect the manner in which the recited compound, composition, method or use functions. The term "consisting of" if used herein in connection with a feature of a compound, composition, use or method, excludes the presence of additional elements and/or method steps in that feature. A compound, composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the context clearly dictates otherwise. The use of the word "a" or "an" when used herein in conjunction with the term "comprising" may mean "one," but it is also consistent with the meaning of "one or more," "at least one" and "one or more than one."

The term "about" can mean within an acceptable error range for the particular value as determined by one of ordinary skill in the art, which will depend in part on how the value is measured or determined, i.e., the limitations of the measurement system. For example, "about" can refer to a range of ±20%, 15%, 10%, 5%, or +1% of a given value.

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, etcetera.

As used herein, the terms "treat", "treatment", "therapeutic" and the like includes ameliorating symptoms, reducing disease progression, improving prognosis and reducing recurrence.

As used herein, the term "diagnostic agent" includes an "imaging agent". As such, a "diagnostic radionuclide" includes radionuclides that are suitable for use in imaging agents.

The term "subject" refers to an animal (e.g., a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include base-free forms, solvates, salts or pharmaceutically acceptable salts thereof. Unless otherwise specified or indicated, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g., protonated) state or may be shown without specifying formal charges. As will be appreciated by a person of skill in the art, the ionization state of certain groups within a compound (e.g., without limitation, COOH, and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g., without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, for administration to a subject. As used herein, "pharmaceutically acceptable" means suitable for in vivo use in a subject, and is not necessarily restricted to therapeutic use, but also includes diagnostic use. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (*J. Pharm Sci.* 66:1-19), or Remington—The Science and Practice of Pharmacy, 21st edition (Gennaro et al editors. Lippincott Williams & Wilkins Philadelphia), each of which is incorporated by reference in its entirety.

As used herein, the expression "$C_n$" where n is an integer (e.g., 1, 2, 3, 4, 5, 6, 7, 8, 9, 10, 11, 12, 13, 14, 15, 16, 17, 18, 19, 20, and the like) or where n is defined as a range of integers (e.g., 1-20, 1-18, 2-15, 3-20, and the like) refers to the number of carbons in a compound, R-group, L-group, or substituent, or refers to the number of carbons plus heteroatoms in a compound, R-group, L-group, or substituent. A range of integers includes all integers in the range; e.g., the range 1-20 includes the integers 1, 2, 3, 4, 5, 6, 7, 8, 9, 10, 11, 12, 13, 14, 15, 16, 17, 18, 19, and 20. Unless otherwise defined, heteroatoms may include any, some or all possible heteroatoms. For example, in some embodiments, the heteroatoms may be selected from N, O, S, P and Se. In some embodiments, the heteroatoms are selected from N, S, or O. Such embodiments are non-limiting. The alternative expression "Cy-Cz", where y and z are integers (e.g., $C_3$-$C_{15}$ and the like), is equivalent to "$C_n$" where n is a range of integers from y to z.

The terms "alkyl", "alkylenyl", "alkenylenyl", and "alkynylenyl" have their usual meanings in organic chemistry. For example, an "alkyenylenyl" has at least one carbon-carbon double bond, and may have any number of carbon-carbon single bonds. Similarly, an "alkynylenyl" has at least one carbon-carbon triple bond, and may have any number of carbon-carbon single bonds. The expressions "alkylenyl, alkenylenyl and/or alkynylenyl" and "alkylenyl, alkenylenyl or alkynylenyl" are intended to be equivalent and each includes hydrocarbon chains that can have any reasonable number or combination of carbon-carbon single bonds, double bonds, and triple bonds. These hydrocarbon chains can be linear, branched, cyclic, or any combination of linear and branched, linear and cyclic, cyclic and branched, branched and cyclic, or linear, branched and cyclic. Cyclic hydrocarbons may be nonaromatic, partially aromatic, or aromatic. Unless otherwise specified, the term "cyclic" includes single rings, multiple non-fused rings, fused rings, bridged rings, and combinations thereof.

The expression "wherein any carbon . . . is optionally independently replaced by N, S, or O" and other similar expressions means that the defined hydrocarbon (e.g., "alkyl", "alkylenyl", "alkenylenyl", or "alkynylenyl") includes zero, one, more than one, or any reasonable combination of two or more heteroatoms selected from N, S, and O. The above expression therefore expands the defined hydrocarbon to additionally encompass heteroalkyls, heteroalkylenyls, heteroalkenylenyls, and heteroalkynylenyls, etc. A person of skill in the art would understand that various combinations of different heteroatoms may be used. The expression "wherein any carbon bonded to two other carbons is optionally independently replaced by N, S, or O" and other similar expressions means that any carbon in the defined hydrocarbon bonded to two other carbons (e.g., the underlined carbon in —C—C—C—), whether those bonds are single, double, or triple bonds, may be a heteroatom, but excludes heteroatoms bonded to other heteroatoms (e.g., excludes —C—N—S—, —S—S—N—, —N—S—C—, and the like).

Various R-groups (e.g., $R^1$, $R^2$, $R^3$, etc.) and L-groups (e.g., $L^1$, $L^2$, $L^3$, etc.) are defined in this disclosure. Some groups are divalent (e.g., —S—, —NH—C(O)—, —C(O)—NH—, —N(alkyl)-C(O)—, —C(O)—N(alkyl)-, —NH—C(O)—NH—, —NH—C(S)—NH—,

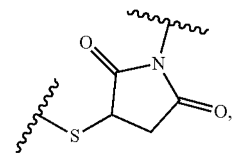,
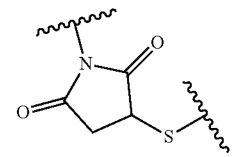,
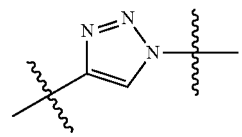, or
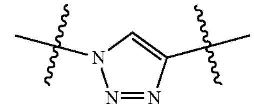).

If unspecified, the size of an R-group or L-group is what would be considered reasonable to a person of skill in the art. For example, but without limitation, if unspecified, the size of an alkyl may be 1, 2, 3, 4, 5, 6, 7, 8, 9, 10, 11, 12, 13, 14, 15, 16, 17, 18, 19, 20 or more than 20 carbons in length, subject to the common general knowledge of the person of skill in the art. Further, but without limitation, if unspecified, the size of a heteroalkyl may be 1, 2, 3, 4, 5, 6, 7, 8, 9, 10, 11, 12, 13, 14, 15, 16, 17, 18, 19, 20 or more than 20 carbons and heteroatoms in length, subject to the common general knowledge of the person of skill in the art. In the context of the expression "alkyl, alkenyl or alkynyl" and similar expressions, the "alkyl" would be understood to be a saturated alkyl, and the "alkenyl" and the "alkynyl" would be understood to be unsaturated.

As used herein, in the context of an alkyl/heteroalkyl group of a compound, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl.

As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

The term "alkylenyl" refers to a divalent analog of an alkyl group. In the context of the expression "alkylenyl, alkenylenyl and/or alkynylenyl", and similar expressions, the "alkylenyl" would be understood to be a saturated alkylenyl, and the "alkenylenyl" and the "alkynylenyl" would be understood to be unsaturated. The term "heteroalkylenyl" refers to a divalent analog of a heteroalkyl group. The term "heteroalkenylenyl" refers to a divalent analog of a heteroalkenyl group. The term "heteroalkynylenyl" refers to a divalent analog of a heteroalkynyl group.

As used herein, the term "saturated" when referring to a chemical entity may be used as it is normally understood to a person of skill in the art and generally refers to a chemical entity that comprises only single bonds, and may include linear, branched, and/or cyclic groups. Non-limiting examples of a saturated $C_1$-$C_{20}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, I-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl, t-decyl, cyclopropanyl, cyclobutanyl, cyclopentanyl, cyclohexanyl, cycloheptanyl, cyclooctanyl, cyclononanyl, cyclodecanyl, and the like. Unless otherwise specified, a $C_1$-$C_{20}$ alkylenyl therefore encompasses, without limitation, all divalent analogs of the above-listed saturated alkyl groups.

As used herein, the term "unsaturated" when referring to a chemical entity may be used as it is normally understood to a person of skill in the art and generally refers to a chemical entity that comprises at least one double or triple bond, and may include linear, branched, and/or cyclic groups. Non-limiting examples of a $C_2$-$C_{20}$ alkenyl group may include vinyl, allyl, isopropenyl, I-propene-2-yl, 1-butene-1-yl, I-butene-2-yl, I-butene-3-yl, 2-butene-1-yl, 2-butene-2-yl, octenyl, decenyl, cyclopropenyl, cyclobutenyl, cyclopentenyl, cyclohexenyl, cycloheptenyl, cyclooctenyl, cyclononanenyl, cyclodecanenyl, and the like. Unless otherwise specified, a $C_1$-$C_{20}$ alkenylenyl therefore encompasses, without limitation, all divalent analogs of the above-listed alkenyl groups. Non-limiting examples of a $C_2$-$C_{20}$ alkynyl group may include ethynyl, propynyl, butynyl, pentynyl, hexynyl, heptynyl, octynyl, nonynyl, decynyl, and the like. Unless otherwise specified, a $C_1$-$C_{20}$ alkynylenyl therefore encompasses, without limitation, all divalent analogs of the above-listed alkynyl groups.

Non-limiting examples of non-aromatic cyclic groups include cylcopropyl, cyclobutyl, cyclopentyl, cyclohexyl, and the like. Non-limiting examples of non-aromatic heterocyclic groups include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, oxathiolanyl, and the like.

Unless further specified, an "aryl" group includes both single aromatic rings as well as fused rings containing at least one aromatic ring. non-limiting examples of $C_3$-$C_{20}$ aryl groups include phenyl (Ph), pentalenyl, indenyl, naphthyl and azulenyl. Non-limiting examples of aromatic heterocyclic groups of similar size include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, isoxazolyl, and the like.

As used herein, the term "substituted" is used as it would normally be understood to a person of skill in the art and generally refers to a compound or chemical entity that has one chemical group replaced with a different chemical group. Unless otherwise specified, a substituted alkyl, alkylenyl, alkenylenyl, or alkynylenyl has one or more hydrogen atom(s) independently replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g., R-group or L-group) may be substituted with any chemical group reasonable to a person of skill in the art. For example, but without limitation, a hydrogen bonded to a carbon or heteroatom (e.g., N) may be substituted with halide (e.g., F, I, Br, Cl), amine, amide, oxo, hydroxyl, thiol, phosphate, phosphonate, sulfate, $SO_2H$, $SO_3H$, alkyls, heteroalkyls, aryl, heteroaryl, ketones, carboxaldehyde, carboxylates, carboxamides, nitriles, monohalomethyl, dihalomethyl or trihalomethyl. In some embodiments, each carbon may be independently substituted or unsubstituted with oxo, hydroxyl, sulfhydryl, amine, amide, urea, halogen, guanidino, carboxylic acid, sulfonic acid, sulfinic acid, or phosphoric acid. In some embodiments, the amide substituent is —C(O)—$NH_2$.

As used herein, the term "unsubstituted" is used as it would normally be understood to a person of skill in the art. Non-limiting examples of unsubstituted alkyls include methyl, ethyl, tert-butyl, pentyl and the like. The expression "optionally substituted" is used interchangeably with the expression "unsubstituted or substituted". The expression "optionally independently substituted" means that each location may be substituted or may not be substituted, and when substituted each substituent may be the same or different.

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

The term "Xaa" refers to an amino acid residue in a peptide chain or an amino acid that is otherwise part of a compound. Amino acids have both an amino group and a carboxylic acid group, either or both of which can be used for covalent attachment. In attaching to the remainder of the compound, the amino group and/or the carboxylic acid group may be converted to an amide or other structure; e.g., a carboxylic acid group of a first amino acid is converted to an amide (i.e. a peptide bond) when bonded to the amino group of a second amino acid. As such, Xaa may have the formula —N($R^a$)$R^b$C(O)—, where $R^a$ and $R^b$ are R-groups. $R^a$ will typically be hydrogen or alkyl (e.g., methyl) or $R^a$ and $R^b$ may form a cyclic structure. The amino acid residues of a peptide may comprise typical peptide (amide) bonds and may further comprise bonds between side chain functional groups and the side chain or main chain functional group of another amino acid. For example, the side chain carboxylate of one amino acid residue in the peptide (e.g., Asp, Glu, etc.) may be bonded to and the amine of another amino acid residue in the peptide (e.g., Dap, Dab, Orn, Lys). Further details are provided below. Unless otherwise indicated, "Xaa" may be any amino acid, including a proteinogenic or nonproteinogenic amino acid. Non-limiting examples of nonproteinogenic amino acids are shown in Table A and include: D-amino acids (including without limitation any D-form of the following amino acids), ornithine (Orn), 3-(1-naphtyl)alanine (Nal), 3-(2-naphtyl)alanine (2-Nal), α-aminobutyric acid, norvaline, norleucine (Nle), homonorleucine, beta-(1,2,3-triazol-4-yl)-L-alanine, 1,2,4-triazole-3-alanine, Phe(4-F), Phe(4-Cl), Phe(4-Br), Phe(4-I), Phe(4-$NH_2$), Phe(4-$NO_2$), homoarginine (hArg), 2-amino-4-guanidinobutyric acid (Agb), 2-amino-3-guanidinopropionic acid (Agp), B-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl)propanoic acid, 2-amino-3-(anthracen-9-yl) propanoic acid, 2-amino-3-(pyren-1-yl)propanoic acid, Trp (5-Br), Trp(5-$OCH_3$), Trp(6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys ($N_3$)), azido-ornithine (Orn($N_3$)), 2-amino-4-azidobutanoic acid Dab($N_3$), Dap($N_3$), 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp), tranexamic acid, tert-leucine (Tle), 4-chlorophenylalanine (Cpa), thiazoline-4-carboxylic acid (Thz), αMe-Trp, p-aminomethylaniline-diglycolic acid (pABzA-DIG), 4-amino-1-carboxymethyl-piperidine (Pip), $NH_2(CH_2)_2O(CH_2)_2C(O)OH$, $NH_2(CH_2)_2[O(CH_2)_2]_2C(O)OH$ (dPEG2), $NH_2(CH_2)_2[O(CH_2)_2]_3C(O)OH$, $NH_2(CH_2)_2[O(CH_2)_2]_4C(O)OH$, $NH_2(CH_2)_2[O(CH_2)_2]_5C(O)OH$, $NH_2(CH_2)_2[O(CH_2)_2]_6C(O)OH$, oxazolidine-4-carboxylic acid (4-oxa-L-Pro), 4,4-difluoroproline (diFPro), statine (Sta), β-(3-benzothienyl) alanine (Bta), citrulline (Cit), Trp(Me), Trp (7-Me), Trp(6-Me), Trp(5-Me), Trp(4-Me), Trp(2-Me), Trp(7-F), Trp(5-F), Trp(4-F) or cyclopentylglycine (Cpa). If not specified as an L- or D-amino acid, then the amino acid includes both L- and D-amino acid. If an unspecified (with respect to L- or D-) amino acid is listed together with its corresponding D-amino acid (e.g., Pro and D-Pro), then the unspecified amino acid is understood to be an L-amino acid.

TABLE A

List of non-limiting examples of non-proteinogenic amino acids.

| | |
|---|---|
| p-aminomethylaniline-diglycolic acid (pABzA-DIG) | 2-amino-3-(anthracen-2-yl)propanoic acid |
| ornithine (Orn) | 2-amino-3-(anthracen-9-yl)propanoic acid |
| 3-(1-naphtyl)alanine (Nal) | 2-amino-3-(pyren-1-yl)propanoic acid |
| 3-(2-naphtyl)alanine (2-Nal) | Trp(5-Br) |
| α-aminobutyric acid | Trp(5-$OCH_3$) |
| norvaline | Trp(6-F) |
| norleucine (Nle) | Trp(5-OH) |
| homonorleucine | Trp(CHO) |
| beta-(1,2,3-triazol-4-yl)-L-alanine | $N^\epsilon$,$N^\epsilon$,$N^\epsilon$-trimethyl-lysine |
| 1,2,4-triazole-3-alanine | cysteic acid |
| Phe(4-F), Phe(2-F), Phe(3-F), | 2-aminoadipic acid (2-Aad) |
| Phe(4-Cl), Phe(2-Cl), Phe(3-Cl), | 3-aminoadipic acid (3-Aad) |
| Phe(4-Br), Phe(2-Br), Phe(3-Br), | propargylglycine (Pra) |
| Phe(4-I), Phe(2-I), Phe(2-I), | homopropargylglycine (Hpg) |
| Phe(4-$NH_2$), Phe(2-$NH_2$), Phe(3-$NH_2$), | beta-homopropargylglycine (Bpg) |
| Phe(4-$NO_2$), Phe(2-$NO_2$), Phe(2-$NO_2$), | 2,3-diaminopropionic acid (Dap) |
| homoarginine (hArg) | 2,4-diaminobutyric acid (Dab) |
| 4-(2-aminoethyl)-1-carboxymethyl-piperazine (Acp) | azidolysine (Lys($N_3$)) |
| 2-(5'-azidopentyl)alanine, 2-(6'-azidohexyl)alanine | azido-ornithine (Orn($N_3$)) |
| 2-amino-4-guanidinobutyric acid (Agb) | amino-4-azidobutanoic acid (Dab($N_3$)) |
| 2-amino-3-guanidinopropionic acid (Agp) | tranexamic acid |
| β-alanine | 4-amino-1-carboxymethyl-piperidine (Pip) |
| 4-aminobutyric acid | $NH_2(CH_2)_2O(CH_2)_2C(O)OH$ |
| 5-aminovaleric acid | $NH_2(CH_2)_2[O(CH_2)_2]_2C(O)OH$ (dPEG2) |
| 6-aminohexanoic acid | $NH_2(CH_2)_2[O(CH_2)_2]_3C(O)OH$ |
| 7-aminoheptanoic acid | $NH_2(CH_2)_2[O(CH_2)_2]_4C(O)OH$ |
| 8-aminooctanoic acid | $NH_2(CH_2)_2[O(CH_2)_2]_5C(O)OH$ |
| 9-aminononanoic acid | $NH_2(CH_2)_2[O(CH_2)_2]_6C(O)OH$ |
| 10-aminodecanoic acid | citrulline (Cit), norcitrulline (nCit) |
| 2-aminooctanoic acid | β-(3-benzothienyl)alanine (Bta) |
| tert-leucine (Tle) | oxazolidine-4-carboxylic acid (4-oxa-L-Pro) |
| 4-chlorophenylalanine (Cpa) | cyclopentylglycine (Cpg) |
| thiazoline-4-carboxylic acid (Thz) | αMe-Trp |
| any N-methylated version of a proteinogenic amino acid or non-proteinogenic amino acid in this Table | any D-amino acid of a proteinogenic amino acid or any D-amino acid of a non-proteinogenic amino acid in this Table |
| Trp(Me), Trp(2-Me) | Trp(7-F), Trp(6-F), Trp(5-F), Trp(4-F) |
| Trp(7-Me), Trp(6-Me), Trp(5-Me), Trp(4-Me), | Trp(7-Cl), Trp(6-Cl), Trp(5-Cl), Trp(4-Cl) |
| 2-Pyridylalanine (2-Pal), 3-Pyridylalanine (3-Pal) | Trp(7-Br), Trp(6-Br), Trp(5-Br), Trp(4-Br) |
| 4-Pyridylalanine (4-Pal) | Trp(7-I), Trp(6-I), Trp(5-I), Trp(4-I) |
| 2-Quinoylalanine, 3-Quinoylalanine (3-Quin-Ala) | cyclobutylglycine |
| 2,3,4,9-tetrahydro-1H-pyrido[3,4-b]indol-3-carboxylic acid (Tpi) | 5,5-dimethyl-1,3-thiazolidine-4-carboxylic acid ($Me_2$Thz) |
| 7-Aza (7-azatryptophan) | 2,3-dehyrdo-Val |
| 4,4-difluoroproline (diFPro) | cyclopropylglycine |
| cis-4-cyclohexyloxy-D-Pro (cis-4-OCy-D-Pro) | statine (Sta) |
| cis-4-cyclohexylamino-D-Pro (cis-4-NHCy-D-Pro) | 2-amino-4-ureidobutanoic acid (Aub) |

The wavy line "∿∿" symbol shown through or at the end of a bond in a chemical formula (e.g., in the definitions $L^1$ or $R^A$ of Formula I) is intended to define the group on one side of the wavy line, without modifying the definition of the structure on the opposite side of the wavy line. Where an R-group or L-group is bonded on two or more sides, any atoms shown outside the wavy lines are intended to clarify orientation of the defined group. As such, only the atoms between the two wavy lines constitute the definition of the R-group or L-group. When atoms are not shown outside the wavy lines (e.g., $L^1$), or for a chemical group shown without wavy lines but does have bonds on multiple sides (e.g., —C(O)NH—, and the like), the chemical group should be read from left to right matching the orientation in the formula that the group relates to; e.g., for formula —$R^a$—$R^b$—$R^c$—, the definition of $R^b$ as —C(O)NH— would be incorporated into the formula as —$R^a$—C(O)NH—$R^c$— not as —$R^a$—NHC(O)—$R^c$—.

The term "therapeutically effective amount" as used herein refers to an amount effective at the dosage and duration necessary to achieve the desired therapeutic result. A therapeutically effective amount of the composition may vary depending on factors such as the individual's condition, age, sex, and weight, and the ability of the protein to elicit the desired response of the individual. A therapeutically effective amount can also be an amount that exceeds any toxic or deleterious effect of the composition that would have a beneficial effect on the treatment.

Compounds

Previously, a series of bombesin analogs modifying its C-terminal $Leu^{13}$-$Met^{14}$ have been developed. See, Rousseau, E. et al. *Journal of Labelled Compounds and Radiopharmaceuticals* 63, 56-64 (2020), Lau, J. et al. *ACS omega* 4, 1470-1478 (2019), and Bratanovic, I. J. et al. *J. of Nuclear Medicine* July 2021, jnumed.120.257758, each of which is hereby incorporated by reference in its entirety for all purposes.

In one aspect, this disclosure provides a peptidic compound of Formula (A), (I), (IA), (IA-1), (IB), (IB-1), (IC), (IC-1), (ID), (ID-1), (IE), (IE-1), (IF), (IF-1), (II), (IIA), (B), or (B-1) (each as defined below), or a salt or solvate thereof.

In some embodiments, the present disclosure relates to a peptidic compound of Formula (A), or a salt or solvate of Formula (A), $$R^{rad}_{n6}—R^L\text{-[linker]-}R^L—Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (A)$$

wherein:

- $Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;
- $Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;
- $Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);
- $Xaa^4$ is Ala, D-Ala, or Ser;
- $Xaa^5$ is Val, 2,3-dehydro-Val, cyclopentylglycine (Cpg), L-cyclopropylglycine, L-cyclobutylglycine, or tert-leucine (Tle);
- $Xaa^6$ is Gly or D-Ala;
- $Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);
- $Xaa^8$ is statine (Sta), Leu, D-Pro, Phe, cis-4-NH$R^a$-D-Pro or cis-4-O$R^a$-D-Pro, wherein $R^a$ is alkyl, cycloalkyl, or aryl;
- R is —$NH_2$ or —NHOH;
- m1 is 0 or 1;
- m2 is 0 or 1;
  - when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoro-Pro), cis-4-NH$R^a$-D-Pro, cis-4-O$R^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;
  - when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;
- ψ represents a peptide bond or reduced peptide bond joining $Xaa^8$ to $Xaa^9$;
- each $R^L$ is independently absent, —($C_{1-6}$ alkyl)-, —($C_{1-6}$ alkyl)-C(O)—, —C(O)—, —NH—C(O)—, or —NH—C(S)—;
- the linker is a linear or branched chain of n1 units of -$Xaa^{11}$-, and/or -$L^1R^1$— and/or -$(L^1)_2R^1$—, wherein:
  - n1 is 1-20;
  - each $Xaa^{11}$ is independently an amino acid;
  - each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;
  - $L^1$ bonds to carbon, wherein each $L^1$ is independently —S—, —N($R^2$)C(O)—, —C(O)N($R^2$)—, —NH—C(O)—NH—, —NH—C(S)—NH—,

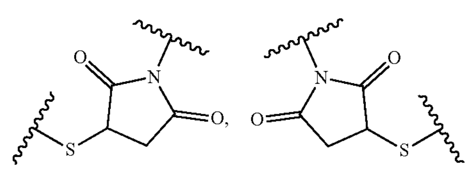
,

-continued

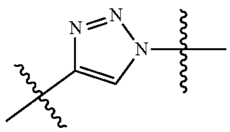

, or

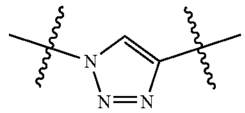

;

and $R^2$ is H, methyl or ethyl;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

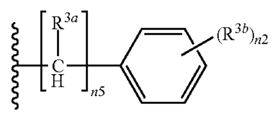

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

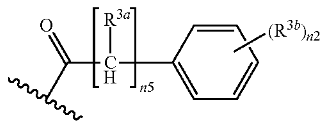

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

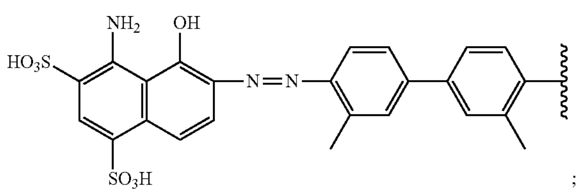 [SMILES: *c1ccc(-c2ccc(N=Nc3ccc4c(S(=O)(=O)O)cc(S(=O)(=O)O)c(N)c4c3O)c(C)c2)cc1C]

;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, the present disclosure relates to a peptidic compound of Formula (I), or a salt or solvate of Formula (I), wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, $Me_2Thz$ (5,5-dimethyl-1,3-thiazolidine-4-carboxylic acid), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

$$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

the linker is a linear or branched chain of n1 units of $-Xaa^{11}-$;

n1 is 1-20;

each $Xaa^{11}$ is independently an amino acid;

optionally, the linker comprises an albumin binder ($R^{alb}$), wherein the albumin binder is:

$-(CH_2)_{n3}-CH_3$ wherein n3 is 8-20;

$-(CH_2)_{n4}-C(O)OH$ wherein n4 is 8-20;

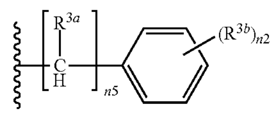

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

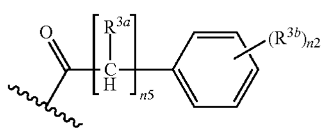

wherein n2 is 1-5, n5 is 1-4, $R^{3a}$ is H or methyl, and $R^{31}$ is I, Br, F, Cl, H, OH, $OCH_3$, $NH_2$, $NO_2$ or $C_1$-$C_6$ alkyl; or

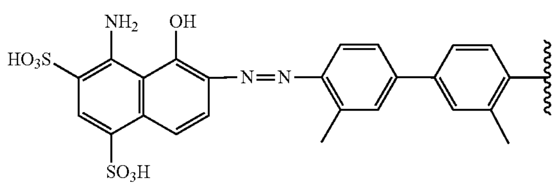

;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments of the compound of formula (A) or (I), or a salt or solvate of formula (A) or (I):

(iii) $Xaa^2$ is Gly, Arg, Asp, Glu, citrulline (Cit), 2-amino-4-ureidobutanoic acid (Aub), or 2-amino-4-guanidinobutyric acid (Agb);

(iv) m2 is 1;

(v) at least one $R^{rad}$ is CROWN, CROWNGA, TCMC, PSC, a prosthetic group containing a trifluoroborate, an aryl or heteroaryl substituted with at least one radiohalogen, or an aryl or heteroaryl substituted with at least one fluorine precursor leaving group;

(vi) m1 is 0; or (vii) any combinations of (i)-(vi).

In some embodiments of the compound of formula (A) or (I), or a salt or solvate of formula (A) or (I), at least one $R^{rad}$ is CROWN, CROWNGA, TCMC, PSC, a prosthetic group containing a trifluoroborate, an aryl or heteroaryl substituted with at least one radiohalogen, or an aryl or heteroaryl substituted with at least one fluorine precursor leaving group. In some embodiments of the compound of formula (A) or (I), or a salt or solvate of formula (A) or (I), at least one $R^{rad}$ is CROWN, TCMC, PSC, a prosthetic group containing a trifluoroborate, an aryl or heteroaryl substituted with at least one radiohalogen, or an aryl or heteroaryl substituted with at least one fluorine precursor leaving group.

In some embodiments, $Xaa^1$ being an N-terminal amino acid residue D-Phe indicates $Xaa^1$ having the structure

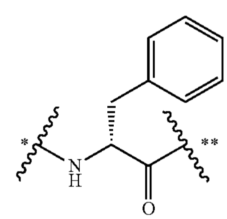

, where * indicates the connectivity to the -[linker]- or to the -[linker]-$R^L$— and ** indicates the connectivity to $Xaa^2$. In embodiments, similar configuration is understood with other $Xaa^1$ amino acids.

In some embodiments of the compound of formula (A) or (I), or salt or solvate of formula (A) or (I), each $Xaa^{11}$ is independently selected from any proteinogenic amino acid or nonproteinogenic amino acid disclosed in Table A.

In some embodiments, the present disclosure relates to a peptidic compound of Formula (IA), or a salt or solvate of Formula (IA), $$R^{rad}_{n6}\text{-[linker]-}Xaa^1-Xaa^2-Xaa^3-Xaa^4-Xaa^5-Xaa^6-Xaa^7-Xaa^8-[\psi-Xaa^9-(Xaa^{10})_{m2}]_{m1}-R \quad \text{(IA)}$$

(i) $Xaa^3$ is αMe-Trp, provided that the compound is not AMTG, AMTG2, and/or LW01186;

(ii) $Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is αMe-Trp;

$Xaa^4$ is Ala, D-Ala, or Ser;

$Xaa^5$ is Val or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;

R is —$NH_2$ or —NHOH;

m1 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, or Leu, wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

$R^L$ is absent, —($C_{1-6}$ alkyl)-, —($C_{1-6}$ alkyl)-C(O)—, —C(O)—, —NH—C(O)—, or —NH—C(S)—; the linker is a linear or branched chain of n1 units of -$Xaa^{11}$-:

n1 is 1-20;

each $Xaa^{11}$ is independently an amino acid;

optionally, the linker is bonded to an albumin binder ($R^{alb}$), wherein $R^{alb}$ is:

—$(CH_2)_{n3}$—$CH_3$ wherein n3 is 8-20;

—$(CH_2)_{n4}$—C(O)OH wherein n4 is 8-20;

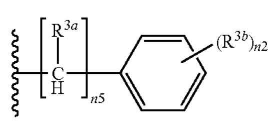

wherein n2 is 1-5, n5 is 1-4, each $R^{3a}$ is independently H or methyl, and each $R^{3b}$ is independently I, Br, F, Cl, H, OH, $OCH_3$, $NH_2$, $NO_2$ or $C_1$-$C_6$ alkyl;

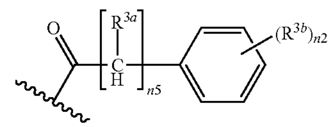

wherein n2 is 1-5, n5 is 1-4, each $R^{3a}$ is independently H or methyl, and each $R^{3b}$ is independently I, Br, F, Cl, H, OH, $OCH_3$, $NH_2$, $NO_2$ or $C_1$-$C_6$ alkyl; or

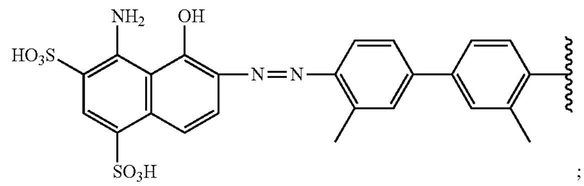 [SMILES: *c1ccc(-c2ccc(N=Nc3ccc4c(S(=O)(=O)O)cc(S(=O)(=O)O)c(N)c4c3O)c(C)c2)cc1C]

;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof;

wherein when $Xaa^5$ is Val, $R^L$ is absent, and the linker is 4-amino-(1-carboxymethyl)piperidine (Pip), then $R^{rad}$ is not DOTA or DOTAGA; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments of the compounds of Formula (A), (I) or (IA), the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethyl-piperazine (Acp) linker.

In some embodiments, the present disclosure relates to a peptidic compound of Formula (IA-1), or a salt or solvate of Formula (IA-1), (SEQ ID NO: 2)

$$R^{rad}\text{-[linker]-}Xaa^1—Xaa^2—Xaa^3—Xaa^4—Xaa^5—Xaa^6—Xaa^7—Xaa^8\text{-}\psi\text{-}Xaa^9—(Xaa^{10})_{m2}—R \quad \text{(IA-1)}$$

wherein:

$Xaa^1$ is an N-terminal amino acid residue of D-Phe;

$Xaa^2$ is Gln;

$Xaa^3$ is αMe-Trp;

$Xaa^4$ is Ala;

$Xaa^5$ is Val or Tle;

$Xaa^6$ is Gly;

$Xaa^7$ is His;

$Xaa^8$ is Sta or Leu;

R is —$NH_2$ or —NHOH;

when m2 is 0, $Xaa^9$-R is a C-terminally amidated (R is —$NH_2$) or a C-terminally hydroxylamidated (R is —NHOH) amino acid residue selected from Pro or Leu;

when m2 is 1, $Xaa^9$ is Pro or Leu; and $Xaa^{10}$-R is a C-terminally amidated (R is —$NH_2$) or a C-terminally hydroxylamidated (R is —NHOH) amino acid residue selected from Val or Tle;

ψ represents a peptide bond or reduced peptide bond joining $Xaa^8$ to $Xaa^9$;

the linker is

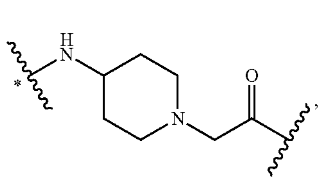

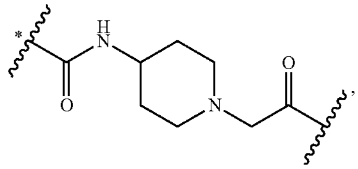

or

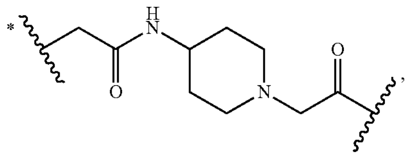

wherein * indicates the connectivity to $R^{rad}$;

$R^{rad}$ is a radiometal chelator;

wherein when $Xaa^5$ is Val, then $R^{rad}$ is not DOTA or DOTAGA; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, the present disclosure relates to a peptidic compound of Formula (IB), or a salt or solvate of Formula (IB), $$R^{rad}_{n6}\text{-[linker]-}R^{L}\text{—}Xaa^1\text{—}Xaa^2\text{—}Xaa^3\text{—}Xaa^4\text{—}Xaa^5\text{—}Xaa^6\text{—}Xaa^7\text{—}Xaa^8\text{-[}\psi\text{-}Xaa^9\text{—}(Xaa^{10})_{m2}]_{m1}\text{—}R \quad \text{(IB)}$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-$NHR^a$-D-Pro or cis-4-$OR^a$-D-Pro, wherein $R^a$ is alkyl, cycloalkyl, or aryl R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2Thz$), or thiazoline-4-carboxylic acid (Thz);

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

$R^L$ is absent, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, $C_{2-20}$ alkenylenyl and/or $C_{2-20}$ alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —$N(R^2)C(O)$—, —$C(O)N(R^2)$—, —NH—C(O)—NH—, —NH—C(S)—NH—,

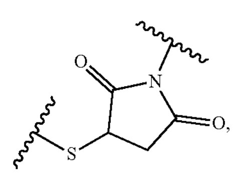

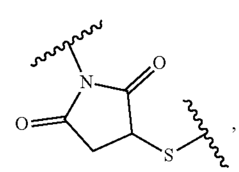

-continued

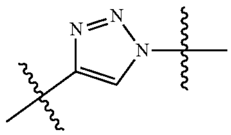

, or

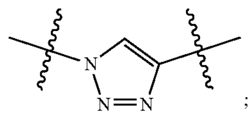

;

and $R^2$ is H, methyl or ethyl;

optionally, the linker is bonded to an albumin binder ($R^{alb}$), wherein $R^{alb}$ is:

$-(CH_2)_{n3}-CH_3$ wherein n3 is 8-20;

$-(CH_2)_{n4}-C(O)OH$ wherein n4 is 8-20;

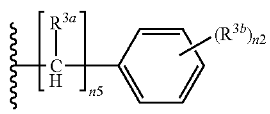

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

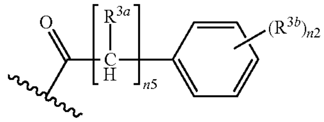

wherein n2 is 1-5, n5 is 1-4, $R^{3a}$ is H or methyl, and $R^{31}$ is I, Br, F, Cl, H, OH, $OCH_3$, $NH_2$, $NO_2$ or $C_1$-$C_6$ alkyl; or

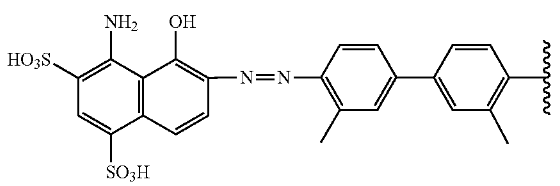

;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, the present disclosure relates to a peptidic compound of Formula (IB-1), or a salt or solvate of Formula (IB-1), wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe;

R is $-NH_2$ or $-NHOH$;

m2 is 0 or 1;

when m2 is 0, $Xaa^9$-R is a C-terminally amidated (R is $-NH_2$) or a C-terminally hydroxylamidated (R is $-NHOH$) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m2 is 1, $Xaa^9$ is Pro, Phe, oxazolidine-4-carboxylic acid (4-oxa-L-Pro), 4,4-difluoroproline (difluoroPro), Leu, $Me_2Thz$ (5,5-dimethyl-1,3-thiazolidine-4-carboxylic acid), or thiazoline-4-carboxylic acid (Thz); and $Xaa^{10}$-R is a C-terminally amidated (R is $-NH_2$) or a C-terminally hydroxylamidated (R is $-NHOH$) amino acid residue selected from Val, Leu, Tle, lie, Nle, Ala, Gly, or Met;

(IB-1)

$$R^{rad}\text{-[linker]-}R^L-Xaa^1-Xaa^2-Xaa^3-Xaa^4-Xaa^5-Xaa^6-Xaa^7-Xaa^8\text{-}\psi\text{-}Xaa^9-(Xaa^{10})_{m2}-R$$

ψ represents a peptide bond or reduced peptide bond joining $Xaa^8$ to $Xaa^9$;

the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethyl-piperazine (Acp) linker;

$R^{rad}$ is a radiometal chelator; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

Trp, Trp(7-F), Trp(6-F), Trp(5-F), Trp(4-F), 3-Quin-Ala, or 2-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is Trp, Trp(5-F), or 3-Quin-Ala; and $Xaa^8$ is Sta or Leu.

In some embodiments, the present disclosure relates to a peptidic compound of Formula (I), or a salt or solvate of Formula (I):

$$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

In some embodiments of the compounds of formula (IB) or (IB-1), $Xaa^7$ is Trp, Trp(7-F), Trp(6-F), Trp(5-F), Trp(4-F), 3-Quin-Ala, or 2-Quin-Ala. In some embodiments, $Xaa^7$ is Trp, Trp(5-F), or 3-Quin-Ala.

In some embodiments of the compounds of formula (IB) or (IB-1), $Xaa^1$ is an N-terminal amino acid residue D-Phe. In some embodiments, $Xaa^2$ is Gln or Cit. In some embodiments, $Xaa^2$ is Gln. In some embodiments, $Xaa^3$ is Trp or αMe-Trp. In some embodiments, $Xaa^4$ is Ala. In some embodiments, $Xaa^5$ is Val or Tle. In some embodiments, $Xaa^6$ is Gly or NMe-Gly. In some embodiments, $Xaa^8$ is Sta or Leu. In some embodiments, m2 is 0 and $Xaa^9$-R is a C-terminally amidated (R is $—NH_2$) amino acid residue Pro or Leu. In some embodiments, m2 is 1 and $Xaa^9$ is Pro or Leu.

In some embodiments of the compounds of formula (IB) or (IB-1), $Xaa^1$ is an N-terminal amino acid residue D-Phe and $Xaa^2$ is Gln or Cit. In some embodiments, $Xaa^1$ is an N-terminal amino acid residue D-Phe; $Xaa^2$ is Gln or Cit; and $Xaa^3$ is Trp or αMe-Trp. In some embodiments, $Xaa^1$ is an N-terminal amino acid residue D-Phe; $Xaa^2$ is Gln or Cit; $Xaa^3$ is Trp or αMe-Trp; and $Xaa^4$ is Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; and $Xaa^5$ is Val or Tle. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; and $Xaa^6$ is Gly or NMe-Gly. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is wherein:

$Xaa^1$ is an N-terminal amino acid residue selected from D-Phe, D-Cpa, D-Nal, or D-2-Nal;

$Xaa^2$ is Asp, Asn, Gln, or Glu;

$Xaa^3$ is Trp, Trp(Me), αMe-Trp, Trp(7-F), Trp(6-F), Trp (5-F), or Trp(4-F);

$Xaa^4$ is Ala or D-Ala;

$Xaa^5$ is Val or tert-leucine (Tle);

$Xaa^6$ is Gly or D-Ala;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), or αMe-Trp;

$Xaa^8$ is Leu;

m1 is 1 and m2 is 0;

$Xaa^9$ is Pro, oxazolidine-4-carboxylic acid (4-oxa-L-Pro), or 4,4-difluoroproline (difluoroPro);

R is $—NH_2$;

ψ represents a peptide bond or reduced peptide bond joining $Xaa^8$ to $Xaa^9$;

the linker comprises p-aminomethylaniline-diglycolic acid (pABzA-DIG), 4-amino-(1-carboxymethyl)piperidine (Pip, 9-amino-4,7-dioxanonanoic acid (dPEG2), or 4-(2-aminoethyl)-1-carboxymethyl-piperazine (Acp), wherein the linker optionally comprises an albumin binder;

n6 is 1;

$R^{rad}$ is a radiometal chelator; and wherein $Xaa^1$, $Xaa^2$, $Xaa^3$, $Xaa^4$, $Xaa^5$, $Xaa^6$, $Xaa^7$, $Xaa^8$, or $Xaa^9$ is each optionally N-methylated.

In some embodiments, the compound is selected from the group consisting of:
(Compound 6; SEQ ID NO: 26)
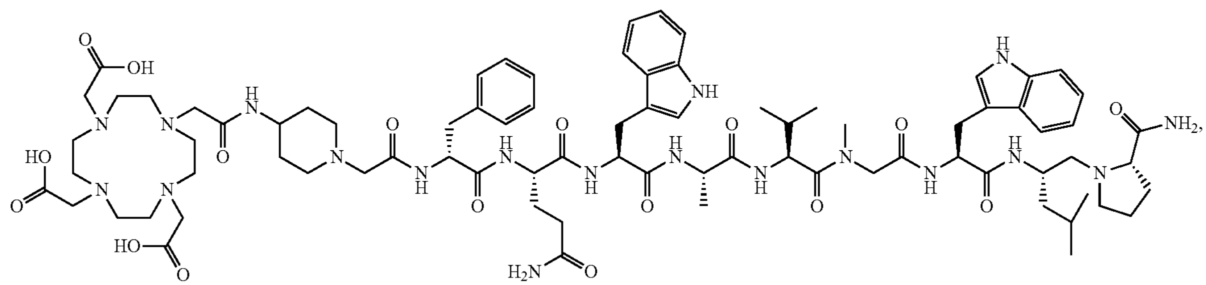
(Compound 6A; SEQ ID NO: 27)
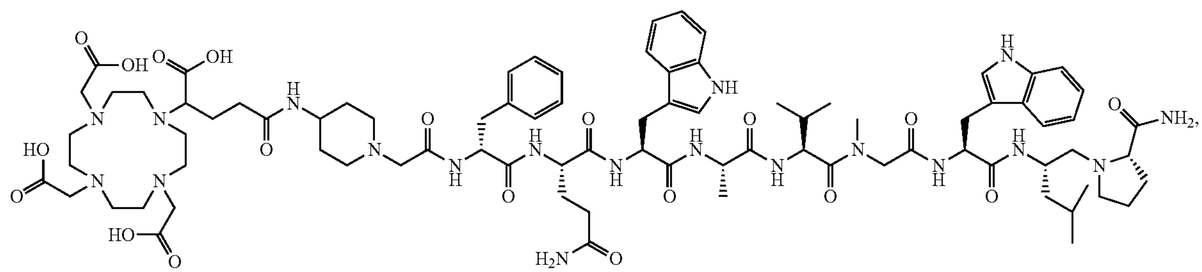
(Compound 8; SEQ ID NO: 30)
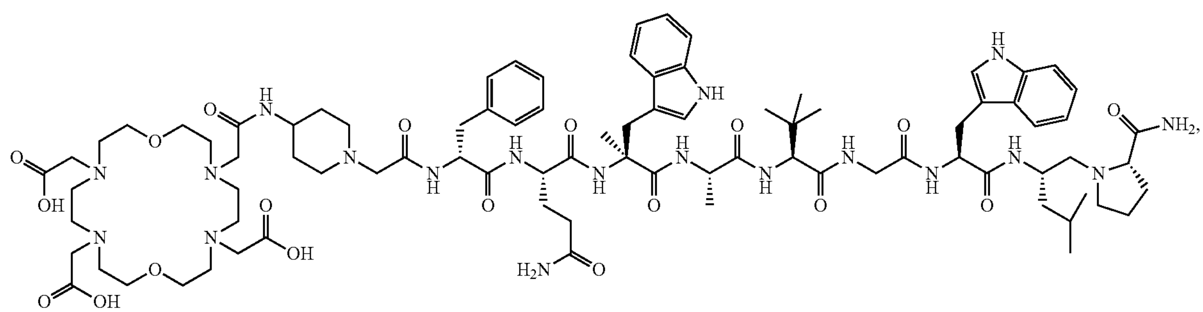
(Compound 8A; SEQ ID NO: 31)
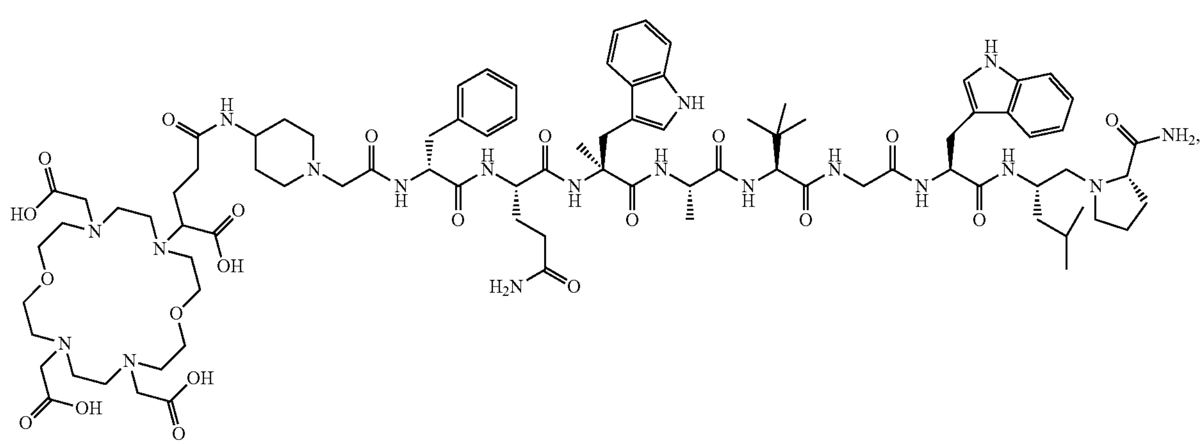

-continued (Compound 9; SEQ ID NO: 28)

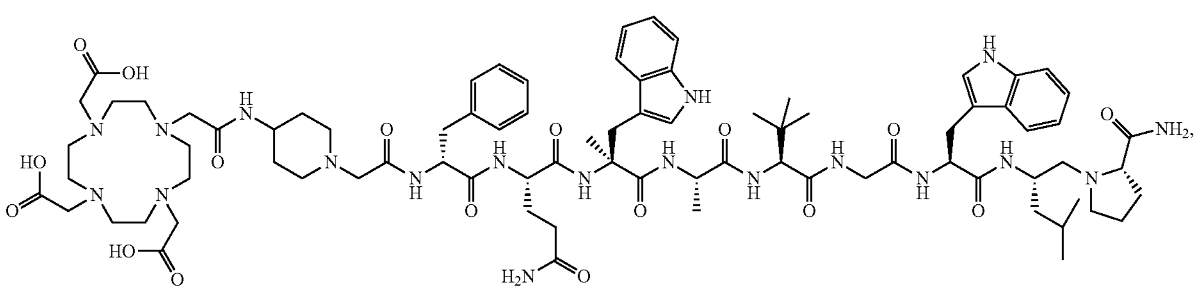

(Compound 9A; SEQ ID NO: 29)

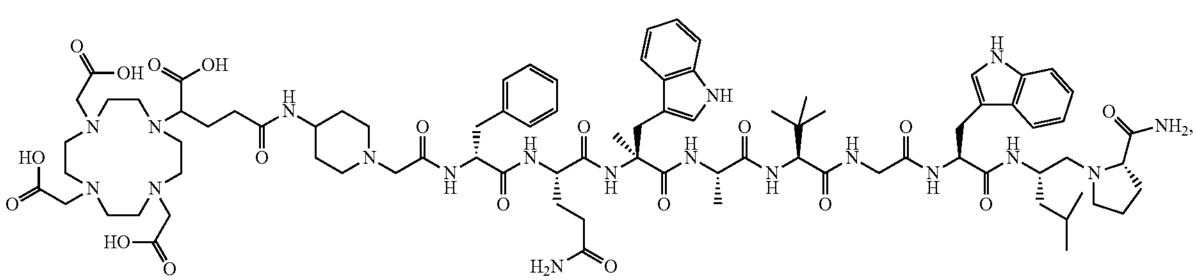

(Compound 10; SEQ ID NO: 32)

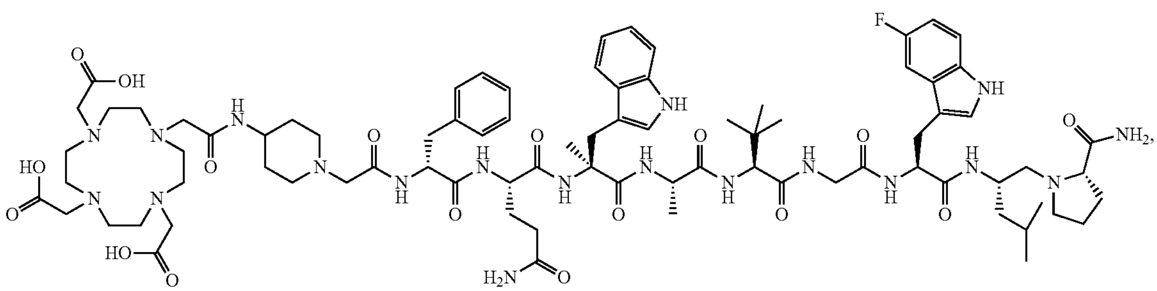

and (Compound 10A; SEQ ID NO: 33)

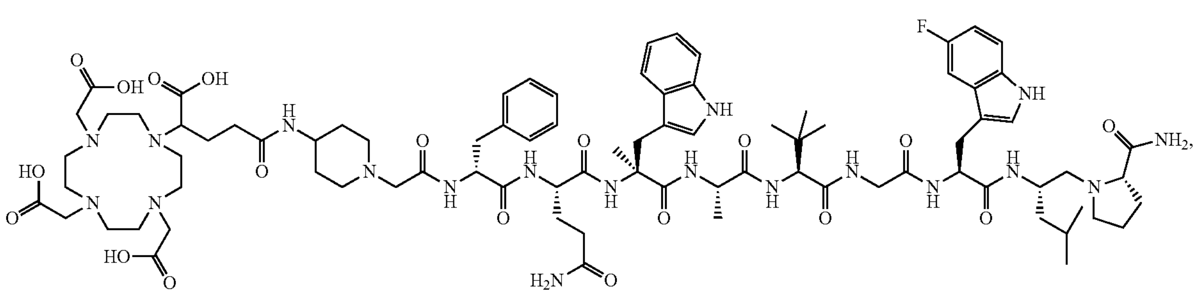

or a salt or solvate thereof. In some embodiments, the compound is conjugated by a radiometal. In some embodiments, the radiometal is $^{68}$Ga, $^{177}$Lu, or $^{225}$Ac.

In some embodiments, the present disclosure relates to a peptidic compound of Formula (IC), or a salt or solvate of Formula (IC), $$R^{rad}_{n6}\text{-[linker]-}R^{L}—Xaa^{1}—Xaa^{2}—Xaa^{3}—Xaa^{4}—Xaa^{5}—Xaa^{6}—Xaa^{7}—Xaa^{8}\text{-}[\psi\text{-}Xaa^{9}—(Xaa^{10})_{m2}]_{m1}—R \quad \text{(IC)}$$

wherein:

Xaa$^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

Xaa$^2$ is Gly, Arg, Asp, Glu, citrulline (Cit), 2-amino-4-ureidobutanoic acid (Aub), or 2-amino-4-guanidinobutyric acid (Agb);

Xaa$^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

$R^L$ is —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, $C_{2-20}$ alkenylenyl and/or $C_{2-20}$ alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —N($R^2$)C(O)—, —C(O)N($R^2$)—, —NH—C(O)—NH—, —NH—C(S)—NH—,

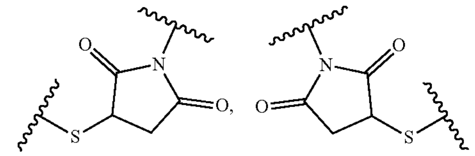

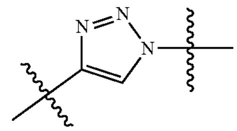

, or

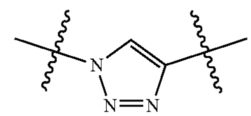

;

and $R^2$ is H, methyl or ethyl;

optionally, the linker is bonded to an albumin binder ($R^{alb}$), wherein $R^{alb}$ is:

—$(CH_2)_{n3}$—$CH_3$ wherein n3 is 8-20;

—$(CH_2)_{n4}$—C(O)OH wherein n4 is 8-20;

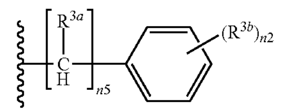

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

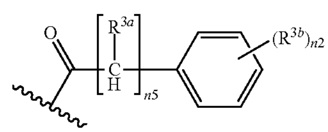

wherein n2 is 1-5, n5 is 1-4, $R^{3a}$ is H or methyl, and $R^{31}$ is I, Br, F, Cl, H, OH, $OCH_3$, $NH_2$, $NO_2$ or $C_1$-$C_6$ alkyl; or

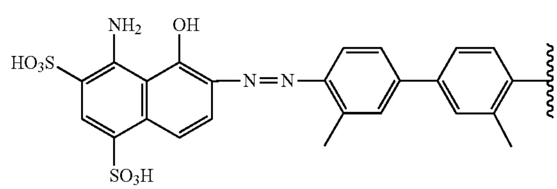

;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, the present disclosure relates to a peptidic compound of Formula (IC-1), or a salt or solvate of Formula (IC-1), (IC-1)

$$R^{rad}\text{-[linker]-}R^{L}—Xaa^1—Xaa^2—Xaa^3—Xaa^4—Xaa^5—Xaa^6—Xaa^7—Xaa^8\text{-}\psi\text{-}Xaa^9—(Xaa^{10})_{m2}—R$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Glu, citrulline (Cit), 2-amino-4-ureidobutanoic acid (Aub), or 2-amino-4-guanidinobutyric acid (Agb);

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe;

R is $—NH_2$ or —NHOH;

m2 is 0 or 1;

when m2 is 0, $Xaa^9$-R is a C-terminally amidated (R is $—NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz); and $Xaa^{10}$-R is a C-terminally amidated (R is $—NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethyl-piperazine (Acp) linker;

$R^{rad}$ is a radiometal chelator; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments of the compounds of formula (IC) or (IC-1), $Xaa^2$ is Cit, Glu, or Agb. In some embodiments, $Xaa^2$ is Cit.

In some embodiments of the compounds of formula (IC) or (IC-1), $Xaa^1$ is an N-terminal amino acid residue D-Phe. In some embodiments, $Xaa^3$ is Trp or αMe-Trp. In some embodiments, $Xaa^4$ is Ala. In some embodiments, $Xaa^5$ is Val or Tle. In some embodiments, $Xaa^6$ is Gly or NMe-Gly. In some embodiments, $Xaa^7$ is His, Trp, Trp(5-F), 3-Quin-Ala, or 2-Quin-Ala. In some embodiments, $Xaa^8$ is Sta or Leu. In some embodiments, m2 is 0 and $Xaa^9$-R is a C-terminally amidated (R is $—NH_2$) amino acid residue Pro or Leu. In some embodiments, m2 is 1 and $Xaa^9$ is Pro or Leu.

In some embodiments of the compounds of formula (IC) or (IC-1), $Xaa^1$ is an N-terminal amino acid residue D-Phe and $Xaa^3$ is Trp or αMe-Trp. In some embodiments, $Xaa^1$ is an N-terminal amino acid residue D-Phe; $Xaa^3$ is Trp or αMe-Trp; and $Xaa^4$ is Ala. In some embodiments, $Xaa^1$ is an N-terminal amino acid residue D-Phe; $Xaa^3$ is Trp or αMe-Trp; $Xaa^4$ is Ala; and $Xaa^5$ is Val or Tle. In some embodiments, $Xaa^1$ is an N-terminal amino acid residue D-Phe; $Xaa^3$ is Trp or αMe-Trp; $Xaa^4$ is Ala; $Xaa^5$ is Val or Tle; and $Xaa^6$ is Gly or NMe-Gly. In some embodiments, $Xaa^1$ is an N-terminal amino acid residue D-Phe; $Xaa^3$ is Trp or αMe-Trp; $Xaa^4$ is Ala; $Xaa^5$ is Val or Tle; $Xaa^6$ is Gly or NMe-Gly; and $Xaa^7$ is His, Trp, Trp(5-F), 3-Quin-Ala, or 2-Quin-Ala. In some embodiments, $Xaa^1$ is an N-terminal amino acid residue D-Phe; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), 3-Quin-Ala, or 2-Quin-Ala; and $Xaa^8$ is Sta or Leu. In some embodiments, $Xaa^1$ is an N-terminal amino acid residue D-Phe; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(7-F), Trp(6-F), Trp(5-F), Trp(4-F), 3-Quin-Ala, or 2-Quin-Ala; and $Xaa^8$ is Sta or Leu. In some embodiments, $Xaa^1$ is an N-terminal amino acid residue D-Phe; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$ is Sta or Leu. In some embodiments, $Xaa^1$ is an N-terminal amino acid residue D-Phe; $Xaa^2$ is Cit, Glu, or Agb; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$ is Sta or Leu. In some embodiments, $Xaa^1$ is an N-terminal amino acid residue D-Phe; $Xaa^2$ is Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$ is Sta or Leu.

In some embodiments, the present disclosure relates to a peptidic compound of Formula (ID), or a salt or solvate of Formula (ID), $R^{rad}_{n6}$-[linker]-$R^L$—$Xaa^1$—$Xaa^2$—$Xaa^3$—$Xaa^4$—$Xaa^5$—$Xaa^6$—$Xaa^7$—$Xaa^8$-ψ-$Xaa^9$—$(Xaa^{10})_{m2}$—R (ID)

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe;

$Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz);

R is —$NH_2$ or —NHOH;

m2 is 1;

$Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

$R^L$ is —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, $C_{2-20}$ alkenylenyl and/or $C_{2-20}$ alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —$N(R^2)C(O)$—, —$C(O)N(R^2)$—, —NH—C(O)—NH—, —NH—C(S)—NH—,

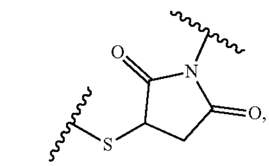, 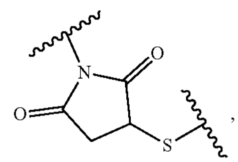,

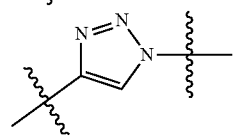, or 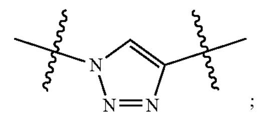;

and $R^2$ is H, methyl or ethyl;

optionally, the linker is bonded to an albumin binder ($R^{alb}$), wherein $R^{alb}$ is:

—$(CH_2)_{n3}$—$CH_3$ wherein n3 is 8-20;

—$(CH_2)_{n4}$—C(O)OH wherein n4 is 8-20;

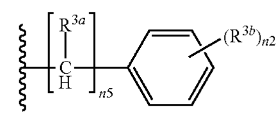

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

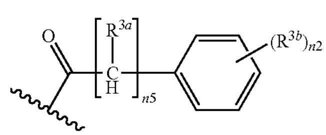

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

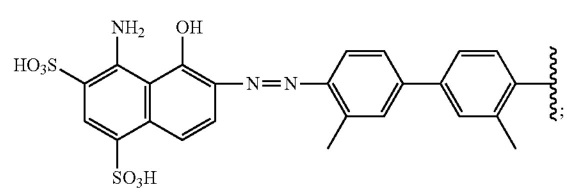 [SMILES: *c1ccc(-c2ccc(N=Nc3ccc4c(S(=O)(=O)O)cc(S(=O)(=O)O)c(N)c4c3O)c(C)c2)cc1C];

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, the present disclosure relates to a peptidic compound of Formula (ID-1), or a salt or solvate of Formula (ID-1), (ID-1)

$$R^{rad}\text{-[linker]-}R^{L}\text{—Xaa}^{1}\text{—Xaa}^{2}\text{—Xaa}^{3}\text{—Xaa}^{4}\text{—Xaa}^{5}\text{—Xaa}^{6}\text{—Xaa}^{7}\text{—Xaa}^{8}\text{-}\psi\text{-Xaa}^{9}\text{—(Xaa}^{10})_{m2}\text{—R}$$

wherein:

- $Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;
- $Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;
- $Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);
- $Xaa^4$ is Ala, D-Ala, or Ser;
- $Xaa^5$ is Val, 2,3-dehydro-Val, cyclopentylglycine (Cpg), L-cyclopropylglycine, L-cyclobutylglycine, or tert-leucine (Tle);
- $Xaa^6$ is Gly or D-Ala;
- $Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);
- $Xaa^8$ is statine (Sta), Leu, D-Pro, or Phe;
- $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz);
- R is —$NH_2$ or —NHOH;
- m2 is 1;
- $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;
- ψ represents a peptide bond or reduced peptide bond joining $Xaa^8$ to $Xaa^9$;
- the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethyl-piperazine (Acp) linker;
- $R^{rad}$ is a radiometal chelator; and
- wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments of the compounds of formula (ID) or (ID-1), $Xaa^1$ is an N-terminal amino acid residue D-Phe. In some embodiments, $Xaa^2$ is Gln or Cit. In some embodiments, $Xaa^3$ is Trp or αMe-Trp. In some embodiments, $Xaa^4$ is Ala. In some embodiments, $Xaa^5$ is Val or Tle. In some embodiments, $Xaa^6$ is Gly or NMe-Gly. In some embodiments, $Xaa^7$ is His, Trp, Trp(5-F), 3-Quin-Ala, or 2-Quin-Ala. In some embodiments, $Xaa^8$ is Sta or Leu. In some embodiments, $Xaa^9$ is Pro or Leu. In some embodiments, $Xaa^{10}$ is Val or Tle.

In some embodiments of the compounds of formula (ID) or (ID-1), $Xaa^1$ is an N-terminal amino acid residue D-Phe and $Xaa^2$ is Gln or Cit. In some embodiments, $Xaa^1$ is an N-terminal amino acid residue D-Phe; $Xaa^2$ is Gln or Cit; and $Xaa^3$ is Trp or αMe-Trp. In some embodiments, $Xaa^1$ is an N-terminal amino acid residue D-Phe; $Xaa^2$ is Gln or Cit; ad $Xaa^3$ is Trp or αMe-Trp; and $Xaa^4$ is Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; and $Xaa^5$ is Val or Tle. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; and $Xaa^6$ is Gly or NMe-Gly. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; and $Xaa^7$ is His, Trp, Trp(5-F), 3-Quin-Ala, or 2-Quin-Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), 3-Quin-Ala, or 2-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp(5-F), or 3-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(7-F), Trp(6-F), Trp(5-F), Trp(4-F), 3-Quin-Ala, or 2-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(7-F), Trp(6-F), Trp(5-F), Trp(4-F), 3-Quin-Ala, or 2-Quin-Ala; $Xaa^8$ is Sta or Leu; and $Xaa^9$ is Pro or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp(5-F), or 3-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp(5-F), or 3-Quin-Ala; $Xaa^8$ is Sta or Leu; and $Xaa^9$ is Pro or Leu.

In some embodiments, the present disclosure relates to a peptidic compound of Formula (IE), or a salt or solvate of Formula (IE), $$R^{rad}_{n6}—R^{L}\text{-[linker]-}R^{L}—Xaa^{1}—Xaa^{2}—Xaa^{3}—Xaa^{4}—Xaa^{5}—Xaa^{6}—Xaa^{7}—Xaa^{8}\text{-}[\psi\text{-}Xaa^{9}—(Xaa^{10})_{m2}]_{m1}—R \quad \text{(IE)}$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoro-Pro), cis-4-NHR$^a$-D-Pro, cis-4-OR$^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —N($R^2$)C(O)—, —C(O)N($R^2$)—, —NH—C(O)—NH—, —NH—C(S)—NH—,

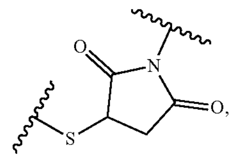,
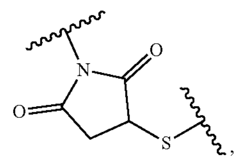,

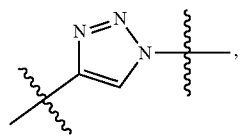, or 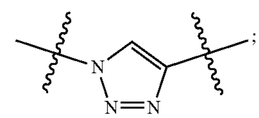;

and $R^2$ is H, methyl or ethyl;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

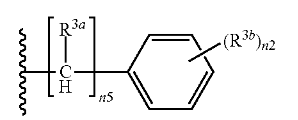

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

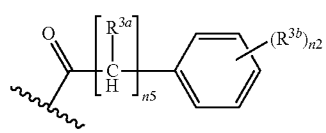

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

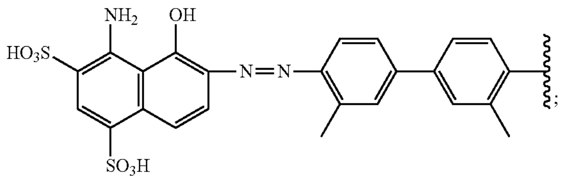 [SMILES: *c1ccc(-c2ccc(N=Nc3ccc4c(S(=O)(=O)O)cc(S(=O)(=O)O)c(N)c4c3O)c(C)c2)cc1C];

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; wherein at least one $R^{rad}$ is CROWN, CROWNGA, TCMC, PSC, a prosthetic group containing a trifluoroborate, an aryl or heteroaryl substituted with at least one radiohalogen, or an aryl or heteroaryl substituted with at least one fluorine precursor leaving group; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, of a compound of Formula (IE), or a salt or solvate of Formula (IE), at least one $R^{rad}$ is CROWN, TCMC, PSC, a prosthetic group containing a trifluoroborate, an aryl or heteroaryl substituted with at least one radiohalogen, or an aryl or heteroaryl substituted with at least one fluorine precursor leaving group.

In some embodiments, the present disclosure relates to a peptidic compound of Formula (IE-1), or a salt or solvate of Formula (IE-1), Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe

R is —$NH_2$ or —NHOH;

m2 is 0 or 1;

when m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NH$R^a$-D-Pro, cis-4-O$R^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;

when m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

$R^L$ is independently absent, —($C_{1-3}$ alkyl)-, —($C_{1-3}$ alkyl)-C(O)—, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-6;

each $Xaa^{11}$ is independently an amino acid;

(IE-1)

$$R^{rad}—R^L\text{-[linker]-}R^L—Xaa^1—Xaa^2—Xaa^3—Xaa^4—Xaa^5—Xaa^6—Xaa^7—Xaa^8\text{-}\psi\text{-}Xaa^9—(Xaa^{10})_{m2}—R$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4- each $R^1$ is, independently, a linear, branched, and/or cyclic $C_{1-6}$ alkylenyl, $C_{2-6}$ alkenylenyl and/or $C_{2-6}$ alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —N($R^2$)C(O)—, —C(O)N($R^2$)—, —NH—C(O)—NH—, —NH—C(S)—NH—,

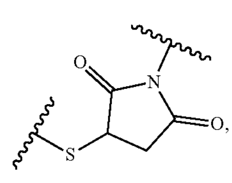,

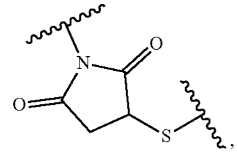,

-continued

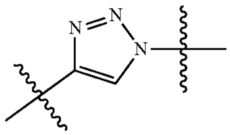, or 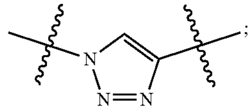;

and $R^2$ is H, methyl or ethyl;

$R^{rad}$ is CROWN, CROWNGA, TCMC, PSC, a prosthetic group containing a trifluoroborate, an aryl or heteroaryl substituted with at least one radiohalogen, or an aryl or heteroaryl substituted with at least one fluorine precursor leaving group; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, a compound of Formula (IE-1), or a salt or solvate of Formula (IE-1), at least one $R^{rad}$ is CROWN, TCMC, PSC, a prosthetic group containing a trifluoroborate, an aryl or heteroaryl substituted with at least one radiohalogen, or an aryl or heteroaryl substituted with at least one fluorine precursor leaving group.

In some embodiments of the compounds of formula (IE) or (IE-1), the linker is -$Xaa^{11}$-. In some embodiments, the linker is -$Xaa^{11}$- and $R^L$ is absent. In some embodiments, the linker is Pip and $R^L$ is absent. In some embodiments, the linker is -$Xaa^{11}$- and $R^L$ is —($C_{1-3}$ alkyl)-, —($C_{1-3}$ alkyl)-C(O)—, or —C(O)—. In some embodiments, the linker is -$Xaa^{11}$- and $R^L$ is —C(O)—. In some embodiments, the linker is Pip and $R^L$ is —C(O)—.

In some embodiments of the compounds of formula (IE) or (IE-1), the linker is a linear or branched chain of n1 units of -$Xaa^{11}$- and/or -$L^1R^1$—. In some embodiments, n1 is 1-3. In some embodiments, n1 is 1 or 2.

In some embodiments of the compounds of formula (IE) or (IE-1), the linker is -$Xaa^{11}$-$R^1L^1$-. In some embodiments, the linker is *-$Xaa^{11}$-$R^1L^1$-, where * indicates the connectivity to $Xaa^1$. In some embodiments, the linker is *-$Xaa^{11}$-C(O)$CH_2$-$L^1$-, where * indicates the connectivity to $Xaa^1$. In some embodiments, the linker is *-$Xaa^{11}$-C(O)$CH_2$-$L^1$-, where * indicates the connectivity to $Xaa^1$ and $L^1$ is

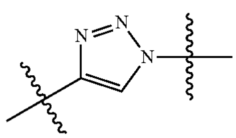, or 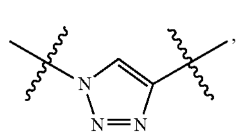,

In some embodiments, $R^L$ is —($C_{1-3}$ alkyl)-, —($C_{1-3}$ alkyl)-C(O)—, or —C(O)—. In some embodiments, $R^L$ is —($C_{1-3}$ alkyl)-. In some embodiments, $R^L$ is —$CH_2$—. In some embodiments, $R^L$ is absent.

In some embodiments of the compounds of formula (IE) or (IE-1), $Xaa^1$ is an N-terminal amino acid residue D-Phe. In some embodiments, $Xaa^2$ is Gln or Cit. In some embodiments, $Xaa^3$ is Trp or αMe-Trp. In some embodiments, $Xaa^4$ is Ala. In some embodiments, $Xaa^5$ is Val or Tle. In some embodiments, $Xaa^6$ is Gly or NMe-Gly. In some embodiments, $Xaa^7$ is His, Trp, Trp(5-F), 3-Quin-Ala, or 2-Quin-Ala. In some embodiments, $Xaa^8$ is Sta or Leu. In some embodiments, m2 is 0 and $Xaa^9$-R is a C-terminally amidated (R is —$NH_2$) amino acid residue Pro or Leu. In some embodiments, m2 is 1 and $Xaa^9$ is Pro or Leu.

In some embodiments of the compounds of formula (IE) or (IE-1), $Xaa^1$ is an N-terminal amino acid residue D-Phe and $Xaa^2$ is Gln or Cit. In some embodiments, $Xaa^1$ is an N-terminal amino acid residue D-Phe; $Xaa^2$ is Gln or Cit; and $Xaa^3$ is Trp or αMe-Trp. In some embodiments, $Xaa^1$ is an N-terminal amino acid residue D-Phe; $Xaa^2$ is Gln or Cit; ad $Xaa^3$ is Trp or αMe-Trp; and $Xaa^4$ is Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; and $Xaa^5$ is Val or Tle. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; and $Xaa^6$ is Gly or NMe-Gly. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; and $Xaa^7$ is His, Trp, Trp(5-F), 3-Quin-Ala, or 2-Quin-Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), 3-Quin-Ala, or 2-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(7-F), Trp(6-F), Trp(5-F), Trp(4-F), 3-Quin-Ala, or 2-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(7-F), Trp(6-F), Trp(5-F), Trp(4-F), 3-Quin-Ala, or 2-Quin-Ala; $Xaa^8$ is Sta or Leu; and $Xaa^9$ is Pro or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; $Xaa^8$ is Sta or Leu; and $Xaa^9$ is Pro or Leu. In some embodiments, the present disclosure relates to a peptidic compound of Formula (IF), or a salt or solvate of Formula (IF), $$R^{rad}_{n6}—R^L\text{-[linker]-}R^L—Xaa^1—Xaa^2—Xaa^3—Xaa^4—Xaa^5—Xaa^6—Xaa^7—Xaa^8—R \quad \text{(IF)}$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), αMe-Trp, Nal, 2-pyridylalanine (2-Pal), 3-pyridylalanine (3-Pal), 4-pyridylalanine (4-Pal), 2-quinoylalanine, or 3-quinoylalanine;

R is —$NH_2$ or —NHOH;

$Xaa^8$-R is a C-terminally amidated (R is —$NH_2$) or a C-terminally hydroxylamidated (R is —NHOH) amino acid residue selected from statine (Sta), Leu, D-Pro, Phe, cis-4-$NHR^a$-D-Pro or cis-4-$OR^a$-D-Pro, wherein $R^a$ is alkyl, cycloalkyl, or aryl;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —N($R^2$)C(O)—, —C(O)N($R^2$)—, —NH—C(O)—NH—, —NH—C(S)—NH—S,

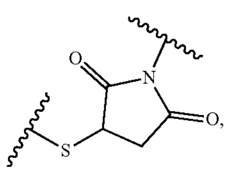
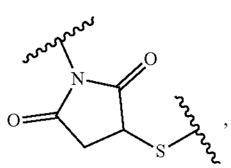
,
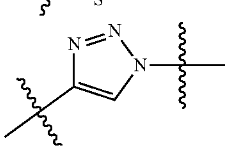
, or
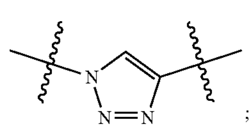
;

and $R^2$ is H, methyl or ethyl;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

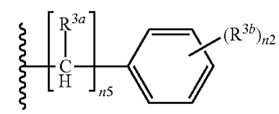

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

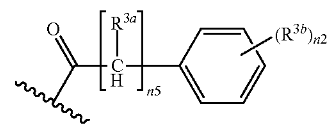

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

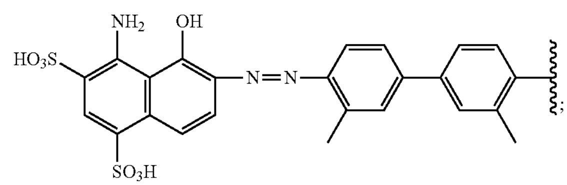
;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, or $Xaa^8$ is each optionally methylated.

In some embodiments, the present disclosure relates to a peptidic compound of Formula (IF-1), or a salt or solvate of Formula (IF-1), $$R^{rad}\text{-}R^{L}\text{—[linker]—}Xaa^1\text{-}Xaa^2\text{-}Xaa^3\text{-}Xaa^4\text{-}Xaa^5\text{-}Xaa^6\text{-}Xaa^7\text{-}Xaa^8\text{-}R \quad \text{(IF-1)}$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^3$ is Trp or αMe-Trp; and $Xaa^4$ is Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; and $Xaa^5$ is Val or Tle. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; and $Xaa^6$ is Gly or NMe-Gly. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; and $Xaa^7$ is His, Trp, Trp(5-F), or 3-Quin-Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$-R is a C-terminally amidated (R is —$NH_2$) amino acid residue selected from cis-4-cyclohexyloxy-D-Pro or cis-4-cyclohexylamino-D-Pro.

In some embodiments, the present disclosure relates to a peptidic compound of Formula (II), or a salt or solvate of Formula (II), $$R^{rad}_{n6}\text{—[linker]—}Xaa^1\text{—}Xaa^2\text{—}Xaa^3\text{—}Xaa^4\text{—}Xaa^5\text{—}Xaa^6\text{—}Xaa^7\text{—}Xaa^8\text{—}[\varphi\text{—}Xaa^9\text{—}(Xaa^{10})_{m2}]_{m1}\text{—}R \quad \text{(II)}$$

R is —$NH_2$ or —NHOH;

$Xaa^8$-R is a C-terminally amidated (R is —$NH_2$) or a C-terminally hydroxylamidated (R is —NHOH) amino acid residue selected from is statine (Sta), Leu, D-Pro, Phe, cis-4-$NHR^a$-D-Pro or cis-4-$OR^a$-D-Pro, wherein $R^a$ is alkyl, cycloalkyl, or aryl; the linker and $R^L$ together form a p-aminomethylaniline-diglycolic acid (pABzA-DIG) linker, a 4-amino-(1-carboxymethyl)piperidine (Pip) linker, a 9-amino-4,7-dioxanonanoic acid (dPEG2) linker, or a 4-(2-aminoethyl)-1-carboxymethyl-piperazine (Acp) linker;

$R^{rad}$ is a radiometal chelator; and wherein $Xaa^1$, $Xaa^2$, $Xaa^3$, $Xaa^4$, $Xaa^5$, $Xaa^6$, $Xaa^7$, or $Xaa^8$, is each optionally N-methylated.

In some embodiments of the compounds of formula (IF) or (IF-1), $Xaa^8$-R is a C-terminally amidated (R is —$NH_2$) or a C-terminally hydroxylamidated (R is —NHOH) amino acid residue selected from D-Pro, cis-4-$NHR^a$-D-Pro or cis-4-$OR^a$-D-Pro, wherein $R^a$ is alkyl, cycloalkyl, or aryl. In some embodiments, $R^a$ is $C_1$-$C_6$ alkyl, $C_3$-$C_7$ cycloalkyl, or phenyl. In some embodiments, $R^a$ is $C_3$-$C_7$ cycloalkyl. In some embodiments, $R^a$ is $C_6$ cycloalkyl.

In some embodiments of the compounds of formula (IF) or (IF-1), $Xaa^8$-R is a C-terminally amidated (R is —$NH_2$) amino acid residue selected from cis-4-cyclohexyloxy-D-Pro or cis-4-cyclohexylamino-D-Pro.

In some embodiments of the compounds of formula (IF) or (IF-1), $Xaa^1$ is an N-terminal amino acid residue D-Phe. In some embodiments, $Xaa^2$ is Gln or Cit. In some embodiments, $Xaa^3$ is Trp or αMe-Trp. In some embodiments, $Xaa^4$ is Ala. In some embodiments, $Xaa^5$ is Val or Tle. In some embodiments, $Xaa^6$ is Gly or NMe-Gly. In some embodiments, $Xaa^7$ is His, Trp, Trp(7-F), Trp(6-F), Trp(5-F), Trp (4-F), 3-Quin-Ala, or 2-Quin-Ala. In some embodiments, $Xaa^7$ is His, Trp, Trp(5-F), or 3-Quin-Ala.

In some embodiments of the compounds of formula (IF) or (IF-1), $Xaa^1$ is an N-terminal amino acid residue D-Phe and $Xaa^2$ is Gln or Cit. In some embodiments, $Xaa^1$ is an N-terminal amino acid residue D-Phe; $Xaa^2$ is Gln or Cit; and $Xaa^3$ is Trp or αMe-Trp. In some embodiments, $Xaa^1$ is an N-terminal amino acid residue D-Phe; $Xaa^2$ is Gln or Cit;

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b] indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-$NHR^a$-D-Pro or cis-4-$OR^a$-D-Pro, wherein $R^a$ is alkyl, cycloalkyl, or aryl; $R^a$ is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoro- Pro), cis-4-NHR$^a$-D-Pro, cis-4-OR$^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, Xaa$^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz); and Xaa$^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining Xaa$^8$ to Xaa$^9$;

the linker is a linear or branched chain of n1 units of -Xaa$^{11}$-, wherein at least one Xaa$^{11}$ is bonded to albumin binder ($R^{alb}$);

n1 is 1-20;

each Xaa$^{11}$ is independently an amino acid;

$R^{alb}$ is:

—$(CH_2)_{n3}$—$CH_3$ wherein n3 is 8-20;

—$(CH_2)_{n4}$—C(O)OH wherein n4 is 8-20;

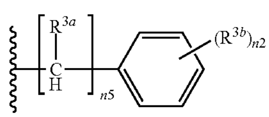

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

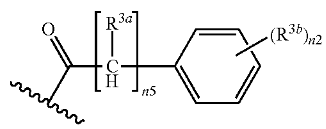

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

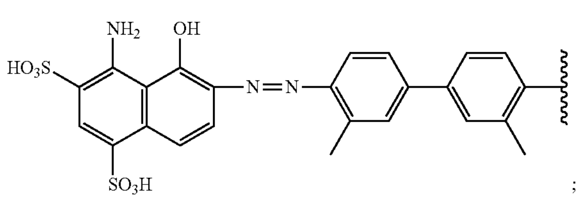 [SMILES: *c1ccc(-c2ccc(N=Nc3ccc4c(S(=O)(=O)O)cc(S(=O)(=O)O)c(N)c4c3O)c(C)c2)cc1C]

;

acceptor moiety; or a prosthetic group containing a fluorophosphate, fluorosulfate, sulfonyl fluoride, or a combination thereof; and wherein Xaa$^1$, Xaa$^2$, Xaa$^3$, Xaa$^4$, Xaa$^5$, Xaa$^6$, Xaa$^7$, Xaa$^8$, or Xaa$^{10}$ is each optionally methylated.

In some embodiments of the compounds of formula (II) the linker is a linear peptide of 3 to 6 amino acid residues, -Xaa$^{11A}$-Xaa$^{11B}$-(Xaa$^{11C}$)$_{1-4}$-, wherein Xaa$^{11A}$ Xaa$^{11B}$, and Xaa$^{11C}$ are each independently an amino acid and wherein the radiolabeling group and the albumin-binding group are bonded to the free N-terminus of Xaa$^{11A}$ and the side chain of Xaa$^{11B}$, respectively, or are bonded to the side chain of Xaa$^{11B}$ and the free N-terminus of Xaa$^{11A}$, respectively. In some embodiments, Xaa$^{11A}$ is Gly, Glu, D-Glu, Asp, D-Asp, 2-Aad, D-2-Aad, 3-Aad, or D-3-Aad. In some embodiments, Xaa$^{11A}$ is Gly, Glu or D-Glu. In some embodiments, Xaa$^{11A}$ is Gly. In some embodiments, Xaa$^{11B}$ is Lys, Orn, D-Orn, Dab, D-Dab, Dap or D-Dap, any of which can form an amide bond with a carboxylate of a radiolabeling group or an albumin binding group. In some embodiments, Xaa$^{11B}$ is Lys or D-Lys. In some such embodiments, (Xaa$^{11C}$)$_{1-4}$ is diglycine. In some such embodiments, (Xaa$^{11C}$)$_{1-4}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, (Xaa$^{11C}$)$_{1-4}$ is Pip. In some embodiments, the C-terminus of Xaa$^{11C}$ and the N-terminus of Xaa$^1$ are bonded.

In some embodiments of the compounds of formula (II) the linker is a branched peptide of 3 to 6 amino acid residues, -Xaa$^{11B}$(Xaa$^{11A}$)-(Xaa$^{11C}$)$_{1-4}$-, wherein Xaa$^{11A}$ Xaa$^{11B}$, and Xaa$^{11C}$ are each independently an amino acid and wherein the C-terminus of Xaa$^{11A}$ forms an amide with the side chain of Xaa$^{11B}$, and wherein the radiolabeling group and the albumin-binding group are bonded to the free N-termini of Xaa$^{11A}$ and Xaa$^{11B}$, respectively, or are bonded to the free N-termini of Xaa$^{11B}$ and Xaa$^{11A}$, respectively. In some embodiments, Xaa$^{11A}$ is Gly, Glu, D-Glu, Asp, D-Asp, 2-Aad, D-2-Aad, 3-Aad, or D-3-Aad. In some embodiments, Xaa$^{11A}$ is Glu or D-Glu. In some embodiments, Xaa$^{11B}$ is Lys, D-Lys, Orn, D-Orn, Dab, D-Dab, Dap or D-Dap. In some embodiments, Xaa$^{11B}$ is Lys or D-Lys. In some such embodiments, (Xaa$^{11C}$)$_{1-4}$ is diglycine. In some such embodiments, (Xaa$^{11C}$)$_{1-4}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, (Xaa$^{11C}$)$_{1-4}$ is Pip. In some embodiments, the C-terminus of Xaa$^{11C}$ and the N-terminus of Xaa$^1$ are bonded.

In some embodiments, the present disclosure relates to a peptidic compound of Formula (IIA), or a salt or solvate of Formula (IIA), $$R^{rad}—[\text{linker}]—Xaa^1—Xaa^2—Xaa^3—Xaa^4—Xaa^5—Xaa^6—Xaa^7—Xaa^8—\varphi—Xaa^9—(Xaa^{10})_{m2}—R \quad \text{(IIA)}$$

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorinewherein:

Xaa$^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe;

R is —$NH_2$ or —NHOH;

m2 is 0 or 1;

when m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, $Me_2$Thz (5,5-dimethyl-1,3-thiazolidine-4-carboxylic acid), or thiazoline-4-carboxylic acid (Thz), wherein $R^a$ is alkyl, cycloalkyl, or aryl;

when m2 is 1, $Xaa^9$ is Pro, Phe, oxazolidine-4-carboxylic acid (4-oxa-L-Pro), 4,4-difluoroproline (difluoroPro), Leu, $Me_2$Thz (5,5-dimethyl-1,3-thiazolidine-4-carboxylic acid), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

the linker is:

a linear peptide of 3 to 6 amino acid residues, -$Xaa^{11A}$-$Xaa^{11B}$-$(Xaa^{11C})_{1-4}$-, wherein $Xaa^{11A}$ $Xaa^{11B}$, and $Xaa^{11C}$ are each independently an amino acid and wherein the radiolabeling group and the albumin-binding group are bonded to the free N-terminus of $Xaa^{11A}$ and the side chain of $Xaa^{11B}$, respectively, or are bonded to the side chain of $Xaa^{11B}$ and the free N-terminus of $Xaa^{11A}$, respectively; or a branched peptide of 3 to 6 amino acid residues, -$Xaa^{11B}(Xaa^{11A})$-$(Xaa^{11C})_{1-4}$-, wherein $Xaa^{11A}$, $Xaa^{11B}$, and $Xaa^{11C}$ are each independently an amino acid and wherein the C-terminus of $Xaa^{11A}$ forms an amide with the side chain of $Xaa^{11B}$, and wherein the radiolabeling group and the albumin-binding group are bonded to the free N-termini of $Xaa^{11A}$ and $Xaa^{11B}$ respectively, or are bonded to the free N-termini of $Xaa^{11B}$ and $Xaa^{11A}$, respectively;

$R^{alb}$ is

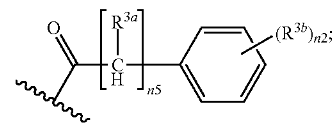

n2 is 1-5;

n5 is 1-4;

each $R^{3a}$ is independently H or methyl;

each $R^{3b}$ is independently I, Br, F, Cl, H, OH, $OCH_3$, $NH_2$, $NO_2$ or $C_1$-$C_6$ alkyl;

$R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, or $Xaa^{10}$ is each optionally methylated.

In some embodiments of the compounds of formula (II) or (IIA), n2 is 1. In some embodiments, $R^{alb}$ is

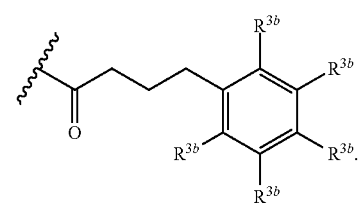

In some embodiments, $R^{alb}$ is

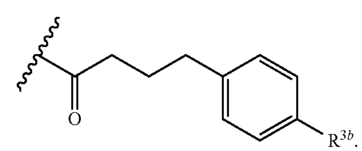

In some embodiments of the compounds of formula (II) or (IIA) the linker is a linear peptide of 3 amino acid residues, -$Xaa^{11A}$-$Xaa^{11B}$-$Xaa^{11C}$-, wherein $Xaa^{11A}$, $Xaa^{11B}$, and $Xaa^{11C}$ are each independently an amino acid and wherein the radiolabeling group and the albumin-binding group are bonded to the free N-terminus of $Xaa^{11A}$ and the side chain of $Xaa^{11B}$, respectively, or are bonded to the side chain of $Xaa^{11B}$ and the free N-terminus of $Xaa^{11A}$, respectively. In some embodiments, $Xaa^{11A}$ is Gly, Glu, D-Glu, Asp, D-Asp, 2-Aad, D-2-Aad, 3-Aad, or D-3-Aad. In some embodiments, $Xaa^{11A}$ is Gly, Glu or D-Glu. In some embodiments, $Xaa^{11A}$ is Gly. In some embodiments, $Xaa^{11B}$ is Lys, D-Lys, Orn, D-Orn, Dab, D-Dab, Dap or D-Dap, any of which can form an amide bond with a carboxylate of a radiolabeling group or an albumin binding group. In some embodiments, $Xaa^{11B}$ is Lys or D-Lys. In some such embodiments, $Xaa^{11C}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, $Xaa^{11C}$ is Pip. In some embodiments, the C-terminus of $Xaa^{11C}$ and the N-terminus of $Xaa^1$ are bonded.

In some embodiments of the compounds of formula (II) or (IIA) the linker is -Gly-Lys-Pip-. In some embodiments, the radiolabeling group is bonded to the free N-terminus of $Xaa^{11A}$ and the albumin-binding group is bonded to the side chain of $Xaa^{11B}$. In some embodiments, the radiolabeling group is bonded to the free N-terminus of Gly and the albumin-binding group is bonded to the side chain of Lys.

In some embodiments of the compounds of formula (II) or (IIA) the linker is a branched peptide of 3 amino acid residues, -$Xaa^{11B}$($Xaa^{11A}$)-$Xaa^{11C}$-, wherein $Xaa^{11A}$, $Xaa^{11B}$, and $Xaa^{11C}$ are each independently an amino acid and wherein the C-terminus of $Xaa^{11A}$ forms an amide with the side chain of $Xaa^{11B}$, and wherein the radiolabeling group and the albumin-binding group are bonded to the free N-termini of $Xaa^{11A}$ and $Xaa^{11B}$, respectively, or are bonded to the free N-termini of $Xaa^{11B}$ and $Xaa^{11A}$, respectively. In some embodiments, $Xaa^{11A}$ is Gly, Glu, D-Glu, Asp, D-Asp, 2-Aad, D-2-Aad, 3-Aad, or D-3-Aad. In some embodiments, $Xaa^{11A}$ is Glu or D-Glu. In some embodiments, $Xaa^{11B}$ is Lys, D-Lys, Orn, D-Orn, Dab, D-Dab, Dap or D-Dap. In some embodiments, $Xaa^{11B}$ is Lys or D-Lys. In some such embodiments, $Xaa^{11C}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, $Xaa^{11C}$ is Pip. In some embodiments, the C-terminus of $Xaa^{11C}$ and the N-terminus of $Xaa^1$ are bonded.

In some embodiments of the compounds of formula (II) or (IIA), $Xaa^1$ is an N-terminal amino acid residue D-Phe. In some embodiments, $Xaa^2$ is Gln or Cit. In some embodiments, $Xaa^2$ is Gln. In some embodiments, $Xaa^3$ is Trp or αMe-Trp. In some embodiments, $Xaa^4$ is Ala. In some embodiments, $Xaa^5$ is Val or Tle. In some embodiments, $Xaa^6$ is Gly or NMe-Gly. In some embodiments, $Xaa^7$ is His, Trp, Trp(7-F), Trp(6-F), Trp(5-F), or Trp(4-F). In some embodiments, $Xaa^8$ is Sta or Leu. In some embodiments, m2 is 0 and $Xaa^9$-R is a C-terminally amidated (R is —$NH_2$) amino acid residue Pro or Leu. In some embodiments, m2 is 1 and $Xaa^9$ is Pro or Leu.

In some embodiments of the compounds of formula (II) or (IIA), $Xaa^1$ is an N-terminal amino acid residue D-Phe and $Xaa^2$ is Gln or Cit. In some embodiments, $Xaa^1$ is an N-terminal amino acid residue D-Phe; $Xaa^2$ is Gln or Cit; and $Xaa^3$ is Trp or αMe-Trp. In some embodiments, $Xaa^1$ is an N-terminal amino acid residue D-Phe; $Xaa^2$ is Gln or Cit; $Xaa^3$ is Trp or αMe-Trp; and $Xaa^4$ is Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; and $Xaa^5$ is Val or Tle. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; and $Xaa^6$ is Gly or NMe-Gly. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; and $Xaa^7$ is His, Trp, Trp(5-F), or 3-Quin-Ala. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(5-F), or 3-Quin-Ala; and $Xaa^8$ is Sta or Leu. In some embodiments, $Xaa^1$ is an N-terminal amino acid residue D-Phe; $Xaa^2$ is Gln or Cit; $Xaa^3$ is Trp or αMe-Trp; $Xaa^4$ is Ala; $Xaa^5$ is Val or Tle; $Xaa^6$ is Gly or NMe-Gly; $Xaa^7$ is His, Trp, Trp(7-F), Trp(6-F), Trp(5-F), Trp(4-F), 3-Quin-Ala, or 2-Quin-Ala; and $Xaa^8$ is Sta or Leu.

In some embodiments, the present disclosure relates to a peptidic compound of Formula (B), or a salt or solvate of Formula (B), (B)

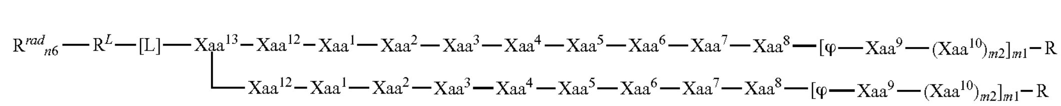

wherein:

each $Xaa^{12}$ is independently an N-terminal amino acid residue selected from p-aminomethylaniline-diglycolic acid (pABzA-DIG), 4-amino-(1-carboxymethyl)piperidine (Pip), 9-amino-4,7-dioxanonanoic acid (dPEG2), or 4-(2-aminoethyl)-1-carboxymethyl-piperazine (Acp);

each $Xaa^1$ is independently D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

each $Xaa^2$ is independently Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

each $Xaa^3$ is independently Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

each $Xaa^4$ is independently Ala, D-Ala, or Ser;

each $Xaa^5$ is independently Val, 2,3-dehydro-Val, cyclopentylglycine (Cpg), L-cyclopropylglycine, L-cyclobutylglycine, or tert-leucine (Tle);

each $Xaa^6$ is independently Gly or D-Ala;

each $Xaa^7$ is independently His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

each $Xaa^8$ is independently statine (Sta), Leu, D-Pro, Phe, cis-4-$NHR^a$-D-Pro or cis-4-$OR^a$-D-Pro, wherein $R^a$ is alkyl, cycloalkyl, or aryl;

each R is independently —$NH_2$ or —NHOH;

each m1 is independently 0 or 1;

each m2 is independently 0 or 1;

when m1 is 1 and m2 is 0, each $Xaa^9$-R is independently a C-terminally amidated (R is $-NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, each $Xaa^9$ is independently Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz); and $Xaa^{10}$-R is a C-terminally amidated (R is $-NH_2$) or a C-terminally hydroxylamidated (R is —NHOH) amino acid residue selected from Val, Leu, Tle, lie, Nle, Ala, Gly, or Met;

$Xaa^{13}$ is an amino acid with a sidechain comprising a carboxylic acid, wherein one $Xaa^{12}$ is bonded to the C-terminus of $Xaa^{13}$ and the other $Xaa^{12}$ is bonded to the sidechain of $Xaa^{13}$;

ψ represents a peptide bond or reduced peptide bond joining $Xaa^8$ to $Xaa^9$;

$R^L$ is absent, —($C_{1-6}$ alkyl)-, —($C_{1-6}$ alkyl)-C(O)—, —C(O)—, —NH—C(O)—, or —NH—C(S)—;

L is a linker and the linker absent or is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —$N(R^2)C(O)$—, —$C(O)N(R^2)$—, —NH—C(O)—NH—, —NH—C(S)—NH—,

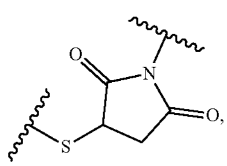, 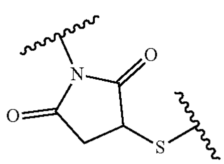,

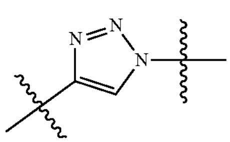, or 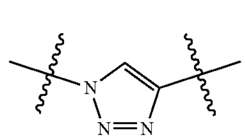;

and $R^2$ is H, methyl or ethyl;

optionally, the linker comprises an albumin binder ($R^{alb}$), wherein the albumin binder is:

$-(CH_2)_{n3}-CH_3$ wherein n3 is 8-20;

$-(CH_2)_{n4}-C(O)OH$ wherein n4 is 8-20;

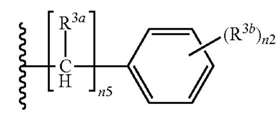

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

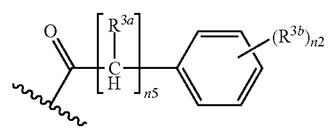

wherein n2 is 1-5, n5 is 1-4, $R^{3a}$ is H or methyl, and $R^{31}$ is I, Br, F, Cl, H, OH, $OCH_3$, $NH_2$, $NO_2$ or $C_1$-$C_6$ alkyl; or

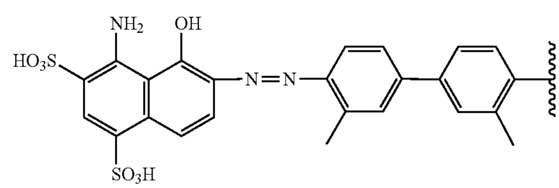;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments, the present disclosure relates to a peptidic compound of Formula (B-1), or a salt or solvate of formula (B-1), (B-1)

$$R^{rad}\text{-[linker]-}Xaa^{13}-[Xaa^{12}-Xaa^1-Xaa^2-Xaa^3-Xaa^4-Xaa^5-Xaa^6-Xaa^7-Xaa^8\text{-}\psi\text{-}Xaa^9-(Xaa^{10})_{m2}-R]_2$$

wherein:

$Xaa^{12}$ is an N-terminal amino acid residue selected from p-aminomethylaniline-diglycolic acid (pABzA-DIG), 4-amino-(1-carboxymethyl)piperidine (Pip), 9-amino-4,7-dioxanonanoic acid (dPEG2), or 4-(2-aminoethyl)-1-carboxymethyl-piperazine (Acp);

$Xaa^1$ is D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, or Phe;

R is —$NH_2$ or —NHOH;

m2 is 0 or 1;

when m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2Thz$), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

$Xaa^{13}$ is an amino acid with a sidechain comprising a carboxylic acid, wherein one $Xaa^{12}$ is bonded to the C-terminus of $Xaa^{13}$ and the other $Xaa^{12}$ is bonded to the sidechain of $Xaa^{13}$;

ψ represents a peptide bond or reduced peptide bond joining $Xaa^8$ to $Xaa^9$;

the linker absent or is a linear or branched chain of n1 units of -$Xaa^{11}$-, wherein:

n1 is 1-6;

each $Xaa^{11}$ is independently an amino acid;

$R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated.

In some embodiments of the peptidic compound of formula (B), the compound has the structure: $R^{rad}{}_{n6}$-$R^L$-[linker]-$Xaa^3$-[$Xaa^{12}$-$Xaa^1$-$Xaa^2$-$Xaa^3$-$Xaa^4$-$Xaa^5$-$Xaa^6$-$Xaa^7$-$Xaa^8$-ψ-$Xaa^9$-$(Xaa^{10})_m$-R$]_2$.

In some embodiments of the peptidic compound of formula (B) or (B-1), both $Xaa^{12}$ is the same amino acid. In some embodiments, each $Xaa^{12}$ is the same or different amino acids.

In some embodiments of the peptidic compound of formula (B) or (B-1), both $Xaa^1$ is the same amino acid. In some embodiments, each $Xaa^1$ is the same or different amino acids.

In some embodiments of the peptidic compound of formula (B) or (B-1), both $Xaa^2$ is the same amino acid. In some embodiments, each $Xaa^2$ is the same or different amino acids.

In some embodiments of the peptidic compound of formula (B) or (B-1), both $Xaa^3$ is the same amino acid. In some embodiments, each $Xaa^3$ is the same or different amino acids.

In some embodiments of the peptidic compound of formula (B) or (B-1), both $Xaa^4$ is the same amino acid. In some embodiments, each $Xaa^4$ is the same or different amino acids.

In some embodiments of the peptidic compound of formula (B) or (B-1), both $Xaa^5$ is the same amino acid. In some embodiments, each $Xaa^5$ is the same or different amino acids.

In some embodiments of the peptidic compound of formula (B) or (B-1), both $Xaa^6$ is the same amino acid. In some embodiments, each $Xaa^6$ is the same or different amino acids.

In some embodiments of the peptidic compound of formula (B) or (B-1), both $Xaa^7$ is the same amino acid. In some embodiments, each $Xaa^7$ is the same or different amino acids.

In some embodiments of the peptidic compound of formula (B) or (B-1), both $Xaa^8$ is the same amino acid. In some embodiments, each $Xaa^8$ is the same or different amino acids.

In some embodiments of the peptidic compound of formula (B) or (B-1), both $Xaa^9$ is the same amino acid. In some embodiments, each $Xaa^9$ is the same or different amino acids.

In some embodiments of the peptidic compound of formula (B) or (B-1), both $Xaa^{10}$ is the same amino acid. In some embodiments, each $Xaa^{10}$ is the same or different amino acids.

In some embodiments of the compounds of formula (B) or (B-1), $Xaa^1$ is D-Phe. In some embodiments, $Xaa^1$ is Cpa or D-Cpa. In some embodiments, $Xaa^1$ is Nal, D-Nal, 2-Nal, D-2-Nal. In some embodiments, $Xaa^1$ is D-Cpa, Tpi, D-Tpi or D-Nal.

In some embodiments of the compounds of formula (B) or (B-1), $Xaa^{12}$ is Pip.

In some embodiments of the compounds of formula (B) or (B-1), $Xaa^{13}$ is Glu, D-Glu, Asp, or D-Asp. In some embodiments, $Xaa^{13}$ is Glu.

In some embodiments of the compounds of formula (B) or (B-1), the linker is absent.

In some embodiments of the compounds of formula (B) or (B-1), the linker is a linear or branched chain of n1 units of -Xaa$^{11}$-, wherein n1 is 1-3, and each Xaa$^{11}$ is independently 2-aminoadipic acid (2-Aad) or 3-aminoadipic acid (3-Aad). In some embodiments, each Xaa$^{11}$ is 2-Aad. In some embodiments, the linker is -2-Aad-2-Aad-.

In some embodiments of the compounds of formula (B) or (B-1), n1 is 1, 2, or 3.

In some embodiments of the compounds of formula (B) or (B-1), $R^{rad}$ is a radiometal chelator. In some embodiments, the radiometal chelator is bound to a radiometal. As used herein, phrases that a radiometal is "bound to a chelator," "chelated to a chelator," "conjugated to a chelator," "conjugated with a chelator," and "associated with a chelator" are used interchangeably.

In some embodiments of the peptidic compound (e.g., compounds of formula (A), (I), (IA), (IA-1), (IB), (IB-1), (IC), (IC-1), (ID), (ID-1), (IE), (IE-1), (IF), (IF-1), (II), (IIA), (B), or (B-1) or salt or solvate thereof), R is —$NH_2$.

In some embodiments of the peptidic compound, ψ represents a reduced peptide bond. In some embodiments, ψ represents a peptide bond.

In some embodiments of the peptidic compound, Xaa$^1$ is an N-terminal amino acid residue selected from D-Phe.

In some embodiments of the peptidic compound, Xaa$^2$ is Gln. In some embodiments, Xaa$^2$ is Cit. In some embodiments, Xaa$^2$ is Glu. In some embodiments, Xaa$^2$ is Agb. In some embodiments, Xaa$^2$ is Asn, Gln, or Hse. In some embodiments, Xaa$^2$ is Gln, Cit, Glu, or Agb. In some embodiments, Xaa$^2$ is Gln or Cit.

In some embodiments of the peptidic compound, Xaa$^3$ is Trp. In some embodiments, Xaa$^3$ is αMe-Trp. In some embodiments, Xaa$^3$ is Trp, Trp(Me), Trp(7-Me), Trp(6-Me), Trp(5-Me), Trp(4-Me), Trp(2-Me), Trp(7-F), Trp(6-F), Trp (5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala). In some embodiments, Xaa$^3$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(5-OH), or αMe-Trp. In some embodiments, Xaa$^3$ is Trp, Trp(7-F), or αMe-Trp.

In some embodiments of the peptidic compound, Xaa$^4$ is Ala. In some embodiments, Xaa$^4$ is Ser.

In some embodiments of the peptidic compound, Xaa$^5$ is Val or Tle. In some embodiments, Xaa$^5$ is Val. In some embodiments, Xaa$^5$ is Tle. In some embodiments, Xaa$^5$ is Cpg.

In some embodiments of the peptidic compound, Xaa$^6$ is Gly or NMe-Gly. In some embodiments, Xaa$^6$ is Gly. In some embodiments, Xaa$^6$ is NMe-Gly. In some embodiments, Xaa$^6$ is Gly, NMe-Gly, or D-Ala.

In some embodiments of the peptidic compound, Xaa$^7$ is His. In some embodiments of the peptidic compound, Xaa$^7$ is Trp. In some embodiments of the peptidic compound, Xaa$^7$ is Trp(5-F). In some embodiments, Xaa$^7$ is Trp, Trp (Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp (6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), or αMe-Trp. In some embodiments, Xaa$^7$ is Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala). In some embodiments, Xaa$^7$ is His, Trp, Trp(5-F), or 3-Quin-Ala.

In some embodiments of the peptidic compound, Xaa$^8$ is Leu. In some embodiments, Xaa$^8$ is Sta. In some embodiments, Xaa$^8$ is D-Pro or Phe. In some embodiments, Xaa$^8$ is cis-4-cyclohexyloxy-D-Pro or cis-4-cyclohexylamino-D-Pro.

In some embodiments of the peptidic compound, Xaa$^8$-R is a C-terminally amidated cis-4-cyclohexyloxy-D-Pro or cis-4-cyclohexylamino-D-Pro.

In some embodiments of the peptidic compound, Xaa$^9$-R is a C-terminally amidated Pro or Leu. In some embodiments of the peptidic compound, Xaa$^9$-R is a C-terminally amidated Pro. In some embodiments of the peptidic compound, Xaa$^9$-R is a C-terminally amidated Leu. In some embodiments of the peptidic compound, Xaa$^9$-R is a C-terminally amidated Phe, diFPro, 4-oxa-Pro, $Me_2$Thz, or Thz. In some embodiments, Xaa$^9$-R is a C-terminally amidated cis-4-cyclohexyloxy-D-Pro or cis-4-cyclohexylamino-D-Pro.

In some embodiments of the peptidic compound, Xaa$^9$ is Pro or Leu. In some embodiments of the peptidic compound, Xaa$^9$ is Pro. In some embodiments of the peptidic compound, Xaa$^9$ is Leu.

In some embodiments of the peptidic compound, Xaa$^{10}$-R is a C-terminally amidated Val or Tle. some embodiments of the peptidic compound, Xaa$^{10}$-R is a C-terminally amidated Val. some embodiments of the peptidic compound, Xaa$^{10}$-R is a C-terminally amidated Tle.

In some embodiments of the peptidic compound, Xaa$^1$ is an N-terminal amino acid residue selected from D-Phe; Xaa$^2$ is Gln, Cit, Glu, or Agb; Xaa$^3$ is Trp or αMe-Trp; Xaa$^4$ is Ala; Xaa$^5$ is Val or Tle; Xaa$^6$ is Gly or NMe-Gly; Xaa$^7$ is His, Trp, Trp(5-F), or 3-Quin-Ala; Xaa$^8$ is Leu or Sta; and Xaa$^9$-R is a C-terminally amidated Pro or Leu.

In some embodiments of the peptidic compound, Xaa$^1$ is an N-terminal amino acid residue selected from D-Phe; Xaa$^2$ is Gln, Cit, Glu, or Agb; Xaa$^3$ is Trp or αMe-Trp; Xaa$^4$ is Ala; Xaa$^5$ is Val or Tle; Xaa$^6$ is Gly or NMe-Gly; Xaa$^7$ is His, Trp, or Trp(5-F); Xaa$^8$ is Leu or Sta; Xaa$^9$ is Pro or Leu; and Xaa$^{10}$-R is a C-terminally amidated Val or Tle.

In some embodiments of the peptidic compound, at least one of Xaa$^1$, Xaa$^2$, Xaa$^3$, Xaa$^4$, Xaa$^5$, Xaa$^6$, Xaa$^7$, Xaa$^8$, Xaa$^9$ or Xaa$^{10}$ is N-methylated. In some embodiments, at least one of Xaa$^1$, Xaa$^2$, Xaa$^3$, Xaa$^4$, Xaa$^5$, Xaa$^6$, Xaa$^7$, or Xaa$^8$ is N-methylated. For example, if the compound has a definition of Xaa$^4$ as Ala, D-Ala, or Ser, then it also includes options for NMe-Ala, NMe-D-Ala, or NMe-Ser as Xaa$^4$.

In some embodiments, Xaa$^6$ is N-methylated.

In a specific embodiment, the compounds of formula (A), (I), (IA), (IB), (IC), (ID), (IE), (B), (B-1) do not comprise an albumin binder $R^{alb}$ in the linker.

In some embodiments of the peptidic compound (e.g., compound of formula (A), (I), (IA), (IA-1), (IB), (IB—I), (IC), (IC-1), (ID), (ID-1), (IE), (IE-1), (IF), (IF-1), (II), (IIA), (B), or (B-1)), ψ is a reduced peptide bond joining Xaa$^8$ to Xaa$^9$, wherein Xaa$^8$ is Leu and Xaa$^9$ is Pro. In some embodiments, the reduced peptide bond joining Xaa$^8$ and Xaa$^9$ means that the main chain amide (e.g., 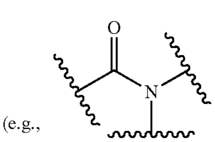 )

formed between $Xaa^8$ and $Xaa^9$ is replaced by

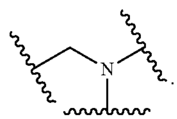 [SMILES: *CN(*)*]

In some embodiments of the peptidic compound, ψ is a peptide bond joining $Xaa^8$ and $Xaa^9$.

In some embodiments of the peptidic compound, $R^L$ is a linkage moiety joining the linker to the N-terminus of $Xaa^1$ or joining the linker and $R^{rad}$ In some embodiments, $R^L$ is —C(O)—. In other embodiments, $R^L$ is —NH—C(O)—. In yet other embodiments, $R^L$ is —NH—C(S)—. In some embodiments, $R^L$ is-($C_{1-3}$alkyl)-. In some embodiments, $R^L$ is-$CH_2$—. In some embodiments, $R^L$ is —($C_{1-3}$ alkyl)-C(O)—. In some embodiments, $R^L$ is —$CH_2$—C(O)—.

In some embodiments of the peptidic compound, the linker and $R^L$ together form a Pip linker. In some embodiments, the linker and $R^L$ together comprises a Pip linker.

In some embodiments of the peptidic compound, a non-limiting example of a suitable linker is a peptide linker. More generally, the linker is a linear or branched chain of n1 units of -$L^1R^1$— and/or -$(L^1)_2R^1$— (i.e. each unit is independently -$L^1R^1$— or -$(L^1)_2R^1$—), wherein n1 is 1-20. In alternative embodiments, n1 is 1, 2, 3, 4, 5, 6, 7, 8, 9, 10, 11, 12, 13, 14, 15, 16, 17, 18, 19, or 20. In some embodiments, n1 is 1-7. In some embodiments, n1 is 1. In other embodiments, n1 is 2. In other embodiments, n1 is 3. In other embodiments, n1 is 4. In other embodiments, n1 is 5. In other embodiments, n1 is 6. In other embodiments, n1 is 7.

In some embodiments of the peptidic compound, the linker is a linear or branched chain of n1 units of -$Xaa^{11}$-, wherein each $Xaa^{11}$ is independently an amino acid and n1 is 1-10. In some embodiments, the linker is a linear or branched chain of n1 units of -$Xaa^{11}$-, wherein each $Xaa^{11}$ is independently an amino acid and n1 is 1-6. In some embodiments, the linker comprises $R^{alb}$ bonded to a free N-terminus of a $Xaa^{11}$. In some embodiments, the linker comprises $R^{alb}$ bonded to a side chain of a $Xaa^{11}$. In some embodiments, at least one $Xaa^{11}$ is Lys. In some embodiments, at least one $Xaa^{11}$ is Lys and $R^{alb}$ is bonded to the side chain the Lys.

In some embodiments of the peptidic compound, the linker is a linear peptide of 3 to 6 amino acid residues, -$Xaa^{11A}$-$Xaa^{11B}$-$(Xaa^{11C})_{1-4}$-, wherein $Xaa^{11A}$ $Xaa^{11B}$, and $Xaa^{11C}$ are each independently an amino acid and wherein the radiolabeling group and the albumin-binding group are bonded to the free N-terminus of $Xaa^{11A}$ and the side chain of $Xaa^{11B}$, respectively, or are bonded to the side chain of $Xaa^{11B}$ and the free N-terminus of $Xaa^{11A}$, respectively. In some embodiments, $Xaa^{11A}$ is Gly, Glu, D-Glu, Asp, D-Asp, 2-Aad, D-2-Aad, 3-Aad, or D-3-Aad. In some embodiments, $Xaa^{11A}$ is Gly, Glu or D-Glu. In some embodiments, $Xaa^{11A}$ is Gly. In some embodiments, $Xaa^{11B}$ is Lys, Orn, D-Orn, Dab, D-Dab, Dap or D-Dap, any of which can form an amide bond with a carboxylate of a radiolabeling group or an albumin binding group. In some embodiments, $Xaa^{11B}$ is Lys or D-Lys. In some such embodiments, $(Xaa^{11C})_{1-4}$ is diglycine. In some such embodiments, $(Xaa^{11C})_{1-4}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, $(Xaa^{11C})_{1-4}$ is Pip. In some embodiments, the C-terminus of $Xaa^{11C}$ and the N-terminus of $Xaa^1$ are bonded.

In some embodiments of the peptidic compound, the linker is a branched peptide of 3 to 6 amino acid residues, -$Xaa^{11B}(Xaa^{11A})$-$(Xaa^{11C})_{1-4}$-, wherein $Xaa^{11A}$ $Xaa^{11B}$, and $Xaa^{11C}$ are each independently an amino acid and wherein the C-terminus of $Xaa^{11A}$ forms an amide with the side chain of $Xaa^{11B}$, and wherein the radiolabeling group and the albumin-binding group are bonded to the free N-termini of $Xaa^{11A}$ and $Xaa^{11B}$, respectively, or are bonded to the free N-termini of $Xaa^{11B}$ and $Xaa^{11A}$, respectively. In some embodiments, $Xaa^{11A}$ is Gly, Glu, D-Glu, Asp, D-Asp, 2-Aad, D-2-Aad, 3-Aad, or D-3-Aad. In some embodiments, $Xaa^{11A}$ is Glu or D-Glu. In some embodiments, $Xaa^{11B}$ is Lys, D-Lys, Orn, D-Orn, Dab, D-Dab, Dap or D-Dap. In some embodiments, $Xaa^{11B}$ is Lys or D-Lys. In some such embodiments, $(Xaa^{11C})_{1-4}$ is diglycine. In some such embodiments, $(Xaa^{11C})_{1-4}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, $(Xaa^{11C})_{1-4}$ is Pip. In some embodiments, the C-terminus of $Xaa^{11C}$ and the N-terminus of $Xaa^1$ are bonded.

In some embodiments of the peptidic compound, the linker is a linear peptide of 3 amino acid residues, -$Xaa^{11A}$-$Xaa^{11B}$-$Xaa^{11C}$-, wherein $Xaa^{11A}$, $Xaa^{11B}$, and $Xaa^{11C}$ are each independently an amino acid and wherein the radiolabeling group and the albumin-binding group are bonded to the free N-terminus of $Xaa^{11A}$ and the side chain of $Xaa^1$B, respectively, or are bonded to the side chain of $Xaa^{11B}$ and the free N-terminus of $Xaa^{11A}$, respectively. In some embodiments, $Xaa^{11A}$ is Gly, Glu, D-Glu, Asp, D-Asp, 2-Aad, D-2-Aad, 3-Aad, or D-3-Aad. In some embodiments, $Xaa^{11A}$ is Gly, Glu or D-Glu. In some embodiments, $Xaa^{11A}$ is Gly. In some embodiments, $Xaa^{11B}$ is Lys, D-Lys, Orn, D-Orn, Dab, D-Dab, Dap or D-Dap, any of which can form an amide bond with a carboxylate of a radiolabeling group or an albumin binding group. In some embodiments, $Xaa^{11B}$ is Lys or D-Lys. In some such embodiments, $Xaa^{11C}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, $Xaa^{11C}$ is Pip. In some embodiments, the C-terminus of $Xaa^{11C}$ and the N-terminus of $Xaa^1$ are bonded.

In some embodiments of the peptidic compound, the linker is -Gly-Lys-Pip-. In some embodiments, the radiolabeling group is bonded to the free N-terminus of $Xaa^{11A}$ and the albumin-binding group is bonded to the side chain of $Xaa^{11B}$. In some embodiments, the radiolabeling group is bonded to the free N-terminus of Gly and the albumin-binding group is bonded to the side chain of Lys. In some embodiments, the C-terminus of Pip and the N-terminus of $Xaa^1$ are bonded.

In some embodiments of the peptidic compound, the linker is a branched peptide of 3 amino acid residues, -$Xaa^{11B}(Xaa^{11A})$-$Xaa^{11C}$-, wherein $Xaa^{11A}$, $Xaa^{11B}$, and $Xaa^{11C}$ are each independently an amino acid and wherein the C-terminus of $Xaa^{11A}$ forms an amide with the side chain of $Xaa^{11B}$, and wherein the radiolabeling group and the albumin-binding group are bonded to the free N-termini of $Xaa^{11A}$ and $Xaa^{11B}$, respectively, or are bonded to the free N-termini of $Xaa^{11B}$ and $Xaa^{11A}$, respectively. In some embodiments, $Xaa^{11A}$ is Gly, Glu, D-Glu, Asp, D-Asp, 2-Aad, D-2-Aad, 3-Aad, or D-3-Aad. In some embodiments, $Xaa^{11A}$ is Glu or D-Glu. In some embodiments, $Xaa^{11B}$ is Lys, D-Lys, Orn, D-Orn, Dab, D-Dab, Dap or D-Dap. In some embodiments, $Xaa^{11B}$ is Lys or D-Lys. In some such embodiments, $Xaa^{11C}$ is p-aminomethylaniline-diglycolic acid (pABzA-DIG), a 4-amino-(1-carboxymethyl)piperidine (Pip), a 9-amino-4,7-dioxanonanoic acid (dPEG2), or a 4-(2-aminoethyl)-1-carboxymethyl-piperazine (Acp). In some such embodiments, $Xaa^{11C}$ is Pip. In some embodiments, the C-terminus of $Xaa^{11C}$ and the N-terminus of $Xaa^1$ are bonded.

In some embodiments of the peptidic compound, $R^{11C}$ between $Xaa^{11}$ of the linker and $Xaa^1$ is absent and $Xaa^{11}$ of the linker joins with the N-terminus of $Xaa^1$. In some embodiments, $R^L$ between $Xaa^{11}$ of the linker and $Xaa^1$ is absent and $Xaa^{11}$ of the linker joins with the N-terminus of $Xaa^1$ by forming an amide bond (i.e., peptide bond between $Xaa^{11}$-$Xaa^1$).

In some embodiments of the peptidic compound, the linker and $R^L$ together form

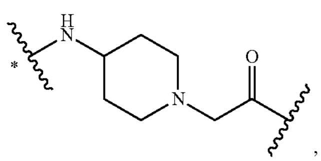
,
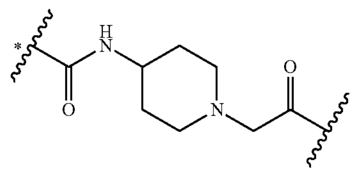
or
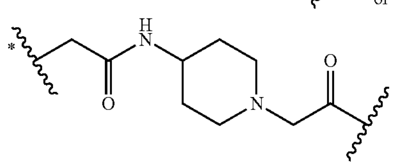
.

In some embodiments the linker is

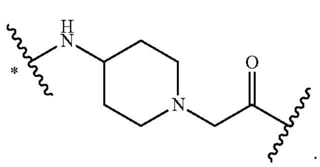 [SMILES: *NC1CCN(CC(*)=O)CC1]
.

In some embodiments of the peptidic compound, an albumin binder ($R^{alb}$) is bonded to the linker. In some embodiments of the peptidic compound, the linker does not comprise $R^{alb}$.

In some embodiments of the peptidic compound, n6 is 1-5. In some embodiments, n6 is 1. In other embodiments, n6 is 2. In other embodiments, n6 is 3. In other embodiments, n6 is 4. In other embodiments, n6 is 5.

In some embodiments of the peptidic compound, n6 is 1 and n1 is 1. In some embodiments, n6 is 1, n1 is 1, and $L^1$ is —C(O)NH—. In some embodiments, n6 is 1, n1 is 1, $L^1$ is —C(O)NH—, and $R^L$ is —C(O)—. In some embodiments, n6 is 1, n1 is 1, $L^1$ is —C(O)NH—, $R^L$ is —C(O)—, and $R^1$ is a linear $C_{1-5}$ alkylenyl or $—(CH_2)_2—[O(CH_2)_2]_{1-6}—(CH_2)_{0-2}$.

In some embodiments of the peptidic compound, $R^{rad}{}_{n6}$-[linker]- is configured as shown in Formula (a):

(a)

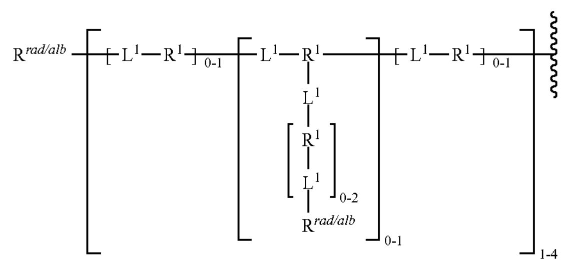
, wherein $L^1$ and $R^1$ are as defined in the definition of the linker in Formula a, and $R^{rad/alb}$ is either $R^{rad}$ or $R^{alb}$, and wherein 0-1 $R^{rad/alb}$ is $R^{alb}$.

In some embodiments of the peptidic compound, $R^1$ is, independently, a linear, branched, and/or cyclic $C_{1-20}$ alkylenyl, $C_{2-20}$ alkenylenyl and/or $C_{2-20}$ alkynylenyl, wherein any carbon bonded to two other carbons is optionally independently replaced by N, S, or O, and carbons are optionally independently substituted. In some embodiments, $R^1$ is, independently, a linear, branched, and/or cyclic $C_{1-15}$ alkylenyl, $C_{2-15}$ alkenylenyl and/or $C_{2-15}$ alkynylenyl, wherein any carbon bonded to two other carbons is optionally independently replaced by N, S, or O, and carbons are optionally independently substituted. In some embodiments, $R^1$ is, independently, a linear, branched, and/or cyclic $C_{1-10}$ alkylenyl, $C_{2-10}$ alkenylenyl and/or $C_{2-10}$ alkynylenyl, wherein any carbon bonded to two other carbons is optionally independently replaced by N, S, or O, and carbons are optionally independently substituted. In some embodiments, $R^1$ is, independently, a linear, branched, and/or cyclic $C_{1-10}$ alkylenyl. In some embodiments, each $R^1$ is independently a linear $C_{1-5}$ alkylenyl or $—(CH_2)_2—[O(CH_2)_2]_{1-6}—(CH_2)_{0-2}—$.

In some embodiments of the peptidic compound, n1 is 1-7. In some embodiments, each $R^1$ is independently $—C(R^{aa})H—$, wherein each $R^{aa}$ is independently the sidechain of a proteinogenic amino acid or the sidechain of an alpha amino acid from Table A. In some embodiments, each $R^1$ is independently a proteinogenic amino acid or an amino acid from Table A omitting the backbone amino and carboxylic acid groups of the amino acid.

In some embodiments of the peptidic compound, $L^1$ is a linkage group. In some embodiments, at least one $L^1$ is —S—. In some embodiments, at least one $L^1$ is $—N(R^2)C(O)—$; in some of these embodiments, at least one $R^2$ is hydrogen. In some embodiments, at least one $L^1$ is $—C(O)N(R^2)$_; in some of these embodiments, at least one $R^2$ is hydrogen. In some embodiments, at least one $L^1$ is —NH—C(O)—NH—. In some embodiments, at least one $L^1$ is —NH—C(S)—NH—. In some embodiments, at least one $L^1$ is

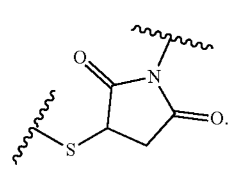 [SMILES: *SC1CC(=O)N(*)C1=O]
.

In some embodiments, at least one $L^1$ is

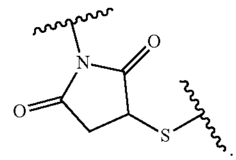 [SMILES: *SC1CC(=O)N(*)C1=O]

In some embodiments, at least one $L^1$ is

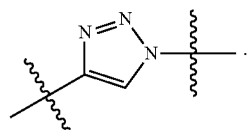 [SMILES: *c1cn(*)nn1]

In some embodiments, at least one $L^1$ is

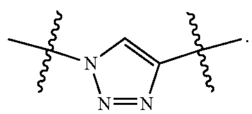 [SMILES: *c1cn(*)nn1]

In some embodiments of the peptidic compound, the linker has the configuration shown in Formula a, and each $R^1$ is independently a linear $C_{1-5}$ alkylenyl or $-(CH_2)_2-[O(CH_2)_2]_{1-6}-(CH_2)_{0-2}-$.

In some embodiments of the peptidic compound, n6 is 1, the linker is $L^1R^1$ and together with $R^L$ forms —C(O)-$Xaa^{11}$- wherein $Xaa^{11}$ is a proteinogenic amino acid residue or an amino acid residue selected from Table A. In some embodiments, $Xaa^{11}$ is pABzA-DIG. In other embodiments, $Xaa^{11}$ is Pip. In other embodiments, $Xaa^{11}$ is dPEG2. In other embodiments, $Xaa^{11}$ is Acp.

In some embodiments of the peptidic compound, the linker together with $R^L$ forms a peptide linker, wherein peptide (amide) bonds are independently optionally methylated, optionally replacing one or more amide bonds with 1,2,3-triazole linkages (product of a reaction between an azide and an alkyne). In some embodiments, the peptide linker is a linear peptide linker, optionally replacing one or more amide bonds with 1,2,3-triazole linkages. In some embodiments, the peptide linker is a branched peptide linker, where the amino acid residues may be connected through a combination of main chain amide (peptide) bonds and 'side chain'-to-'main chain' or 'side chain'-to-'side chain' bonds. For example, a branched peptide may be connected by one or more of: backbone (main chain) peptide (amide) bonds, 'main chain'-to-side chain amide bonds (between an amino group and a carboxylic acid group), optionally replacing one or more amide bonds with 1,2,3-triazole linkages. In some such embodiments, the peptide linker is $(Xaa^A)_{1-20}$, wherein each $Xaa^A$ is independently a proteinogenic amino acid residue or a non-proteinogenic amino acid residue (e.g., selected from Table A) linked together as a linear or branched peptide linker. In some embodiments, $(Xaa^A)_{1-20}$ is a linear peptide linker. In some embodiments, $(Xaa^A)_{1-20}$ is a branched peptide linker. $R^{rad}$ is bonded to the peptide linker through an amide bond or another $L^1$ linkage group; in some embodiments, $R^{rad}$ is bonded to the peptide linker through an amide bond.

In some embodiments, each $Xaa^A$ is independently $-N(R^a)R^bC(O)-$ wherein: $R^a$ may be H or methyl; $R^b$ may be a 1- to 30-atom alkylenyl, heteroalkylenyl, alkenylenyl, heteroalkenylenyl, alkynylenyl, or heteroalkynylenyl, including linear, branched, and/or cyclic (whether aromatic or nonaromatic as well as mono-cyclic, multicyclic or fused cyclic) structures; or N, $R^a$ and $R^b$ together may form a 5- to 7-atom heteroalkylenyl or heteroalkenylenyl.

In some embodiments, $(Xaa^A)_{1-20}$ consists of a single amino acid or residue. In some embodiments, $(Xaa^A)_{1-20}$ is a dipeptide, wherein each $Xaa^A$ may be the same or different. In some embodiments, $(Xaa^A)_{1-20}$ is a tripeptide, wherein each $Xaa^A$ may be the same, different or a combination thereof. In some embodiments, $(Xaa^A)_{1-20}$ consists of 4 amino acid residues connected by peptide bonds, wherein each $Xaa^A$ may be the same, different or a combination thereof. In some embodiments, each $Xaa^A$ is independently selected from proteinogenic amino acids and the non-proteinogenic amino acids listed in Table A, wherein each peptide backbone amino group of the peptide linker is independently optionally methylated. In some embodiments, all peptide backbone amino groups of the peptide linker are methylated. In other embodiments, only one peptide backbone amino group of the peptide linker is methylated. In other embodiments, only two peptide backbone amino groups of the peptide linker are methylated. In other embodiments, no peptide backbone amino groups of the peptide linker are methylated.

In some embodiments of the peptidic compound, $R^{alb}$ is $-(CH_2)_{n3}-CH_3$ wherein n3 is 8-20. In some embodiments, n3 is 8-15.

In some embodiments of the peptidic compound, $R^{alb}$ is $-(CH_2)_{n4}-C(O)OH$ wherein n4 is 8-20. In some embodiments, n4 is 8-15.

In some embodiments of the peptidic compound, $R^{alb}$ is

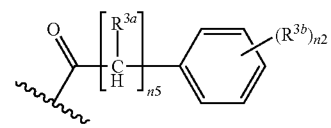

wherein n2 is 1-5, n5 is 1-4, and each $R^{3a}$ is independently H or methyl, and each $R^{3b}$ independently is I, Br, F, Cl, H, OH, $OCH_3$, $NH_2$, $NO_2$ or $C_1$-$C_6$ alkyl. In some embodiments, n2 is 1. In some embodiments, n5 is 1, 2, 3, or 4. In some embodiments, each $R^{3a}$ is H. In some embodiments, each $R^{3a}$ is methyl. In some embodiments, each $R^{3b}$ is I, Br, F, or Cl, optionally in para position. In some embodiments, $R^{3b}$ is H. In some embodiments, $R^{3b}$ is OH, optionally in para position. In some embodiments, $R^{3b}$ is $OCH_3$, optionally in para position. In certain embodiments, $R^{3b}$ is $NH_2$, optionally in para position. In some embodiments, $R^{3b}$ is $NO_2$, optionally in para position. In some embodiments, $R^{3b}$ is $C_1$-$C_6$ alkyl, optionally in para position. In some embodiments, $R^{3a}$ is H and $R^{3b}$ is $OCH_3$ or $NO_2$.

In some embodiments of the peptidic compound, $R^{alb}$ is

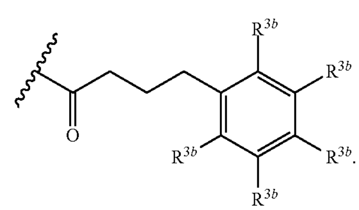

In some embodiments, $R^{alb}$ is

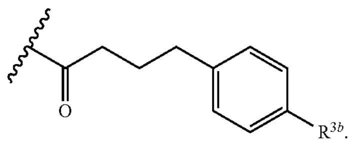

In some embodiments, $R^{3b}$ is I, Br, F, Cl, H, OH, $OCH_3$, $NH_2$, or $NO_2$.

In some embodiments of the peptidic compound, $R^{alb}$ is

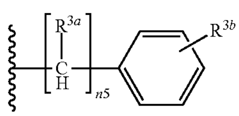

wherein n5 is 1-4 and each $R^{3a}$ is independently H or methyl, and $R^{3b}$ is I, Br, F, Cl, H, OH, $OCH_3$, $NH_2$, $NO_2$ or $C_1$-$C_6$ alkyl. In some embodiments, each $R^{3a}$ is H. In some embodiments, each $R^{3a}$ is methyl. In some embodiments, $R^{3b}$ is I, Br, F, or Cl, optionally in para position. In some embodiments, $R^{3b}$ is H. In some embodiments, $R^{3b}$ is OH, optionally in para position. In some embodiments, $R^{3b}$ is $OCH_3$, optionally in para position. In some embodiments, $R^{3b}$ is $NH_2$, optionally in para position. In certain embodiments, $R^{3b}$ is $NO_2$, optionally in para position. In some embodiments, $R^{3b}$ is $C_1$-$C_6$ alkyl, optionally in para position. In some embodiments, $R^{3a}$ is H and $R^{3b}$ is $OCH_3$ or $NO_2$.

In some embodiments of the peptidic compound, $R^{alb}$ is

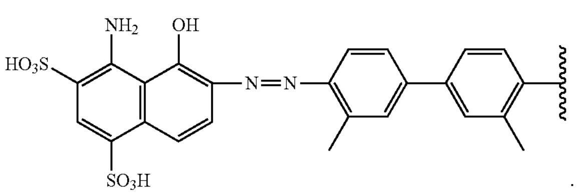 [SMILES: *c1ccc(-c2ccc(N=Nc3ccc4c(S(=O)(=O)O)cc(S(=O)(=O)O)c(N)c4c3O)c(C)c2)cc1C]

In some embodiments, at least one $R^{rad}$ is or comprises a radiometal chelator. The radiometal chelator may be any chelator suitable for binding a radiometal, a radionuclide-bound metal, or a radionuclide-bound metal-containing prosthetic group, and which is attached to the linker by forming an amide bond (between an amino group and a carboxylic acid group) or a 1,2,3-triazole (reaction between an azide and an alkyne), or by reaction between a maleimide and a thiol group. Many suitable radiometal chelators are known, e.g., as summarized in Price and Orvig, *Chem. Soc. Rev.,* 2014, 43, 260-290. In some embodiments, but without limitation, each radiometal chelator is independently selected from the group consisting of: DOTA and DOTA derivatives; DOTAGA (2-(4,7,10-tris(carboxymethyl)-1,4,7,10-tetraazacyclododecan-1-yl)pentanedioic acid); PSC (1,4,7,10-tetraazacyclododecane-1,4,7,10-tetriacetic acid); NOTA; NODAGA; NODASA; CB-DO2A; 3p-C-DEPA; TCMC (also known as DOTAM); DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; $H_2$dedpa, $H_4$octapa, $H_4$py4pa, $H_4$Pypa, $H_2$azapa, $H_5$decapa, and other picolinic acid derivatives; CP256; PCTA; C-NETA; C-NE3TA; HBED; SHBED; BCPA; CP256; YM103; desferrioxamine (DFO) and DFO derivatives; $H_6$phospa; a trithiol chelate; mercaptoacetyl; hydrazinonicotinamide; dimercaptosuccinic acid; 1,2-ethylenediylbis-L-cysteine diethyl ester; methylenediphosphonate; hexamethylpropyleneamineoxime; and hexakis (methoxy isobutyl isonitrile). In some embodiments, at least one radiometal chelator is DOTA or a DOTA derivative.

In some embodiments, when $R^{rad}$ is a radiometal chelator, an atom or a chemical group of the radiometal chelator is replaced to form a covalent bond to the linker. For example, a hydroxyl group (—OH) of a carboxylic acid of DOTA is replaced with a covalent bond to the linker. In another example, an amine group (—$NH_2$) of an acetamide of TCMC is replaced with a covalent bond to the linker.

In some embodiments, when $R^{rad}$ is DOTA and —$R^L$-[linker]-$R^L$—, -[linker]-$R^L$—, or -[linker]- is Pip, and $R^{rad}$-[linker]-$R^L$— has the structure:

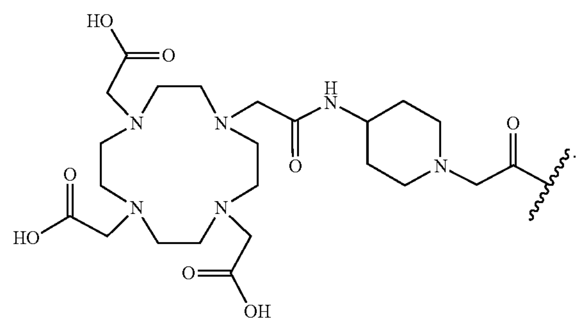 [SMILES: *C(=O)CN1CCC(NC(=O)CN2CCN(CC(=O)O)CCN(CC(=O)O)CCN(CC(=O)O)CC2)CC1]

In some embodiments, when $R^{rad}$ is DOTA and $R^L$-[linker]-$R^L$—, -[linker]-$R^L$—, or -[linker]- is Pip, and $R^{rad}$—$R^L$-[linker]-$R^L$-Xaa$^1$-$R^{rad}$-[linker]-$R^L$-Xaa$^1$- or $R^{rad}$-[linker]-Xaa$^1$- has the structure:

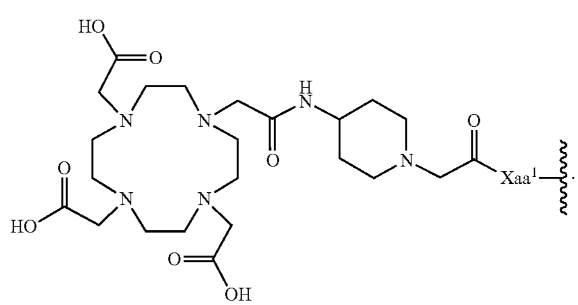

In some embodiments, when $R^{rad}$ is DOTAGA and —$R^L$-[linker]-$R^L$—, -[linker]-$R^L$—, or -[linker]- is Pip, and $R^{rad}$-[linker]-$R^L$— has the structure:

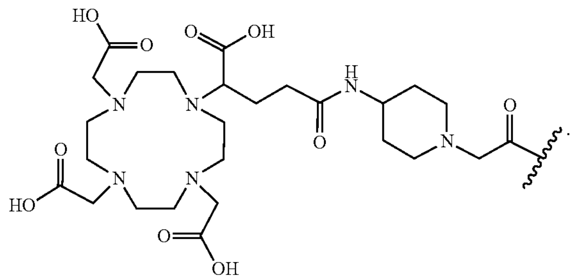 [SMILES: *C(=O)CN1CCC(NC(=O)CCC(C(=O)O)N2CCN(CC(=O)O)CCN(CC(=O)O)CCN(CC(=O)O)CC2)CC1]

In some embodiments, when $R^{rad}$ is DOTAGA and $R^{L}$-[linker]-$R^{L}$—, -[linker]-$R^{L}$—, or -[linker]- is Pip, and $R^{rad}$—$R^{L}$-[linker]-$R^{L}$-Xaa$^{1}$-$R^{rad}$-[linker]-$R^{L}$-Xaa$^{1}$- or $R^{rad}$-[linker]-Xaa$^{1}$- has the structure:

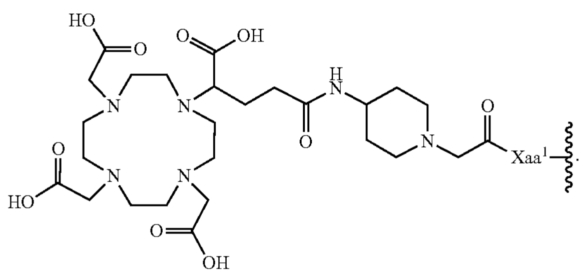

In some embodiments, when $R^{rad}$ is CROWN and —$R^{L}$-[linker]-$R^{L}$—, -[linker]-$R^{L}$—, or -[linker]- is Pip, and $R^{rad}$—$R^{L}$-[linker]-$R^{L}$-Xaa$^{1}$-$R^{rad}$-[linker]-$R^{L}$-Xaa$^{1}$- or $R^{rad}$-[linker]-Xaa$^{1}$- has the structure:

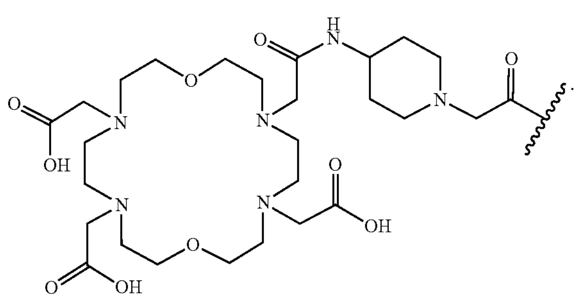 [SMILES: *C(=O)CN1CCC(NC(=O)CN2CCOCCN(CC(=O)O)CCN(CC(=O)O)CCOCCN(CC(=O)O)CC2)CC1]

In some embodiments, when $R^{rad}$ is CROWN and —$R^{L}$-[linker]-$R^{L}$—, -[linker]-$R^{L}$—, or -[linker]- is Pip, and $R^{rad}$ $R^{rad}$—$R^{L}$-[linker]-$R^{L}$-Xaa$^{1}$-$R^{rad}$-[linker]-$R^{L}$-Xaa$^{1}$- or $R^{rad}$-[linker]-Xaa$^{1}$- has the structure:

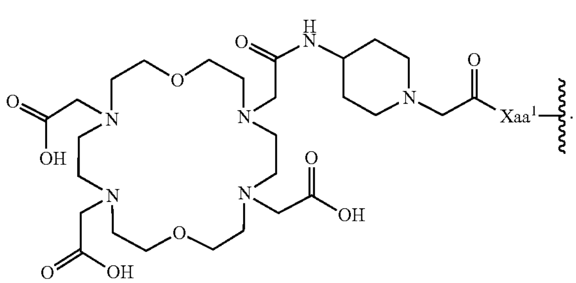

In some embodiments, when $R^{rad}$ is CROWNGA and —$R^{L}$-[linker]-$R^{L}$—, -[linker]-$R^{L}$—, or -[linker]- is Pip, and $R^{rad}$—$R^{L}$-[linker]-$R^{L}$-Xaa$^{1}$-$R^{rad}$-[linker]-$R^{L}$-Xaa$^{1}$- or $R^{rad}$-[linker]-Xaa$^{1}$- has the structure:

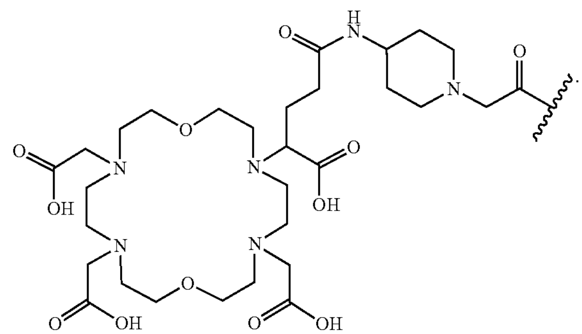 [SMILES: *C(=O)CN1CCC(NC(=O)CCC(C(=O)O)N2CCOCCN(CC(=O)O)CCN(CC(=O)O)CCOCCN(CC(=O)O)CC2)CC1]

In some embodiments, when $R^{rad}$ is CROWNGA and —$R^{L}$-[linker]-$R^{L}$—, -[linker]-$R^{L}$—, or -[linker]- is Pip, and $R^{rad}$ $R^{rad}$—$R^{L}$-[linker]-$R^{L}$-Xaa$^{1}$-$R^{rad}$-[linker]-$R^{L}$-Xaa$^{1}$- or $R^{rad}$-[linker]-Xaa$^{1}$- has the structure:

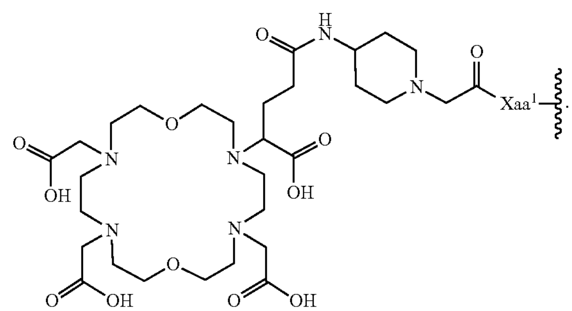

In some embodiments, when $R^{rad}$ is TCMC and —$R^{L}$-[linker]-$R^{L}$, -[linker]-$R^{L}$—, or -[linker]- is Pip, and $R^{rad}$-[linker]-$R^{L}$— has the structure:

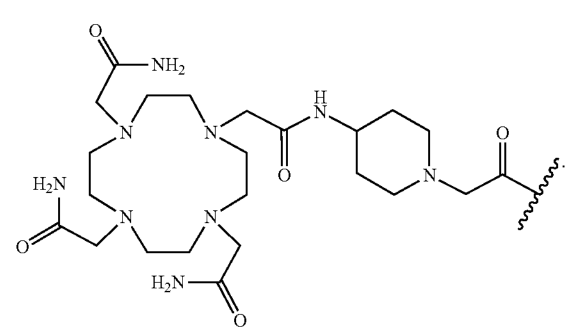 [SMILES: *C(=O)CN1CCC(NC(=O)CN2CCN(CC(N)=O)CCN(CC(N)=O)CCN(CC(N)=O)CC2)CC1]

In some embodiments, when $R^{rad}$ is PSC and —$R^{L}$-[linker]-$R^{L}$—, -[linker]-$R^{L}$—, or -[linker]- is Pip, and $R^{rad}$—$R^{L}$-[linker]-$R^{L}$-Xaa$^{1}$-$R^{rad}$-[linker]-$R^{L}$-Xaa$^{1}$- or $R^{rad}$-[linker]-$R^{L}$-Xaa$^{1}$- has the structure:

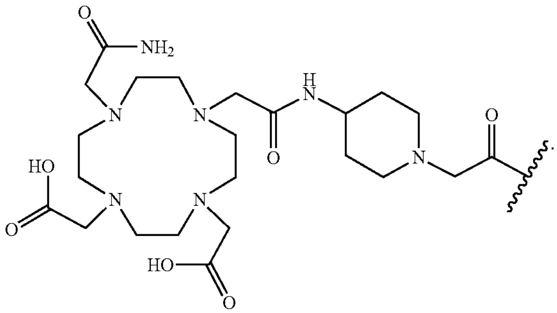 [SMILES: *C(=O)CN1CCC(NC(=O)CN2CCN(CC(N)=O)CCN(CC(=O)O)CCN(CC(=O)O)CC2)CC1]

TABLE B

| Exemplary radiometal chelators and exemplary radiometals | |
|---|---|
| Chelator | Radiometal |
| 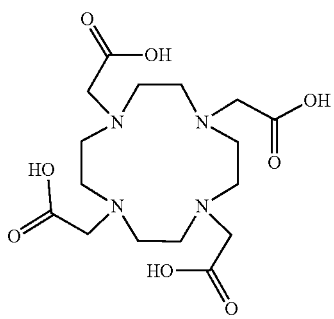 [SMILES: O=C(O)CN1CCN(CC(=O)O)CCN(CC(=O)O)CCN(CC(=O)O)CC1]<br>DOTA, 1,4,7,10-tetraazacyclododecane-1,4,7,10-tetraacetic acid | Cu-64/67<br>Ga-67/68<br>In-111<br>Lu-177<br>Y-86/90<br>Bi-203/212/213<br>Pb-212<br>Ac-225<br>Gd-159<br>Yb-175<br>Ho-166<br>As-211<br>Sc-44/47<br>Pm-149<br>Pr-142<br>Sn-117m<br>Sm-153<br>Tb-149/152/155/161<br>Er-165<br>Ra-223/224<br>Th-227 |
| 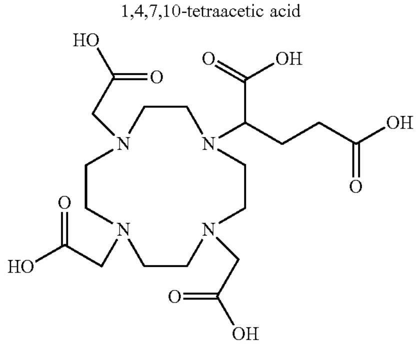<br>DOTAGA, 2-(4,7,10-tris(carboxymethyl)-1,4,7,10-tetraazacyclododecan-1-yl) pantanedioic acid | |
| 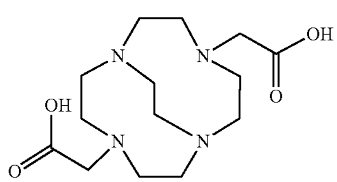 [SMILES: O=C(O)CN1CCN2CCN(CC1)CCN(CC(=O)O)CC2]<br>CB-DO2A, 4,10-bis(carboxymethyl)-1,4,7,10-tetraazabicyclo[5.5.2]tetradecane | Cu-64/67 |

TABLE B-continued
| Exemplary radiometal chelators and exemplary radiometals | |
|---|---|
| Chelator | Radiometal |
| 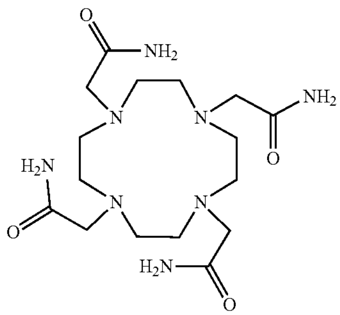 [SMILES: NC(=O)CN1CCN(CC(N)=O)CCN(CC(N)=O)CCN(CC(N)=O)CC1]<br>TCMC, 1,4,7,10-tetrakis(carbamoylmethyl)-1,4,7,10-tetraazacyclododecane | Pb-212 |
| 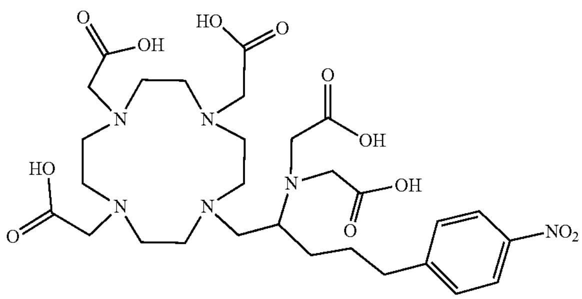 [SMILES: O=C(O)CN1CCN(CC(=O)O)CCN(CC(CCCc2ccc([N+](=O)[O-])cc2)N(CC(=O)O)CC(=O)O)CCN(CC(=O)O)CC1]<br>3p-C-DEPA | Bi-212/213 |
| 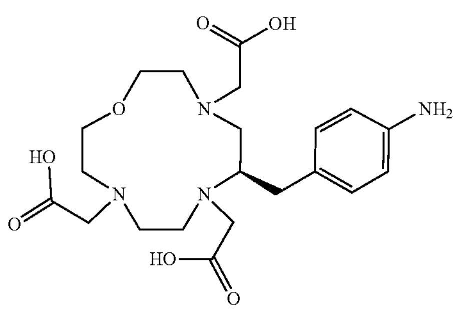 [SMILES: Nc1ccc(C[C@@H]2CN(CC(=O)O)CCOCCN(CC(=O)O)CCN2CC(=O)O)cc1]<br>p-$NH_2$-Bn-Oxo-DO3A | Cu-64/67 |
| 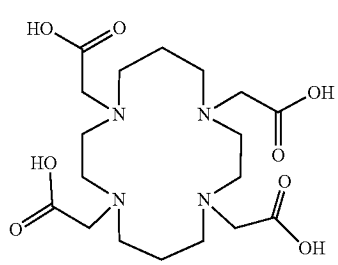 [SMILES: O=C(O)CN1CCCN(CC(=O)O)CCN(CC(=O)O)CCCN(CC(=O)O)CC1]<br>TETA, 1,4,8,11-tetraazacyclotetradecane-1,4,8,11-tetraacetic acid | Cu-64/67 |

TABLE B-continued
| Exemplary radiometal chelators and exemplary radiometals | |
|---|---|
| Chelator | Radiometal |
| 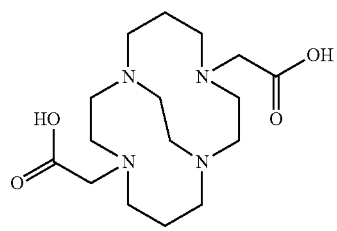 [SMILES: O=C(O)CN1CCCN2CCN(CCCN(CC(=O)O)CC2)CC1] CB-TE2A, 4,11-bis-(carboxymethyl)-1,4,8,11-tetraazabicyclo[6.6.2]-hexadecane | Cu-64/67 |
| 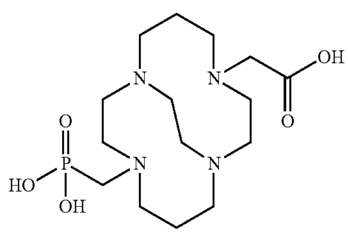 [SMILES: O=C(O)CN1CCCN2CCN(CCCN(CP(=O)(O)O)CC2)CC1] CB-TE1A1P | Cu-64/67 |
| 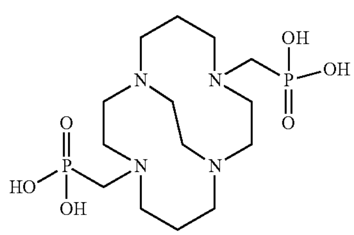 [SMILES: O=P(O)(O)CN1CCCN2CCN(CCCN(CP(=O)(O)O)CC2)CC1] CB-TE2P | Cu-64/67 |
| 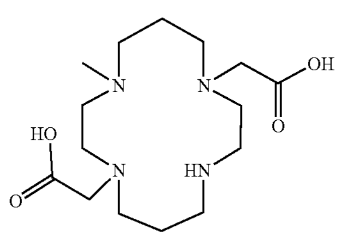 [SMILES: CN1CCCN(CC(=O)O)CCNCCCN(CC(=O)O)CC1] MM-TE2A | Cu-64/67 |
| 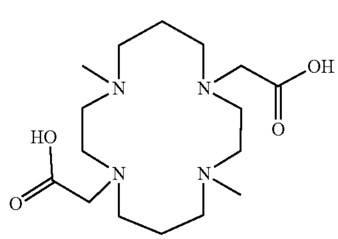 [SMILES: CN1CCCN(CC(=O)O)CCN(C)CCCN(CC(=O)O)CC1] DM-TE2A | Cu-64/67 |

TABLE B-continued
| Exemplary radiometal chelators and exemplary radiometals | |
|---|---|
| Chelator | Radiometal |
| 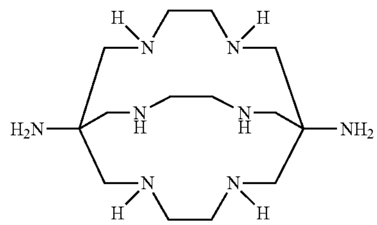 [SMILES: NC12CNCCNCC(N)(CNCCNC1)CNCCNC2]<br>Diamsar | Cu-64/67 |
| 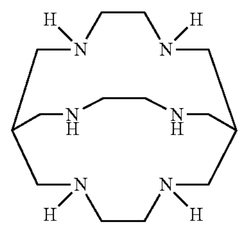 [SMILES: C1CNCC2CNCCNCC(CN1)CNCCNC2]<br>Sarcophagine | Cu-64/67 |
| 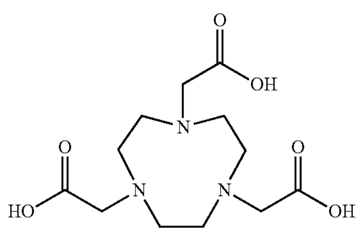 [SMILES: O=C(O)CN1CCN(CC(=O)O)CCN(CC(=O)O)CC1]<br>NOTA, 1,4,7-triazacyclononane-1,4,7-triacetic acid | Cu-64/67<br>Ga-68<br>In-111<br>Sc-44/47 |
| 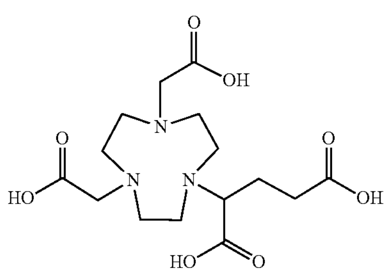 [SMILES: O=C(O)CCC(C(=O)O)N1CCN(CC(=O)O)CCN(CC(=O)O)CC1]<br>NODAGA, 1,4,7-triazacyclononane, 1-glutaric acid-4,7-acetic acid | Cu-64/67<br>Ga-68<br>In-111<br>Sc-44/47 |
| 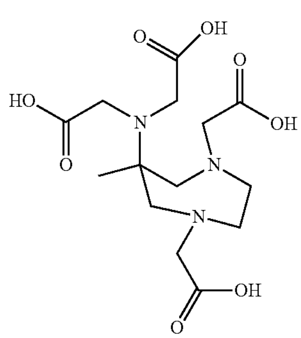 [SMILES: CC1(N(CC(=O)O)CC(=O)O)CN(CC(=O)O)CCN(CC(=O)O)C1]<br>AAZTA | Cu-64/67<br>Ga-68<br>In-111<br>Lu-177 |

TABLE B-continued
Exemplary radiometal chelators and exemplary radiometals
| Chelator | Radiometal |
|---|---|
| 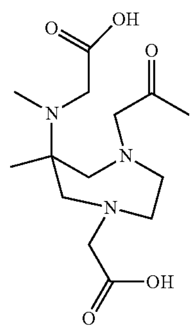 DATA | Cu-64/67<br>Ga-68<br>In-111 |
| 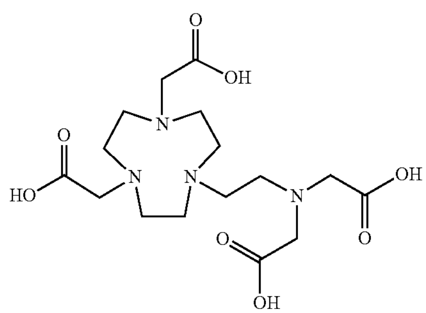 NETA, {4-[(2-(bis-carboxymethylamino)-ethyl]-7-carboxymethyl-[1,4,7]triazonan-1-yl}-acetic acid | Cu-64/67<br>Ga-68<br>Lu-177<br>Y-86/90<br>Bi-213<br>Pb-212 |
| 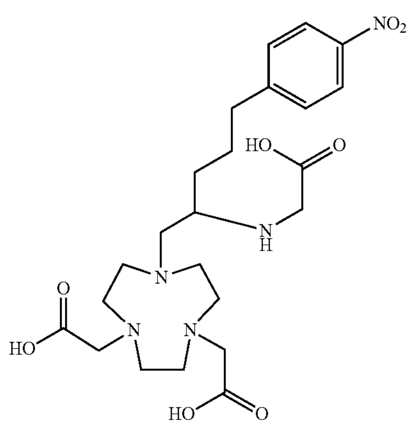 3p-C-NE3TA | Cu-64/67<br>Ga-68<br>Lu-177<br>Y-86/90<br>Bi-213<br>Pb-212 |
| 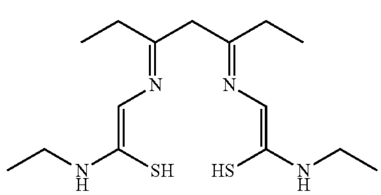 HxTSE | Au-198/199 |

TABLE B-continued

| Exemplary radiometal chelators and exemplary radiometals | |
|---|---|
| Chelator | Radiometal |
| 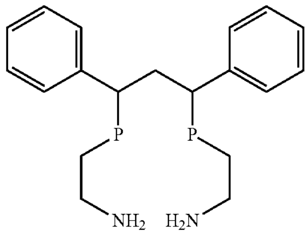 P$_2$N$_2$Ph$_2$ | Rh-105 |
| 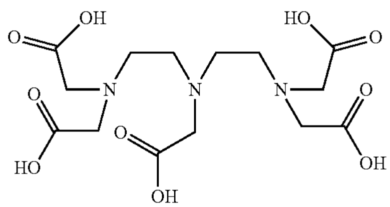 [SMILES: O=C(O)CN(CCN(CC(=O)O)CC(=O)O)CCN(CC(=O)O)CC(=O)O] DTPA, diethylenetriaminepentaacetic acid | In-111<br>Sc-44/47<br>Lu-177<br>Y-86/90<br>Sn-117m<br>Pd-109 |
| 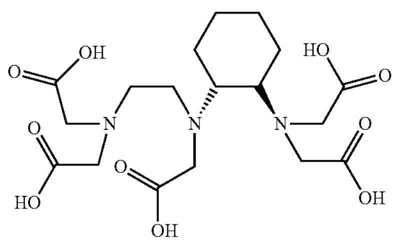 CHX-A00-DTPA, 2-(p-isothiocyanatobenzyl)cyclohexyl-diethylenetriaminepentaacetic acid | In-111<br>Lu-177<br>Y-86/90<br>Bi-212/213 |
| 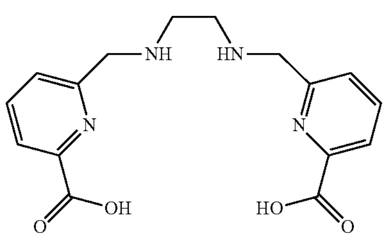 [SMILES: O=C(O)c1cccc(CNCCNCc2cccc(C(=O)O)n2)n1] H$_2$dedpa, 1,2-[[6-(carboxy)-pyridin-2-yl]-methylamino]ethane | Cu-64/67 |
| 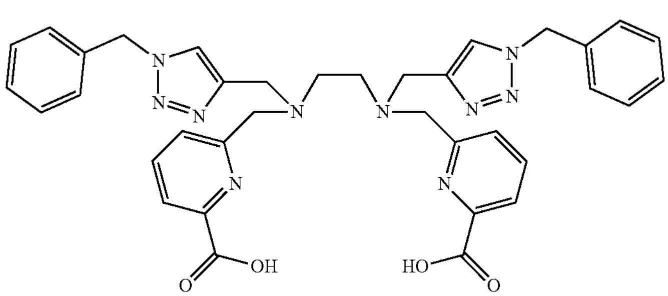 [SMILES: O=C(O)c1cccc(CN(CCN(Cc2cn(Cc3ccccc3)nn2)Cc2cccc(C(=O)O)n2)Cc2cn(Cc3ccccc3)nn2)n1] H$_2$azapa, N,N'-[1-benzyl-1,2,3-triazole-4-yl]methyl-N,N'-[6-(carboxy)pyridin-2-yl]-1,2-diaminoethane | Cu-64/67 |

TABLE B-continued
| Exemplary radiometal chelators and exemplary radiometals | |
|---|---|
| Chelator | Radiometal |
| 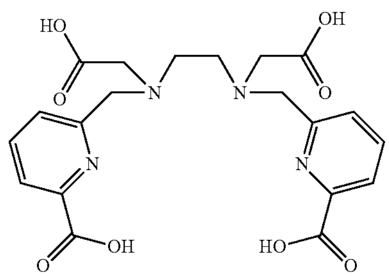 [SMILES: O=C(O)CN(CCN(CC(=O)O)Cc1cccc(C(=O)O)n1)Cc1cccc(C(=O)O)n1]<br>$H_4$octapa | In-111<br>Lu-177<br>Y-86/90<br>Ac-225 |
| 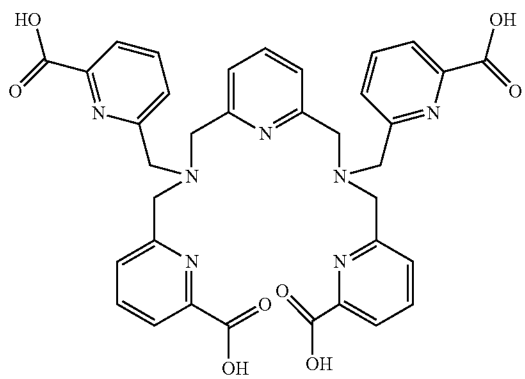 [SMILES: O=C(O)c1cccc(CN(Cc2cccc(CN(Cc3cccc(C(=O)O)n3)Cc3cccc(C(=O)O)n3)n2)Cc2cccc(C(=O)O)n2)n1]<br>$H_4$py4pa | Ac-225 |
| 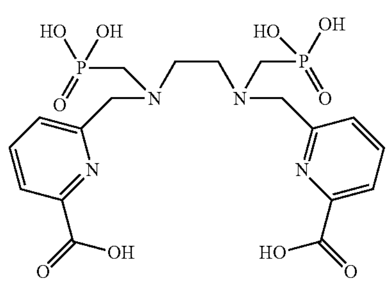 [SMILES: O=C(O)c1cccc(CN(CCN(Cc2cccc(C(=O)O)n2)CP(=O)(O)O)CP(=O)(O)O)n1]<br>$H_6$phospa | Ac-225 |
| 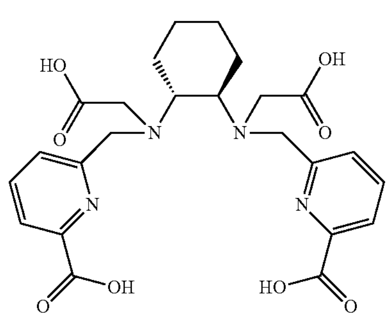 [SMILES: O=C(O)CN(Cc1cccc(C(=O)O)n1)[C@@H]1CCCC[C@H]1N(CC(=O)O)Cc1cccc(C(=O)O)n1]<br>$H_4$CHXoctapa | In-111<br>Ac-225 |

TABLE B-continued
| Exemplary radiometal chelators and exemplary radiometals | |
|---|---|
| Chelator | Radiometal |
| 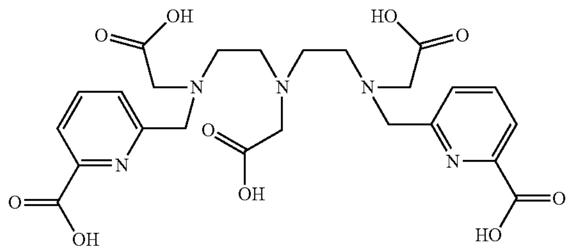 [SMILES: O=C(O)CN(CCN(CC(=O)O)Cc1cccc(C(=O)O)n1)CCN(CC(=O)O)Cc1cccc(C(=O)O)n1]<br>$H_5$decapa | In-111<br>Lu-177<br>Ac-225 |
| 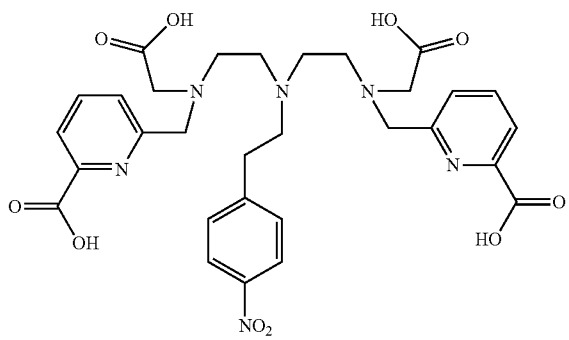 [SMILES: O=C(O)CN(CCN(CCc1ccc([N+](=O)[O-])cc1)CCN(CC(=O)O)Cc1cccc(C(=O)O)n1)Cc1cccc(C(=O)O)n1]<br>$H_4$neunpa-p-Bn-$NO_2$ | In-111<br>Lu-177<br>Ac-225 |
| 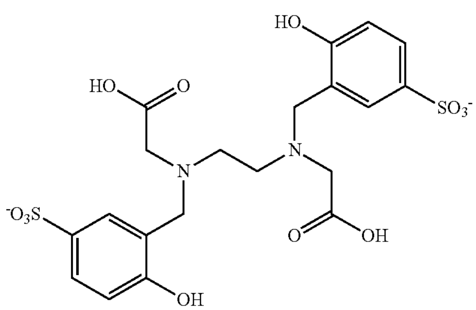<br>SHBED, N,N'-bis(2-hydroxy-5-sulfobenzyl)-ethylenediamine-N,N'-diacetic acid | In-111<br>Ga-68 |
| 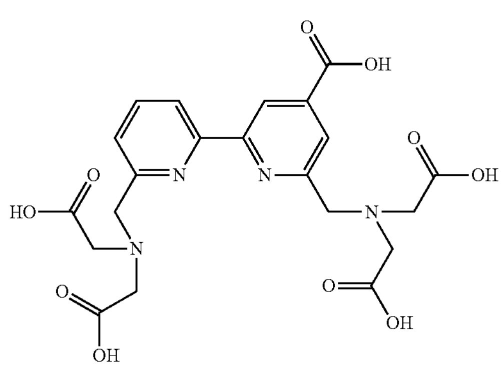 [SMILES: O=C(O)CN(CC(=O)O)Cc1cccc(-c2cc(C(=O)O)cc(CN(CC(=O)O)CC(=O)O)n2)n1]<br>BPCA | In-111 |

TABLE B-continued
| Exemplary radiometal chelators and exemplary radiometals | |
|---|---|
| Chelator | Radiometal |
| 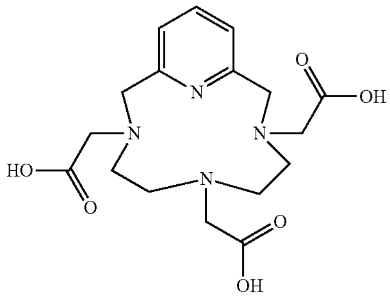 [SMILES: O=C(O)CN1CCN(CC(=O)O)Cc2cccc(n2)CN(CC(=O)O)CC1] PCTA, 3,6,9,15-tetraazabicyclo[9.3.1]-pentadeca-1(15),11,13-triene-3,6,9,-triacetic acid | Cu-64/67 |
| 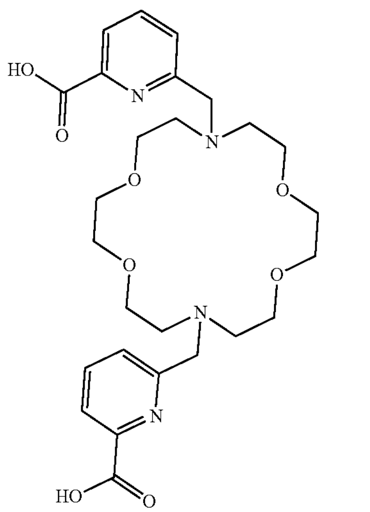 [SMILES: O=C(O)c1cccc(CN2CCOCCOCCN(Cc3cccc(C(=O)O)n3)CCOCCOCC2)n1] H2-MACROPA (N,N'-bis[(6-carboxy-2-pyridil)methyl]-4,13-diaza-18-crown-6) | Ac-225 |
| 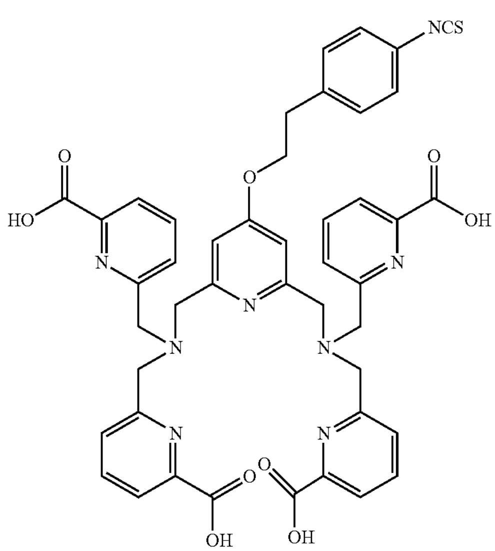 H4py4pa-phenyl-NCS | Ac-225 |

TABLE B-continued
| Exemplary radiometal chelators and exemplary radiometals | |
|---|---|
| Chelator | Radiometal |
| 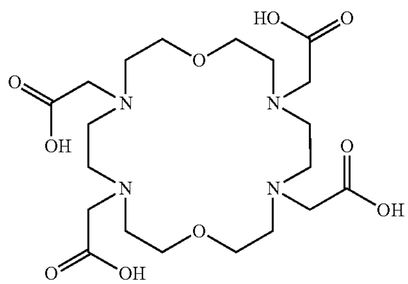 [SMILES: O=C(O)CN1CCOCCN(CC(=O)O)CCN(CC(=O)O)CCOCCN(CC(=O)O)CC1]<br>CROWN | Ac-225<br>Tb-155<br>Tb-161<br>Th-227 |
| 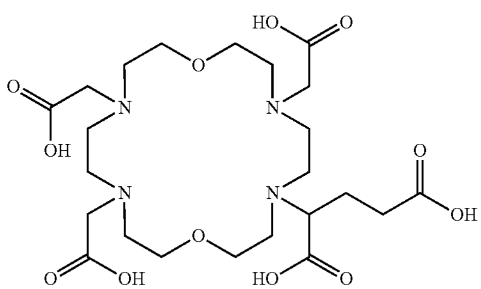 [SMILES: O=C(O)CCC(C(=O)O)N1CCOCCN(CC(=O)O)CCN(CC(=O)O)CCOCCN(CC(=O)O)CC1]<br>CROWNGA | Ac-225<br>Tb-155<br>Tb-161<br>Th-227 |
| 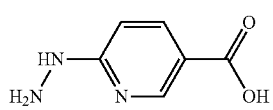<br>HYNIC | Tc-99m<br>Tc-94m |
| 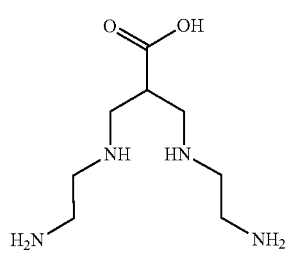 [SMILES: NCCNCC(CNCCN)C(=O)O]<br>N4 (6-carboxy-1,4,7,11-tetraazaundecane) | Tc-99m<br>Tc-94m |
| 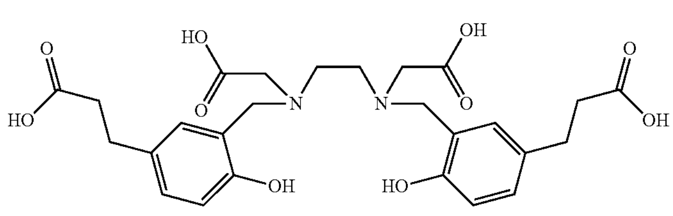 [SMILES: O=C(O)CCc1ccc(O)c(CN(CCN(CC(=O)O)Cc2cc(CCC(=O)O)ccc2O)CC(=O)O)c1]<br>HBED-CC | Ga-68 |

TABLE B-continued
| Exemplary radiometal chelators and exemplary radiometals | |
|---|---|
| Chelator | Radiometal |
| 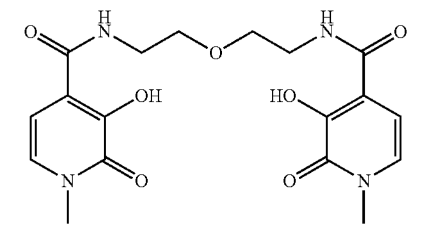 [SMILES: Cn1ccc(C(=O)NCCOCCNC(=O)c2ccn(C)c(=O)c2O)c(O)c1=O] Me-3,2-HOPO (3-hydroxy-N-methyl-2-pyridinone) | Th-227 |
| 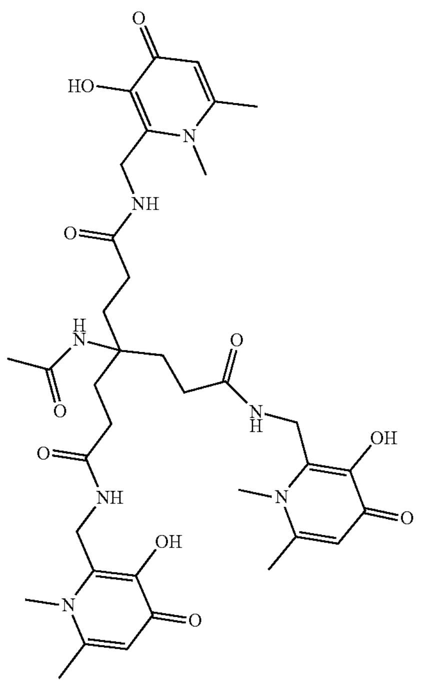 [SMILES: CC(=O)NC(CCC(=O)NCc1c(O)c(=O)cc(C)n1C)(CCC(=O)NCc1c(O)c(=O)cc(C)n1C)CCC(=O)NCc1c(O)c(=O)cc(C)n1C] CP256 | Ga-68 |
| 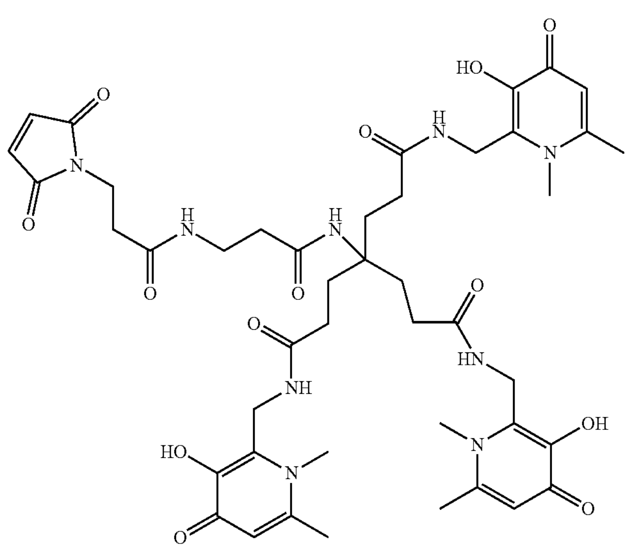 [SMILES: Cc1cc(=O)c(O)c(CNC(=O)CCC(CCC(=O)NCc2c(O)c(=O)cc(C)n2C)(CCC(=O)NCc2c(O)c(=O)cc(C)n2C)NC(=O)CCNC(=O)CCN2C(=O)C=CC2=O)n1C] YM103 | Ga-68 |

TABLE B-continued

| Exemplary radiometal chelators and exemplary radiometals | |
|---|---|
| Chelator | Radiometal |
| 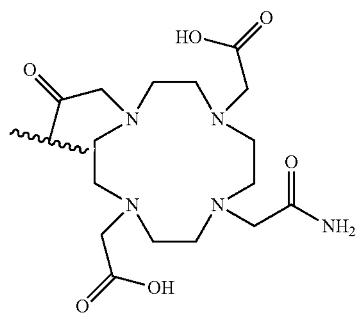 [SMILES: *C(=O)CN1CCN(CC(=O)O)CCN(CC(N)=O)CCN(CC(=O)O)CC1]<br>Pb Specific Chelator (PSC) | Pb-203<br>Pb-212 |

In some embodiments of the peptidic compound, each radiometal chelator is independently selected from Table B, wherein each chelator is optionally bound by a radiometal. In some embodiments, each radiometal chelator is bound by one of the corresponding radiometal shown in Table B. In some embodiments, the radiometal chelator is bound by a radiometal, a radionuclide-bound metal, or a radionuclide-bound metal-containing prosthetic group.

In some embodiments of the peptidic compound, at least one $R^{rad}$ is DOTA, or a derivative thereof, linked via an amide (e.g., formed from one of the carboxyl groups shown in Table B. In some embodiments, at least one $R^{rad}$ is CB-DO2A, or a derivative thereof, linked via an amide (e.g., formed from one of the carboxyl groups shown in Table B). In some embodiments, at least one $R^{rad}$ is TCMC, or a derivative thereof, linked via an amide (e.g., formed from one of the —$CONH_2$ groups shown in Table B). In some embodiments, the chelator at least one $R^{rad}$ is 3p-C-DEPA, or a derivative thereof, linked via an amide (e.g., formed from one of the carboxyl groups shown in Table B). In some embodiments, at least one $R^{rad}$ is p-$NH_2$—Bn-Oxo-DO3A or a derivative thereof, linked via an amide (e.g., formed from one of the carboxyl groups shown in Table B). In some embodiments, at least one $R^{rad}$ is TETA, or a derivative thereof, linked via an amide (e.g., formed from one of the carboxyl groups shown in Table B). In some embodiments, at least one $R^{rad}$ is CB-TE2A, or a derivative thereof, linked via an amide (e.g., formed from one of the carboxyl groups shown in Table B). In some embodiments, at least one $R^{rad}$ is Diamsar, or a derivative thereof, linked via an amide (e.g., formed from one of the amino groups shown in Table B). In some embodiments, at least one $R^{rad}$ is NOTA, or a derivative thereof, linked via an amide (e.g., formed from one of the carboxyl groups shown in Table B). In some embodiments, at least one $R^{rad}$ is NETA, or a derivative thereof, linked via an amide (e.g., formed from one of the carboxyl groups shown in Table B). In some embodiments, at least one $R^{rad}$ is HxTSE, or a derivative thereof, linked via an amide (e.g., formed from one of the amino groups shown in Table B). In some embodiments, at least one $R^{rad}$ is $P_2N_2Ph_2$, or a derivative thereof, linked via an amide (e.g., formed from one of the amino groups shown in Table B). In some embodiments, at least one $R^{rad}$ is DTPA, or a derivative thereof, linked via an amide (e.g., formed from one of the carboxyl groups shown in Table B). In some embodiments, at least one $R^{rad}$ is CHX-A00-DTPA, or a derivative thereof, linked via an amide (e.g., formed from one of the carboxyl groups shown in Table B). In some embodiments, at least one $R^{rad}$ is $H_2$dedpa, or a derivative thereof, linked via an amide (e.g., formed from one of the carboxyl groups shown in Table B). In some embodiments, at least one $R^{rad}$ is $H_2$azapa, or a derivative thereof, linked via an amide (e.g., formed from one of the carboxyl groups shown in Table B). In some embodiments, at least one $R^{rad}$ is $H_4$octapa, or a derivative thereof, linked via an amide (e.g., formed from one of the carboxyl groups shown in Table B). In some embodiments, at least one $R^{rad}$ is $H_6$phospa, or a derivative thereof, linked via an amide (e.g., formed from one of the carboxyl groups shown in Table B). In some embodiments, at least one $R^{rad}$ is $H_4$CHXoctapa, or a derivative thereof, linked via an amide (e.g., formed from one of the carboxyl groups shown in Table B). In some embodiments, at least one $R^{rad}$ is $H_5$decapa, or a derivative thereof, linked via an amide (e.g., formed from one of the carboxyl groups shown in Table B). In some embodiments, at least one $R^{rad}$ is $H_4$neunpa-p-Bn-NO2, or a derivative thereof, linked via an amide (e.g., formed from one of the carboxyl groups shown in Table B). In some embodiments, at least one $R^{rad}$ is SHBED, or a derivative thereof, linked via an amide (e.g., formed from one of the carboxyl groups shown in Table B). In some embodiments, at least one $R^{rad}$ is BPCA, or a derivative thereof, linked via an amide (e.g., formed from one of the carboxyl groups shown in Table B). In some embodiments, at least one $R^{rad}$ is PCTA, or a derivative thereof, linked via an amide (e.g., formed from one of the carboxyl groups shown in Table B). In some embodiments, at least one $R^{rad}$ is H2-MACROPA, or a derivative thereof, linked via an amide (e.g., formed from one of the carboxyl groups shown in Table B). In some embodiments, at least one $R^{rad}$ is CROWN, or a derivative thereof, linked via an amide (e.g., formed from one of the carboxyl groups shown in Table B). In some embodiments, at least one $R^{rad}$ is CROWNGA, or a derivative thereof, linked via an amide (e.g., formed from one of the carboxyl groups shown in Table B). In some embodiments, at least one $R^{rad}$ is HYNIC, or a derivative thereof, linked via an amide (e.g., formed from the carboxyl group shown in Table B). In some embodiments, at least one $R^{rad}$ is N4, or a derivative thereof, linked via an amide (e.g., formed from the carboxyl group shown in Table B). In some embodiments, at least one $R^{rad}$ is HBED-CC, or a derivative thereof, linked via an amide (e.g., formed from one of the carboxyl groups shown in Table B).

In some embodiments of the peptidic compound, the radiometal chelator (or one of the radiometal chelators) is a derivative of a radiometal chelator shown in Table B. A derivative may include, e.g., (1) modification of a functional group of the chelator (e.g., a carboxyl group, an amino group, etc.) or (2) attachment of a new functional group (e.g., attachment of an R-group to an ethylene carbon located between two nitrogen atoms, wherein the R-group is a functional group fused to a spacer). In some embodiments, a carboxyl functional group shown in Table B is replaced with azidopropyl ethylacetamide (e.g., azido-mono-amide-DOTA), butynylacetamide (e.g., butyne-DOTA), thioethylacetamide (e.g., DO3A-thiol), maleimidoethylacetamide (e.g., maleimido-mono-amide-DOTA), or N-hydroxysuccinimide ester (e.g., DOTA-NHS-ester). When linked, these derivative chelators can be linked either via an amide (formed from a remaining carboxyl group) or via —C(O)—NH—$(CH_2)_{2-3}$-(triazole) or —C(O)—NH—$(CH_2)_{2-3}$-(thiomaleimide). In other embodiments, a backbone carbon (e.g., in an ethylene positioned between two backbone nitrogen atoms) in the chelator ring is fused to an R-group containing a functional group, optionally wherein the R-group is —$(CH_2)_{1-3}$-(phenyl)-N═C═S or —$(CH_2)_{1-3}$-(phenyl)-N═C═O, optionally 1,4-isothiocyanatobenzyl; e.g., p-SCN-Bn-DOTA (S-2-(4-isothiocyanatobenzyl)-1,4,7,10-tetraazacyclododecane tetraacetic acid), p-SCN-Bn-NOTA (2-S-(4-isothiocyanatobenzyl)-1,4,7-triazacyclononane-1,4,7-triacetic acid), and the like. When linked, these derivatives can form a urea linkage (formed from isocyanate) or a thiourea linkage (formed from isothiocyanate).

In some embodiments of the peptidic compound, the radiometal chelator is 1,4,7,10-tetraazacyclotetradecane-1,4,7,10-tetraacetic acid (DOTA), 2-(4,7,10-tris(carboxymethyl)-1,4,7,10-tetraazacyclododecan-1-yl)pentanedioic acid (DOTAGA), 1,4,7-triazacyclononane-triacetic acid (NOTA), 1,4,7-triazacyclononane-1-glutaric acid-4,7-diacetic acid (NODAGA), 1,4,7-Triazacyclononane-1-succinic acid-4,7-diacetic acid (NODASA), 1,8-N,N'-bis-(carboxymethyl)-1,4,8,11-tetraazacyclotetradecane (TE2A), 3,6,9,15-tetraazabicyclo[9.3.1]pentadeca-1(15),11,13-triene-3,6,9-triacetic acid (PCTA), 1-substituted 1,4,7-tricarboxymethyl-1,4,7,10-teraazacyclododecane triacetic acid (DO3A), DEDPA (6,6'-[1,2-ethanediylbis(iminomethylene)] bis(2-pyridinecarboxylic acid) and 1,4,8,11-tetraazacyclotetradecane-1,4,8,11-tetraacetic acid (TETA), ethylenediaminetetraacetic acid (EDTA), diethylenetriamine pentaacetic acid (DTPA), CB-DO2A, 3p-C-DEPA, TCMC, DO3A, DTPA, CHX-A"-DTPA, 1B4M-DTPA, TETA, NOPO, Me-3,2-HOPO, CB-TE1A1P, CB-TE2P, MM-TE2A, DM-TE2A, sarcophagine, SarAr, SarAr-NCS, diamSar, AmBaSar, BaBaSar, TRAP, AAZTA, DATA, H2-macropa, H2dedpa, H4octapa, H4py4pa, H4Pypa, H2azapa, H5decapa, H4CHXoctapa, H4neunpa-p-Bn-NO2, CP256, PCTA, {4-[2-(bis-carboxymethylamino)-ethyl]-7-carboxymethyl-[1,4,7]triazonan-1-yl}-acetic acid (NETA), C-NETA, C-NE3TA, HBED, HBED-CC, BCPA, CP256, YM103, desferrioxamine (DFO), H6phospa, a trithiol chelate, mercaptoacetyl, hydrazinonicotinamide, dimercaptosuccinic acid, 1,2-ethylenediylbis-L-cysteine diethyl ester, methylenediphosphonate, N, N'-bis(2-hydroxy-5-sulfobenzyl)-ethylenediamine-N,N-diacetic acid (SHBED), hexamethylpropyleneamineoxime, hexakis(methoxy isobutyl isonitrile), 2,2',2",2'-(1,10-dioxa-4,7,13,16-tetraazacyclooctadecane-4,7,13,16-tetrayl) tetraacetic acid (CROWN), 2-(7,13,16-tris(carboxymethyl)-1,10-dioxa-4,7,13,16-tetraazacyclooctadecan-4-yl)pentanedioic acid (CROWNGA), H4py4pa-phenyl-NCS, PSC, bis-aminoethanethiol (BAT), TE3A, TE2A, CB-TE2A, triazacyclononane (TACN), 1,4,7-Trimethyl-1,4,7-triazacyclononane (TM-TACN), BPCA, HEHA, PEPA, H6phospha, noneunpa, or DOTAM.

In some embodiments of the peptidic compound, the radiometal chelator is TETA (1,4,8,11-tetraazacyclotetradecane-1,4,8,11-tetraacetic acid), SarAr (1-N-(4-Aminobenzyl)-3,6,10,13,16,19-hexaazabicyclo[6.6.6]-eicosane-1,8-diamine), NOTA (1,4,7-triazacyclononane-1,4,7-triacetic acid), TRAP (1,4,7-triazacyclononane-1,4,7-tris[methyl(2-carboxyethyl)phosphinic acid), HBED (N,N'-bis(2-hydroxybenzyl)-ethylenediamine-N,N'-diacetic acid), 2,3-HOPO (3-hydroxypyridin-2-one), PCTA (3,6,9,15-tetraazabicyclo[9.3.1]-pentadeca-1 (15),11,13-triene-3,6,9-triacetic acid), DFO (desferrioxamine), DTPA (diethylenetriaminepentaacetic acid), OCTAPA (N,N'-bis(6-carboxy-2-pyridylmethyl)-ethylenediamine-N,N'-diacetic acid) or another picolinic acid derivative.

In some embodiments of the peptidic compound, the radiometal chelator is DOTA, PSC (1,4,7,10-tetraazacyclododecane-1,4,7,10-tetriacetic acid), TCMC, or CROWN. In some embodiments, the radiometal chelator is DOTA, DOTAGA, PSC, TCMC, CROWN or CROWNGA. In some embodiments, the radiometal chelator is DOTA or CROWN. In some embodiments, the radiometal chelator is DOTA, DOTAGA, CROWN, or CROWNGA.

In some embodiments of the peptidic compound, a $R^{rad}$ is a radiometal chelator for radiolabelling with $^{99m}$Tc, $^{94m}$Tc, $^{186}$Re, or $^{188}$Re, such as mercaptoacetyl, hydrazinonicotinamide, dimercaptosuccinic acid, 1,2-ethylenediylbis-L-cysteine diethyl ester, methylenediphosphonate, hexamethylpropyleneamineoxime and hexakis(methoxy isobutyl isonitrile), and the like. In some embodiments, a $R^{rad}$ is mercaptoacetyl, hydrazinonicotinamide, dimercaptosuccinic acid, 1,2-ethylenediylbis-L-cysteine diethyl ester, methylenediphosphonate, hexamethylpropyleneamineoxime or hexakis(methoxy isobutyl isonitrile). In some of these embodiments, the chelator is bound by a radiometal selected from $^{99m}$Tc, $^{94m}$Tc, $^{186}$Re, or $^{188}$Re.

In some embodiments of the peptidic compound, $R^{rad}$ is a chelator that can bind $^{18}$F-aluminum fluoride ([$^{18}$F]AlF), such as 1,4,7-triazacyclononane-1,4-diacetate (NODA) and the like. In some embodiments, the chelator is NODA. In some embodiments, the chelator is bound by [$^{18}$F]AlF.

In some embodiments of the peptidic compound, $R^{rad}$ is a chelator that can bind $^{72}$As or $^{77}$As, such as a trithiol chelate and the like. In some embodiments, the chelator is a trithiol chelate. In some embodiments, the chelator is conjugated to $^{72}$As. In some embodiments, the chelator is conjugated to $^{77}$As.

In some embodiments, the radiometal chelator is DOTA or a derivative thereof conjugated with $^{44}$Sc, $^{47}$Sc, $^{64}$Cu, $^{67}$Cu, $^{68}$Ga, $^{86}$Y, $^{90}$Y, $^{111}$In, $^{117m}$Sn, $^{149}$Tb, $^{152}$Tb, $^{153}$Sm, $^{155}$Tb, $^{161}$Tb, $^{165}$Er, $^{177}$Lu, $^{203}$Pb, $^{212}$Pb, $^{212}$Bi, $^{213}$Bi, $^{224}$Ra, $^{225}$Ac, $^{227}$Th, or $^{223}$Ra. In some embodiments, the radiometal chelator is DOTA or a derivative thereof conjugated with $^{68}$Ga or $^{177}$Lu. In some embodiments, the radiometal chelator is DOTAGA or a derivative thereof conjugated with $^{44}$Sc, $^{47}$Sc, $^{64}$Cu, $^{67}$Cu, $^{68}$Ga, $^{86}$Y, $^{90}$Y, $^{111}$In, $^{117m}$Sn, $^{149}$Tb, $^{152}$Tb, $^{153}$Sm, $^{155}$Tb, $^{161}$Tb, $^{165}$Er, $^{177}$Lu, $^{203}$Pb, $^{212}$Pb, $^{212}$Bi, $^{213}$Bi, $^{224}$Ra, $^{225}$Ac, $^{227}$Th, or $^{223}$Ra. In some embodiments, the radiometal chelator is DOTAGA or a derivative thereof conjugated with $^{68}$Ga or $^{177}$Lu.

In some embodiments, the radiometal chelator is CROWN conjugated with $^{225}$Ac, $^{177}$Lu or $^{68}$Ga. In some embodiments, the radiometal chelator is CROWNGA conjugated with $^{225}Ac$, $^{177}Lu$ or $^{68}Ga$.

In some embodiments, the radiometal chelator is TCMC conjugated with $^{203}Pb$ or $^{212}Pb$. In some embodiments, the radiometal chelator is PSC conjugated with $^{203}Pb$ or $^{212}Pb$.

In some embodiments, the radiometal chelator is H2-MACROPA conjugated with $^{225}Ac$. In some embodiments, the radiometal chelator is Me-3,2-HOPO conjugated with $^{227}Th$. In some embodiments, the radiometal chelator is $H_4$py4pa conjugated with $^{225}Ac$, $^{227}Th$ or $^{177}Lu$. In some embodiments, the radiometal chelator is $H_4$pypa conjugated with $^{177}Lu$. In some embodiments, the radiometal chelator is NODAGA conjugated with $^{68}Ga$. In some embodiments, the radiometal chelator is DTPA conjugated with $^{111}In$. In some embodiments, the radiometal chelator is or DFO conjugated with $^{89}Zr$.

In some embodiments, an $R^{rad}$ is a chelator that can bind $^{18}F$-aluminum fluoride ([$^{18}F$]AlF), such as 1,4,7-triazacyclononane-1,4-diacetate (NODA) and the like. In some embodiments, the chelator is NODA. In some embodiments, the chelator is bound by [$^{18}F$]AlF.

In some embodiments, an $R^{rad}$ is a chelator that can bind $^{72}As$ or $^{77}As$, such as a trithiol chelate and the like. In some embodiments, the chelator is a trithiol chelate. In some embodiments, the chelator is conjugated to $^{72}As$. In some embodiments, the chelator is conjugated to $^{77}As$.

In some embodiments, $R^{rad}{}_{n6}$-[linker]-$R^L$— is DOTA-Pip-, DOTAGA-Pip-, CROWN-Pip-, or CROWNGA-Pip-.

In some embodiments of the peptidic compound, at least one $R^{rad}$ is a prosthetic group containing a trifluoroborate ($BF_3$), capable of $^{18}F/^{19}F$ exchange radiolabeling. In some embodiments, $R^{rad}$ is $BF_3$—$R^5$—$R^4$—, wherein $R^4$ is —$(CH_2)_{1-5}$— and wherein $BF_3$—$R^5$-forms:

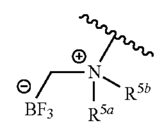

wherein $R^{5a}$ and $R^{5b}$ are each independently a $C_1$-$C_5$ linear or branched alkyl group. In some embodiments, $R^4$ is —$CH_2$—. In some embodiments, $R^{5a}$ is methyl. In some embodiments, $R^{5a}$ is ethyl. In some embodiments, $R^{5a}$ is propyl. In some embodiments, $R^{5a}$ is isopropyl. In some embodiments, $R^{5a}$ is butyl. In some embodiments, $R^{5a}$ is n-butyl. In some embodiments, $R^{5a}$ is pentyl. In some embodiments, $R^{5b}$ is methyl. In some embodiments, $R^{5b}$ is ethyl. In some embodiments, $R^{5b}$ is propyl. In some embodiments, $R^{5b}$ is isopropyl. In some embodiments, $R^{5b}$ is butyl. In some embodiments, $R^{5b}$ is n-butyl. In some embodiments, $R^{5b}$ is pentyl. In some embodiments, $R^{5a}$ and $R^{5b}$ are both methyl. In some embodiments, $BF_3$—$R^5$— is

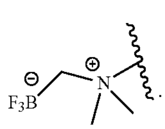

In some embodiments, at least one $R^{rad}$ is

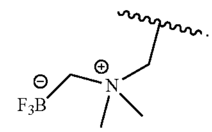

In some embodiments, one fluorine in $BF_3$ is $^{18}F$. In some embodiments, one, two, or three fluorines in $BF_3$ are $^{18}F$. In some embodiments, all three fluorines in $BF_3$ are $^{18}F$. In some embodiments, all three fluorines in $BF_3$ are $^{19}F$.

In some embodiments of the peptidic compound, at least one $R^{rad}$ has the structure listed in Table C or Table D. in Tables C and D, each R in —OR, —SR, —NR—, —NHR or —$NR_2$ is independently a $C_1$-$C_5$ linear or branched alkyl. In some embodiments, one fluorine in $BF_3$ is $^{18}F$. In some embodiments, one, two, or three fluorines in $BF_3$ are $^{18}F$. In some embodiments, all three fluorines in $BF_3$ are $^{18}F$. In some embodiments, all three fluorines in $BF_3$ are $^{19}F$.

TABLE C

| Exemplary $BF_3$—$R^5$— groups. |
| --- |
| 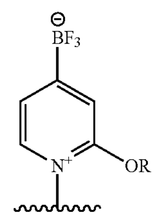 |
| 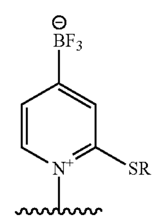 |
| 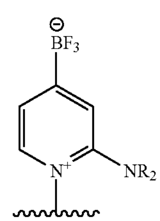 |
| 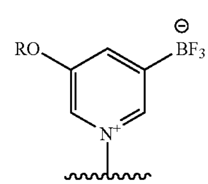 |
| 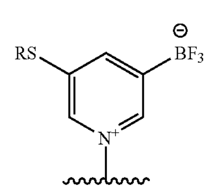 |

TABLE C-continued
Exemplary $BF_3$—$R^5$— groups.
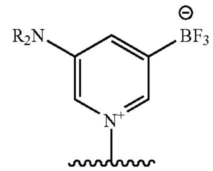
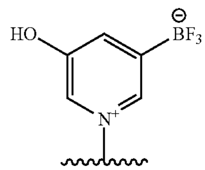
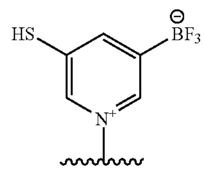
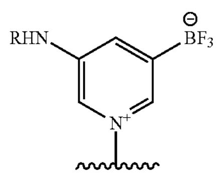
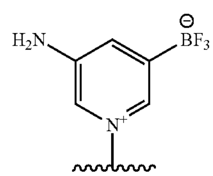
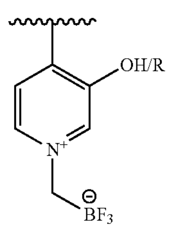
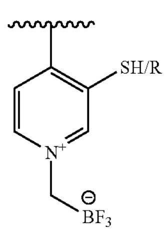
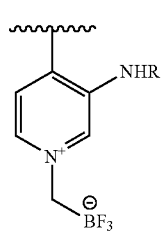
TABLE C-continued
Exemplary $BF_3$—$R^5$— groups.
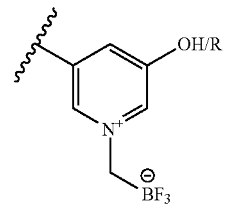
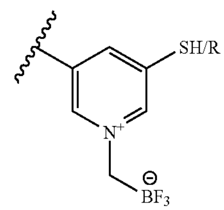
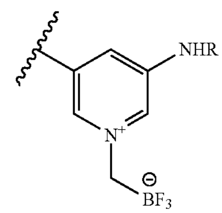
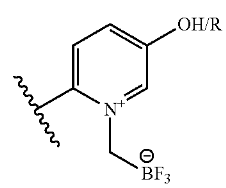
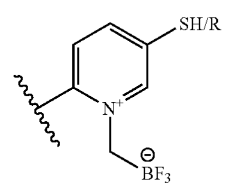
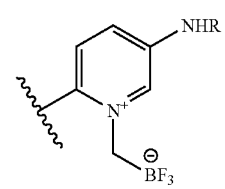
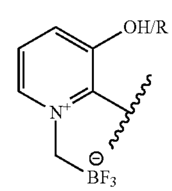
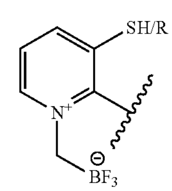

TABLE C-continued
Exemplary $BF_3$—$R^5$— groups.
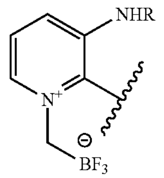
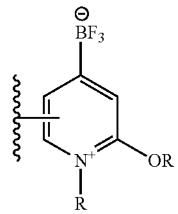
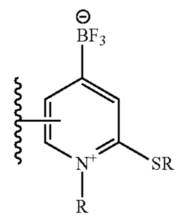
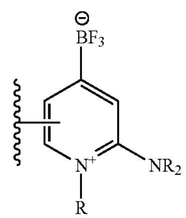
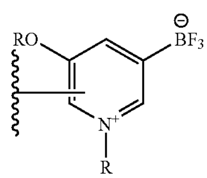
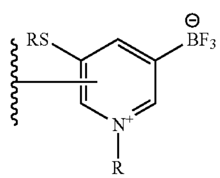
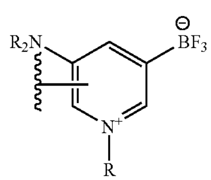
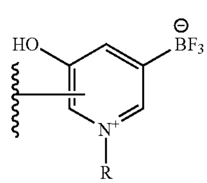
TABLE C-continued
Exemplary $BF_3$—$R^5$— groups.
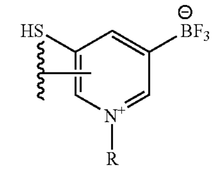
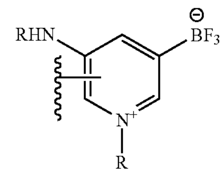
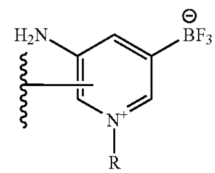
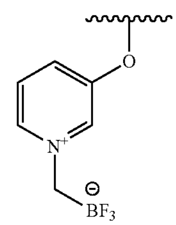
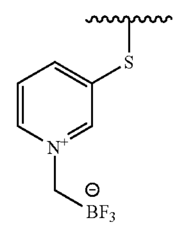
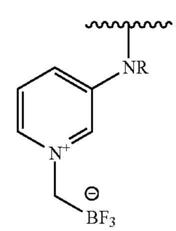
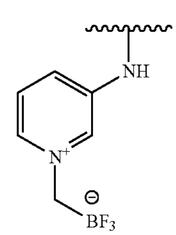

TABLE C-continued
| Exemplary $BF_3$—$R^5$— groups. |
|---|
| 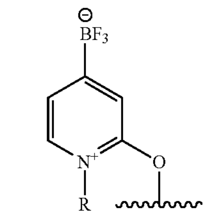 |
| 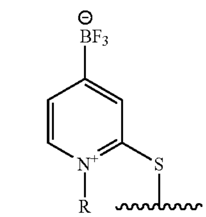 |
| 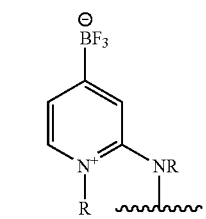 |
| 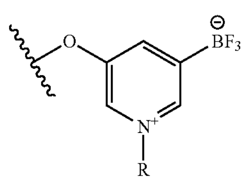 |
| 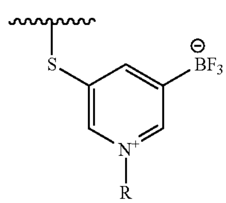 |
| 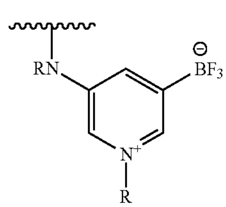 |
| 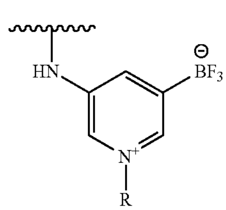 |
| 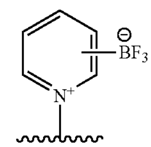 |
TABLE D
| Exemplary $BF_3$—$R^5$— groups. |
|---|
| 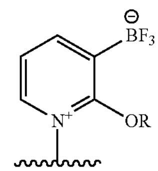 |
| 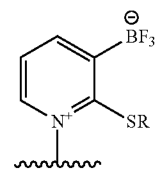 |
| 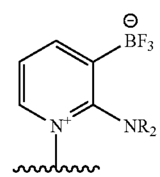 |
| 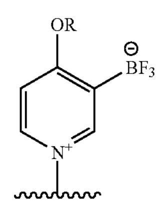 |
| 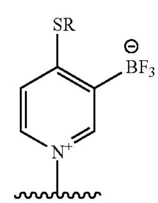 |
| 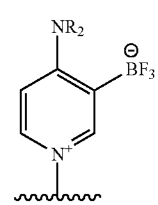 |

TABLE D-continued
| Exemplary $BF_3$—$R^5$— groups. |
|---|
| 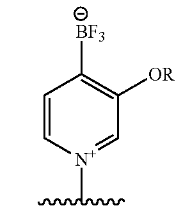 |
| 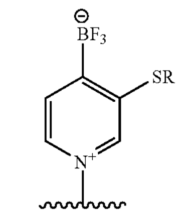 |
| 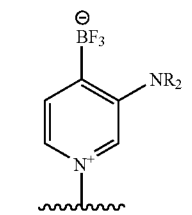 |
| 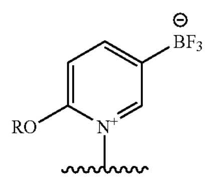 |
| 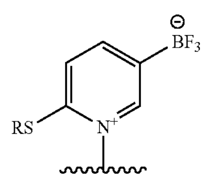 |
| 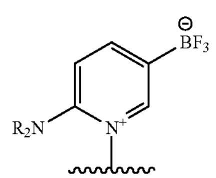 |
| 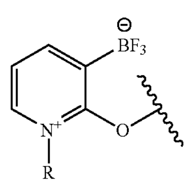 |
| 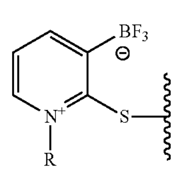 |
TABLE D-continued
| Exemplary $BF_3$—$R^5$— groups. |
|---|
| 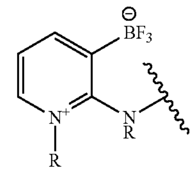 |
| 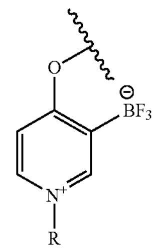 |
| 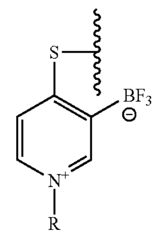 |
| 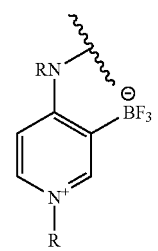 |
| 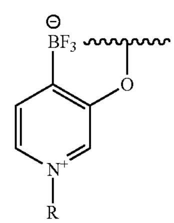 |
| 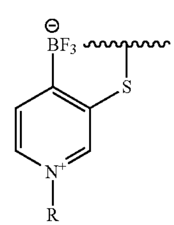 |
| 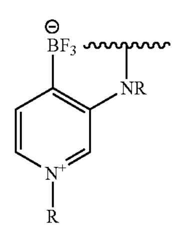 |

TABLE D-continued
| Exemplary $BF_3$—$R^5$— groups. |
| --- |
| 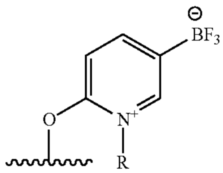 |
| 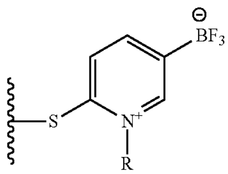 |
| 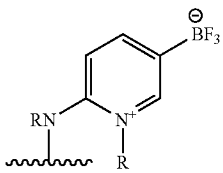 |
| 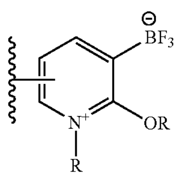 |
| 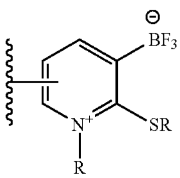 |
| 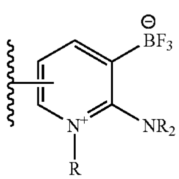 |
| 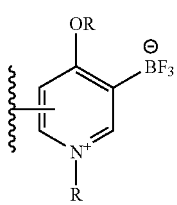 |
| 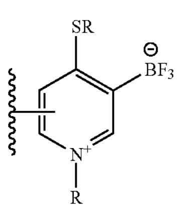 |
TABLE D-continued
| Exemplary $BF_3$—$R^5$— groups. |
| --- |
| 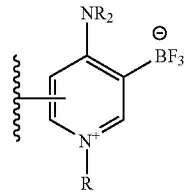 |
| 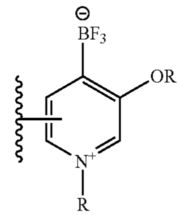 |
| 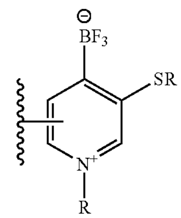 |
| 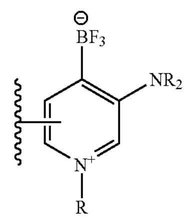 |
| 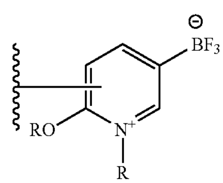 |
| 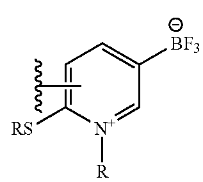 |
| 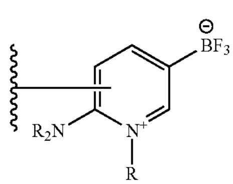 |

TABLE D-continued
Exemplary $BF_3$—$R^5$— groups.
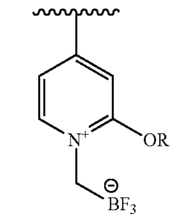
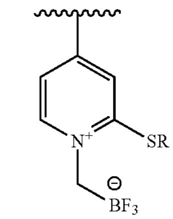
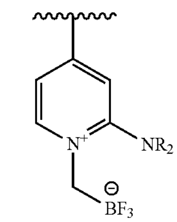
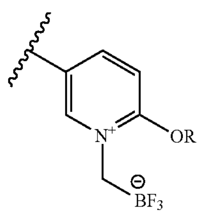
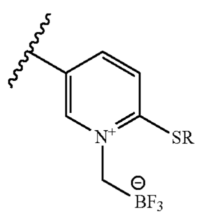
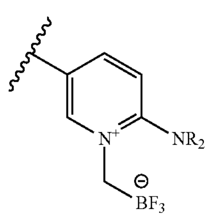
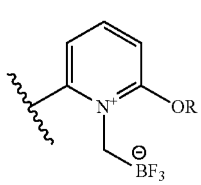
TABLE D-continued
Exemplary $BF_3$—$R^5$— groups.
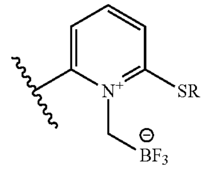
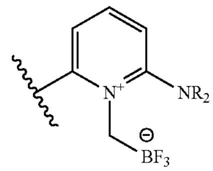
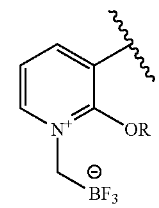
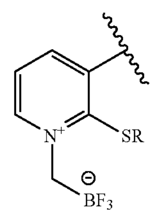
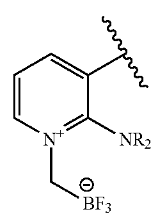
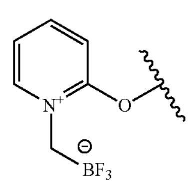

TABLE D-continued

| Exemplary $BF_3$—$R^5$— groups. |
| --- |
| 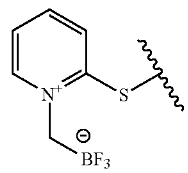 |
| 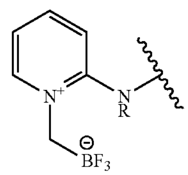 |
| 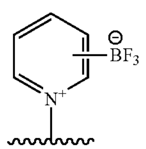 |

In some embodiments, a $BF_3$—$R^5$— may independently selected from Table C, in which each R (when present) in the pyridine substituted —OR, —SR, —NR—, —NHR or —$NR_2$ is independently a linear or branched $C_1$-$C_5$ alkyl. In some embodiments, R is methyl. In some embodiments, R is ethyl. In some embodiments, R is propyl. In some embodiments, R is isopropyl. In some embodiments, R is n-butyl. The trifluoroborate-containing prosthetic group(s) may comprise $^{18}F$. In some embodiments, one fluorine is a $BF_3$—$R^5$— is $^{18}F$. In some embodiments, all three fluorines in a $BF_3$—$R^5$— are $^{18}F$. In some embodiments, all three fluorines in a $BF_3$—$R^5$— are $^{19}F$.

In some embodiments, a $BF_3$—$R^5$— may independently form selected from Table D, in which each R (when present) in the pyridine substituted —OR, —SR, —NR—, —NHR or —$NR_2$ is independently a linear or branched $C_1$-$C_5$ alkyl. In some embodiments, R is methyl. In some embodiments, R is ethyl. In some embodiments, R is propyl. In some embodiments, R is isopropyl. In some embodiments, R is n-butyl. In some embodiments, a $BF_3$—$R^5$— is

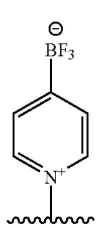

.

In some embodiments, all three fluorines in a $BF_3$—$R^5$— are $^{18}F$. In some embodiments, one fluorine in a $BF_3$—$R^5$— is $^{18}F$. In some embodiments, all three fluorines in a $BF_3$—$R^5$— are $^{19}F$.

In some embodiments, at least one $R^{rad}$ is an aryl or heteroaryl substituted with at least one radiohalogen. In some embodiments, at least one $R^{rad}$ is an aryl or an N-heteroaryl substituted with at least one radiohalogen. In some embodiments, at least one $R^{rad}$ is an aryl or a 6-membered heteroaryl substituted with at least one radiohalogen. In some embodiments, at least one $R^{rad}$ is a phenyl, a pyridyl, or a quinoyl substituted with at least one radiohalogen. In some embodiments, at least one $R^{rad}$ is a pyridyl or a quinoyl substituted with at least one radiohalogen. In some embodiments, at least one $R^{rad}$ is a pyridyl or a quinoyl substituted with at least one $^{18}F$. In some embodiments, at least one $R^{rad}$ is a pyridyl or a quinoyl substituted with a $^{18}F$. In some embodiments, at least one $R^{rad}$ is a pyridyl substituted with a $^{18}F$. In some embodiments, at least one $R^{rad}$ is

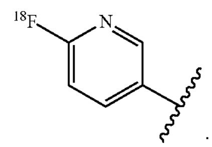

.

In some embodiments, at least one $R^{rad}$ is an aryl or heteroaryl substituted with at least one fluorine precursor leaving group. In some embodiments, the fluorine precursor leaving group is an electron-withdrawing leaving group. In some embodiments, the fluorine precursor leaving group is a sulfonate leaving group, aryl iodonium group, diazonium group, —$NMe_3^+$, —$NO_2$, F, Cl, Br, I, —CN, or —$CF_3$. In some embodiments, the fluorine precursor leaving group is a -OTs (tosylate), -OMe (mesylate), -Ons (nosylate), —$NMe_3^+$, —$NO_2$, F, Cl, Br, I, —CN, or —$CF_3$. In some embodiments, at least one $R^{rad}$ is an aryl or heteroaryl substituted with at least one —$NMe_3^+$, —$NO_2$, F, Cl, Br, I, —CN, or —$CF_3$. In some embodiments, at least one $R^{rad}$ is an aryl or an N-heteroaryl substituted with at least one —$NMe_3^+$, —$NO_2$, F, Cl, Br, I, —CN, or —$CF_3$. In some embodiments, at least one $R^{rad}$ is an aryl or a 6-membered heteroaryl substituted with at least one —$NMe_3^+$, —$NO_2$, F, Cl, Br, I, —CN, or —$CF_3$. In some embodiments, at least one $R^{rad}$ is an aryl or a pyridyl substituted with at least one —$NMe_3^+$, —$NO_2$, F, Cl, Br, I, —CN, or —$CF_3$. In some embodiments, at least one $R^{rad}$ is an aryl or a pyridyl substituted with at least one —$NMe_3^+$. In some embodiments, at least one $R^{rad}$ is

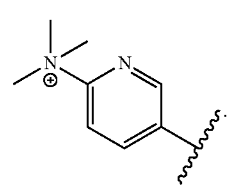 [SMILES: *c1ccc([N+](C)(C)C)nc1]

.

In some embodiments, -Xaa[1]-Xaa[2]-Xaa[3]-Xaa[4]-Xaa[5]-Xaa[6]-Xaa[7]-Xaa[8]-ψ-Xaa[9]-R is:

(SEQ ID NO: 3)
D-Phe-Gln-αMeTrp-Ala-Tle-Gly-His-LeuψPro-$NH_2$;

(SEQ ID NO: 4)
D-Phe-Gln-αMeTrp-Ala-Val-Gly-His-Sta-Leu-$NH_2$;

(SEQ ID NO: 5)
D-Phe-Gln-αMeTrp-Ala-Tle-Gly-His-Sta-Leu-$NH_2$;

(SEQ ID NO: 6)
D-Phe-Gln-Trp-Ala-Val-N-MeGly-Trp-LeuψPro-$NH_2$;

(SEQ ID NO: 7)
D-Phe-Gln-αMeTrp-Ala-Tle-Gly-Trp-LeuψPro-$NH_2$;

(SEQ ID NO: 8)
D-Phe-Gln-αMeTrp-Ala-Tle-Gly-Trp(5-F)-LeuψPro-$NH_2$;

(SEQ ID NO: 9)
D-Phe-Gln-αMeTrp-Ala-Tle-Gly-Trp-Sta-Leu-$NH_2$;

(SEQ ID NO: 10)
D-Phe-Gln-αMeTrp-Ala-Tle-Gly-Trp(5-F)-Sta-Leu-$NH_2$;

(SEQ ID NO: 11)
D-Phe-Cit-αMeTrp-Ala-Tle-Gly-His-LeuψPro-$NH_2$;

(SEQ ID NO: 12)
D-Phe-Glu-αMeTrp-Ala-Tle-Gly-His-LeuψPro-$NH_2$;

(SEQ ID NO: 13)
D-Phe-Agb-αMeTrp-Ala-Tle-Gly-His-LeuψPro-$NH_2$;

(SEQ ID NO: 14)
D-Phe-Gln-αMeTrp-N-MeGly-Tle-Gly-His-LeuψPro-$NH_2$;
or (SEQ ID NO: 15)
D-Phe-Gln-αMeTrp-N-MeGly-Tle-Gly-Trp-LeuψPro-$NH_2$,
wherein ψ is a reduced peptide bond.

In some embodiments, -Xaa[1]-Xaa[2]-Xaa[3]-Xaa[4]-Xaa[5]-Xaa[6]-Xaa[7]-Xaa[8]-ψ-Xaa[9]-Xaa[10]-R is (SEQ ID NO: 16)
D-Phe-Gln-Trp-Ala-Val-N-MeGly-His-LeuψPro-$NH_2$.

In some embodiments, -Xaa[1]-Xaa[2]-Xaa[3]-Xaa[4]-Xaa[5]-Xaa[6]-Xaa[7]-Xaa[8]-ψ-Xaa[9]-Xaa[10]-R is (SEQ ID NO: 17)
D-Phe-Gln-Trp-Ala-Val-N-MeGly-Trp-LeuψPro-Val-$NH_2$;

(SEQ ID NO: 18)
D-Phe-Gln-Trp-Ala-Val-N-MeGly-His-LeuψPro-Val-$NH_2$;

(SEQ ID NO: 19)
D-Phe-Gln-αMeTrp-Ala-Tle-Gly-Trp-LeuψPro-Tle-$NH_2$;
or (SEQ ID NO: 20)
D-Phe-Gln-αMeTrp-Ala-Tle-Gly-His-LeuψPro-Tle-$NH_2$,
wherein ψ is a reduced peptide bond.

In some embodiments, [Xaa[12]-Xaa[1]-Xaa[2]-Xaa[3]-Xaa[4]-Xaa[5]-Xaa[6]-Xaa[7]-Xaa[8]-ψ-Xaa[9]-R] is (SEQ ID NO: 21)
Pip-D-Phe-Gln-7FTrp-Ala-Tle-Gly-His-LeuψPro-$NH_2$.

In some embodiments, the compounds of formula (A), (I), (IA), (IA-1), (IB), (IB-1), (IC), (IC-1), (ID), (ID-1), (IE), or (IE-1), excludes compounds disclosed in WO2009/109332. PCT application publication WO2009/109332 is incorporated by reference in its entirety herein.

In some embodiments, the compounds of formula (A), (I), (IA), (IA-1), (IB), (IB-1), (IC), (IC-1), (ID), (ID-1), (IE), or (IE-1), excludes compounds disclosed in WO2021/068051. PCT application publication WO2021/068051 is incorporated by reference in its entirety herein.

In some embodiments, the compounds of formula (A), (I), (IA), (IA-1), (IB), (IB-1), (IC), (IC-1), (ID), (ID-1), (IE), or (IE-1), excludes compounds described in Wang, L et al., Molecules, 2022 27, 3777, which is incorporated by reference in its entirety herein.

In some embodiments, the compounds of formula (A), (I), (IA), (IA-1), (IB), (IB-1), (IC), (IC-1), (ID), (ID-1), (IE), or (IE-1), excludes compounds described in Wang, L et al., Molecules, 2022 27, 3777, which is incorporated by reference in its entirety herein.

In some embodiments, the compounds of formula (A), (I), (IA), (IA-1), (IB), (IB-1), (IC), (IC-1), (ID), (ID-1), (IE), or (IE-1), excludes LW01186.

In some embodiments, the compounds of formula (A), (I), (IA), (IA-1), (IB), (IB-1), (IC), (IC-1), (ID), (ID-1), (IE), or (IE-1), excludes AMTG having the structure (SEQ ID NO: 66)

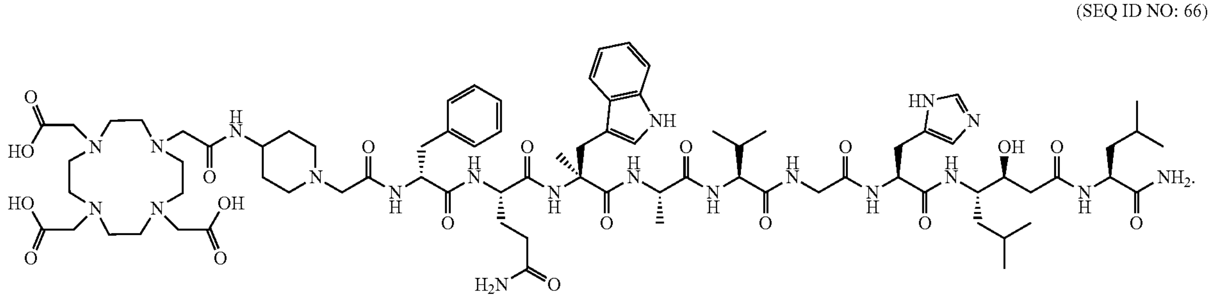 [SMILES: CC(C)C[C@H](NC(=O)C[C@H](O)[C@H](CC(C)C)NC(=O)[C@H](Cc1cnc[nH]1)NC(=O)CNC(=O)[C@@H](NC(=O)[C@H](C)NC(=O)[C@](C)(Cc1c[nH]c2ccccc12)NC(=O)[C@H](CCC(N)=O)NC(=O)[C@@H](Cc1ccccc1)NC(=O)CN1CCC(NC(=O)CN2CCN(CC(=O)O)CCN(CC(=O)O)CCN(CC(=O)O)CC2)CC1)C(C)C)C(N)=O]

In some embodiments, the compounds of formula (A), (I), (IA), (IA-1), (IB), (IB-1), (IC), (IC-1), (ID), (ID-1), (IE), or (IE-1), excludes AMTG2 having the structure
(SEQ ID NO: 67)
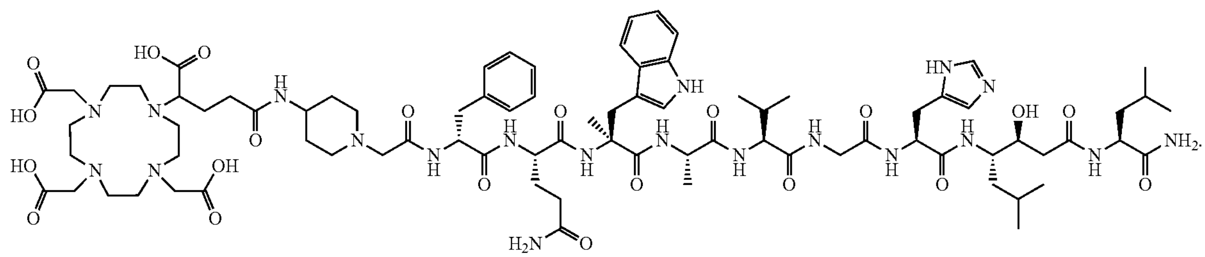
In some embodiments, the peptidic compound described herein is:
(Compound 1; SEQ ID NO: 22)
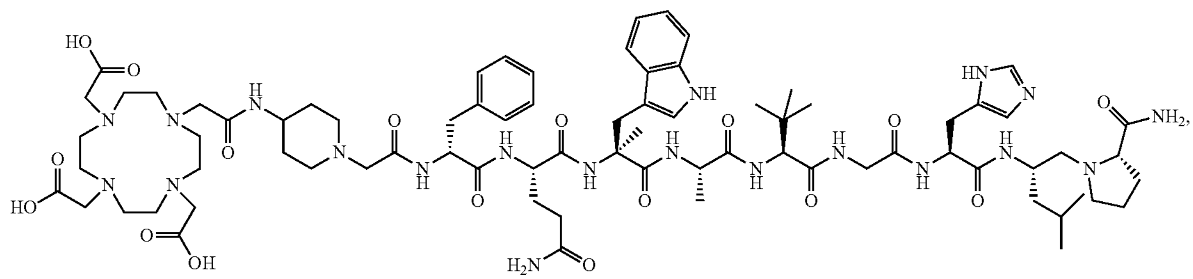
(Compound 2; SEQ ID NO: 23)
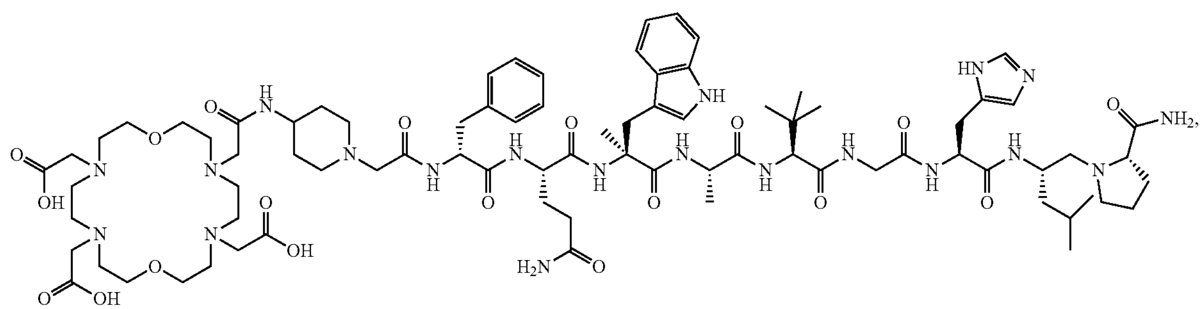
(Compound 3; SEQ ID NO: 24)
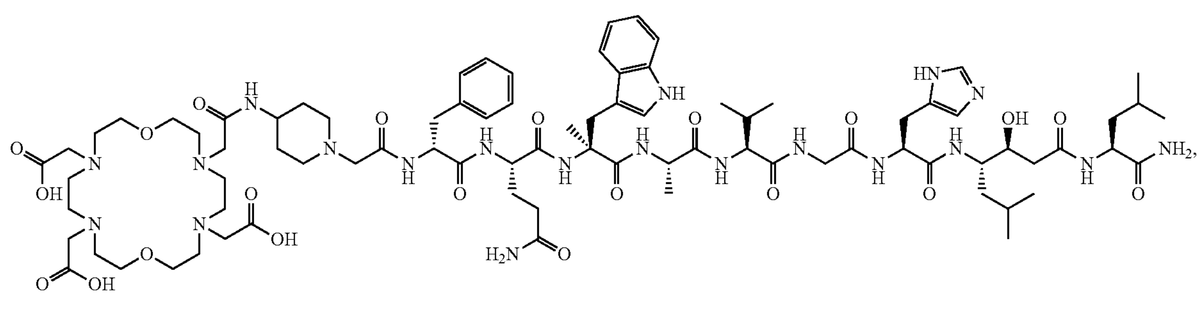

-continued
(Compound 4; SEQ ID NO: 25)
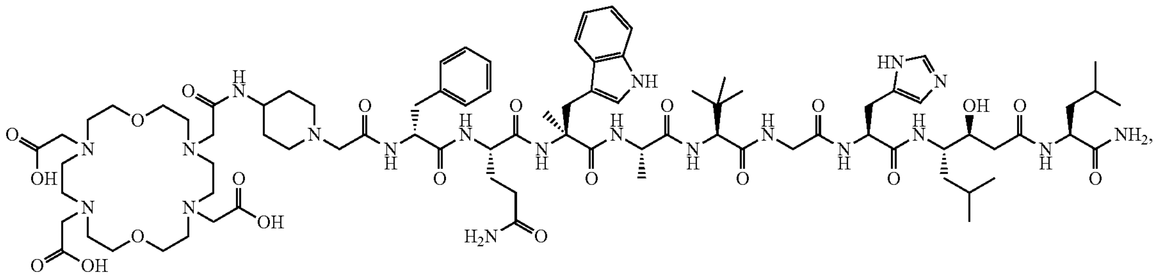
or
(Compound 5; SEQ ID NO: 52)
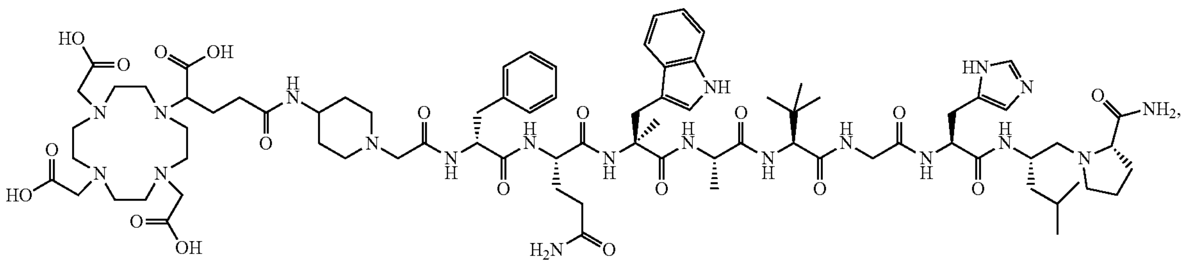
,
or a salt or a solvate thereof. In some embodiments, the compound is conjugated by a radiometal. In some embodiments, the radiometal is $^{68}$Ga, $^{177}$Lu, or $^{225}$Ac.
In some embodiments, the peptidic compound described herein is:
(Compound 6; SEQ ID NO: 26)
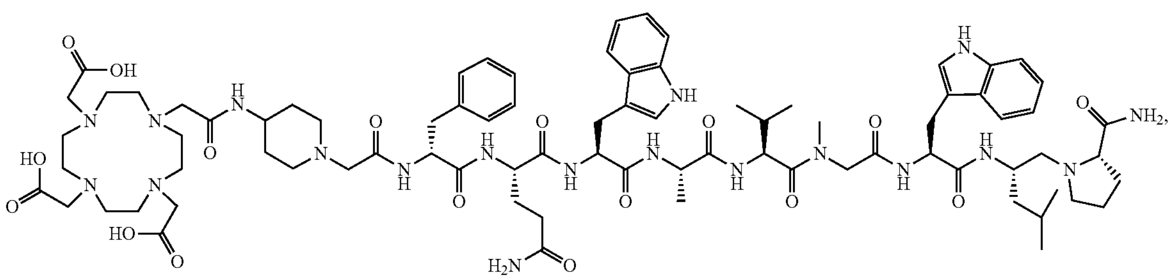
,
(Compound 7; SEQ ID NO: 47)
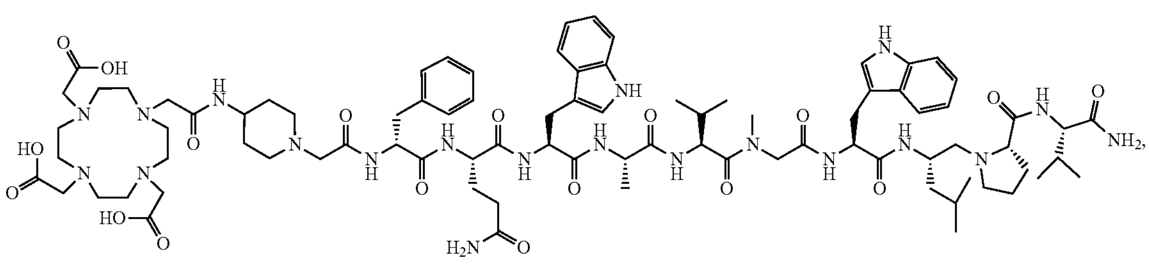
, -continued
(Compound 8; SEQ ID NO: 30)
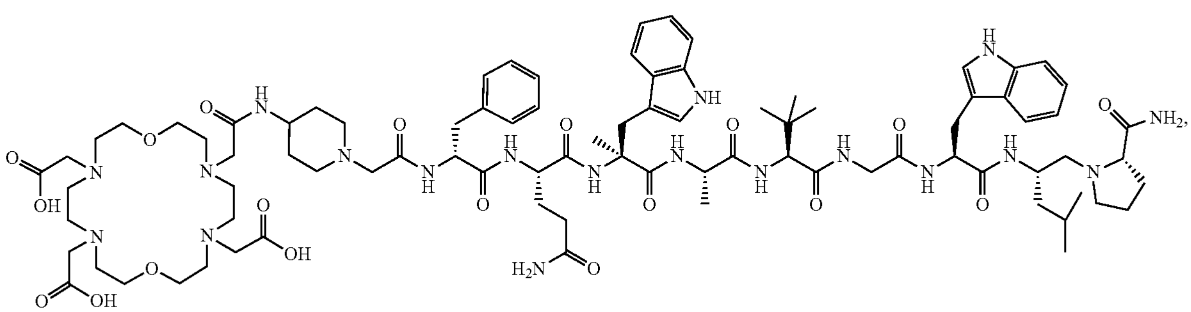
(Compound 9; SEQ ID NO: 28)
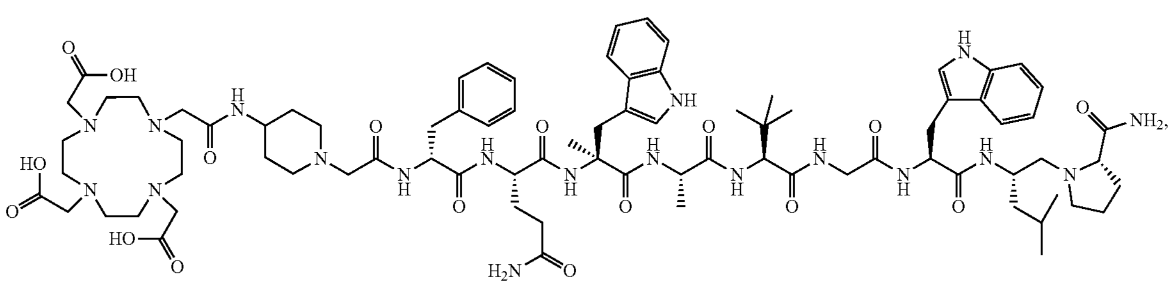
(Compound 10; SEQ ID NO: 32)
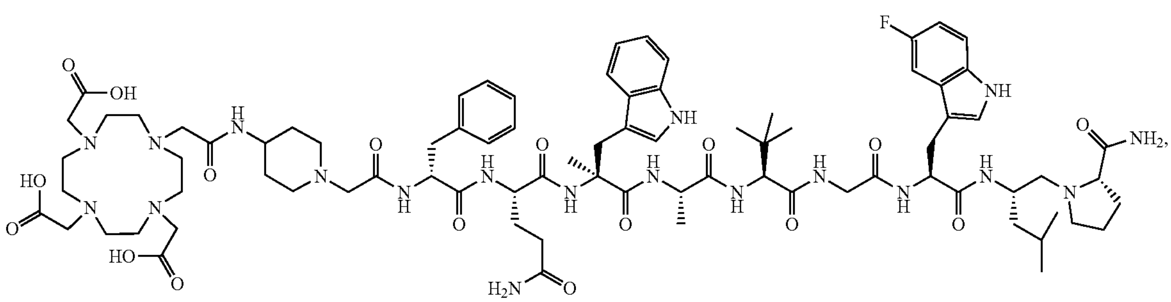
(Compound 11: SEQ ID NO: 49)
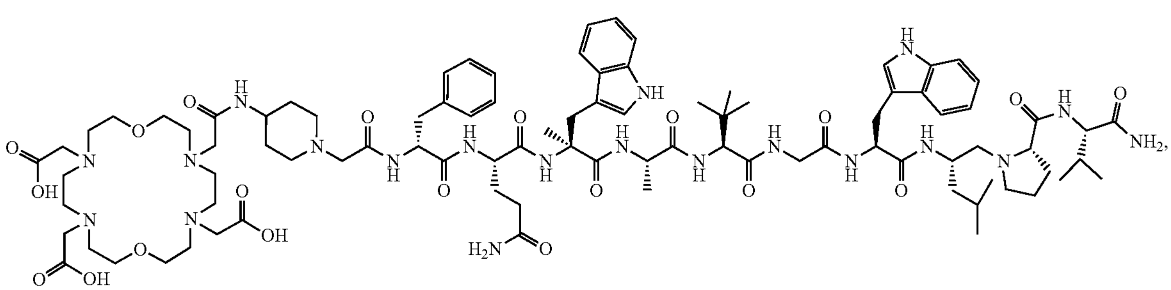
(Compound 12; SEQ ID NO: 34)
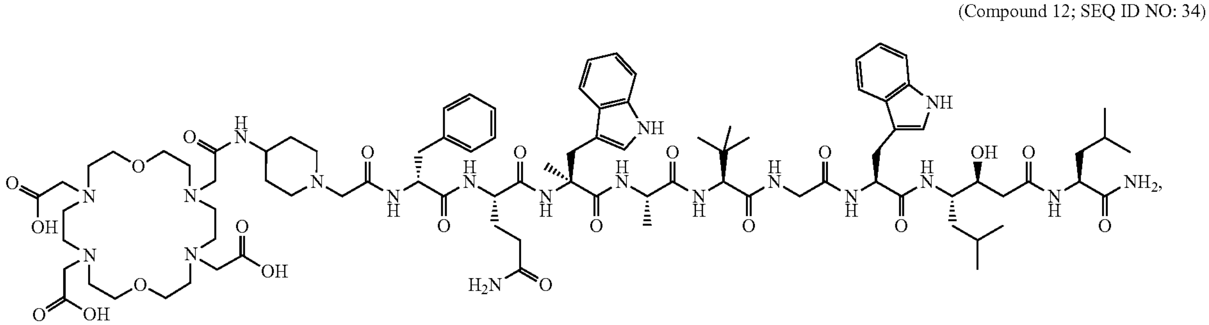

-continued
(Compound 13; SEQ ID NO: 35)
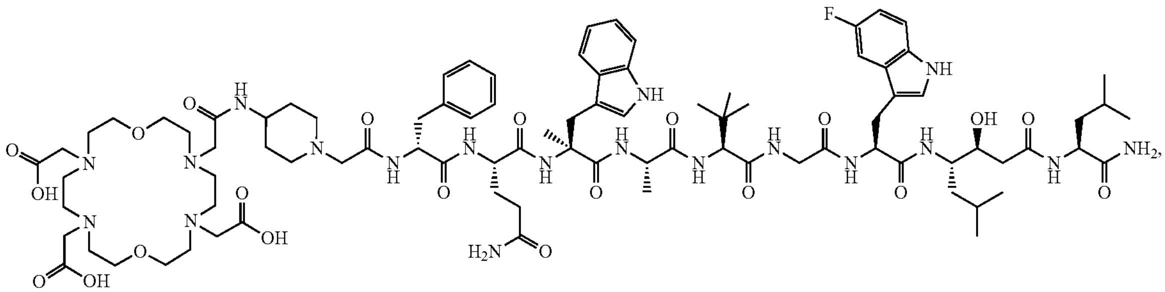
(Compound 14; SEQ ID NO: 58)
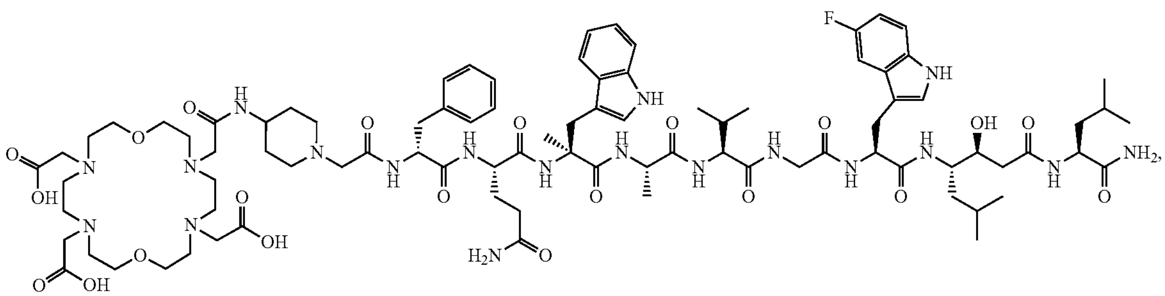
(Compound 15; SEQ ID NO: 51)
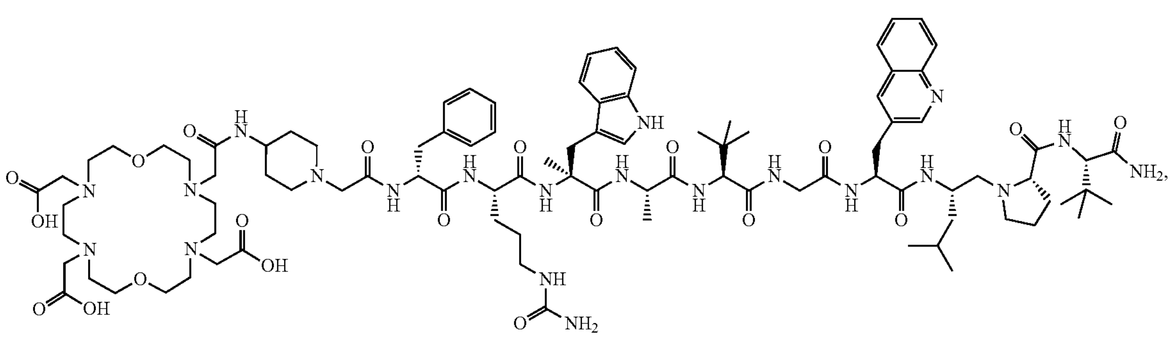
(Compound 16; SEQ ID NO: 41)
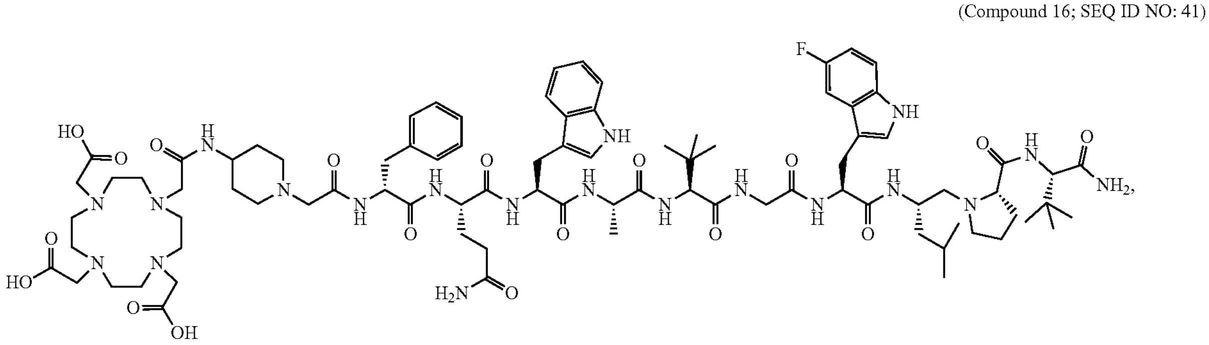

-continued
(Compound 17; SEQ ID NO: 42)
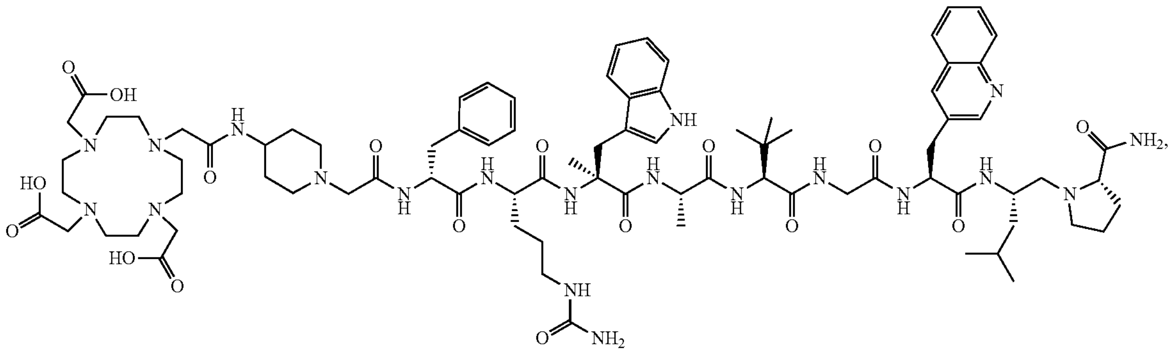
or
(Compound 18; SEQ ID NO: 44)
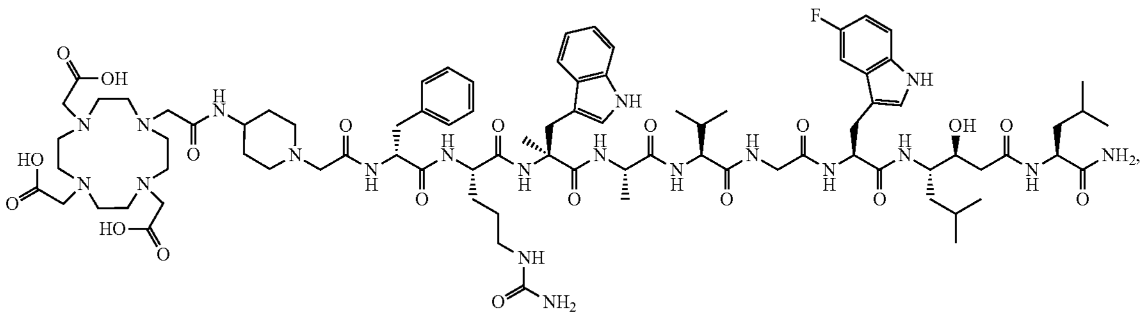
,
or a salt or a solvate thereof. In some embodiments, the compound is conjugated by a radiometal. In some embodiments, the radiometal is $^{68}Ga$, $^{177}Lu$, or $^{225}Ac$.
In some embodiments, the peptidic compound described herein is:
(Compound 19: SEQ ID NO: 36)
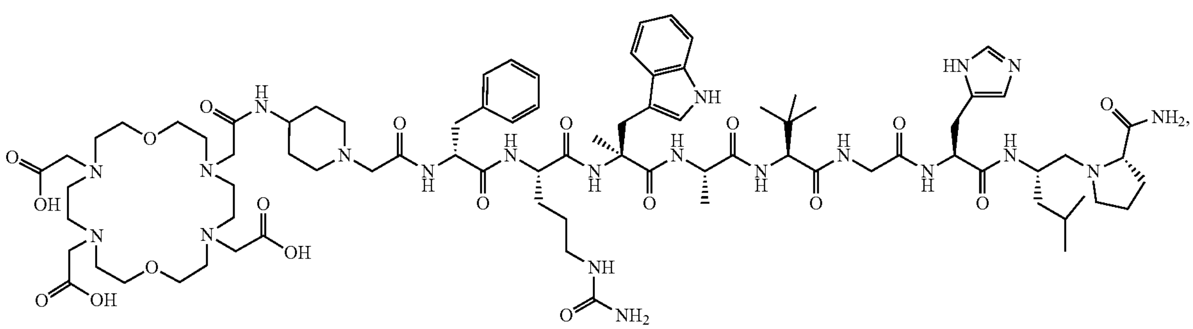
,
(Compound 20; SEQ ID NO: 37)
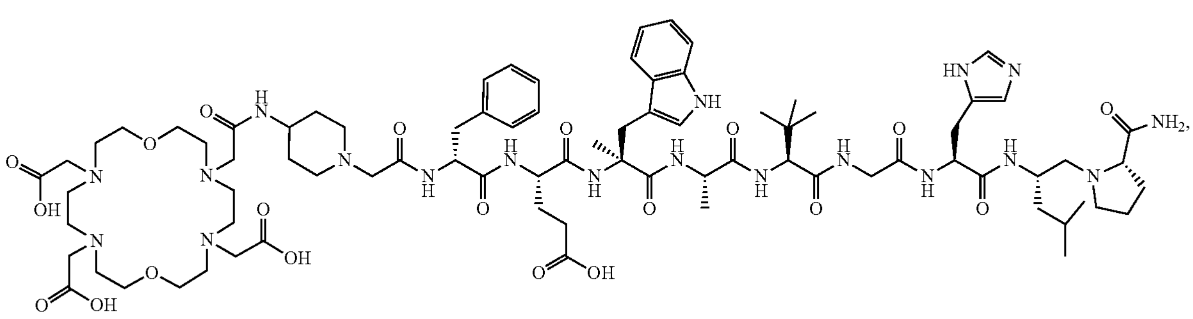
, -continued
(Compound 21: SEQ ID NO: 38)
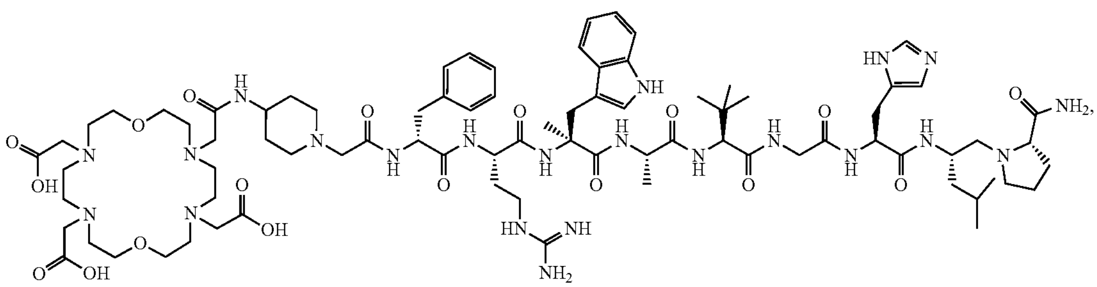
or
(Compound 22: SEQ ID NO: 43)
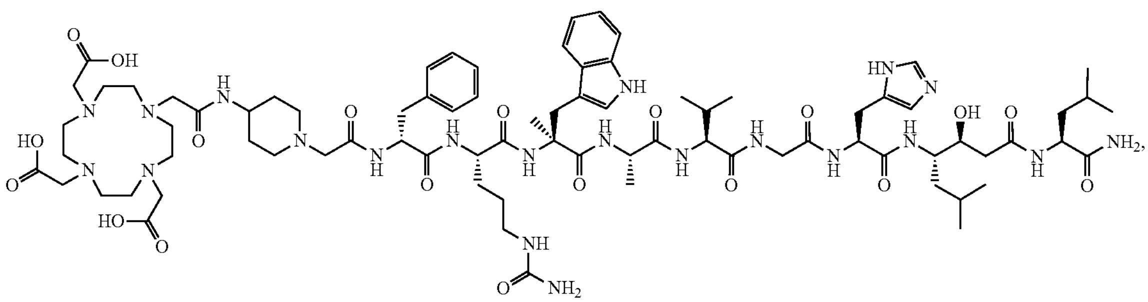
or a salt or a solvate thereof. In some embodiments, the compound is conjugated by a radiometal. In some embodiments, the radiometal is $^{68}$Ga, $^{177}$Lu, or $^{225}$Ac.
In some embodiments, the peptidic compound described herein is:
(Compound 7; SEQ ID NO: 47)
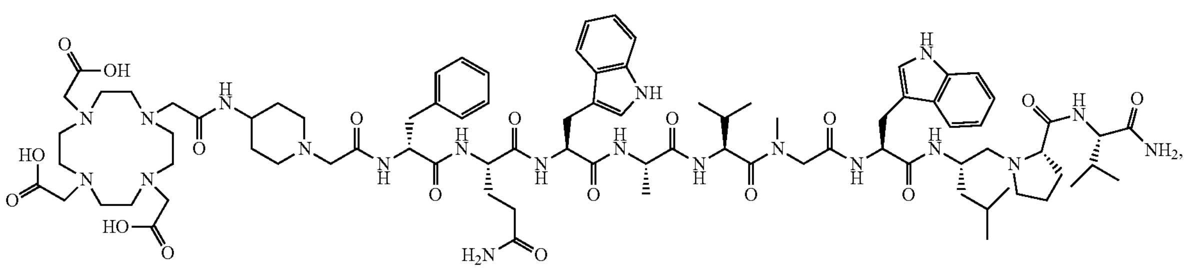
(Compound 23; SEQ ID NO: 48)
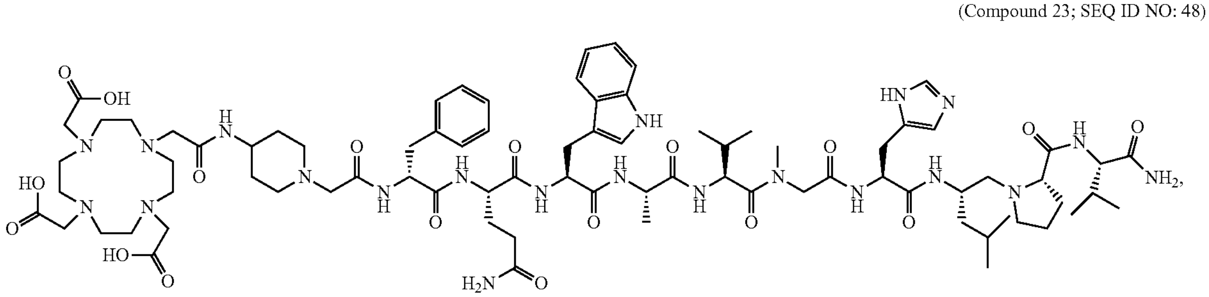

-continued
(Compound 11; SEQ ID NO: 49)
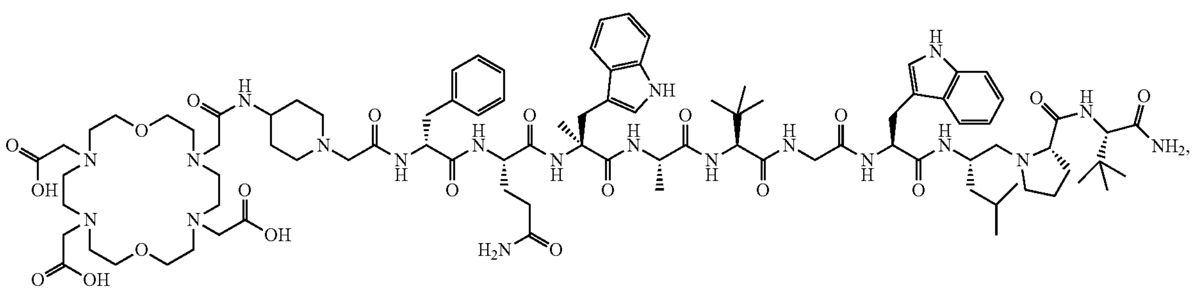
(Compound 24; SEQ ID NO: 50)
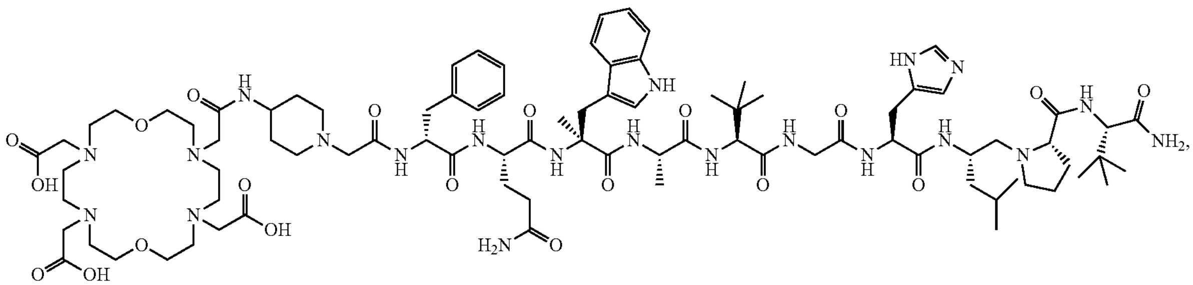
(Compound 15; SEQ ID NO: 51)
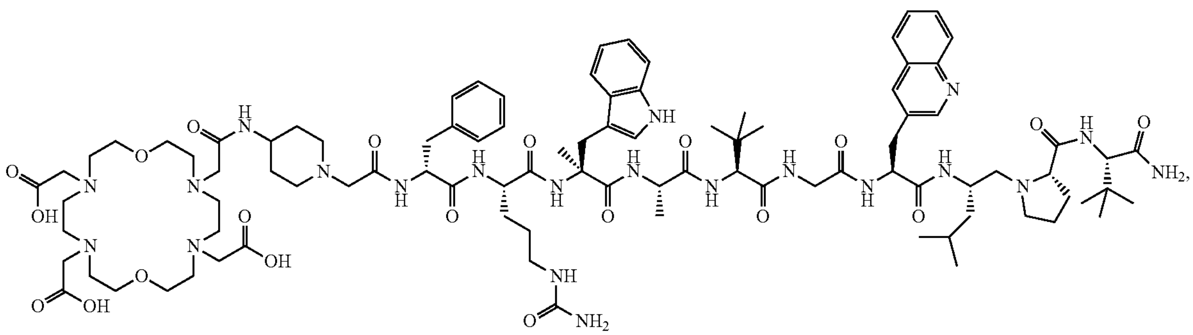
(Compound 16; SEQ ID NO: 41)
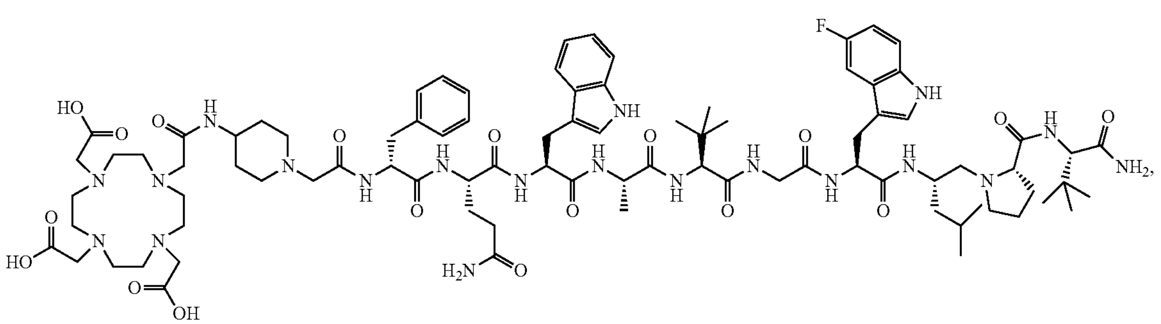
or
(Compound 25; SEQ ID NO: 53)
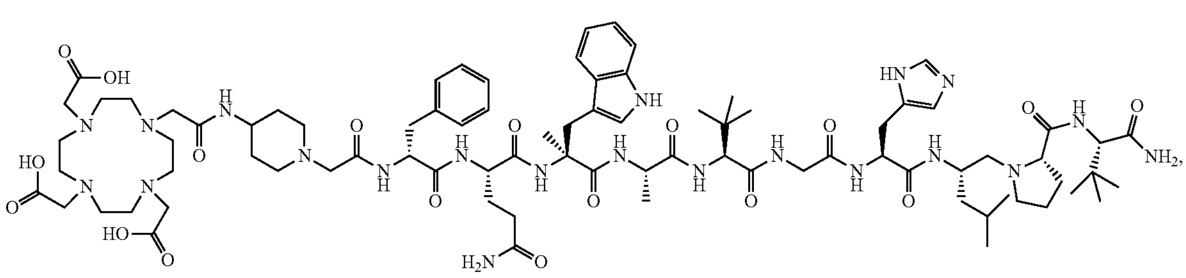

or a salt or a solvate thereof. In some embodiments, the compound is conjugated by a radiometal. In some embodiments, the radiometal is $^{68}$Ga, $^{177}$Lu, or $^{225}$Ac.

In some embodiments, the peptidic compound described herein is:

(Compound 26; SEQ ID NO: 39)

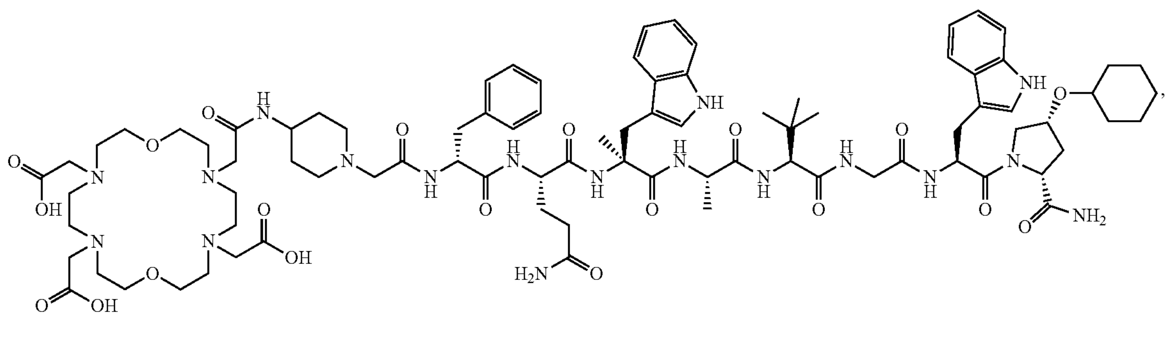

, or (Compound 27; SEQ ID NO: 40)

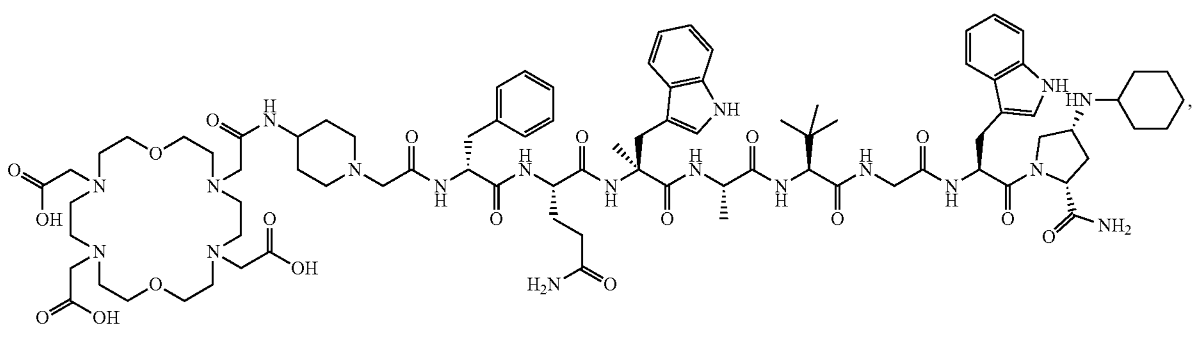

, or a salt or a solvate thereof. In some embodiments, the compound is conjugated by a radiometal. In some embodiments, the radiometal is $^{68}$Ga, $^{177}$Lu, or $^{225}$Ac.

In some embodiments, the peptidic compound described herein is:

(Compound 28; SEQ ID NO: 59)

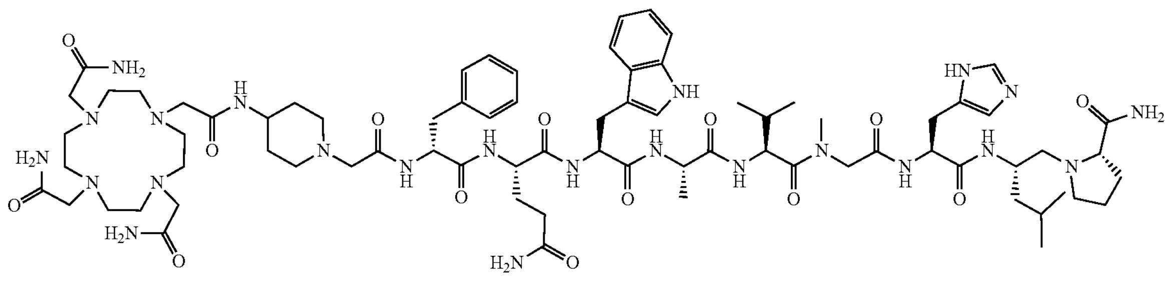

or

-continued (Compound 29; SEQ ID NO: 46)

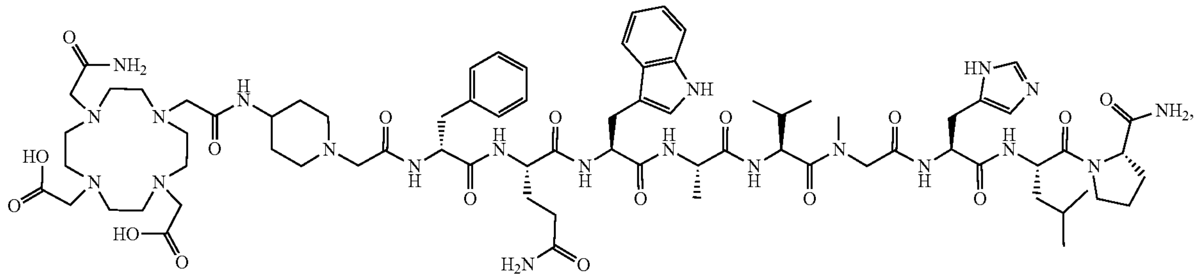

or a salt or a solvate thereof. In some embodiments, the compound is conjugated by a radiometal. In some embodiments, the compound is conjugated with $^{203}Pb$ or $^{212}Pb$.

In some embodiments, the peptidic compound described herein is:

(Compound 30; SEQ ID NO: 60)

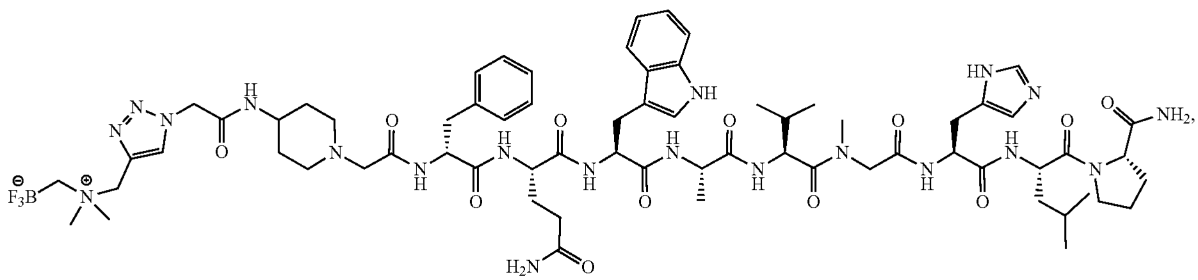

or a salt or a solvate thereof. In some embodiments, at least one fluorine in $—BF_3^-$ is $^{18}F$. In some embodiments, one or more fluorines in $—BF_3^-$ is $^{18}F$. In some embodiments, all fluorines in $—BF_3^-$ is $^{18}F$.

In some embodiments, the peptidic compound described herein is:

(Compound 31; SEQ ID NO: 61)

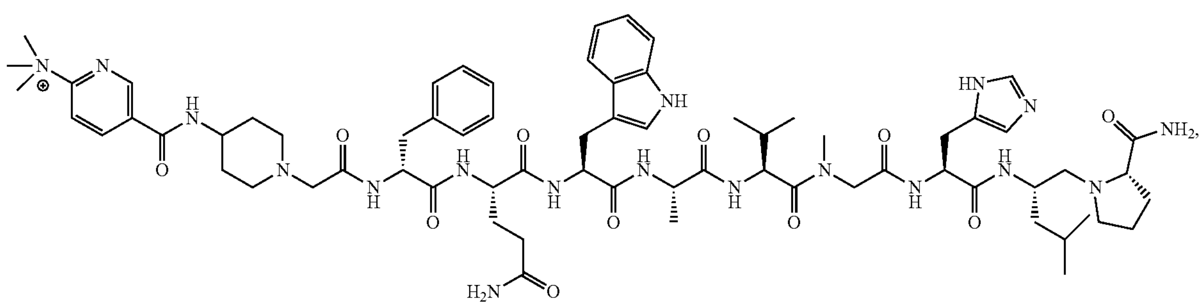

or a salt or a solvate thereof.

In some embodiments, the peptidic compound described herein is:

(Compound 32; SEQ ID NO: 62)

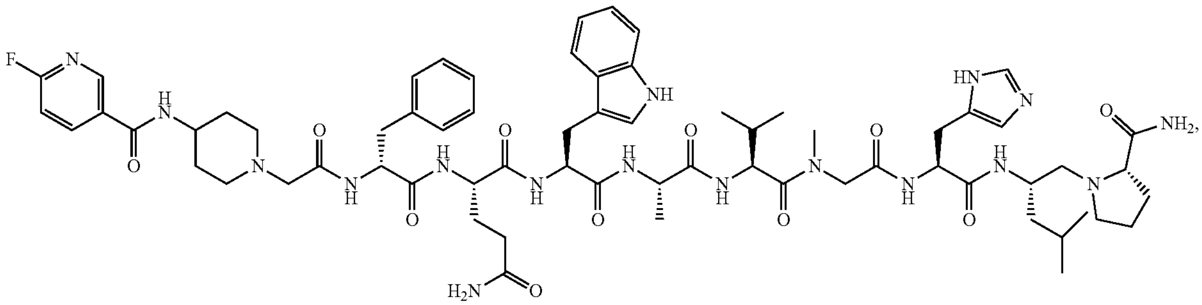

or a salt or a solvate thereof. In some embodiments, the fluorine (substituted on pyridine) is $^{18}$F.

In some embodiments, the peptidic compound described herein is:

(Compound 33; SEQ ID NO: 63)

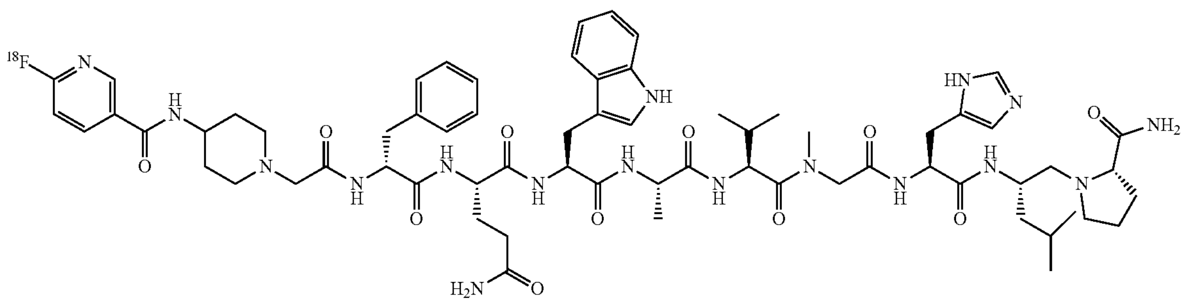

or a salt or a solvate thereof.

In some embodiments, the peptidic compound described herein is:

(Compound 34; SEQ ID NO: 64)

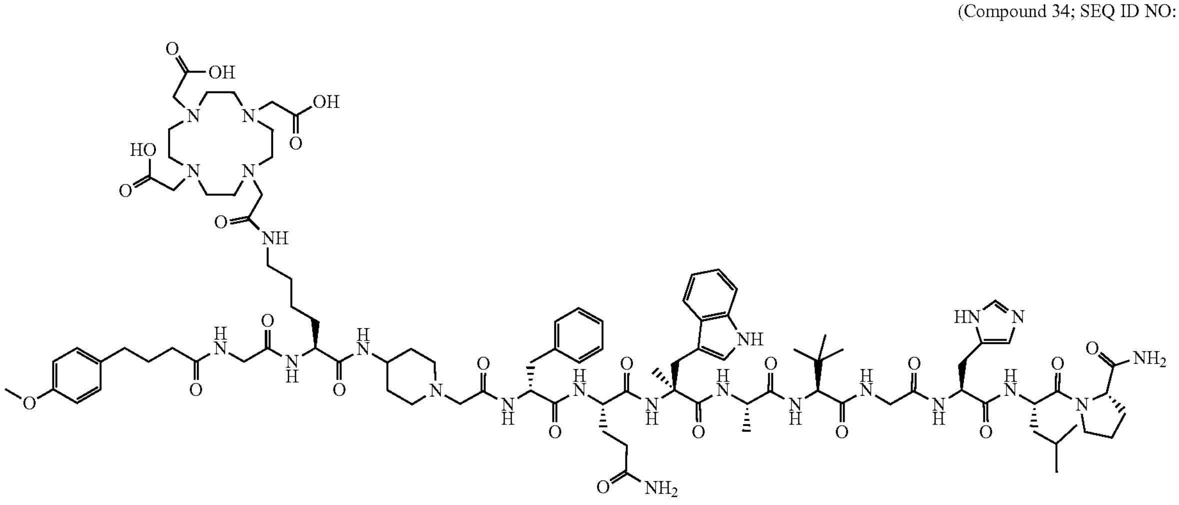

or

-continued
(Compound 35; SEQ ID NO: 65)
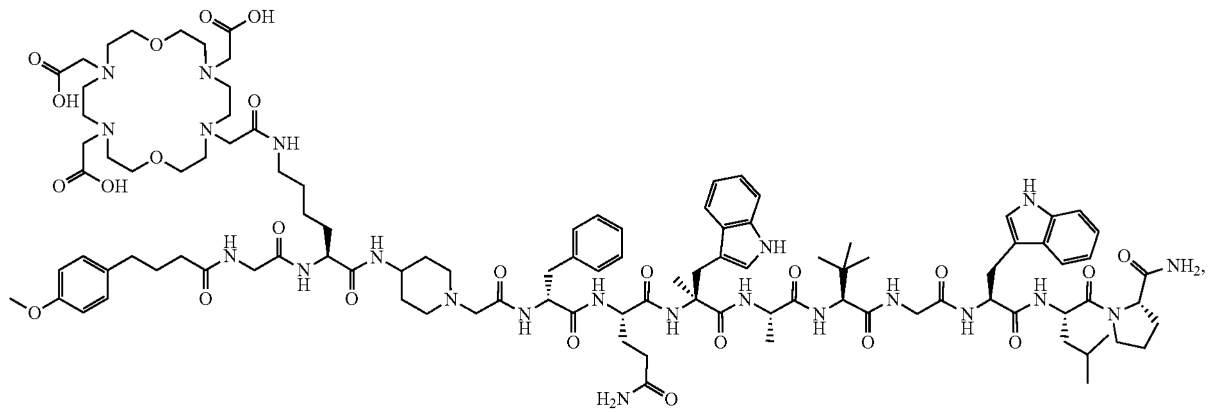
or a salt or a solvate thereof. In some embodiments, the compound is conjugated by a radiometal. In some embodiments, the radiometal is $^{68}Ga$, $^{177}Lu$, or $^{225}Ac$.
In some embodiments, the peptidic compound described herein is:
(Compound 36; SEQ ID NOs: 54 and 55)
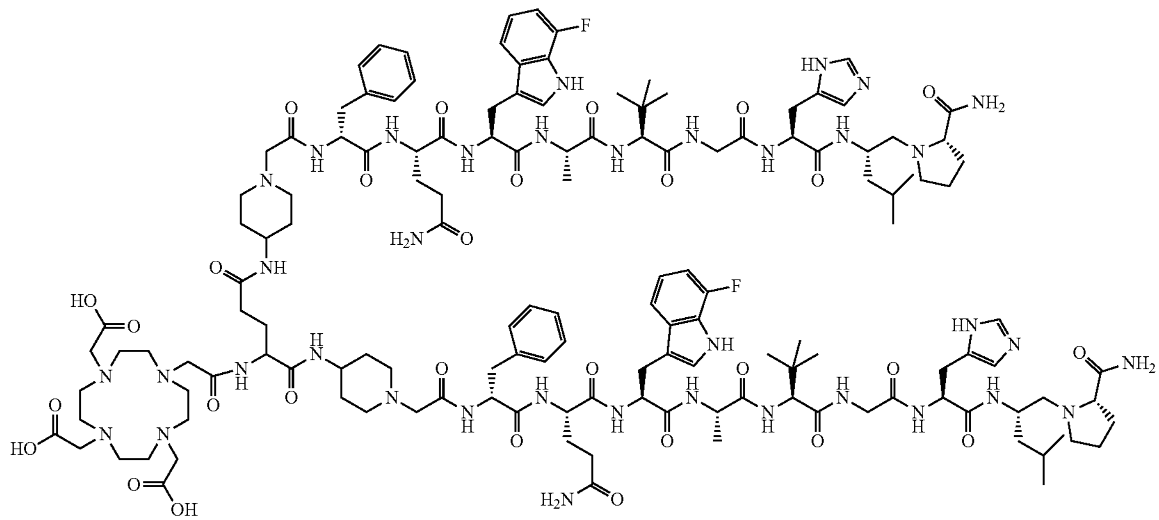
or
(Compound 37; SEQ ID NOs: 56 and 57)
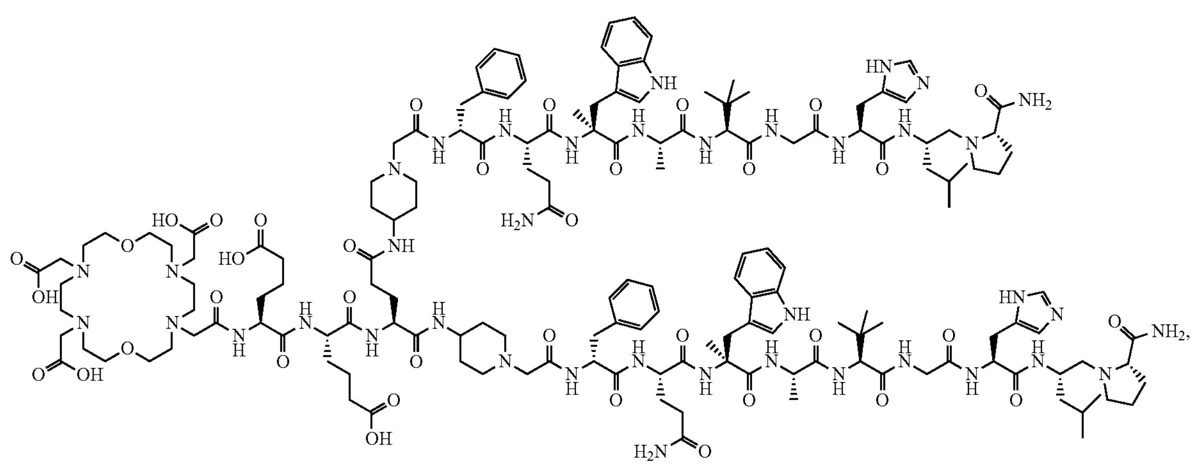
, or a salt or a solvate thereof. In some embodiments, the compound is conjugated by a radiometal. In some embodiments, the radiometal is $^{68}Ga$, $^{177}Lu$, or $^{225}Ac$.

In some embodiments, the peptidic compound described herein is selected from any one of Compounds 1-37 (including Compounds 6A, 8A, 9A, and 10A).

In some embodiments, the peptidic compound is (SEQ ID NO: 22)
DOTA-Pip-D-Phe-Gln-αMeTrp-Ala-Tle-Gly-His-LeuψPro-$NH_2$;

(SEQ ID NO: 23)
CROWN-Pip-D-Phe-Gln-αMeTrp-Ala-Tle-Gly-His-LeuψPro-$NH_2$;

(SEQ ID NO: 24)
CROWN-Pip-D-Phe-Gln-αMeTrp-Ala-Val-Gly-His-Sta-Leu-$NH_2$;

(SEQ ID NO: 25)
CROWN-Pip-D-Phe-Gln-αMeTrp-Ala-Tle-Gly-His-Sta-Leu-$NH_2$;

(SEQ ID NO: 26)
DOTA-Pip-D-Phe-Gln-Trp-Ala-Val-N-MeGly-Trp-LeuψPro-$NH_2$;

(SEQ ID NO: 27)
DOTAGA-Pip-D-Phe-Gln-Trp-Ala-Val-N-MeGly-Trp-LeuψPro-$NH_2$;

(SEQ ID NO: 28)
DOTA-Pip-D-Phe-Gln-αMeTrp-Ala-Tle-Gly-Trp-LeuψPro-$NH_2$;

(SEQ ID NO: 29)
DOTAGA-Pip-D-Phe-Gln-αMeTrp-Ala-Tle-Gly-Trp-LeuψPro-$NH_2$;

(SEQ ID NO: 30)
CROWN-Pip-D-Phe-Gln-αMeTrp-Ala-Tle-Gly-Trp-LeuψPro-$NH_2$;

(SEQ ID NO: 31)
CROWNGA-Pip-D-Phe-Gln-αMeTrp-Ala-Tle-Gly-Trp-LeuψPro-$NH_2$;

(SEQ ID NO: 32)
DOTA-Pip-D-Phe-Gln-αMeTrp-Ala-Tle-Gly-Trp(5-F)-LeuψPro-$NH_2$;

(SEQ ID NO: 33)
DOTAGA-Pip-D-Phe-Gln-αMeTrp-Ala-Tle-Gly-Trp(5-F)-LeuψPro-$NH_2$;

(SEQ ID NO: 34)
CROWN-Pip-D-Phe-Gln-αMe Trp-Ala-Tle-Gly-Trp-Sta-Leu-$NH_2$;

(SEQ ID NO: 35)
CROWN-Pip-D-Phe-Gln-αMeTrp-Ala-Tle-Gly-Trp(5-F)-Sta-Leu-$NH_2$;

(SEQ ID NO: 36)
CROWN-Pip-D-Phe-Cit-αMeTrp-Ala-Tle-Gly-His-LeuψPro-$NH_2$;

(SEQ ID NO: 37)
CROWN-Pip-D-Phe-Glu-αMeTrp-Ala-Tle-Gly-His-LeuψPro-$NH_2$;

(SEQ ID NO: 38)
CROWN-Pip-D-Phe-Agb-αMeTrp-Ala-Tle-Gly-His-LeuψPro-$NH_2$;

(SEQ ID NO: 39)
CROWN-Pip-D-Phe-Gln-αMeTrp-Ala-Tle-Gly-Trp-(cis-4-OCy-D-Pro)-$NH_2$;

(SEQ ID NO: 40)
CROWN-Pip-D-Phe-Gln-αMeTrp-Ala-Tle-Gly-Trp-(cis-4-NHCy-D-Pro)-$NH_2$;

(SEQ ID NO: 41)
DOTA-Pip-D-Phe-Gln-αMeTrp-Ala-Tle-Gly-5FTrp-LeuψPro-Tle-$NH_2$;

(SEQ ID NO: 42)
DOTA-Pip-D-Phe-Cit-αMeTrp-Ala-Tle-Gly-(3-Quin-Ala)-LeuψPro-$NH_2$;

(SEQ ID NO: 43)
DOTA-Pip-D-Phe-Cit-αMeTrp-Ala-Val-Gly-His-Sta-Leu-$NH_2$;
or (SEQ ID NO: 44)
DOTA-Pip-D-Phe-Cit-αMeTrp-Ala-Val-Gly-5FTrp-Sta-Leu-$NH_2$;

wherein ψ is a reduced peptide bond. In some embodiments, the compound is conjugated by a radiometal. In some embodiments, the radiometal is $^{68}$Ga, $^{177}$Lu, or $^{225}$Ac.

In some embodiments, the peptidic compound is TCMC-Pip-D-Phe-Gln-Trp-Ala-Val-N-MeGly-His-LeuψPro-NH2 (SEQ ID NO: 45) or PSC-Pip-D-Phe-Gln-Trp-Ala-Val-N-MeGly-His-LeuψPro-NH2 (SEQ ID NO: 46), wherein ψ is a reduced peptide bond. In some embodiments, the compound is conjugated by a radiometal. In some embodiments, the radiometal is $^{68}$Ga, $^{177}$Lu, $^{203}$Pb, $^{212}$Pb, or $^{225}$Ac. In some embodiments, the radiometal is $^{203}$Pb or $^{212}$Pb.

In some embodiments, the peptidic compound is DOTA-Pip-D-Phe-Gln-Trp-Ala-Val-N-MeGly-Trp-LeuψPro-Val-$NH_2$ (SEQ ID NO: 47); DOTA-Pip-D-Phe-Gln-Trp-Ala-Val-N-MeGly-His-LeuψPro-Val-$NH_2$ (SEQ ID NO: 48); CROWN-Pip-D-Phe-Gln-αMeTrp-Ala-Tle-Gly-Trp-LeuψPro-Tle-$NH_2$ (SEQ ID NO: 49); or CROWN-Pip-D-Phe-Gln-αMeTrp-Ala-Tle-Gly-His-LeuψPro-Tle-$NH_2$ (SEQ ID NO: 50); CROWN-Pip-D-Phe-Cit-αMeTrp-Ala-Tle-Gly-(3-Quin-Ala)-LeuψPro-Tle-$NH_2$ (SEQ ID NO: 51); DOTAGA-Pip-D-Phe-Gln-αMeTrp-Ala-Tle-Gly-His-LeuψPro-$NH_2$ (SEQ ID NO: 52); or DOTA-Pip-D-Phe-Gln-αMeTrp-Ala-Tle-Gly-His-LeuψPro-Tle-$NH_2$ (SEQ ID NO: 53); wherein ψ is a reduced peptide bond. In some embodiments, the compound is conjugated by a radiometal. In some embodiments, the radiometal is $^{68}$Ga, $^{177}$Lu, or $^{225}$Ac.

In some embodiments, the peptidic compound is DOTA-Glu(Pip-$^{D}$Phe-Gln-7FTrp-Ala-Tle-Gly-His-LeupPro-$NH_2$)$_2$ (SEQ ID NOs: 54 and 55) or CROWN-Aad-Aad-Glu(Pip-$^{D}$Phe-Gln-αMeTrp-Ala-Tle-Gly-His-LeuψPro-$NH_2$)$_2$ (SEQ ID NOs: 56 and 57), wherein ψ is a reduced peptide bond. In some embodiments, the compound is conjugated by a radiometal. In some embodiments, the radiometal is $^{68}$Ga, $^{177}$Lu, or $^{225}$Ac.

In some embodiments of the peptidic compound described herein (e.g., compounds of formula (A), (I), (IA), (IA-1), (IB), (IB-1), (IC), (IC-1), (ID), (ID-1), (IE), (IE-1), (IF), (IF-1), (II), (IIA), (B), or (B-1) or salt or solvate thereof), the compound is bound to (or conjugated with) or include a radiometal, a radiohalogen, or a radiohalogen containing metal. In some embodiments, the radiometal, the radiohalogen, or the radiohalogen containing metal is [$^{18}$F]AlF, $^{44}$Sc, $^{47}$Sc, $^{61}$Cu, $^{64}$Cu, $^{67}$Cu, $^{67}$Ga, $^{68}$Ga, $^{72}$As, $^{77}$As, $^{86}$Y $^{89}$Zr, $^{90}$Y $^{90}$Nb, $^{94m}$Tc, $^{99m}$Tc, $^{105}$Rh, $^{109}$Pd, $^{110m}$In, $^{111}$In, $^{114m}$In, $^{117m}$Sn, $^{123}$I, $^{124}$I, $^{131}$I, $^{132}$La, $^{133}$La, $^{134}$La, $^{134}$Ce, $^{135}$La, $^{142}$Pr, $^{149}$Tb, $^{149}$Pm, $^{152}$Tb, $^{153}$Sm, $^{155}$Tb, $^{159}$Gd, $^{161}$Tb, $^{165}$Er, $^{166}$Ho, $^{175}$Yb, $^{177}$Lu $^{186}$Re, $^{188}$Re, $^{198}$Au, $^{199}$Au, $^{203}$Pb, $^{211}$At, $^{212}$Pb, $^{212}$Bi, $^{213}$Bi, $^{223}$Ra, $^{224}$Ra, $^{225}$Ac, or $^{227}$Th. In some embodiments, the radiometal, the radiohalogen, or the radiohalogen containing metal is [$^{18}$F]AlF, $^{44}$Sc, $^{61}$Cu, $^{64}$CU $^{67}$Ga, $^{68}$Ga, $^{72}$As, $^{86}$Y $^{89}$Zr, $^{90}$Nb, $^{99m}$Tc, $^{110m}$In, $^{111}$In, $^{123}$I, $^{124}$I, $^{131}$I, $^{152}$Tb, $^{155}$Tb, $^{177}$Lu $^{203}$Pb, $^{212}$Pb, or $^{225}$Ac. In some embodiments, the radiometal is $^{47}$Sc, $^{64}$Cu, $^{67}$Cu, $^{77}$As, $^{90}$Y, $^{105}$Rh, $^{109}$Pd, $^{111}$In, $^{117m}$Sn, $^{142}$Pr, $^{149}$Pm, $^{149}$Tb, $^{153}$Sm, $^{159}$Gd, $^{161}$Tb, $^{165}$Er, $^{166}$Ho, $^{175}$Yb, $^{177}$Lu $^{186}$Re, $^{188}$Re, $^{198}$Au, $^{199}$Au, $^{211}$At, $^{212}$Pb, $^{212}$Bi, $^{213}$Bi, $^{223}$Ra, $^{224}$Ra, $^{225}$Ac, or $^{227}$Th. In some embodiments, the radiometal is $^{44}$Sc, $^{47}$Sc, $^{64}$Cu, $^{67}$Ga, $^{67}$Cu, $^{68}$Ga, $^{86}$Y, $^{90}$Y, $^{111}$In, $^{117m}$Sn, $^{149}$Tb, $^{152}$Tb, $^{153}$Sm, $^{155}$Tb, $^{161}$Tb, $^{165}$Er, $^{177}$Lu $^{203}$Pb, $^{212}$Pb, $^{212}$Bi, $^{213}$Bi, $^{223}$Ra, $^{224}$Ra, $^{225}$Ac, or $^{227}$Th. In some embodiments, the radiometal is $^{44}$Sc, $^{61}$Cu, $^{64}$Cu, $^{67}$Cu, $^{67}$Ga, $^{68}$Ga, $^{86}$Y, $^{90}$Y, $^{111}$In, $^{177}$Lu, $^{213}$Bi, $^{212}$Bi, or $^{225}$Ac. In some embodiments, the radiometal is $^{68}$Ga, $^{177}$Lu, $^{203}$Pb, $^{212}$Pb, or $^{225}$Ac. In some embodiments, the radiometal is $^{68}$Ga, $^{177}$Lu, or $^{225}$Ac.

In some embodiments, the peptidic compounds described herein are gastrin-releasing peptide receptor (GRPR) antagonists.

In some embodiments, the peptidic compounds described herein the compound is conjugated with a radiometal, a radiohalogen, or a radiohalogen for positron emission tomography (PET) or single photon emission computed tomography (SPECT) imaging of GRPR expressing tumors, wherein the compound is conjugated with a radiometal, a radiohalogen, or a radiohalogen that is a positron emitter or a gamma emitter. In some embodiments, the positron or gamma emitter is $^{18}$F, $^{44}$Sc, $^{61}$Cu, $^{64}$Cu, $^{67}$Ga, $^{68}$Ga, $^{72}$As, $^{86}$Y, $^{89}$Zr, $^{90}$Nb, $^{99m}$Tc, $^{110m}$In, $^{111}$In, $^{123}$I, $^{124}$I, $^{131}$I, $^{132}$La, $^{133}$La, $^{134}$La, $^{134}$Ce, $^{152}$Tb, $^{155}$Tb, or $^{203}$Pb.

In some embodiments, the peptidic compounds described herein the compound is conjugated with a radiometal that is used for therapy. In some embodiments, the radiometal is $^{47}$Sc, $^{64}$Cu, $^{67}$Cu, $^{77}$As, $^{90}$Y, $^{105}$Rh, $^{109}$Pd, $^{111}$In, $^{117m}$Sn, $^{135}$La, $^{142}$Pr, $^{149}$Pm, $^{149}$Tb, $^{153}$Sm, $^{159}$Gd, $^{161}$Tb, $^{165}$Er, $^{166}$Ho, $^{175}$Yb, $^{177}$Lu $^{186}$Re, $^{188}$Re, $^{198}$Au, $^{199}$Au, $^{211}$At, $^{212}$Pb, $^{212}$Bi, $^{213}$Bi, $^{223}$Ra, $^{224}$Ra, $^{225}$Ac, or $^{227}$Th.

The peptidic compounds described herein can be prepared by known peptide synthesis methods, such as methods employing 9-fluorenylmethoxycarbonyl (Fmoc) and/or t-butyloxycarbonyl (Boc) protecting groups. In some embodiments, peptide synthesis is solid-phase peptide synthesis. Fmoc protecting groups can be removed from the amino acid on the solid support under basic conditions. The amino acid to be added can be activated for coupling using activating reagents such as 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-aza-benzotriazole (HOAt). In some embodiments, the amino acid coupling reaction is performed in the presence of a suitable base to form a typical peptide bond.

Other than the formation of a typical amino acid peptide bond, amino acids can be coupled at their sidechain functional groups including carboxylic acid and amino groups. Amino acids with carboxylic acid or an amino group in their side chain can be used to form branched peptide chain. In some embodiments, an amino acid with a side chain with a carboxylic acid is Asp, D-Asp, Glu, or D-Glu. In some embodiments, an amino acid with a side chain with an amine is Lys, D-Lys, Orn, D-Orn, Dab, D-Dab, Dap, or D-Dap.

An amino acid with an azide side chain can be used to form a triazole with another amino acid or an input with an alkyne group. In some embodiments, an amino acid with a side chain with an azide is Lys($N_3$) or D-Lys($N_3$). In some embodiments, an amino acid with a side chain with an alkyne group is Pra or D-Pra.

In some embodiments of the peptidic compounds, Xaa$^1$, Xaa$^2$, Xaa$^3$, Xaa$^4$, Xaa$^5$, Xaa$^6$, Xaa$^7$, Xaa$^8$, Xaa$^9$ or Xaa$^{10}$ is each optionally N-methylated. In some embodiments, N-methylation can be achieved by directly using Fmoc-N-methylated amino acids during peptide synthesis.

In some embodiments, the radiolabeling group or the albumin binder is coupled to the peptide N-terminus while the peptide is attached to the solid support.

A prosthetic group containing a trifluoroborate, such as $BF_3—R^5—R^4—$ component, can be prepared according to reported procedures (Liu et al. Angew Chem Int Ed 2014 53:11876-11880; Liu et al. J Nucl Med 2015 55:1499-1505; Liu et al. Nat Protoc 2015 10:1423-1432; Kuo et al. J Nucl Med, 2019 60:1160-1166; each of which is incorporated by reference in its entirety).

$^{18}$F-labeling of the $BF_3$-containing compounds via $^{18}$F-$^{19}$F isotope exchange reaction can be performed following reported procedures (Liu et al. Nat Protoc 2015 10:1423-1432, incorporated by reference in its entirety).

Binding and Function

A person having ordinary skill in the art would appreciate that the compounds disclosed herein are bombesin derivatives and therefore function in a similar manner to bombesin. Bombesin and its derivatives are known to bind to GRPR by inserting their C-termini into the binding pocket of the receptor (Peng, et al. 2023 *Proc Natl Acad Sci USA* 120). Bombesin derivatives comprising a chelated radionuclide also bind to GRPR in a similar fashion while delivering a cytotoxic radiation dose to a cell (e.g., a tumor cell). A skilled person also appreciates that the disclosed compounds selectively bind to tumors that overexpress GRPR over healthy tissues and organs (e.g., pancreas and kidneys) based on the Examples disclosed herein.

In an aspect, the peptidic compounds of the invention comprise a means for binding to a GRPR-expressing tumor in a subject, wherein the peptidic compound exhibits a tumor/pancreas uptake ratio of at least 1. In some embodiments, the peptidic compound exhibits a tumor/pancreas uptake ratio of about 1.5 or higher. In some embodiments, the peptidic compound exhibits a tumor/pancreas uptake ratio of about 2 or higher. In some embodiments, the peptidic compound exhibits a tumor/pancreas uptake ratio of about 4 or higher. In some embodiments, the peptidic compound exhibits a tumor/pancreas uptake ratio of about 5 or higher. In some embodiments, the peptidic compound exhibits a tumor/pancreas uptake ratio of about 6 or higher. In some embodiments, the peptidic compound exhibits a tumor/pancreas uptake ratio of about 7 or higher. In some embodiments, the peptidic compound exhibits a tumor/pancreas uptake ratio of about 10 or higher. In some embodiments, the peptidic compound exhibits a tumor/pancreas uptake ratio of about 16. In some embodiments, the peptidic compound comprises a radiolabeling group. In some embodiments, the radiolabeling group is a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof. In some embodiments, the peptidic compound comprises a radiometal chelator optionally comprising or complexed with a radionuclide.

In another aspect, the peptidic compounds of the invention comprise a means for binding to a GRPR-expressing tumor in a subject, wherein the peptidic compound exhibits a tumor comparative time-activity integration ($AUC_{tumor}$) of at least 1000% ID/g·h. In some embodiments, the peptidic compound exhibits an $AUC_{tumor}$ of at least 1100% ID/g·h. In some embodiments, the peptidic compound exhibits an $AUC_{tumor}$ of at least 1200% ID/g·h. In some embodiments, the peptidic compound exhibits an $AUC_{tumor}$ of at least 1300% ID/g·h. In some embodiments, the peptidic compound exhibits an $AUC_{tumor}$ of at least 1400% ID/g·h. In some embodiments, the peptidic compound exhibits an $AUC_{tumor}$ of at least 1500% ID/g·h. In some embodiments, the peptidic compound exhibits an $AUC_{tumor}$ of at least 1600% ID/g·h. In some embodiments, the peptidic compound exhibits an $AUC_{tumor}$ of at least 1700% ID/g·h. In some embodiments, the peptidic compound exhibits an $AUC_{tumor}$ of at least 1800% ID/g·h. In some embodiments, the peptidic compound exhibits an $AUC_{tumor}$ of at least 1900% ID/g·h. In some embodiments, the peptidic compound exhibits an $AUC_{tumor}$ of at least 2000% ID/g·h. In some embodiments, the peptidic compound exhibits an $AUC_{tumor}$ of at least 2100% ID/g·h. In some embodiments, the peptidic compound comprises a radiolabeling group. In some embodiments, the radiolabeling group is a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof. In some embodiments, the peptidic compound comprises a radiometal chelator optionally comprising or complexed with a radionuclide.

In yet another aspect, the peptidic compounds of the invention comprise a means for binding to a GRPR-expressing tumor in a subject, wherein the peptidic compound exhibits a tumor/kidney uptake ratio of at least 10. In some embodiments, the peptidic compound exhibits a tumor/kidney uptake ratio of at least 11. In some embodiments, the peptidic compound exhibits a tumor/kidney uptake ratio of at least 12. In some embodiments, the peptidic compound exhibits a tumor/kidney uptake ratio of at least 13. In some embodiments, the peptidic compound exhibits a tumor/kidney uptake ratio of at least 14. In some embodiments, the peptidic compound exhibits a tumor/kidney uptake ratio of at least 15. In some embodiments, the peptidic compound exhibits a tumor/kidney uptake ratio of at least 16. In some embodiments, the peptidic compound exhibits a tumor/kidney uptake ratio of at least 17. In some embodiments, the peptidic compound exhibits a tumor/kidney uptake ratio of at least 18. In some embodiments, the peptidic compound exhibits a tumor/kidney uptake ratio of at least 19. In some embodiments, the peptidic compound exhibits a tumor/kidney uptake ratio of at least 20. In some embodiments, the peptidic compound comprises a radiolabeling group. In some embodiments, the radiolabeling group is a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof. In some embodiments, the peptidic compound comprises a radiometal chelator optionally comprising or complexed with a radionuclide.

In an additional aspect, the peptidic compounds of the invention comprise a means for binding to a GRPR-expressing tumor in a subject, wherein the peptidic compound comprises a chelator optionally complexed with a radionuclide and wherein the peptidic compound exhibits a tumor/pancreas uptake ratio of at least 1. In some embodiments, the peptidic compound exhibits a tumor/pancreas uptake ratio of 1.5 or higher. In some embodiments, the peptidic compound exhibits a tumor/pancreas uptake ratio of 2 or higher. In some embodiments, the peptidic compound exhibits a tumor/pancreas uptake ratio of 4 or higher. In some embodiments, the peptidic compound exhibits a tumor/pancreas uptake ratio of 5 or higher. In some embodiments, the peptidic compound exhibits a tumor/pancreas uptake ratio of 6 or higher. In some embodiments, the peptidic compound exhibits a tumor/pancreas uptake ratio of about 7 or higher. In some embodiments, the peptidic compound exhibits a tumor/pancreas uptake ratio of about 10 or higher. In some embodiments, the peptidic compound exhibits a tumor/pancreas uptake ratio of about 16.

In a further aspect, the peptidic compounds of the invention comprise a means for binding to a GRPR-expressing tumor in a subject, wherein the peptidic compound comprises a chelator optionally complexed with a radionuclide and wherein the peptidic compound exhibits a tumor comparative time-activity integration ($AUC_{tumor}$) of at least 1000% ID/g·h. In some embodiments, the peptidic compound exhibits an $AUC_{tumor}$ of at least 1100% ID/g·h. In some embodiments, the peptidic compound exhibits an $AUC_{tumor}$ of at least 1200% ID/g·h. In some embodiments, the peptidic compound exhibits an $AUC_{tumor}$ of at least 1300% ID/g·h. In some embodiments, the peptidic compound exhibits an $AUC_{tumor}$ of at least 1400% ID/g·h. In some embodiments, the peptidic compound exhibits an $AUC_{tumor}$ of at least 1500% ID/g·h. In some embodiments, the peptidic compound exhibits an $AUC_{tumor}$ of at least 1600% ID/g·h. In some embodiments, the peptidic compound exhibits an $AUC_{tumor}$ of at least 1700% ID/g·h. In some embodiments, the peptidic compound exhibits an $AUC_{tumor}$ of at least 1800% ID/g·h. In some embodiments, the peptidic compound exhibits an $AUC_{tumor}$ of at least 1900% ID/g·h. In some embodiments, the peptidic compound exhibits an $AUC_{tumor}$ of at least 2000% ID/g·h. In some embodiments, the peptidic compound exhibits an $AUC_{tumor}$ of at least 2100% ID/g·h.

In yet another aspect, the peptidic compounds of the invention comprise a means for binding to a GRPR-expressing tumor in a subject, wherein the peptidic compound comprises a chelator optionally complexed with a radionuclide and wherein the peptidic compound exhibits a tumor/kidney uptake ratio of at least 10. In some embodiments, In some embodiments, the peptidic compound exhibits a tumor/kidney uptake ratio of at least 11. In some embodiments, the peptidic compound exhibits a tumor/kidney uptake ratio of at least 12. In some embodiments, the peptidic compound exhibits a tumor/kidney uptake ratio of at least 13. In some embodiments, the peptidic compound exhibits a tumor/kidney uptake ratio of at least 14. In some embodiments, the peptidic compound exhibits a tumor/kidney uptake ratio of at least 15. In some embodiments, the peptidic compound exhibits a tumor/kidney uptake ratio of at least 16. In some embodiments, the peptidic compound exhibits a tumor/kidney uptake ratio of at least 17. In some embodiments, the peptidic compound exhibits a tumor/kidney uptake ratio of at least 18. In some embodiments, the peptidic compound exhibits a tumor/kidney uptake ratio of at least 19. In some embodiments, the peptidic compound exhibits a tumor/kidney uptake ratio of at least 20.

In an additional aspect, the peptidic compounds of the invention comprise a means for binding to a GRPR-expressing tumor in a subject, wherein the peptidic compound comprises a chelator optionally complexed with a radionuclide and wherein the peptidic compound exhibits a tumor/pancreas uptake ratio of at least 1 (e.g., at least 1.5, at least 2, at least 4, at least 5, at least 6, at least 8, at least 10) and a tumor comparative time-activity integration ($AUC_{tumor}$) of at least 1000% ID/g·h (e.g., at least 1100, at least 1200, at least 1300, at least 1400, at least 1500, at least 1600, at least 1700, at least 1800, at least 1900, or at least 2000% ID/g·h).

In another aspect, a peptidic compound of the invention comprises a means for binding to a GRPR-expressing tumor in a subject, wherein the peptidic compound is a compound of Formula (A), or a salt or solvate of Formula (A):

$$R^{rad}_{n6}—R^{L}\text{-[linker]-}R^{L}—Xaa^{1}—Xaa^{2}—Xaa^{3}—Xaa^{4}—Xaa^{5}—Xaa^{6}—Xaa^{7}—Xaa^{8}—[\psi\text{-}Xaa^{9}—(Xaa^{10})_{m2}]_{m1}—R \quad (A)$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid (Me-Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —$N(R^2)C(O)$—, —$C(O)N(R^2)$—, —NH—C(O)—NH—, —NH—C(S)—NH—,

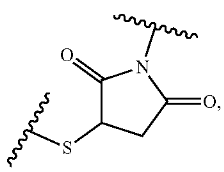
,
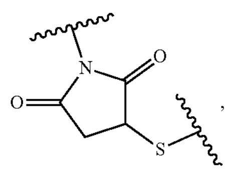
,
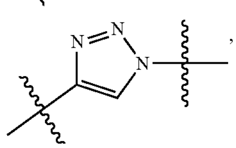
, or
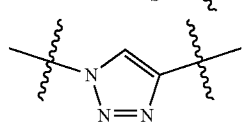
;

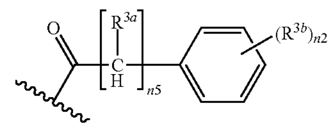

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

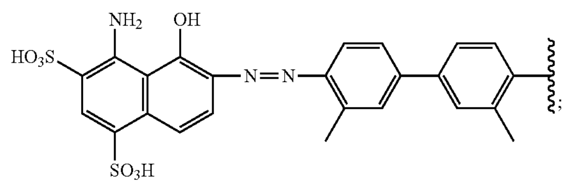
;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound of Formula (A) exhibits a tumor/pancreas uptake ratio of at least 1 (e.g., at least 1.5 or higher, about 2 or higher, about 4 or higher, about 5 or higher, about 6 or higher, about 7 or higher, about 10 or higher, or about 16).

In an aspect, a peptidic compound of the invention comprises a means for binding to a GRPR-expressing tumor in a subject, wherein the peptidic compound is a compound of Formula (A), or a salt or solvate of Formula (A):

$$R^{rad}_{n6}—R^L\text{-[linker]-}R^L—Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (A)$$

and $R^2$ is H, methyl or ethyl;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

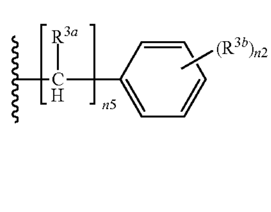

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-$NHR^a$-D-Pro or cis-4-$OR^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{11}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —$N(R^2)C(O)$—, —$C(O)N(R^2)$—, —NH—C(O)—NH—, —NH—C(S)—NH—

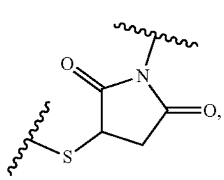,
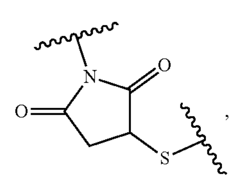,
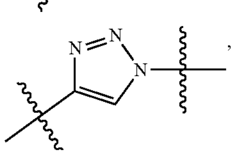, or
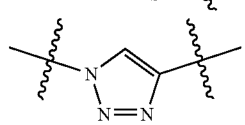;

and $R^2$ is H, methyl or ethyl;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

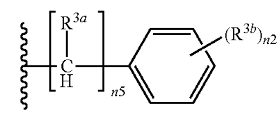

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

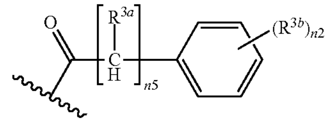

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

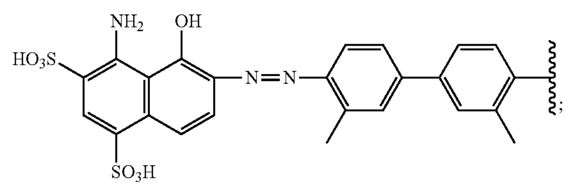 [SMILES: *c1ccc(-c2ccc(N=Nc3ccc4c(S(=O)(=O)O)cc(S(=O)(=O)O)c(N)c4c3O)c(C)c2)cc1C];

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound of Formula (A) exhibits a tumor comparative time-activity integration ($AUC_{tumor}$) of at least 1000% ID/g·h (e.g., at least 1100% ID/g·h, at least 1200% ID/g·h, at least 1300% ID/g·h, at least 1400% ID/g·h, at least 1500% ID/g·h, at least 1600% ID/g·h, at least 1700% ID/g·h, at least 1800% ID/g·h, at least 1900% ID/g·h, at least 2000% ID/g·h, or at least 2100% ID/g·h).

In yet another aspect, a peptidic compound of the invention comprises a means for binding to a GRPR-expressing tumor in a subject, wherein the peptidic compound is a compound of Formula (A), or a salt or solvate of Formula (A):

$$R^{rad}_{n6}—R^{L}\text{-[linker]-}R^{L}—Xaa^{1}—Xaa^{2}—Xaa^{3}—Xaa^{4}—Xaa^{5}—Xaa^{6}—Xaa^{7}—Xaa^{8}—[\psi\text{-}Xaa^{9}—(Xaa^{10})_{m2}]_{m1}—R \qquad (A)$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 2-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is statine (Sta), Leu, D-Pro, Phe, cis-4-NH$R^a$-D-Pro or cis-4-O$R^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NH$R^a$-D-Pro, cis-4-O$R^a$-D-Pro, Leu, 5,5-dimethyl-1,3-thiazolidine-4-carboxylic acid ($Me_2$Thz), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, 5,5-dimethyl-1,3-thiazolidine-4-carboxylic acid ($Me_2$Thz), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain of n1 units of -$Xaa^{11}$-, and/or -$L^1R^1$— and/or -$(L^1)_2R^1$—, wherein:

n1 is 1-20;

each $Xaa^{11}$ is independently an amino acid;

each $R^1$ is, independently, a linear, branched, and/or cyclic $C_{1-20}$ alkylenyl, alkenylenyl and/or alkynylenyl, wherein any carbon bonded to two other carbons is optionally independently replaced by N, S, or O, and carbons are optionally independently substituted with oxo, hydroxyl, sulfhydryl, —SeH, halogen, guanidino, amine, amide, urea, carboxylic acid, sulfonic acid, sulfinic acid, or phosphoric acid;

$L^1$ bonds to carbon, wherein each $L^1$ is independently —S—, —N($R^2$)C(O)—, —C(O)N($R^2$)—, —NH—C(O)—NH—, —NH—C(S)—NH—,

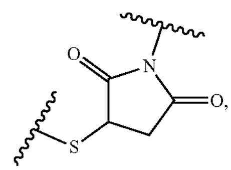

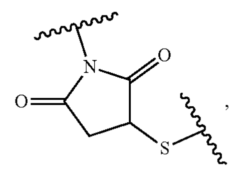

,

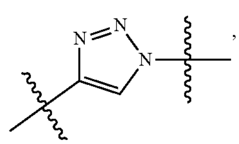

, or

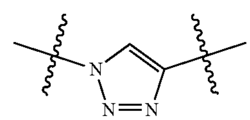

;

and $R^2$ is H, methyl or ethyl;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

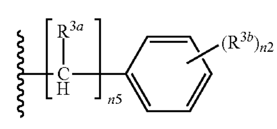

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

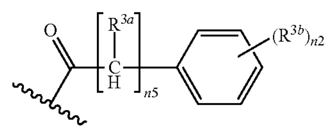

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

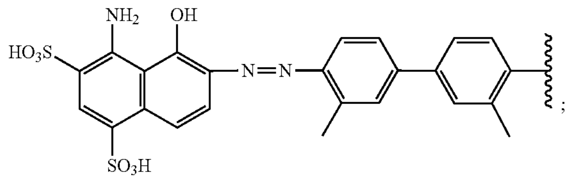 [SMILES: *c1ccc(-c2ccc(N=Nc3ccc4c(S(=O)(=O)O)cc(S(=O)(=O)O)c(N)c4c3O)c(C)c2)cc1C]

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor/pancreas uptake ratio of at least 1 (e.g., at least 1.5, at least 2, at least 4, at least 5, at least 6, at least 8, at least 10) and a tumor comparative time-activity integration ($AUC_{tumor}$) of at least 1000 (e.g., at least 1100, at least 1200, at least 1300, at least 1400, at least 1500, at least 1600, at least 1700, at least 1800, at least 1900, or at least 2000) % ID/g·h.

In another aspect, a peptidic compound of the invention comprises a means for binding to a GRPR-expressing tumor in a subject, wherein the peptidic compound is a compound of Formula (I), or a salt or solvate of Formula (I), $$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 22-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is statine (Sta), Leu, D-Pro, Phe, cis-4-$NHR^a$-D-Pro or cis-4-$OR^a$-D-Pro, wherein $R^a$ is alkyl, cycloalkyl, or aryl;

R is $—NH_2$ or —NHOH;

m1 is 0 or 1;

m2 is 0 or 1;

when m1 is 1 and m2 is 0, $Xaa^9$-R is a C-terminally amidated (R is $—NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, $Me_2Thz$ (5,5-dimethyl-1,3-thiazolidine-4-carboxylic acid), or thiazoline-4-carboxylic acid (Thz); and $Xaa^{10}$-R is a C-terminally amidated (R is $—NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

the linker is a linear or branched chain of n1 units of $-Xaa^{11}$-;

n1 is 1-20;

each $Xaa^{11}$ is independently an amino acid;

optionally, the linker comprises an albumin binder ($R^{alb}$), wherein the albumin binder is:

$—(CH_2)_{n3}—CH_3$ wherein n3 is 8-20;

$—(CH_2)_{n4}—C(O)OH$ wherein n4 is 8-20;

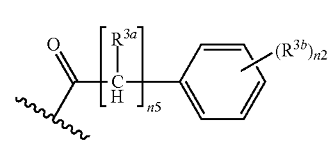

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

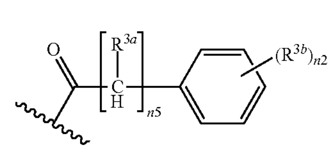

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

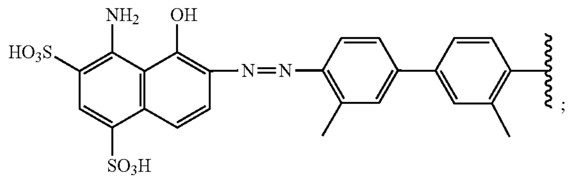 [SMILES: *c1ccc(-c2ccc(N=Nc3ccc4c(S(=O)(=O)O)cc(S(=O)(=O)O)c(N)c4c3O)c(C)c2)cc1C]

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor/pancreas uptake ratio of at least 1 (e.g., at least 1.5 or higher, about 2 or higher, about 4 or higher, about 5 or higher, about 6 or higher, about 7 or higher, about 10 or higher, or about 16).

In another aspect, a peptidic compound of the invention comprises a means for binding to a GRPR-expressing tumor in a subject, wherein the peptidic compound is a compound of Formula (I), or a salt or solvate of Formula (I), $$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 22-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is statine (Sta), Leu, D-Pro, Phe, cis-4-NHR$^a$-D-Pro or cis-4-OR$^a$-D-Pro, wherein $R^a$ is alkyl, cycloalkyl, or aryl;

R is $—NH_2$ or —NHOH;

m1 is 0 or 1;

m2 is 0 or 1;

when m1 is 1 and m2 is 0, $Xaa^9$-R is a C-terminally amidated (R is $—NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-NHR$^a$-D-Pro, cis-4-OR$^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, $Me_2Thz$ (5,5-dimethyl-1,3-thiazolidine-4-carboxylic acid), or thiazoline-4-carboxylic acid (Thz); and $Xaa^{10}$-R is a C-terminally amidated (R is $—NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

the linker is a linear or branched chain of n1 units of $-Xaa^{11}$-;

n1 is 1-20;

each $Xaa^{11}$ is independently an amino acid;

optionally, the linker comprises an albumin binder ($R^{alb}$), wherein the albumin binder is:

$—(CH_2)_{n3}—CH_3$ wherein n3 is 8-20;

$—(CH_2)_{n4}—C(O)OH$ wherein n4 is 8-20;

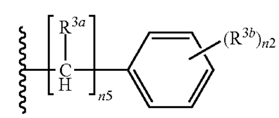

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

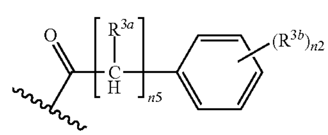

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

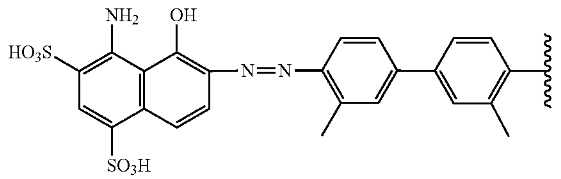;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor comparative time-activity integration ($AUC_{tumor}$) of at least 1000% ID/g·h (e.g., at least 1100% ID/g·h, at least 1200% ID/g·h, at least 1300% ID/g·h, at least 1400% ID/g·h, at least 1500% ID/g·h, at least 1600% ID/g·h, at least 1700% ID/g·h, at least 1800% ID/g·h, at least 1900% ID/g·h, at least 2000% ID/g·h, or at least 2100% ID/g·h).

In another aspect, a peptidic compound of the invention comprises a means for binding to a GRPR-expressing tumor in a subject, wherein the peptidic compound is a compound of Formula (I), or a salt or solvate of Formula (I), $$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

wherein:

$Xaa^1$ is an N-terminal amino acid residue selected from D-Phe, 4-chlorophenylalanine (Cpa), D-Cpa, 3-(1-naphthyl)alanine (Nal), D-Nal, 3-(2-naphthyl)alanine (2-Nal), D-2-Nal, 2,3,4,9-tetrahydro-1H-pyrido[3,4-b]indol-3-carboxylic acid (Tpi), or D-Tpi;

$Xaa^2$ is Gly, Arg, Asp, Asn, Gln, Glu, homoserine (Hse), citrulline (Cit), 2-amino-4-ureidobutanoic acid (Aub), 22-amino-4-guanidinobutyric acid (Agb), or His;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is Ala, D-Ala, or Ser;

$Xaa^5$ is Val, 2,3-dehydro-Val, cyclopentylglycine (Cpg), L-cyclopropylglycine, L-cyclobutylglycine, or tert-leucine (Tle);

$Xaa^6$ is Gly or D-Ala;

$Xaa^7$ is His, Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is statine (Sta), Leu, D-Pro, Phe, cis-4-$NHR^a$-D-Pro or cis-4-$OR^a$-D-Pro, wherein $R^a$ is alkyl, cycloalkyl, or aryl;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue selected from Pro, Phe, oxazolidine-4-carboxylic acid (4-oxa-L-Pro), 4,4-difluoroproline (difluoroPro), cis-4-$NHR^a$-D-Pro, cis-4-$OR^a$-D-Pro, Leu, 5,5-dimethyl-1,3-thiazolidine-4-carboxylic acid ($Me_2Thz$), or thiazoline-4-carboxylic acid (Thz), wherein $R^a$ is alkyl, cycloalkyl, or aryl;

when m1 is 1 and m2 is 1, $Xaa^9$ is Pro, Phe, oxazolidine-4-carboxylic acid (4-oxa-L-Pro), 4,4-difluoroproline (difluoroPro), Leu, $Me_2Thz$ (5,5-dimethyl-1,3-thiazolidine-4-carboxylic acid), or thiazoline-4-carboxylic acid (Thz); and $Xaa^{10}$-R is a C-terminally amidated (R is —$NH_2$) or a C-terminally hydroxylamidated (R is —NHOH) amino acid residue selected from Val, Leu, Tle, lie, Nle, Ala, Gly, or Met;

ψ represents a peptide bond or reduced peptide bond joining $Xaa^8$ to $Xaa^9$;

the linker is a linear or branched chain of n1 units of -$Xaa^{11}$-;

n1 is 1-20;

each $Xaa^{11}$ is independently an amino acid;

optionally, the linker comprises an albumin binder ($R^{alb}$), wherein the albumin binder is:

—$(CH_2)_{n3}$—$CH_3$ wherein n3 is 8-20;

—$(CH_2)_{n4}$—C(O)OH wherein n4 is 8-20;

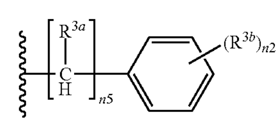

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl;

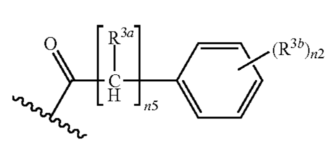

wherein n2 is 1-5, n5 is 1-4, $R^{3a}$ is H or methyl, and $R^{3b}$ is I, Br, F, Cl, H, OH, $OCH_3$, $NH_2$, $NO_2$ or $C_1$-$C_6$ alkyl; or

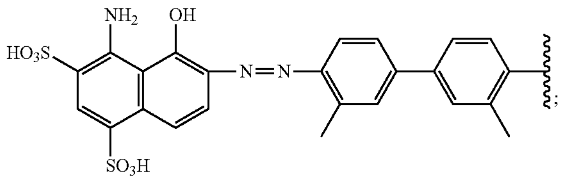 [SMILES: *c1ccc(-c2ccc(N=Nc3ccc4c(S(=O)(=O)O)cc(S(=O)(=O)O)c(N)c4c3O)c(C)c2)cc1C]

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor/pancreas uptake ratio of at least 1 (e.g., at least 1.5, at least 2, at least 4, at least 5, at least 6, at least 8, at least 10) and a tumor comparative time-activity integration ($AUC_{tumor}$) of at least 1000 (e.g., at least 1100, at least 1200, at least 1300, at least 1400, at least 1500, at least 1600, at least 1700, at least 1800, at least 1900, or at least 2000) % ID/g·h.

In yet another aspect, a peptidic compound of the invention comprises a means for binding to a GRPR-expressing tumor in a subject, wherein the peptidic compound is a compound of Formula (A), or a salt or solvate of Formula (A):

$$R^{rad}_{n6}—R^L\text{-[linker]-}R^L—Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (A)$$

wherein:

$Xaa^1$ is an N-terminal residue comprising any proteinogenic or nonproteinogenic amino acid;

$Xaa^2$ is any proteinogenic or nonproteinogenic amino acid;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is any proteinogenic or nonproteinogenic amino acid;

$Xaa^5$ is any proteinogenic or nonproteinogenic amino acid;

$Xaa^6$ is any proteinogenic or nonproteinogenic amino acid;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is any proteinogenic or nonproteinogenic amino acid;

R is $—NH_2$ or —NHOH;

m1 is 0 or 1;

m2 is 0 or 1;

when m1 is 1 and m2 is 0, $Xaa^9$-R is a C-terminally amidated (R is $—NH_2$) or a C-terminally hydroxylamidated (R is —NHOH) amino acid residue;

when m1 is 1 and m2 is 1, $Xaa^9$ is any proteinogenic or nonproteinogenic amino acid; and $Xaa^{10}$-R is a C-terminally amidated (R is $—NH_2$) or a C-terminally hydroxylamidated (R is —NHOH) amino acid residue;

ψ represents a peptide bond or reduced peptide bond joining $Xaa^8$ to $Xaa^9$;

each $R^L$ is independently absent, $—(C_{1-6}\ alkyl)-$, $—(C_{1-6}\ alkyl)-C(O)—$, —C(O)—, —NH—C(O)—, or —NH—C(S)—;

the linker is a linear or branched chain optionally comprising an albumin binder;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound of Formula (A) exhibits a tumor/pancreas uptake ratio of at least 1 (e.g., at least 1.5 or higher, about 2 or higher, about 4 or higher, about 5 or higher, about 6 or higher, about 7 or higher, about 10 or higher, or about 16).

In an aspect, a peptidic compound of the invention comprises a means for binding to a GRPR-expressing tumor in a subject, wherein the peptidic compound is a compound of Formula (A), or a salt or solvate of Formula (A):

$$R^{rad}_{n6}—R^L\text{-[linker]-}R^L—Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (A)$$

wherein:

$Xaa^1$ is an N-terminal residue comprising any proteinogenic or nonproteinogenic amino acid;

$Xaa^2$ is any proteinogenic or nonproteinogenic amino acid;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is any proteinogenic or nonproteinogenic amino acid;

$Xaa^5$ is any proteinogenic or nonproteinogenic amino acid;

$Xaa^6$ is any proteinogenic or nonproteinogenic amino acid;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is any proteinogenic or nonproteinogenic amino acid;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue;

when m1 is 1 and m2 is 1, $Xaa^9$ is any proteinogenic or nonproteinogenic amino acid; and $Xaa^{10}$-R is a C-terminally amidated (R is —$NH_2$) or a C-terminally hydroxylamidated (R is —NHOH) amino acid residue;

ψ represents a peptide bond or reduced peptide bond joining $Xaa^8$ to $Xaa^9$;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain optionally comprising an albumin binder;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound of Formula (A) exhibits a tumor comparative time-activity integration ($AUC_{tumor}$) of at least 1000% ID/g·h (e.g., at least 1100% ID/g·h, at least 1200% ID/g·h, at least 1300% ID/g·h, at least 1400% ID/g·h, at least 1500% ID/g·h, at least 1600% ID/g·h, at least 1700% ID/g·h, at least 1800% ID/g·h, at least 1900% ID/g·h, at least 2000% ID/g·h, or at least 2100% ID/g·h).

In yet another aspect, a peptidic compound of the invention comprises a means for binding to a GRPR-expressing tumor in a subject, wherein the peptidic compound is a compound of Formula (A), or a salt or solvate of Formula (A):

$$R^{rad}_{n6}—R^L\text{-[linker]-}R^L—Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (A)$$

wherein:

$Xaa^1$ is an N-terminal amino acid residue comprising any proteinogenic or nonproteinogenic amino acid;

$Xaa^2$ is any proteinogenic or nonproteinogenic amino acid;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^4$ is any proteinogenic or nonproteinogenic amino acid;

$Xaa^5$ is any proteinogenic or nonproteinogenic amino acid;

$Xaa^6$ is any proteinogenic or nonproteinogenic amino acid;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine (2-Quin-Ala), or 3-quinoylalanine (3-Quin-Ala);

$Xaa^8$ is any proteinogenic or nonproteinogenic amino acid;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue;

when m1 is 1 and m2 is 1, $Xaa^9$ is any proteinogenic or nonproteinogenic amino acid; and $Xaa^{10}$-R is a C-terminally amidated (R is —$NH_2$) or a C-terminally hydroxylamidated (R is —NHOH) amino acid residue;

ψ represents a peptide bond or reduced peptide bond joining $Xaa^8$ to $Xaa^9$;

each $R^L$ is independently absent, —($C_{1-6}$ alkyl)-, —($C_{1-6}$ alkyl)-C(O)—, —C(O)—, —NH—C(O)—, or —NH—C(S)—;

the linker is a linear or branched chain optionally comprising an albumin binder;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor/pancreas uptake ratio of at least 1 (e.g., at least 1.5, at least 2, at least 4, at least 5, at least 6, at least 8, at least 10) and a tumor comparative time-activity integration ($AUC_{tumor}$) of at least 1000 (e.g., at least 1100, at least 1200, at least 1300, at least 1400, at least 1500, at least 1600, at least 1700, at least 1800, at least 1900, or at least 2000) % ID/g·h.

In another aspect, a peptidic compound of the invention comprises a means for binding to a GRPR-expressing tumor in a subject, wherein the peptidic compound is a compound of Formula (I), or a salt or solvate of Formula (I), $$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

wherein:

$Xaa^1$ is an N-terminal amino acid residue comprising any proteinogenic or nonproteinogenic amino acid;

$Xaa^2$ is any proteinogenic or nonproteinogenic amino acid;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is any proteinogenic or nonproteinogenic amino acid;

$Xaa^5$ is any proteinogenic or nonproteinogenic amino acid;

$Xaa^6$ is any proteinogenic or nonproteinogenic amino acid;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is any proteinogenic or nonproteinogenic amino acid;

R is $—NH_2$ or —NHOH;

m1 is 0 or 1;

m2 is 0 or 1;

when m1 is 1 and m2 is 0, $Xaa^9$-R is a C-terminally amidated (R is $—NH_2$) or a C-terminally hydroxylamidated (R is —NHOH) amino acid residue;

when m1 is 1 and m2 is 1, $Xaa^9$ is any proteinogenic or nonproteinogenic amino acid; and $Xaa^{10}$-R is a C-terminally amidated (R is $—NH_2$) or a C-terminally hydroxylamidated (R is —NHOH) amino acid residue;

ψ represents a peptide bond or reduced peptide bond joining $Xaa^8$ to $Xaa^9$;

the linker is a linear or branched chain optionally comprising an albumin binder;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor/pancreas uptake ratio of at least 1 (e.g., at least 1.5 or higher, about 2 or higher, about 4 or higher, about 5 or higher, about 6 or higher, about 7 or higher, about 10 or higher, or about 16).

In another aspect, a peptidic compound of the invention comprises a means for binding to a GRPR-expressing tumor in a subject, wherein the peptidic compound is a compound of Formula (I), or a salt or solvate of Formula (I), $$R^{rad}_{n6}\text{-[linker]-}Xaa^1—Xaa^2—Xaa^3—Xaa^4—Xaa^5—Xaa^6—Xaa^7—Xaa^8—[\psi\text{-}Xaa^9—(Xaa^{10})_{m2}]_{m1}—R \quad (I)$$

wherein:

$Xaa^1$ is an N-terminal amino acid residue comprising any proteinogenic or nonproteinogenic amino acid;

$Xaa^2$ is any proteinogenic or nonproteinogenic amino acid;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is any proteinogenic or nonproteinogenic amino acid;

$Xaa^5$ is any proteinogenic or nonproteinogenic amino acid;

$Xaa^6$ is any proteinogenic or nonproteinogenic amino acid;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I),

Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is any proteinogenic or nonproteinogenic amino acid;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue;

when m1 is 1 and m2 is 1, $Xaa^9$ is any proteinogenic or nonproteinogenic amino acid; and $Xaa^{10}$-R is a C-terminally amidated (R is —$NH_2$) or a C-terminally hydroxylamidated (R is —NHOH) amino acid residue;

ψ represents a peptide bond or reduced peptide bond joining $Xaa^8$ to $Xaa^9$;

the linker is a linear or branched chain optionally comprising an albumin linker;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor comparative time-activity integration ($AUC_{tumor}$) of at least 1000% ID/g·h (e.g., at least 1100% ID/g·h, at least 1200% ID/g·h, at least 1300% ID/g·h, at least 1400% ID/g·h, at least 1500% ID/g·h, at least 1600% ID/g·h, at least 1700% ID/g·h, at least 1800% ID/g·h, at least 1900% ID/g·h, at least 2000% ID/g·h, or at least 2100% ID/g·h).

In another aspect, a peptidic compound of the invention comprises a means for binding to a GRPR-expressing tumor in a subject, wherein the peptidic compound is a compound of Formula (I), or a salt or solvate of Formula (I), $$R^{rad}_{n6}\text{-[linker]-}Xaa^1\text{—}Xaa^2\text{—}Xaa^3\text{—}Xaa^4\text{—}Xaa^5\text{—}Xaa^6\text{—}Xaa^7\text{—}Xaa^8\text{—}[\psi\text{-}Xaa^9\text{—}(Xaa^{10})_{m2}]_{m1}\text{—}R \quad (I)$$

wherein:

$Xaa^1$ is an N-terminal amino acid residue comprising any proteinogenic or nonproteinogenic amino acid;

$Xaa^2$ is any proteinogenic or nonproteinogenic amino acid;

$Xaa^3$ is Trp, β-(3-benzothienyl)alanine (Bta), Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp (4-I), Trp(5-OH), αMe-Trp, Tpi, 7-azatryptophan (7-Aza), Nal, 2-pyridylalanine (2-Pal), 3-pyridylalanine (3-Pal), 4-pyridylalanine (4-Pal), 2-quinoylalanine, or 3-quinoylalanine;

$Xaa^4$ is any proteinogenic or nonproteinogenic amino acid;

$Xaa^5$ is any proteinogenic or nonproteinogenic amino acid;

$Xaa^6$ is any proteinogenic or nonproteinogenic amino acid;

$Xaa^7$ is Trp, Trp(Me), Trp(7-Me), Trp(6-Me), Trp(5-Me), Trp(4-Me), Trp(2-Me), Trp(7-F), Trp(6-F), Trp(5-F), Trp(4-F), Trp(7-Cl), Trp(6-Cl), Trp(5-Cl), Trp(4-Cl), Trp(7-Br), Trp(6-Br), Trp(5-Br), Trp(4-Br), Trp(7-I), Trp(6-I), Trp(5-I), Trp(4-I), Trp(5-OH), αMe-Trp, Nal, 2-pyridylalanine (2-Pal), 3-pyridylalanine (3-Pal), 4-pyridylalanine (4-Pal), 2-quinoylalanine, or 3-quinoylalanine;

$Xaa^8$ is any proteinogenic or nonproteinogenic amino acid;

R is —$NH_2$ or —NHOH;

m1 is 0 or 1;

m2 is 0 or 1;

when m1 is 1 and m2 is 0, $Xaa^9$-R is a C-terminally amidated (R is —$NH_2$) or a C-terminally hydroxylamidated (R is —NHOH) amino acid residue;

when m1 is 1 and m2 is 1, $Xaa^9$ is any proteinogenic or nonproteinogenic amino acid; and $Xaa^{10}$-R is a C-terminally amidated (R is —$NH_2$) or a C-terminally hydroxylamidated (R is —NHOH) amino acid residue;

ψ represents a peptide bond or reduced peptide bond joining $Xaa^8$ to $Xaa^9$;

the linker is a linear or branched chain optionally comprising an albumin binder;

n6 is 1-5;

each $R^{rad}$ is a radiolabeling group independently selected from a radiometal chelator; an aryl or heteroaryl substituted with at least one radiohalogen; a prosthetic group containing a trifluoroborate; an aryl or heteroaryl substituted with at least one fluorine precursor leaving group; a prosthetic group containing a silicon-fluorine-acceptor moiety; or a prosthetic group containing a fluorophosphate, fluorosulfate, sulfonyl fluoride, or a combination thereof; and wherein $Xaa^1$, $Xaa^2$, $Xaa^3$, $Xaa^4$, $Xaa^5$, $Xaa^6$, $Xaa^7$, $Xaa^8$, $Xaa^9$ or $Xaa^{10}$ is each optionally N-methylated; wherein the above peptidic compound exhibits a tumor/pancreas uptake ratio of at least 1 (e.g., at least 1.5, at least 2, at least 4, at least 5, at least 6, at least 8, at least 10) and a tumor comparative time-activity integration ($AUC_{tumor}$) of at least 1000 (e.g., at least 1100, at least 1200, at least 1300, at least 1400, at least 1500, at least 1600, at least 1700, at least 1800, at least 1900, or at least 2000) % ID/g·h.

In some embodiments, the means for binding to a GRPR-expressing tumor in a subject is achieved by a portion of the peptidic compound having any one of SEQ ID NOs: 3-21. In some embodiments, the means for binding to a GRPR-expressing tumor in a subject is achieved by a peptidic compound having SEQ ID NO: 2. In some embodiments, the means for binding to a GRPR-expressing tumor in a subject is achieved by a peptidic compound having any one of SEQ ID NOs: 22-65.

Compositions

In another aspect, a composition comprising any one of the peptidic compounds as described herein is disclosed. In some embodiments, the composition is a pharmaceutical composition. In some embodiments, the composition comprises a pharmaceutically acceptable excipient or carrier.

The GRPR targeting compounds disclosed herein are typically formulated for administration to a patient, either before or after incorporation of a radiolabel. Certain embodiments of the invention thus relate to pharmaceutical compositions comprising one or more of the radio-labelled GRPR targeting compounds, or unlabeled GRPR targeting compounds, and a pharmaceutically acceptable carrier, diluent, or excipient. The pharmaceutical compositions are prepared by known procedures using well-known and readily available ingredients.

The pharmaceutical compositions comprising the GRPR targeting compounds are typically formulated for parenteral administration. The term parenteral as used herein includes subcutaneous, intradermal, intra-articular, intravenous, intraperitoneal, intramuscular, intravascular, intrasternal, intrathecal injection or infusion techniques.

In certain embodiments, the pharmaceutical compositions may be in the form of a sterile injectable aqueous or oleaginous suspension. This suspension may be formulated according to known art using those suitable dispersing or wetting agents and suspending agents that have been mentioned above. The sterile injectable preparation may also be a sterile injectable solution or a suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables. Adjuvants such as local anesthetics, preservatives and buffering agents can also be included in the injectable solution or suspension.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philadelphia, PA (2000).

Diagnostic Applications

In a further aspect, this disclosure relates to diagnostic applications of the radio-labelled GRPR targeting compounds for imaging a cancer or tissue in which GRPR is expressed, aberrantly expressed, ectopically expressed, or overexpressed, for example, in oncology.

Overexpression of GRPR has been demonstrated in many malignancies, including psychiatric disorder, neurological disorder, inflammatory disease, prostate cancer, lung cancer, head and neck cancer, colon cancer, kidney cancer, ovarian cancer, liver cancer, pancreatic cancer, breast cancer, glioma (e.g., glioblastoma), or neuroblastoma. GRPR activation has been shown to potentiate malignant behaviors by inducing cell proliferation, migration, and angiogenesis. Certain embodiments of the invention thus contemplate that the radio-labelled GRPR targeting compounds could be used as imaging probes for cancers of prostate cancer, lung cancer, head and neck cancer, colon cancer, kidney cancer, ovarian cancer, liver cancer, pancreatic cancer, breast cancer, glioma (e.g., glioblastoma), or neuroblastoma, including for use in early diagnosis of solid malignancies that express GRPR, as imaging agents to confirm the diagnostic of malignancy, or to guide focal ablative treatment if the disease is localized. According to certain embodiments, the GRPR targeting compounds could also be used to monitor response to therapy, by providing an independent assessment of the residual cellular content of a tumor known to overexpress GRPR.

Radio-labelled GRPR targeting compounds of this disclosure can show high contrast, rapid renal clearance, minimal non-target organ uptake, and high tumour to normal tissue ratios, which properties make these compounds well-suited for use as imaging agents for cancer diagnosis, including diagnosis of early-stage cancer. In particular, certain GRPR targeting compounds according to embodiments of the invention exhibit relatively low renal retention, and relatively high ratio of tumor:kidney and/or tumor/pancreas uptake, facilitating safe and effective use of the compounds in diagnostic and radiotherapeutic treatments.

In some embodiments of the invention, it is contemplated that the radio-labelled GRPR targeting compounds may be used as PET/SPECT imaging probes to assist with precise localization of primary or recurrent cancer in order to guide and assist with focal ablative therapies.

In some embodiments, the invention contemplates that the radio-labelled GRPR targeting compounds could be used to monitor response to therapy, by providing an independent assessment of the residual cellular content of a tumour known to overexpress GRPR. Overexpression of GRPR may be an indicator of angiogenesis in tumours, as blocking of GRPR activation is known to have antiangiogenic activity.

There is some evidence that GRPR antagonists might cause growth inhibition in some cancers. In certain embodiments, GRPR expression and receptor blockage could be detected by imaging with the radio-labelled GRPR targeting compounds, which could then act as a predictive biomarker for treatment success.

In some embodiments, the use of the radio-labelled GRPR targeting compounds in multimodality imaging of cancers is contemplated, for example, combined functional imaging and anatomical imaging, such as PET/CT or SPECT/CT. Multimodality imaging may be useful in situations in which a cancer is present, but the uptake of imaging agent is low.

Therapeutic Uses

In an additional aspect, the present disclosure provides a method for treating a disease or condition. In some embodiments, the disease or the condition is a GRPR-expressing condition or disease.

In an additional aspect, the present disclosure provides a method for treating a GRPR-expressing condition or disease comprises administering to a subject in need of imaging any one of the peptidic compounds or compositions comprising any one of the peptidic compounds disclosed herein. In some embodiments, the GRPR-expressing condition or disease is cancer. In some embodiments, the GRPR-expressing condition or disease is a psychiatric disorder, neurological disorder, inflammatory disease, prostate cancer, lung cancer, head and neck cancer, colon cancer, kidney cancer, ovarian cancer, liver cancer, pancreatic cancer, breast cancer, glioma (e.g., glioblastoma), or neuroblastoma. In some embodiments, the cancer is prostate cancer. In some embodiments, the cancer is breast cancer. In some embodiments, the cancer is glioblastoma. According to further embodiments, the GRPR targeting compounds can be used for endoradiotherapy targeting cells expressing GRPR, by radiolabelling the compound with a radioisotope, usually a β- or α-particle emitter, to deliver a high local dose of radiation to lesions, to inflict DNA damage and inducing cellular death. Unlike external beam radiation therapy, in certain embodiments this systemic treatment can be effective even in the treatment of metastases.

Pharmaceutical Packs or Kits

Certain embodiments of the invention relate to pharmaceutical packs or kits containing one or more GRPR targeting compounds, for example, therapeutic or diagnostic packs or kits. The compounds may be provided radio-labelled or as precursors suitable for radio-labelling, in which case the kit may optionally include additional reagents for radio-labelling the compounds.

In certain embodiments, one or more of the components of the kit can be lyophilized and the kit can additionally contain a suitable solvent for reconstitution of the lyophilized components. Individual components of the kit would typically be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration.

In certain embodiments, the compound(s) are provided in the kit in the form of pharmaceutical compositions suitable for administration to a subject. In this case, if desired, the container may itself be an inhalant, syringe, pipette, eye dropper, or other such like apparatus, from which the composition may be administered to the subject.

GRPR targeting compounds described herein can be synthesized according to conventional methods known to those of ordinary skill in the art. Exemplary, non-limiting procedures are provided in the Examples below.

It is contemplated that any embodiment discussed herein can be implemented with respect to any method, use or composition of the invention, and vice versa. Furthermore, compositions and kits of the invention can be used to achieve methods and uses of the invention.

To gain a better understanding of the invention described herein, the following examples are set forth. It will be understood that these examples are intended to describe illustrative embodiments of the invention and are not intended to limit the scope of the invention in any way.

EXAMPLES

General Methods

Chemicals were procured from commercial sources and used without further purification. All peptides were synthesized on a peptide synthesizer (Liberty Blue 2.0). Purification and quality control of peptide precursor and nonradioactive Lu-complexed and La-complexed standards were performed on Agilent HPLC and LC/MS systems. HPLC columns used were preparative columns (Luna 5 μm C18(2) 100 Å, LC Column 150×21.2 mm), (Luna 5 μm C18(2) 100 Å, LC Column 50×30 mm), semipreparative columns (Luna C18, 5 μm particle size, 100 Å pore size, 250×10 mm), (Aeris 3.6 μm PEPTIDE XB—C18 100 Å, LC Column 250×4.6 mm) and analytical columns (Luna C18, 5 μm particle size, 100 Å pore size, 250×4.6 mm), (Kinetex 2.6 μm PS C18 100 Å, LC Column 100×3 mm) and (Kinetex 2.6 μm C18 100 Å, LC Column 100×3 mm) from Phenomenex. The collected HPLC eluates containing the desired peptides were lyophilized using a Labconco FreeZone 4.5 Plus freeze drier. Mass analyses were performed using Agilent mass spectrometer.

General Peptide Synthesis:

At a 0.1 mmol scale, Sieber resin or Rink Amide Resin was deprotected by treating the resin with 20% piperidine in DMF (3×8 min). Fmoc-Leu-ψ-Pro-OH (or the first amino acid) was coupled to the resin via solid-phase peptide synthesis using Fmoc-based chemistry. The coupling was carried out in DMF using Fmoc-Leu-ψ-Pro-OH (4 eq.), HATU (4 eq.), HOAt (4 eq.) and DIEPA (11 eq.) at room temperature for overnight (16 hours). The preloaded Fmoc-Leu-ψ-Pro-Sieber resin (or Rink Amide resin) was then loaded onto the Liberty Blue, and the Fmoc was deprotected with 10% Piperidine in DMF at 45° C. (3 min×3) or 20% piperidine in DMF at room temperature (3×8 min). According to the peptide sequence, each Fmoc-protected amino acid (4 eq., 0.4 mmol, 0.2 M in DMF) was subsequently coupled at 45° C. (20 min) using 1 M DIC/1 M Oxyma in DMF or coupled at room temperature (1-3 h) using HATU (4 eq.), HOAt (4 eq.) in DMF, followed by Fmoc-deprotection as described above. Fmoc-Ala-OH was double-coupled at 45° C. (20 min×2) or room temperature (1 h×2). The synthesis continued with the addition of the linker, Fmoc-4-amino-(1-carboxymethyl) piperidine (4 eq.), using double coupling at 45° C. for 1.5 h or couple at room temperature for 3 h and then followed by the chelator DOTA$(tBu)_3$ (4 eq) or Crown$(tBu)_3$ (4 eq) at 25° C. for 18 h. The coupling of the linker and the chelator were carried out using HATU/HOAt/DIPEA (4/4/11 eq). The peptide was then deprotected and simultaneously cleaved from the resin by treating with 95/5 trifluoroacetic acid (TFA)/triisopropylsilane (TIS) for 2 h at room temperature. After filtration, the crude peptide was precipitated by the addition of cold diethyl ether to the TFA solution and lyophilized in a H2O/MeCN mixture.

Cold Lutetium or Lanthanum Cold Complexations Synthesis:

The precursor (1 eq., 5-10 mg) and $LuCl_3$ (5 eq.) or $LaCl_3$ (5 eq.) were dissolved in 0.1 M aq. NaOAc and MeCN (2.5:1, DMSO was added when solubility is low). The reaction mixture was heated to 90° C. for 30 minutes, at which point most reactions were complete (monitored by MS). The reaction mixture was then diluted with $H_2O$/MeCN and directly purified by semi-prep HPLC (0.1% TFA in $H_2O$/MeCN) to afford the Lu or La-cold standard. Isolated amounts ranged from 3-8 mg, and purities (HPLC) were between 95% and 99%.

General Methods of Radiolabeling with $^{177}Lu$:

Generally, a small aliquot of the precursor (1-5 μL, 1-3 nmol) was dissolved in the reaction buffer/solution with a known pH. To the solution was added a known amount/activity of $^{177}LuCl_3$. Then, the reaction was heated to 85° C. for 20-30 minutes. At this point, the reaction was cooled down and further diluted with the suitable formulation or dilution buffer. For analysis, the reaction mixtures and/or diluted solutions were analyzed using radio-TLC (iTLC) and radio-HPLC. Generally, iTLCs were run on SG paper plates, with 0.1 M sodium citrate as the eluent and other optional solvents as needed. The developed plates were then read using a radio-TLC reading instrument. HPLC analyses were performed using a suitable C18 column, with different combinations of $H_2O$ and MeCN (both with 0.1% TFA) as the eluent. The eluting components were visualized by UV (DAD) and radio-detection flow monitors. In all cases, the radiochemical purity of the radiolabeled compound was assessed at the end of synthesis (EOS) and after 3 h (estimated time between end of synthesis and in vivo experiments).

General Methods of Radiolabeling with $^{225}Ac$:

Generally, a small aliquot of the precursor (1-10 μL, 1-10 nmol) was dissolved in the reaction buffer/solution with a known pH. To the solution was added a known amount/activity of $^{225}AcCl_3$ or $^{225}Ac(NO_3)_3$ Then, the reaction was heated to 95° C. for 15-30 minutes. At this point, the reaction was cooled down and further diluted with the suitable formulation or dilution buffer. For analysis, the reaction mixtures and/or diluted solutions were analyzed using radio-TLC (iTLC) and radio-HPLC. Generally, iTLCs were run on SG paper plates, with 0.1 M sodium citrate as the eluent and other optional solvents as needed. The developed plates were then read using a radio-TLC reading instrument. HPLC analyses were performed using a suitable C18 column, with different combinations of $H_2O$ and MeCN (both with 0.1% TFA) as the eluent. The eluting components were visualized by UV (DAD) and radio-detection flow monitors. To detect the emissions resulting from the decay chain of $^{225}$Ac, all collected fractions from HPLC were allowed to equilibrate for 6 h, then were placed in a Gamma counting instrument for subsequent measurements. In all cases, the radiochemical purity of the radiolabeled compound was assessed at the end of synthesis (EOS) and after 3-5 h (estimated time between end of synthesis and in vivo experiments).

Example 1: Synthesis

Synthesis of Compound 1

Sieber resin was deprotected by treating the resin with 20% piperidine in DMF (3×8 min). Fmoc-Leu-ψ-Pro-OH was coupled to the resin via solid-phase peptide synthesis using Fmoc-based chemistry. The coupling was carried out in DMF using Fmoc-Leu-ψ-Pro-OH (4 eq.), HATU (4 eq.), HOAt (4 eq.) and DIEPA (11 eq.) at room temperature for overnight (16 hours). At a 0.15 mmol scale, the preloaded Fmoc-Leu-ψ-Pro-Sieber resin was then loaded onto the peptide synthesizer, and the Fmoc was deprotected with 10% Piperidine in DMF at 45° C. (3 min×3). Then, Fmoc-His(Boc)-OH (4 eq., 0.4 mmol, 0.2 M in DMF) was coupled at 45° C. (10 min) using 1 M DIC/1 M Oxyma in DMF (1 mL/0.5 mL), followed by Fmoc-deprotection as described above. Fmoc-Gly-OH, Fmoc-Tle-OH, Fmoc-Ala-OH (×2), Fmoc-αMeTrp(Boc)-OH, Fmoc-Gln(Trt)-OH (×2), and Fmoc-D-Phe-OH were coupled consecutively in a similar manner, except Fmoc-Gln(Trt)-OH was using HATU/HOAt/DIEPA(4/4/11 eq.) as coupling reagents. The synthesis continued with the addition of the linker, Fmoc-4-amino-(1-carboxymethyl) piperidine (4 eq.), at 45° C. for 1.5 h×2 and then followed by the chelator DOTA(tBu)$_3$ (4 eq) at 25° C. for 18 h. The coupling of the linker and the chelator were carried out by using HATU/HOAt/DIPEA (4/4/11 eq.). The peptide was then deprotected and simultaneously cleaved from the resin by treating with 92.5/2.5/2.5/2.5 TFA/TIS/DODT/H2O for 50 min at 40° C. After filtration, the crude peptide was precipitated by the addition of cold diethyl ether to the TFA solution and lyophilized in a $H_2O$/MeCN mixture. The crude peptide was purified with prep HPLC using solvents A: $H_2O$/0.1% TFA and B: MeCN/0.1% TFA, 20 mL/min (21%-31% B over 7 min, tR=6.5 min). The sample was lyophilized to a white solid. Calc mass $[M+2H]^{2+}/2$: 797.45 m/z; found $[M+2H]^{2+}/2$: 797.50 m/z.

Other compounds were synthesized in similar manner. Table 1 lists the LC-MS data for the synthesized compounds.

TABLE 1

Mass values obtained from LC-MS spectrum of illustrative compounds

| Compound | Calculated mass ($[M + 2H]^{2+}$, m/z) | Found ($[M + 2H]^{2+}$, m/z) |
|---|---|---|
| 1 | 797.45 | 797.5 |
| 2 | 841.45 | 841.7 |
| 3 | 871.49 | 871.8 |
| 4 | 878.5 | 878.8 |

TABLE 1-continued

Mass values obtained from LC-MS spectrum of illustrative compounds

| | | |
|---|---|---|
| 5 | 833.45 | 833.8 |
| 6 | 814.94 | 815.2 |
| 7 | 864.48 | 864.8 |
| 23 | 839.95 | 840.3 |
| 8 | 865.98 | 886.1 |
| 9 | 821.95 | 822.3 |
| 10 | 830.95 | 831.3 |
| 11 | 922.52 | 922.8 |
| 14 | 905.00 | 905.5 |
| 17 | 842.45 | 842.7 |
| 24 | 898.01 | 898.3 |
| 19 | 855.98 | 856.3 |
| 20 | 841.96 | 842.3 |
| 22 | 804.45 | 804.7 |
| 35 | 1046.6 | 1046.9 |
| **Compound** | **Calculated mass ($[M + 3H]^{3+}$, m/z)** | **Found ($[M + 3H]^{3+}$, m/z)** |
| 34 | 652.37 | 652.7 |
| 36 | 973.86 | 974.1 |
| **Compound** | **Calculated mass ($[M + 4H]^{4+}$, m/z)** | **Found ($[M + 4H]^{4+}$, m/z)** |
| 37 | 822.2 | 822.7 |

Synthesis of Lu-Compound 1

The precursor of compound 1 (7.4 mg, 4.6 μmol) was dissolved in 600 μL 0.2 NaOAc buffer (4.5 pH) and to it was added 5 eq of $LuCl_3$ (23 μmol). The solution was heated to 90° C. for 30 minutes and the reaction mixture was then purified by HPLC using the semipreparative column. The HPLC conditions were 24% acetonitrile in water with 0.1% TFA at a flow rate of 4 mL/min ($t_R$=8.3 min). The HPLC eluates containing the desired peptide were collected, pooled, and lyophilized. The yield was 65% with 95% purity. ESI-MS: calculated $[M+2H]^{2+}$ for Lu-Compound 1 $C_{77}H_{215}N_{20}O_{17}$[Lu] 883.4; found $[M+2H]^{2+}$ 883.7.

Synthesis of La-Compound 1

The precursor of compound 1 (5.6 mg, 3.5 μmol) was dissolved in 500 μL 0.2 NaOAc buffer (4.5 pH) and to it was added 5 eq of $LaCl_3$ (23 μmol). The solution was heated to 90° C. for 30 minutes and the reaction mixture was then purified by HPLC using the analytic column. The HPLC conditions were 23% acetonitrile in water with 0.1% TFA at a flow rate of 1 mL/min ($t_R$=10.6 min). The HPLC eluates containing the desired peptide were collected, pooled, and lyophilized. The yield was 29% with 97% purity. ESI-MS: calculated $[M+2H]^{2+}$ for La-Compound 1 $C_{77}H_{215}N_{20}O_{17}$[La]865.4; found $[M+2H]^{2}$+865.7.

Radiolabelling of $^{177}$Lu-Compound 1

2.4 μL aliquot of compound 1 precursor (1 mM, 2.4 nmol) was dissolved in 205.3 μL 0.2 M NaOAc (pH 5.5), followed by 8.3 μL, 126.9 MBq of $^{177}LuCl_3$. Then, the reaction was heated to 95° C. for 15 minutes. After cooling down, the reaction mixture was further diluted with the formulation buffer. For quality control, the formulated solutions were analyzed using radio-TLC (iTLC) and radio-HPLC. iTLCs were run on SG paper plates, with 0.1 M sodium citrate (5% MeOH) as the eluent. The developed plates were then read using a radio-TLC reading instrument. HPLC analyses were performed using an analytical Luna column, the mobile phase condition was using gradient from 5 to 85% acetonitrile in water with 0.1% TFA in 15 minutes at a flow rate of 1 mL/min ($t_R$=10.8 min). The eluting components were visualized by UV (DAD) and radio-detection flow monitors.

The radiochemical purity of $^{177}$Lu-compound 1 at EOS (end of synthesis) and after 3 h were >99% by iTLC and HPLC with molar activity 44.57 MBq/nmol.

Radiolabeling of $^{225}$Ac-Compound 1

5 μL aliquot of compound 1 precursor (1 mM, 5 nmol) was dissolved in 138 μL 0.2 M NaOAc (pH 5.5) and 20 μL EtOH (10%), followed by 37.3 μL, 1.06 MBq of $^{225}AcCl_3$. Then, the reaction was heated to 95° C. for 15 minutes. After cooling down, the reaction mixture was diluted with 3800 μL formulation buffer. For quality control, the formulated solutions were analyzed using radio-TLC (iTLC) and radio-HPLC. iTLCs were run on SG paper plates, with 0.1 M sodium citrate (5% MeOH) as the eluent. The developed plates were then read using a radio-TLC reading instrument. HPLC analyses were performed using an analytical Luna column with fraction collection. The mobile phase condition was using gradient from 5 to 85% acetonitrile in water with 0.1% TFA in 15 minutes at a flow rate of 1 mL/min ($t_R$=10.8 min). The eluting components were visualized by UV (DAD) and radio-detection flow monitors. To detect the emissions resulting from the decay chain of $^{225}$Ac, all collected fractions from HPLC were allowed to equilibrate for 6 h, then were placed in a Gamma counting instrument for subsequent measurements. The radiochemical purity of $^{225}$Ac-compound 1 at EOS (end of synthesis) and after 3 h was >97% by iTLC and >92% by HPLC with molar activity of 0.17 MBq/nmol.

Example 2: In Vitro Competition Binding Assay

PC-3 cells were seeded at 2×10$^5$ cells/well in 24-well poly-D-lysine plates 24-48 hours prior to the experiment. The growth medium was replaced by 400 μL of reaction medium (RPMI 1640 containing 2 mg/mL BSA, 4.8 mg/mL HEPES, 1 U/mL penicillin G and 1 μg/mL streptomycin). Cells were incubated for 30-60 min at 37° C. Peptides as provided in Table 9 below provided in 50 μL of decreasing concentrations (10 μM to 1 pM) and 50 μL of 0.011 nM [$^{125}$I-Tyr$^4$]bombesin were added to wells. The cells were incubated with moderate agitation for 1 h at 27° C., washed twice with ice-cold PBS, harvested by trypsinization, and measured for radioactivity on the gamma counter. Data were analyzed using nonlinear regression (one binding site model for competition assay) with GraphPad Prism 8.

TABLE 2

Binding affinities (Ki, nM) of GRPR-targeting peptides

| Compound | Binding affinities Ki (n = 1-4) |
|---|---|
| La-Compound 1 | 7.80 ± 3.30 |
| Lu-Compound 1 | 11.64 ± 6.69 |

TABLE 2-continued

Binding affinities (Ki, nM) of GRPR-targeting peptides

| Compound | Binding affinities Ki (n = 1-4) |
|---|---|
| La-Compound 2 | 62.47 ± 31.47 |
| La-Compound 3 | 8.70 ± 0.39 |
| La-Compound 4 | 15.83 ± 7.09 |
| La-Compound 5 | 46.02 ± 16.08 |
| Lu-Compound 5 | 20.28 ± 4.36 |
| La-Compound 6 | 4.54 ± 0.78 |
| La-Compound 7 | 1.71 ± 0.46 |
| La-Compound 23 | 18.31 ± 10.05 |
| La-Compound 8 | 1.05 ± 0.52 |
| La-Compound 19 | 9.25 ± 3.27 |
| La-Compound 9 | 1.71 ± 0.95 |
| Lu-Compound 9 | 3.38 ± 0.55 |
| La-Compound 10 | 1.78 ± 1.19 |
| Lu-Compound 10 | 5.03 ± 0.27 |
| La-Compound 11 | 1.12 ± 0.26 |
| La-Compound 14 | >100 |
| La-Compound 17 | >100 |
| La-Compound 20 | 94.45 ± 49.12 |
| La-Compound 24 | 9.26 ± 6.39 |
| La-Compound 34 | 2.00 ± 0.68 |
| Lu-Compound 34 | 7.62 ± 4.45 |
| La-Compound 35 | 3.81 ± 1.93 |
| La-Compound 36 | 12.39 ± 2.21 |
| Lu-Compound 36 | 6.51 ± 2.20 |

Example 3: Ex Vivo Biodistribution in PC-3 Tumor-Bearing Mice

Biodistribution studies were performed using male NOD.Cg-Rag1$^{tm1Mom}$ Il2rg$^{tm1Wjl}$/SzJ (NRG) mice and conducted according to the guidelines established by the Canadian Council on Animal Care and approved by Animal Ethics Committee of the University of British Columbia. For tumor inoculations, mice were anesthetized by inhalation with 2% isoflurane in oxygen and implanted subcutaneously with 5×10$^6$ PC-3 cells below the left shoulder. Imaging and biodistribution studies were performed only after tumors grew to 5-8 mm in diameter.

For ex vivo biodistribution studies, mice were injected with ~20 kBq of the $^{225}$Ac-labeled tracer. Mice were euthanized at various times (1 h, 4 h, 24 h, 48 h, 72 h, 96 h, and/or 120 h p.i.), blood was drawn from heart, and organs/tissues of interest were collected, rinsed with PBS, blotted dry, weighed, and counted using an automated gamma counter. The uptake in each organ/tissue was normalized to the injected dose and expressed as the percentage of the injected dose per gram of tissue (% ID/g).

Biodistribution data is shown in Tables 3-11.

TABLE 3

Biodistribution data (average % ID/g with ± SD at 1 h, 4 h, 24 h, 48 h, and 120 h post-injection) of $^{225}$Ac-Compound 1 in mice bearing PC-3 tumor xenografts (8.15 ± 0.29 kBq).

| | Time (h) | | | | | | | | | | | | | | |
|---|---|---|---|---|---|---|---|---|---|---|---|---|---|---|---|
| | 1 | | | 4 | | | 24 | | | 48 | | | 120 | | |
| Organs | AVG | SD | n | AVG | SD | n | AVG | SD | n | AVG | SD | n | AVG | SD | n |
| Blood | 0.37 | 0.06 | 4 | 0.11 | 0.03 | 4 | — | — | — | — | — | — | — | — | — |
| Tumor | 10.87 | 1.01 | 4 | 14.23 | 3.90 | 4 | 17.09 | 2.41 | 4 | 10.71 | 1.98 | 4 | 3.41 | 0.70 | 4 |
| Pancreas | 57.60 | 9.16 | 4 | 38.62 | 7.54 | 4 | 4.86 | 0.80 | 4 | 3.29 | 0.69 | 4 | 2.05 | 0.41 | 4 |
| Kidneys | 2.11 | 0.45 | 4 | 1.74 | 0.19 | 4 | 0.85 | 0.10 | 4 | 0.51 | 0.17 | 4 | 0.22 | 0.08 | 4 |
| Liver | 0.41 | 0.04 | 4 | 0.42 | 0.10 | 4 | 0.37 | 0.06 | 4 | 0.36 | 0.07 | 4 | 0.43 | 0.08 | 4 |
| Small intestine | 3.57 | 1.64 | 4 | 2.74 | 0.63 | 4 | 0.32 | 0.09 | 4 | 0.12 | 0.04 | 4 | 0.06 | 0.01 | 3 |

TABLE 3-continued

Biodistribution data (average % ID/g with ± SD at 1 h, 4 h, 24 h, 48 h, and 120 h post-injection) of $^{225}$Ac-Compound 1 in mice bearing PC-3 tumor xenografts (8.15 ± 0.29 kBq).

| | Time (h) | | | | | | | | | | | | | | |
|---|---|---|---|---|---|---|---|---|---|---|---|---|---|---|---|
| | 1 | | | 4 | | | 24 | | | 48 | | | 120 | | |
| Organs | AVG | SD | n | AVG | SD | n | AVG | SD | n | AVG | SD | n | AVG | SD | n |
| Large intestine | 3.41 | 0.15 | 4 | 2.31 | 0.54 | 4 | 0.76 | 0.20 | 4 | 0.29 | 0.08 | 4 | 0.10 | 0.03 | 4 |
| Tumor/Blood | 29.92 | 2.78 | 4 | 133.28 | 44.76 | 4 | — | — | — | — | — | — | — | — | — |
| Tumor/Kidneys | 5.27 | 0.74 | 4 | 8.09 | 1.53 | 4 | 20.00 | 1.93 | 4 | 21.53 | 2.93 | 4 | 16.40 | 2.99 | 4 |
| Tumor/liver | 26.74 | 3.16 | 4 | 33.59 | 6.29 | 4 | 46.39 | 2.78 | 4 | 30.33 | 2.85 | 4 | 7.91 | 0.25 | 4 |
| Tumor/pancreas | 0.19 | 0.02 | 4 | 0.37 | 0.05 | 4 | 3.54 | 0.34 | 4 | 3.27 | 0.15 | 4 | 1.66 | 0.03 | 4 |

TABLE 4

Biodistribution data (average % ID/g with ± SD at 1 h, 4 h, 24 h, 48 h, and 120 h post-injection) of $^{225}$Ac-Compound 4 in mice bearing PC-3 tumor xenografts (8.10 ± 1.42 kBq).

| | Time (h) | | | | | | | | | | | | | | |
|---|---|---|---|---|---|---|---|---|---|---|---|---|---|---|---|
| | 1 | | | 4 | | | 24 | | | 48 | | | 120 | | |
| Organs | AVG | SD | n | AVG | SD | n | AVG | SD | n | AVG | SD | n | AVG | SD | n |
| Blood | 0.29 | 0.09 | 4 | 0.08 | 0.04 | 4 | — | — | — | — | — | — | — | — | — |
| Tumor | 9.60 | 2.84 | 4 | 12.15 | 2.92 | 4 | 11.90 | 2.85 | 4 | 6.64 | 2.69 | 4 | 2.67 | 0.80 | 4 |
| Pancreas | 24.51 | 5.58 | 4 | 8.62 | 1.54 | 4 | 0.83 | 0.15 | 4 | 1.00 | 0.33 | 4 | 0.79 | 0.22 | 4 |
| Kidneys | 1.80 | 0.44 | 4 | 2.05 | 0.52 | 4 | 0.93 | 0.14 | 4 | 0.80 | 0.25 | 4 | 0.48 | 0.17 | 4 |
| Liver | 0.28 | 0.05 | 4 | 0.31 | 0.08 | 4 | 0.48 | 0.06 | 4 | 0.60 | 0.24 | 4 | 0.84 | 0.22 | 4 |
| Small intestine | 1.90 | 0.47 | 4 | 1.05 | 0.17 | 4 | 0.13 | 0.04 | 4 | 0.08 | 0.02 | 4 | 0.06 | 0.03 | 4 |
| Large intestine | 1.81 | 0.40 | 4 | 1.02 | 0.28 | 3 | 0.41 | 0.01 | 3 | 0.12 | 0.04 | 4 | 0.15 | 0.10 | 4 |
| Tumor/Blood | 34.89 | 8.76 | 4 | 184.46 | 103.09 | 4 | — | — | — | — | — | — | — | — | — |
| Tumor/Kidneys | 5.32 | 0.52 | 4 | 5.99 | 0.76 | 4 | 12.64 | 1.71 | 4 | 8.26 | 1.75 | 4 | 5.68 | 0.43 | 4 |
| Tumor/liver | 34.57 | 8.51 | 4 | 38.99 | 2.44 | 4 | 24.60 | 5.08 | 4 | 11.17 | 2.18 | 4 | 3.17 | 0.15 | 4 |
| Tumor/pancreas | 0.39 | 0.05 | 4 | 1.40 | 0.10 | 4 | 14.25 | 2.14 | 4 | 6.58 | 0.46 | 4 | 3.41 | 0.45 | 4 |

TABLE 5

Biodistribution data (average % ID/g with ± SD at 1 h, 4 h, 24 h, 48 h, and 96 h post-injection) of $^{225}$Ac-Compound 36 in mice bearing PC-3 tumor xenografts (8.59 ± 0.49 kBq).

| | Time (h) | | | | | | | | | | | | | | |
|---|---|---|---|---|---|---|---|---|---|---|---|---|---|---|---|
| | 1 | | | 4 | | | 24 | | | 48 | | | 96 | | |
| Organs | AVG | SD | n | AVG | SD | n | AVG | SD | n | AVG | SD | n | AVG | SD | n |
| Blood | 1.54 | 0.24 | 4 | 0.13 | 0.05 | 4 | — | — | — | — | — | — | — | — | — |
| Tumor | 7.61 | 1.11 | 4 | 8.07 | 0.77 | 4 | 4.51 | 0.51 | 4 | 2.70 | 0.27 | 4 | 0.98 | 0.05 | 4 |
| Pancreas | 14.51 | 1.92 | 4 | 2.05 | 0.22 | 4 | 0.59 | 0.07 | 4 | 0.60 | 0.13 | 4 | 0.37 | 0.06 | 4 |
| Kidneys | 6.82 | 1.10 | 4 | 5.21 | 0.33 | 4 | 2.51 | 0.35 | 4 | 1.26 | 0.13 | 4 | 0.69 | 0.11 | 4 |
| Liver | 11.85 | 2.18 | 4 | 9.42 | 0.68 | 4 | 7.44 | 0.42 | 4 | 5.94 | 0.68 | 4 | 6.56 | 0.33 | 4 |
| Small intestine | 2.14 | 0.61 | 4 | 0.60 | 0.15 | 4 | 0.16 | 0.02 | 4 | 0.14 | 0.05 | 4 | 0.04 | 0.00 | 3 |
| Large intestine | 1.52 | 0.38 | 4 | 0.99 | 0.25 | 4 | 0.46 | 0.10 | 4 | 0.29 | 0.11 | 4 | 0.12 | 0.03 | 4 |
| Tumor/Blood | 4.95 | 0.48 | 4 | 70.13 | 27.96 | 4 | — | — | — | — | — | — | — | — | — |
| Tumor/Kidneys | 1.12 | 0.12 | 4 | 1.55 | 0.12 | 4 | 1.80 | 0.09 | 4 | 2.16 | 0.31 | 4 | 1.46 | 0.22 | 4 |
| Tumor/liver | 0.65 | 0.05 | 4 | 0.86 | 0.03 | 4 | 0.60 | 0.05 | 4 | 0.46 | 0.07 | 4 | 0.15 | 0.01 | 4 |
| Tumor/pancreas | 0.53 | 0.06 | 4 | 3.95 | 0.22 | 4 | 7.71 | 0.86 | 4 | 4.71 | 1.28 | 4 | 2.73 | 0.42 | 4 |

TABLE 6

Biodistribution data (average % ID/g with ± SD at 1 h, 4 h, 23 h, 102 h, and 120 h post-injection) of $^{225}$Ac-Compound 2 in mice bearing PC-3 tumor xenografts (19.71 ± 0.81 kBq).

| | Time (h) | | | | | | | | | | | | | | |
|---|---|---|---|---|---|---|---|---|---|---|---|---|---|---|---|
| | 1 | | | 4 | | | 23 | | | 102 | | | 120 | | |
| Organs | AVG | SD | n | AVG | SD | n | AVG | SD | n | AVG | SD | n | AVG | SD | n |
| Blood | 0.68 | 0.11 | 4 | — | — | — | — | — | — | — | — | — | — | — | — |
| Tumor | 9.45 | 1.52 | 4 | 7.79 | 0.95 | 4 | 2.32 | 0.11 | 4 | 0.56 | 0.08 | 4 | 0.54 | 0.11 | 4 |
| Muscle | 0.18 | 0.06 | 2 | — | — | — | — | — | — | — | — | — | — | — | — |
| Pancreas | 6.17 | 0.97 | 4 | 0.52 | 0.07 | 4 | 0.22 | 0.09 | 3 | 0.20 | 0.00 | 2 | — | — | — |
| Kidneys | 2.90 | 0.19 | 4 | 1.99 | 0.31 | 4 | 0.93 | 0.07 | 4 | 036 | 0.03 | 4 | 0.36 | 0.08 | 4 |
| Liver | 0.49 | 0.05 | 4 | 0.48 | 0.06 | 4 | 0.53 | 0.04 | 4 | 0.63 | 0.06 | 4 | 0.56 | 0.04 | 4 |
| Small intestine | 0.89 | 0.20 | 4 | 0.32 | 0.17 | 4 | 0.04 | 0.01 | 4 | — | — | — | 0.02 | 0.00 | 2 |
| Large intestine | 0.76 | 0.13 | 4 | 0.16 | 0.03 | 4 | 0.11 | 0.06 | 4 | — | — | — | — | — | — |
| Tumor/Muscle | 54.93 | 15.73 | 2 | — | — | — | — | — | — | — | — | — | — | — | — |
| Tumor/Blood | 14.30 | 3.59 | 4 | — | — | — | — | — | — | — | — | — | — | — | — |
| Tumor/Kidneys | 3.25 | 0.44 | 4 | 3.95 | 0.34 | 4 | 2.50 | 0.27 | 4 | 1.55 | 0.20 | 4 | 1.50 | 0.10 | 4 |
| Tumor/liver | 19.16 | 1.63 | 4 | 16.32 | 1.01 | 4 | 4.37 | 0.38 | 4 | 0.90 | 0.14 | 4 | 0.97 | 0.14 | 4 |
| Tumor/pancreas | 1.55 | 0.26 | 4 | 15.27 | 3.96 | 4 | 11.54 | 4.02 | 3 | 2.75 | 0.61 | 2 | — | — | — |

TABLE 7

Biodistribution data (average % ID/g with ± SD at 1 h, 4 h, 23 h, 46 h, and 166 h post-injection) of $^{225}$Ac-Compound 3 in mice bearing PC-3 tumor xenografts (9.10 ± 0.36 kBq).

| | Time (h) | | | | | | | | | | | | | | |
|---|---|---|---|---|---|---|---|---|---|---|---|---|---|---|---|
| | 1 | | | 4 | | | 23 | | | 46 | | | 166 | | |
| Organs | AVG | SD | n | AVG | SD | n | AVG | SD | n | AVG | SD | n | AVG | SD | n |
| Blood | 0.51 | 0.05 | 4 | 0.09 | 0.01 | 4 | — | — | — | — | — | — | — | — | — |
| Tumor | 15.36 | 0.78 | 4 | 14.14 | 2.16 | 4 | 10.10 | 1.18 | 4 | 5.90 | 1.37 | 4 | 1.22 | 0.38 | 4 |
| Muscle | 0.21 | 0.02 | 3 | — | — | — | — | — | — | — | — | — | — | — | — |
| Spleen | 0.92 | 0.34 | 4 | — | — | — | — | — | — | — | — | — | — | — | — |
| Pancreas | 23.59 | 2.66 | 4 | 5.56 | 1.79 | 4 | 0.68 | 0.10 | 4 | 0.63 | 0.23 | 4 | 0.59 | 0.16 | 4 |
| Kidneys | 3.10 | 0.46 | 4 | 2.37 | 0.22 | 4 | 1.25 | 0.09 | 4 | 0.92 | 0.17 | 4 | 0.38 | 0.06 | 4 |
| Liver | 0.39 | 0.05 | 4 | 0.27 | 0.03 | 4 | 0.39 | 0.02 | 4 | 0.50 | 0.12 | 4 | 0.74 | 0.26 | 4 |
| Small intestine | 2.68 | 0.39 | 4 | 1.08 | 0.38 | 4 | 0.09 | 0.03 | 4 | 0.06 | 0.02 | 4 | 0.04 | 0.01 | 4 |
| Large intestine | 1.78 | 0.12 | 4 | 0.66 | 0.15 | 4 | 0.18 | 0.07 | 4 | 0.12 | 0.01 | 4 | 0.08 | 0.03 | 4 |
| Tumor/Muscle | 76.26 | 4.70 | 3 | — | — | — | — | — | — | — | — | — | — | — | — |
| Tumor/Blood | 30.26 | 2.87 | 4 | 163.79 | 33.44 | 4 | — | — | — | — | — | — | — | — | — |
| Tumor/Kidneys | 5.03 | 0.74 | 4 | 5.96 | 0.44 | 4 | 8.14 | 1.05 | 4 | 6.39 | 0.65 | 4 | 3.18 | 0.58 | 4 |
| Tumor/liver | 39.67 | 4.46 | 4 | 51.27 | 3.62 | 4 | 25.76 | 1.96 | 4 | 12.02 | 1.77 | 4 | 1.91 | 0.24 | 4 |
| Tumor/pancreas | 0.66 | 0.08 | 4 | 2.64 | 0.44 | 4 | 14.92 | 0.69 | 4 | 9.92 | 2.14 | 4 | 2.32 | 0.34 | 4 |

TABLE 8

Biodistribution data (average % ID/g with ± SD at 1 h, 4 h, 24 h, 95 h, and 117 h post-injection) of $^{225}$Ac-Compound 8 in mice bearing PC-3 tumor xenografts (6.71 ± 0.31 kBq).

| | Time (h) | | | | | | | | | | | | | | |
|---|---|---|---|---|---|---|---|---|---|---|---|---|---|---|---|
| | 1 | | | 4 | | | 24 | | | 95 | | | 117 | | |
| Organs | AVG | SD | n | AVG | SD | n | AVG | SD | n | AVG | SD | n | AVG | SD | n |
| Blood | 2.98 | 0.22 | 4 | 0.41 | 0.04 | 4 | — | — | — | — | — | — | 0.06 | 0.01 | 2 |
| Tumor | 16.71 | 2.62 | 4 | 19.59 | 2.62 | 4 | 10.17 | 2.84 | 4 | 3.38 | 0.51 | 4 | 2.66 | 0.01 | 3 |
| Muscle | 0.21 | 0.02 | 4 | — | — | — | — | — | — | — | — | — | 0.30 | 0.12 | 2 |
| Spleen | 1.00 | 0.24 | 3 | — | — | — | — | — | — | — | — | — | 1.92 | 0.58 | 3 |
| Pancreas | 34.51 | 3.18 | 4 | 7.29 | 0.95 | 4 | 1.15 | 0.38 | 3 | 1.00 | 0.15 | 4 | 1.17 | 0.23 | 4 |
| Kidneys | 6.19 | 0.47 | 4 | 3.21 | 0.13 | 4 | 1.80 | 0.33 | 4 | 0.95 | 0.07 | 4 | 0.73 | 0.14 | 4 |
| Liver | 4.35 | 0.37 | 4 | 2.56 | 0.24 | 4 | 2.24 | 0.37 | 4 | 2.66 | 0.26 | 4 | 2.47 | 0.35 | 4 |
| Small intestine | 3.45 | 0.17 | 4 | 0.92 | 0.16 | 4 | 0.16 | 0.03 | 4 | 0.09 | 0.02 | 4 | 0.12 | 0.02 | 4 |
| Large intestine | 3.02 | 0.44 | 4 | 1.04 | 0.07 | 4 | 0.27 | 0.04 | 4 | 0.17 | 0.03 | 4 | 0.25 | 0.03 | 4 |
| Tumor/Muscle | 69.96 | 0.58 | 4 | — | — | — | — | — | — | — | — | — | 9.92 | 4.22 | 2 |
| Tumor/Blood | 5.60 | 0.72 | 4 | 48.12 | 8.10 | 4 | — | — | — | — | — | — | 41.37 | 13.80 | 2 |

TABLE 8-continued

Biodistribution data (average % ID/g with ± SD at 1 h, 4 h, 24 h, 95 h, and 117 h post-injection) of $^{225}$Ac-Compound 8 in mice bearing PC-3 tumor xenografts (6.71 ± 0.31 kBq).

| | Time (h) | | | | | | | | | | | | | | |
|---|---|---|---|---|---|---|---|---|---|---|---|---|---|---|---|
| | 1 | | | 4 | | | 24 | | | 95 | | | 117 | | |
| Organs | AVG | SD | n | AVG | SD | n | AVG | SD | n | AVG | SD | n | AVG | SD | n |
| Tumor/Kidneys | 2.69 | 0.31 | 4 | 6.09 | 0.64 | 4 | 5.60 | 0.79 | 4 | 3.55 | 0.41 | 4 | 3.39 | 0.32 | 3 |
| Tumor/liver | 3.83 | 0.34 | 4 | 7.66 | 1.04 | 4 | 4.47 | 0.57 | 4 | 1.27 | 0.19 | 4 | 1.01 | 0.06 | 3 |
| Tumor/pancreas | 0.48 | 0.07 | 4 | 2.69 | 0.05 | 4 | 8.50 | 0.22 | 3 | 3.37 | 0.36 | 4 | 2.11 | 0.20 | 3 |

TABLE 9

Biodistribution data (average % ID/g with ± SD at 1 h, 4 h, 23 h, 101 h, and 137 h post-injection) of $^{225}$Ac-Compound 10 in mice bearing PC-3 tumor xenografts (16.93 ± 0.35 kBq).

| | Time (h) | | | | | | | | | | | | | | |
|---|---|---|---|---|---|---|---|---|---|---|---|---|---|---|---|
| | 1 | | | 4 | | | 23 | | | 101 | | | 137 | | |
| Organs | AVG | SD | n | AVG | SD | n | AVG | SD | n | AVG | SD | n | AVG | SD | n |
| Blood | 2.93 | 0.24 | 4 | 1.00 | 0.17 | 4 | 0.06 | 0.01 | 3 | — | — | — | — | — | — |
| Tumor | 10.76 | 1.25 | 4 | 18.70 | 1.97 | 4 | 23.33 | 1.98 | 4 | 9.82 | 0.80 | 4 | 6.73 | 0.61 | 4 |
| Muscle | 0.28 | 0.09 | 4 | 0.10 | 0.02 | 3 | — | — | — | — | — | — | — | — | — |
| Spleen | 0.92 | 0.14 | 4 | 0.37 | 0.13 | 3 | 0.46 | 0.12 | 2 | — | — | — | 0.62 | 0.22 | 3 |
| Pancreas | 63.20 | 4.02 | 4 | 42.59 | 4.67 | 4 | 6.96 | 0.60 | 4 | 3.67 | 0.23 | 4 | 3.48 | 1.05 | 4 |
| Kidneys | 5.17 | 0.39 | 4 | 3.18 | 0.32 | 4 | 1.16 | 0.09 | 4 | 0.46 | 0.00 | 3 | 0.39 | 0.05 | 4 |
| Liver | 4.98 | 0.25 | 4 | 3.82 | 0.22 | 4 | 3.26 | 0.12 | 4 | 2.51 | 0.17 | 4 | 2.71 | 0.31 | 4 |
| Small intestine | 4.08 | 0.33 | 4 | 3.18 | 0.48 | 4 | 0.63 | 0.10 | 4 | 0.16 | 0.02 | 4 | 0.14 | 0.00 | 3 |
| Large intestine | 3.09 | 0.76 | 4 | 2.19 | 0.20 | 4 | 1.10 | 0.09 | 4 | 0.31 | 0.03 | 4 | 0.27 | 0.08 | 4 |
| Tumor/Muscle | 41.37 | 10.55 | 4 | 187.24 | 39.67 | 3 | — | — | — | — | — | — | — | — | — |
| Tumor/Blood | 3.69 | 0.44 | 4 | 18.89 | 1.91 | 4 | 390.35 | 40.65 | 3 | — | — | — | — | — | — |
| Tumor/Kidneys | 2.09 | 0.28 | 4 | 5.89 | 0.18 | 4 | 20.18 | 1.92 | 4 | 21.27 | 2.06 | 3 | 17.45 | 2.56 | 4 |
| Tumor/liver | 2.16 | 0.27 | 4 | 4.89 | 0.45 | 4 | 7.15 | 0.53 | 4 | 3.91 | 0.34 | 4 | 2.51 | 0.40 | 4 |
| Tumor/pancreas | 0.17 | 0.02 | 4 | 0.44 | 0.02 | 4 | 3.36 | 0.14 | 4 | 2.68 | 0.27 | 4 | 2.11 | 0.87 | 4 |

TABLE 10

Biodistribution data (average % ID/g with ± SD at 1 h, 4 h, 26 h, 48 h, and 118 h post-injection) of $^{225}$Ac-Compound 19 in mice bearing PC-3 tumor xenografts (20.79 ± 0.34 kBq).

| | Time (h) | | | | | | | | | | | | | | |
|---|---|---|---|---|---|---|---|---|---|---|---|---|---|---|---|
| | 1 | | | 4 | | | 26 | | | 48 | | | 118 | | |
| Organs | AVG | SD | n | AVG | SD | n | AVG | SD | n | AVG | SD | n | AVG | SD | n |
| Blood | 0.62 | 0.08 | 4 | 0.07 | 0.01 | 4 | 0.02 | 0.00 | 2 | — | — | — | — | — | — |
| Tumor | 10.91 | 0.47 | 4 | 4.88 | 0.02 | 4 | 1.47 | 0.24 | 4 | 1.05 | 0.11 | 4 | 0.40 | 0.05 | 4 |
| Muscle | 0.16 | 0.03 | 4 | — | — | — | — | — | — | — | — | — | 0.10 | 0.00 | 2 |
| Spleen | 0.61 | 0.25 | 3 | 0.50 | 0.01 | 2 | — | — | — | — | — | — | 0.49 | 0.09 | 3 |
| Pancreas | 8.63 | 1.47 | 4 | 0.95 | 0.27 | 4 | 0.34 | 0.10 | 4 | 0.37 | 0.05 | 4 | 0.35 | 0.06 | 4 |
| Kidneys | 3.20 | 0.25 | 4 | 2.21 | 0.24 | 4 | 1.13 | 0.24 | 4 | 1.02 | 0.20 | 4 | 0.52 | 0.09 | 4 |
| Liver | 0.72 | 0.06 | 4 | 0.63 | 0.06 | 4 | 0.64 | 0.13 | 4 | 0.87 | 0.23 | 4 | 0.68 | 0.13 | 4 |
| Small intestine | 1.24 | 0.25 | 4 | 0.42 | 0.23 | 4 | 0.08 | 0.02 | 4 | 0.05 | 0.02 | 4 | 0.03 | 0.00 | 4 |
| Large intestine | 1.04 | 0.12 | 4 | 0.36 | 0.08 | 4 | 0.32 | 0.10 | 4 | 0.09 | 0.02 | 4 | 0.04 | 0.01 | 4 |
| Tumor/Muscle | 68.30 | 14.50 | 4 | — | — | — | — | — | — | — | — | — | 4.58 | 0.29 | 2 |
| Tumor/Blood | 17.84 | 1.91 | 4 | 75.14 | 16.60 | 3 | 90.54 | 24.52 | 2 | — | — | — | — | — | — |
| Tumor/Kidneys | 3.42 | 0.25 | 4 | 2.33 | 0.13 | 3 | 1.31 | 0.07 | 4 | 1.06 | 0.21 | 4 | 0.79 | 0.09 | 4 |
| Tumor/liver | 15.25 | 1.19 | 4 | 8.13 | 0.77 | 3 | 2.32 | 0.11 | 4 | 1.24 | 0.18 | 4 | 0.60 | 0.06 | 4 |
| Tumor/pancreas | 1.29 | 0.20 | 4 | 5.99 | 0.80 | 3 | 4.49 | 0.62 | 4 | 2.88 | 0.36 | 4 | 1.20 | 0.03 | 3 |

TABLE 11

Biodistribution data (average % ID/g with ± SD at 1 h, 4 h, 22 h, 45 h, and 165 h post-injection) of $^{225}$Ac-Compound 34 in mice bearing PC-3 tumor xenografts (16.8 ± 0.18 kBq).

| | Time (h) | | | | | | | | | | | | | | |
|---|---|---|---|---|---|---|---|---|---|---|---|---|---|---|---|
| | 1 | | | 4 | | | 22 | | | 45 | | | 165 | | |
| Organs | AVG | SD | n | AVG | SD | n | AVG | SD | n | AVG | SD | n | AVG | SD | n |
| Blood | 6.13 | 0.49 | 4 | 2.95 | 0.49 | 4 | 0.16 | 0.09 | 4 | 0.02 | 0.00 | 3 | — | — | — |
| Tumor | 9.48 | 1.01 | 4 | 18.33 | 2.73 | 4 | 17.85 | 1.34 | 4 | 9.35 | 1.04 | 4 | 2.51 | 0.37 | 4 |
| Muscle | 0.36 | 0.13 | 4 | 0.25 | 0.08 | 4 | — | — | — | — | — | — | — | — | — |
| Spleen | 0.95 | 0.19 | 4 | 0.65 | 0.15 | 4 | 0.71 | 0.12 | 3 | 0.58 | 0.12 | 2 | — | — | — |
| Pancreas | 24.72 | 2.40 | 4 | 17.02 | 3.00 | 4 | 3.51 | 0.74 | 4 | 2.26 | 0.22 | 4 | 1.75 | 0.16 | 4 |
| Kidneys | 6.00 | 0.70 | 4 | 5.17 | 0.63 | 4 | 2.75 | 0.86 | 4 | 1.37 | 0.24 | 4 | 0.47 | 0.09 | 4 |
| Liver | 10.18 | 1.74 | 4 | 7.07 | 1.33 | 4 | 2.88 | 0.20 | 4 | 2.00 | 0.34 | 4 | 1.73 | 0.16 | 4 |
| Small intestine | 2.54 | 0.52 | 4 | 1.92 | 0.35 | 4 | 0.31 | 0.10 | 4 | 0.14 | 0.04 | 4 | 0.06 | 0.01 | 4 |
| Large intestine | 1.71 | 0.26 | 4 | 1.51 | 0.37 | 4 | 0.70 | 0.13 | 4 | 0.26 | 0.05 | 4 | 0.12 | 0.03 | 4 |
| Tumor/Muscle | 29.05 | 9.57 | 4 | 77.20 | 21.68 | 4 | — | — | — | — | — | — | — | — | — |
| Tumor/Blood | 1.56 | 0.26 | 4 | 6.21 | 0.27 | 4 | 142.03 | 77.19 | 4 | 495.84 | 40.31 | 3 | — | — | — |
| Tumor/Kidneys | 1.58 | 0.11 | 4 | 3.55 | 0.30 | 4 | 6.84 | 1.53 | 4 | 6.94 | 1.18 | 4 | 5.36 | 0.32 | 4 |
| Tumor/liver | 0.94 | 0.08 | 4 | 2.61 | 0.18 | 4 | 6.19 | 0.10 | 4 | 4.72 | 0.38 | 4 | 1.46 | 0.27 | 4 |
| Tumor/pancreas | 0.38 | 0.01 | 4 | 1.08 | 0.04 | 4 | 5.24 | 0.98 | 4 | 4.17 | 0.60 | 4 | 1.44 | 0.23 | 4 |

Example 4: Ex Vivo Biodistribution in PC-3 Tumor-Bearing Mice

Biodistribution studies were performed using male NOD.Cg-Rag1$^{tm1Mom}$ Il2rg$^{tm1WJl}$/SzJ (NRG) mice and conducted according to the guidelines established by the Canadian Council on Animal Care and approved by Animal Ethics Committee of the University of British Columbia. For tumor inoculations, mice were anesthetized by inhalation with 2% isoflurane in oxygen and implanted subcutaneously with $5\times10^6$ PC-3 cells below the left shoulder. Imaging and biodistribution studies were performed only after tumors grew to 5-8 mm in diameter.

For ex vivo biodistribution studies, mice were injected with ~1 MBq of the $^{177}$Lu-labeled tracer. Mice were euthanized at various times (1 h, 4 h, 24 h, 48 h, 72 h, and/or 120 h, 144 h p.i.), blood was drawn from heart, and organs/tissues of interest were collected, rinsed with PBS, blotted dry, weighed, and counted using an automated gamma counter. The uptake in each organ/tissue was normalized to the injected dose and expressed as the percentage of the injected dose per gram of tissue (% ID/g).

Biodistribution data is shown in Tables 12-14.

TABLE 12

Biodistribution data (average % ID/g with ± SD at 1 h, 4 h, 24 h, 72 h, and 120 h post-injection) of $^{177}$Lu-Compound 1 in mice bearing PC-3 tumor xenografts (1077.22 ± 32.65 kBq).

| | Time (h) | | | | | | | | | | | | | | |
|---|---|---|---|---|---|---|---|---|---|---|---|---|---|---|---|
| | 1 | | | 4 | | | 24 | | | 72 | | | 120 | | |
| Organs | AVG | SD | n | AVG | SD | n | AVG | SD | n | AVG | SD | n | AVG | SD | n |
| Blood | 0.47 | 0.10 | 4 | 0.03 | 0.01 | 4 | — | — | — | — | — | — | — | — | — |
| Tumor | 12.70 | 2.75 | 4 | 8.36 | 1.14 | 4 | 5.09 | 0.72 | 4 | 1.93 | 0.35 | 4 | 1.00 | 0.23 | 4 |
| Muscle | 0.10 | 0.06 | 4 | 0.03 | 0.02 | 4 | — | — | — | — | — | — | — | — | — |
| Spleen | 0.28 | 0.08 | 4 | 0.11 | 0.05 | 4 | 0.08 | 0.01 | 3 | — | — | — | 0.10 | 0.03 | 2 |
| Pancreas | 11.55 | 1.62 | 4 | 1.18 | 0.42 | 4 | 0.38 | 0.07 | 4 | 0.21 | 0.05 | 3 | 0.12 | 0.00 | 3 |
| Kidneys | 2.63 | 0.53 | 4 | 1.64 | 0.20 | 4 | 0.59 | 0.06 | 4 | 0.20 | 0.03 | 4 | 0.11 | 0.02 | 4 |
| Liver | 0.38 | 0.06 | 4 | 0.21 | 0.03 | 4 | 0.14 | 0.00 | 3 | 0.08 | 0.01 | 4 | 0.07 | 0.01 | 4 |
| Small intestine | 1.51 | 0.24 | 4 | 0.40 | 0.14 | 4 | 0.03 | 0.00 | 3 | 0.04 | 0.01 | 4 | 0.01 | 0.00 | 4 |
| Large intestine | 0.94 | 0.21 | 4 | 0.33 | 0.07 | 4 | 0.12 | 0.10 | 4 | 0.12 | 0.03 | 4 | 0.02 | 0.00 | 4 |
| Tumor/Muscle | 145.30 | 52.22 | 4 | 410.76 | 213.84 | 4 | — | — | — | — | — | — | — | — | — |
| Tumor/Blood | 27.11 | 2.44 | 4 | 325.78 | 74.76 | 4 | — | — | — | — | — | — | — | — | — |
| Tumor/Kidneys | 4.83 | 0.45 | 4 | 5.11 | 0.52 | 4 | 8.63 | 0.62 | 4 | 9.39 | 0.64 | 4 | 9.26 | 1.19 | 4 |
| Tumor/liver | 33.54 | 5.89 | 4 | 40.62 | 4.43 | 4 | 37.31 | 6.44 | 3 | 23.49 | 3.68 | 4 | 13.12 | 2.12 | 4 |
| Tumor/pancreas | 1.09 | 0.12 | 4 | 7.59 | 1.83 | 4 | 13.57 | 0.78 | 4 | 9.12 | 0.95 | 3 | 7.80 | 1.90 | 3 |

TABLE 13

Biodistribution data (average % ID/g with ± SD at 1 h, 4 h, 26 h, 46 h, and 120 h post-injection) of $^{177}$Lu-Compound 9 in mice bearing PC-3 tumor xenografts (0.93 ± 0.04 MBq).

| | Time (h) | | | | | | | | | | | | | | |
|---|---|---|---|---|---|---|---|---|---|---|---|---|---|---|---|
| | 1 | | | 4 | | | 26 | | | 46 | | | 120 | | |
| Organs | AVG | SD | n | AVG | SD | n | AVG | SD | n | AVG | SD | n | AVG | SD | n |
| Blood | 2.28 | 0.24 | 5 | 0.51 | 0.06 | 5 | 0.01 | 0.00 | 4 | 0.01 | 0.00 | 3 | — | — | — |
| Tumor | 17.23 | 1.14 | 5 | 25.59 | 1.65 | 5 | 19.43 | 2.33 | 5 | 15.60 | 2.46 | 5 | 3.85 | 0.42 | 5 |
| Muscle | 0.22 | 0.05 | 5 | 0.08 | 0.02 | 5 | — | — | — | — | — | — | — | — | — |
| Spleen | 0.56 | 0.08 | 4 | 0.39 | 0.06 | 5 | 0.19 | 0.03 | 5 | 0.21 | 0.06 | 5 | — | — | — |
| Pancreas | 53.20 | 3.34 | 5 | 21.58 | 3.97 | 5 | 2.06 | 0.30 | 5 | 1.63 | 0.42 | 5 | 0.27 | 0.03 | 5 |
| Kidneys | 5.48 | 0.10 | 5 | 3.52 | 0.52 | 5 | 1.11 | 0.21 | 5 | 0.76 | 0.18 | 5 | 0.21 | 0.04 | 5 |
| Liver | 3.22 | 0.20 | 5 | 2.05 | 0.24 | 5 | 0.88 | 0.21 | 5 | 0.64 | 0.17 | 5 | 0.17 | 0.02 | 5 |
| Small intestine | 4.52 | 0.45 | 5 | 2.30 | 0.51 | 5 | 0.26 | 0.05 | 5 | 0.13 | 0.03 | 4 | 0.02 | 0.00 | 4 |
| Large intestine | 2.97 | 0.33 | 5 | 1.72 | 0.12 | 5 | 0.78 | 0.32 | 5 | 0.34 | 0.07 | 5 | 0.07 | 0.01 | 5 |
| Tumor/Muscle | 81.74 | 21.37 | 5 | 337.44 | 66.36 | 5 | — | — | — | — | — | — | — | — | — |
| Tumor/Blood | 7.64 | 1.20 | 5 | 50.02 | 3.81 | 5 | 1445.62 | 162.25 | 5 | 2241.28 | 381.41 | 3 | — | — | — |
| Tumor/Kidneys | 3.14 | 0.18 | 5 | 7.35 | 0.69 | 5 | 18.37 | 0.24 | 4 | 20.83 | 2.84 | 5 | 19.19 | 1.84 | 5 |
| Tumor/liver | 5.36 | 0.41 | 5 | 12.55 | 0.67 | 5 | 22.56 | 2.89 | 5 | 25.08 | 3.21 | 5 | 22.26 | 2.46 | 5 |
| Tumor/pancreas | 0.32 | 0.02 | 5 | 1.21 | 0.17 | 5 | 9.49 | 0.61 | 5 | 9.79 | 1.43 | 5 | 14.14 | 1.35 | 5 |

TABLE 14

Biodistribution data (average % ID/g with ± SD at 1 h, 4 h, 27 h, 46 h, and 118 h post-injection) of $^{177}$Lu-Compound 10 in mice bearing PC-3 tumor xenografts (1.09 ± 0.06 MBq).

| | Time (h) | | | | | | | | | | | | | | |
|---|---|---|---|---|---|---|---|---|---|---|---|---|---|---|---|
| | 1 | | | 4 | | | 27 | | | 46 | | | 118 | | |
| Organs | AVG | SD | n | AVG | SD | n | AVG | SD | n | AVG | SD | n | AVG | SD | n |
| Blood | 3.72 | 0.49 | 5 | 0.98 | 0.11 | 5 | 0.02 | 0.00 | 4 | 0.01 | 0.01 | 5 | — | — | — |
| Tumor | 21.55 | 0.97 | 5 | 25.88 | 3.30 | 5 | 10.87 | 1.09 | 5 | 8.23 | 0.91 | 5 | 2.71 | 0.68 | 5 |
| Muscle | 0.24 | 0.03 | 5 | 0.10 | 0.01 | 5 | 0.02 | 0.01 | 5 | — | — | — | — | — | — |
| Spleen | 0.78 | 0.06 | 5 | 0.47 | 0.06 | 5 | 0.26 | 0.04 | 5 | 0.35 | 0.07 | 5 | 0.17 | 0.02 | 4 |
| Pancreas | 17.97 | 1.84 | 5 | 6.94 | 1.56 | 5 | 0.83 | 0.07 | 5 | 0.79 | 0.11 | 5 | 0.19 | 0.06 | 5 |
| Kidneys | 6.68 | 0.50 | 5 | 4.15 | 0.41 | 5 | 1.25 | 0.17 | 5 | 1.02 | 0.16 | 5 | 0.32 | 0.14 | 5 |
| Liver | 5.78 | 0.60 | 5 | 4.05 | 0.41 | 5 | 1.51 | 0.38 | 5 | 1.02 | 0.22 | 5 | 0.34 | 0.10 | 5 |
| Small intestine | 2.44 | 0.23 | 5 | 1.26 | 0.13 | 5 | 0.28 | 0.03 | 5 | 0.15 | 0.03 | 5 | 0.03 | 0.00 | 4 |
| Large intestine | 1.45 | 0.13 | 5 | 0.98 | 0.09 | 5 | 0.51 | 0.10 | 5 | 0.33 | 0.05 | 4 | 0.08 | 0.04 | 5 |
| Tumor/Muscle | 88.90 | 9.18 | 5 | 265.92 | 19.21 | 5 | 481.09 | 98.94 | 5 | — | — | — | — | — | — |
| Tumor/Blood | 5.87 | 0.81 | 5 | 26.55 | 1.97 | 5 | 610.83 | 40.74 | 4 | 687.86 | 278.17 | 5 | — | — | — |
| Tumor/Kidneys | 3.24 | 0.25 | 5 | 6.23 | 0.46 | 5 | 8.76 | 0.48 | 5 | 8.13 | 0.72 | 5 | 9.85 | 2.01 | 5 |
| Tumor/liver | 3.76 | 0.42 | 5 | 6.38 | 0.23 | 5 | 7.37 | 0.95 | 5 | 8.24 | 1.36 | 5 | 8.15 | 1.22 | 5 |
| Tumor/pancreas | 1.21 | 0.10 | 5 | 3.80 | 0.45 | 5 | 13.05 | 0.40 | 5 | 10.57 | 1.73 | 5 | 15.29 | 2.02 | 5 |

Example 5: Ex Vivo Biodistribution in PC-3 Tumor-Bearing Mice

Biodistribution studies were performed using male NOD.Cg-Rag1$^{tm1Mom}$ Il2rg$^{tm1Wjl}$/SzJ (NRG) mice and conducted according to the guidelines established by the Canadian Council on Animal Care and approved by Animal Ethics Committee of the University of British Columbia. For tumor inoculations, mice were anesthetized by inhalation with 2% isoflurane in oxygen and implanted subcutaneously with 5×10$^{6}$ PC-3 cells below the left shoulder. Imaging and biodistribution studies were performed only after tumors grew to 5-8 mm in diameter.

For ex vivo biodistribution studies, mice were injected with ~1 MBq of the $^{177}$Lu or ~20 kBq of the $^{225}$Ac-labeled tracer. Mice were euthanized at various times (1 h, 4 h, 24 h, 48 h, 72 h, and/or 120 h, 144 h p.i.), blood was drawn from heart, and organs/tissues of interest were collected, rinsed with PBS, blotted dry, weighed, and counted using an automated gamma counter. The uptake in each organ/tissue was normalized to the injected dose and expressed as the percentage of the injected dose per gram of tissue (% ID/g).

The biodistribution data was decayed from injection to its corresponding time point. Mono-exponential and/or bi-exponential fits were performed to generate the time-activity-curves for each organ. Activity under the curve (AUC) values were then integrated for each organ.

Comparative Time-Activity Integration (AUC) of various radiotracers is shown in Table 15.

TABLE 15

Comparative Time-Activity Integration (AUC) of Radiotracers Uptake in Tumor, Pancreas, and Kidney.

| Compounds | $AUC_{tumor}$ | $AUC_{Pancreas}$ | $AUC_{Kidney}$ | Tumor/Pan-creas | Tumor/Kidney |
|---|---|---|---|---|---|
| $^{225}$Ac-AMTG | 1004.1 | 1698.2 | 69.3 | 0.59 | 14.49 |
| $^{225}$Ac-RM2 | 564.4 | 1575.7 | 89.0 | 0.36 | 6.34 |
| $^{225}$Ac-Compound 2 | 271.1 | 17.0 | 92.4 | 15.91 | 2.93 |
| $^{225}$Ac-Compound 8 | 939.5 | 478.8 | 200.8 | 1.96 | 4.68 |
| $^{225}$Ac-Compound 10 | 2041.6 | 1403.7 | 121.5 | 1.45 | 16.80 |
| $^{225}$Ac-Compound 34 | 1254.7 | 675.6 | 232.6 | 1.86 | 5.39 |

TABLE 15-continued

Comparative Time-Activity Integration (AUC) of Radiotracers Uptake in Tumor, Pancreas, and Kidney.

| Compounds | $AUC_{tumor}$ | $AUC_{Pancreas}$ | $AUC_{Kidney}$ | Tumor/Pan-creas | Tumor/Kidney |
|---|---|---|---|---|---|
| $^{177}$Lu-AMTG | 879.8 | 167.9 | 55.8 | 5.24 | 15.77 |
| $^{177}$Lu-Compound 9 | 1346.4 | 351.0 | 99.8 | 3.84 | 13.50 |
| $^{177}$Lu-Compound 10 | 860.88 | 138.85 | 127.12 | 6.20 | 6.77 |

AUC unit: % ID/g · h

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes. It will be apparent to persons skilled in the art that a number of variations and modifications can be made without departing from the scope of the invention as defined in the following claims. The scope of the invention should therefore not be limited by the preferred embodiments set forth in the above Examples, but should be given the broadest interpretation consistent with the description as a whole.

What is claimed is:

1. A compound having the structure of Compound 9:

(Compound 9)

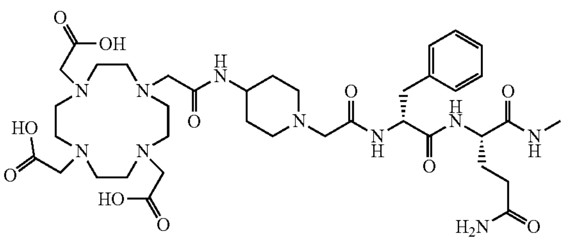

-continued

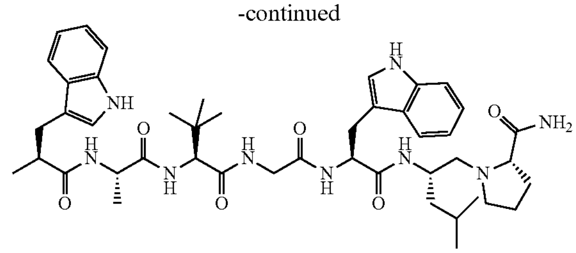

or a salt thereof, wherein the compound is optionally bound by a radiometal.

2. A composition comprising a compound, or a salt thereof, of claim 1 and a pharmaceutically acceptable carrier or excipient.

3. A method of imaging gastrin-releasing peptide receptor (GRPR)-expressing tissue in a subject, the method comprising:

administering to the subject a compound, or a salt thereof, of claim 1; and imaging tissue of the subject.

4. A method of treating cancer in a subject comprising, administering to the subject in need thereof a therapeutically effective amount of a compound, or a salt thereof, of claim 1.

5. The method of claim 4, wherein the cancer is prostate cancer, lung cancer, head and neck cancer, colon cancer, kidney cancer, ovarian cancer, liver cancer, pancreatic cancer, breast cancer, glioma or neuroblastoma.

6. The compound, or a salt thereof, of claim 1, wherein the compound, or a salt thereof, is bound by a radiometal selected from [$^{18}$F]AlF, $^{44}$Sc, $^{47}$Sc, $^{61}$Cu, $^{64}$Cu, $^{67}$Cu, $^{67}$Ga, $^{68}$Ga, $^{72}$As, $^{77}$As, $^{86}$Y $^{89}$Zr, $^{90}$Y $^{90}$Nb, $^{94m}$Tc, $^{99m}$Tc, $^{105}$Rh, $^{109}$Pd, $^{111}$In, $^{114m}$In, $^{117m}$Sn, $^{132}$La, $^{133}$La, $^{134}$La, $^{135}$La, $^{134}$Ce, $^{142}$Pr, $^{149}$Pm, $^{149}$Tb, $^{152}$Tb, $^{155}$Tb, $^{159}$Gd, $^{161}$Tb, $^{165}$Er, $^{166}$Ho, $^{175}$Yb, $^{177}$Lu, $^{186}$Re, $^{188}$Re, $^{198}$Au, $^{199}$Au, $^{203}$Pb, $^{211}$At, $^{212}$Pb, $^{212}$Bi, $^{213}$Bi, $^{225}$Ac, or $^{227}$Th.

7. The method of claim 3, wherein the compound, or salt thereof, is bound by a radiometal selected from $^{68}$Ga or $^{177}$Lu.

8. The method of claim 4, wherein the compound, or salt thereof, is bound by a radiometal selected from $^{177}$Lu or $^{225}$Ac.

9. The compound, or a salt thereof, of claim 1, wherein Compound 9 is bound by $^{177}$Lu.

10. A compound having the structure of Compound 10:

(Compound 10)

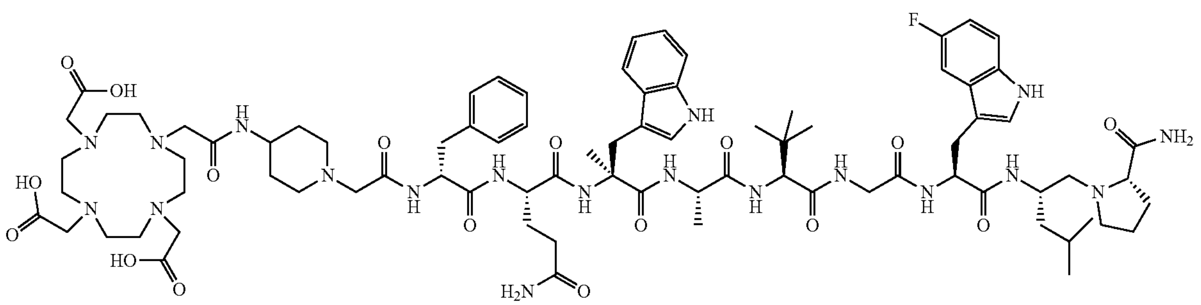

(Compound 10) or a salt thereof, wherein the compound is optionally bound by a radiometal.

11. A composition comprising a compound, or a salt thereof, of claim 10 and a pharmaceutically acceptable carrier or excipient.

12. A method of imaging gastrin-releasing peptide receptor (GRPR)-expressing tissue in a subject, the method comprising:

administering to the subject a compound, or a salt thereof, of claim 10; and imaging tissue of the subject.

13. A method of treating cancer in a subject comprising, administering to the subject in need thereof a therapeutically effective amount of a compound, or a salt thereof, of claim 10.

14. The method of claim 13, wherein the cancer is prostate cancer, lung cancer, head and neck cancer, colon cancer, kidney cancer, ovarian cancer, liver cancer, pancreatic cancer, breast cancer, glioma or neuroblastoma.

15. The compound, or a salt thereof, of claim 10, wherein the compound, or a salt thereof, is bound by a radiometal selected from [$^{18}$F]AlF, $^{44}$Sc, $^{47}$Sc, $^{61}$Cu, $^{64}$Cu, $^{67}$Cu, $^{67}$Ga, $^{68}$Ga, $^{72}$As, $^{77}$As, $^{86}$Y $^{89}$Zr, $^{90}$Y, $^{90}$Nb, $^{94m}$Tc, $^{99m}$Tc, $^{105}$Rh, $^{109}$Pd, $^{111}$In, $^{114m}$In, $^{117m}$Sn, $^{132}$La, $^{133}$La, $^{134}$La, $^{135}$La, $^{134}$Ce, $^{142}$Pr, $^{149}$Pm, $^{149}$Tb, $^{152}$Tb, $^{155}$Tb, $^{159}$Gd, $^{161}$Tb, $^{165}$Er, $^{166}$Ho, $^{175}$Yb, $^{177}$Lu, $^{186}$Re, $^{188}$Re, $^{198}$Au, $^{199}$Au, $^{203}$Pb, $^{211}$At, $^{212}$Pb, $^{212}$Bi, $^{213}$Bi, $^{225}$Ac, or $^{227}$Th.

16. The method of claim 12, wherein the compound, or salt thereof, is bound by a radiometal selected from $^{68}$Ga or $^{177}$Lu.

17. The method of claim 13, wherein the compound, or salt thereof, is bound by a radiometal selected from $^{177}$Lu or $^{225}$Ac.
18. The compound, or a salt thereof, of claim 10, wherein Compound 10 is bound by $^{225}$Ac.
19. A compound selected from:
(Compound 6)
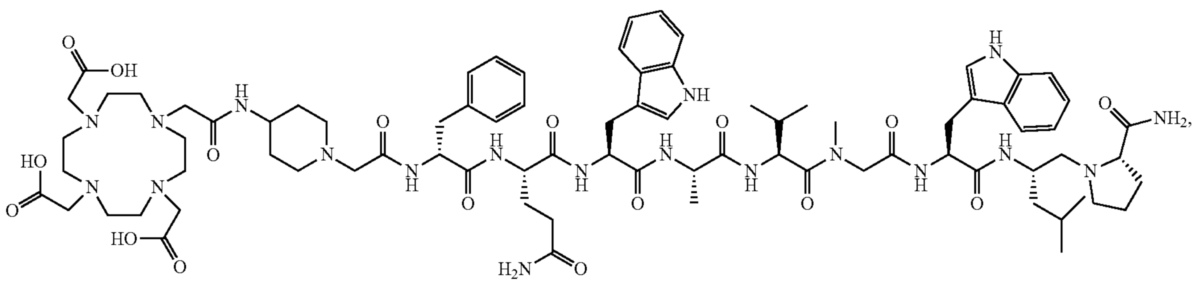
(Compound 6A)
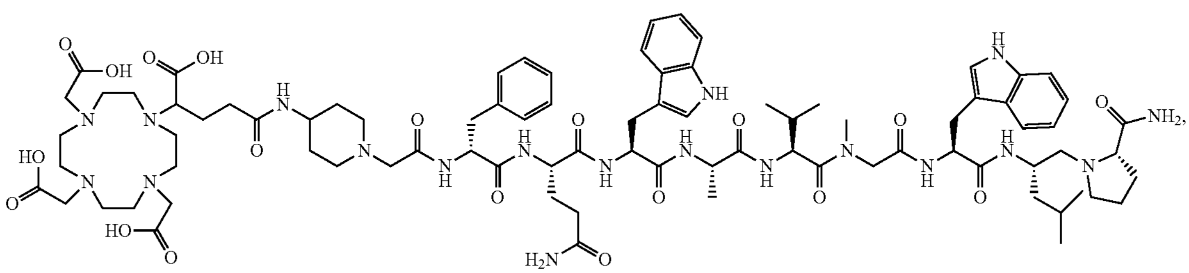
(Compound 8)
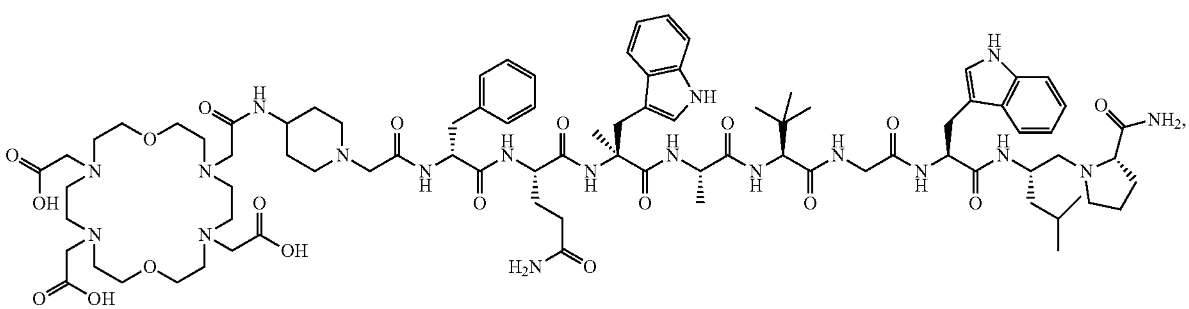
(Compound 8A)
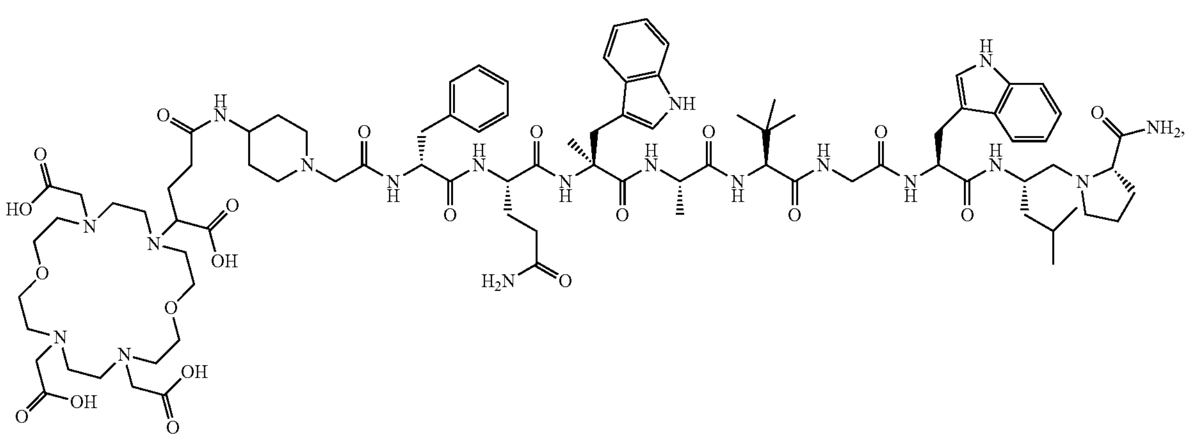

-continued (Compound 9A)

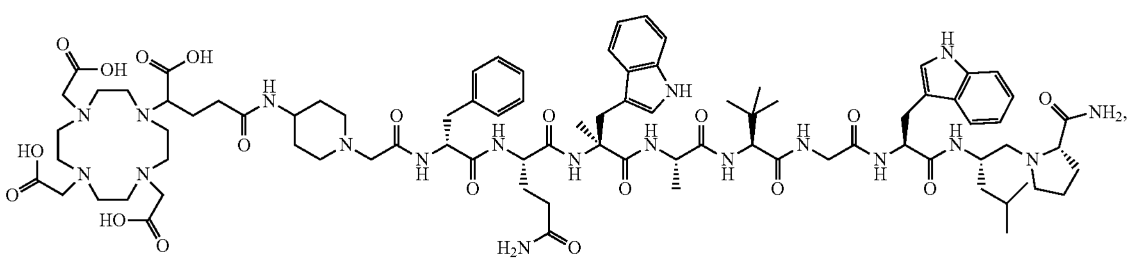

or (Compound 10A)

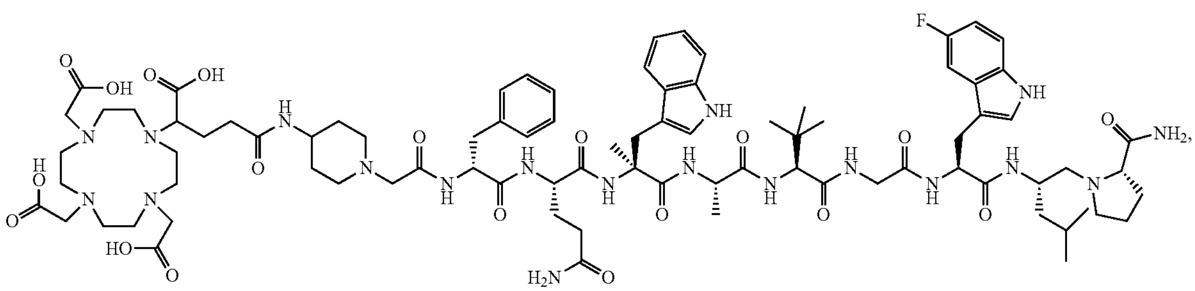

or a salt thereof, wherein the compound is optionally bound by a radiometal.

20. A composition comprising a compound, or a salt thereof, of claim 19 and a pharmaceutically acceptable carrier or excipient.

21. A method of imaging gastrin-releasing peptide receptor (GRPR)-expressing tissue in a subject, the method comprising:

administering to the subject a compound, or a salt thereof, of claim 19; and imaging tissue of the subject.

22. A method of treating cancer in a subject comprising, administering to the subject in need thereof a therapeutically effective amount of a compound, or a salt thereof, of claim 19.

23. The method of claim 22, wherein the cancer is prostate cancer, lung cancer, head and neck cancer, colon cancer, kidney cancer, ovarian cancer, liver cancer, pancreatic cancer, breast cancer, glioma or neuroblastoma.

24. The compound, or a salt thereof, of claim 19, wherein the compound, or a salt thereof, is bound by a radiometal selected from [$^{18}$F]AlF, $^{44}$Sc, $^{47}$Sc, $^{61}$Cu, $^{64}$Cu, $^{67}$Cu, $^{67}$Ga, $^{68}$Ga, $^{72}$As, $^{77}$As, $^{86}$Y $^{89}$Zr, $^{90}$Y, $^{90}$Nb, $^{94m}$Tc, $^{99m}$Tc, $^{105}$Rh, $^{109}$Pd, $^{111}$In, $^{114m}$In, $^{117m}$Sn, $^{132}$La, $^{133}$La, $^{134}$La, $^{135}$La, $^{134}$Ce, $^{142}$Pr, $^{149}$Pm, $^{149}$Tb, $^{152}$Tb, $^{155}$Tb, $^{159}$Gd, $^{161}$Tb, $^{165}$Er, $^{166}$Ho, $^{175}$Yb, $^{177}$Lu, $^{186}$Re, $^{188}$Re, $^{198}$Au, $^{199}$Au, $^{203}$Pb, $^{211}$At, $^{212}$Pb, $^{212}$Bi, $^{213}$Bi, $^{225}$Ac, or $^{227}$Th.

25. The method of claim 21, wherein the compound, or a salt thereof, is bound by a radiometal selected from $^{68}$Ga or $^{177}$Lu.

26. The method of claim 22, wherein the compound, or a salt thereof, is bound by a radiometal selected from $^{177}$Lu or $^{225}$Ac.

27. A compound having the structure of Compound 9:

(Compound 9)

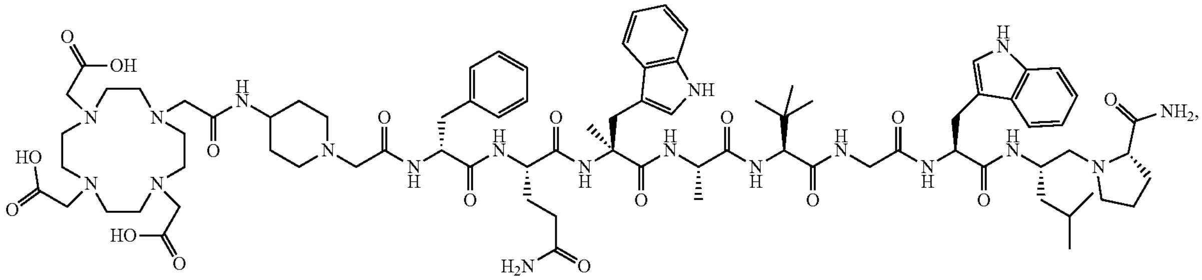

wherein the compound is bound by $^{177}$Lu.

28. A composition comprising a compound of claim 27 and a pharmaceutically acceptable carrier or excipient.

29. A method of treating cancer in a subject comprising, administering to the subject in need thereof a therapeutically effective amount of a compound of claim 27.

30. The method of claim 29, wherein the cancer is prostate cancer, lung cancer, head and neck cancer, colon cancer, kidney cancer, ovarian cancer, liver cancer, pancreatic cancer, breast cancer, glioma or neuroblastoma.

31. A compound having the structure of Compound 10:

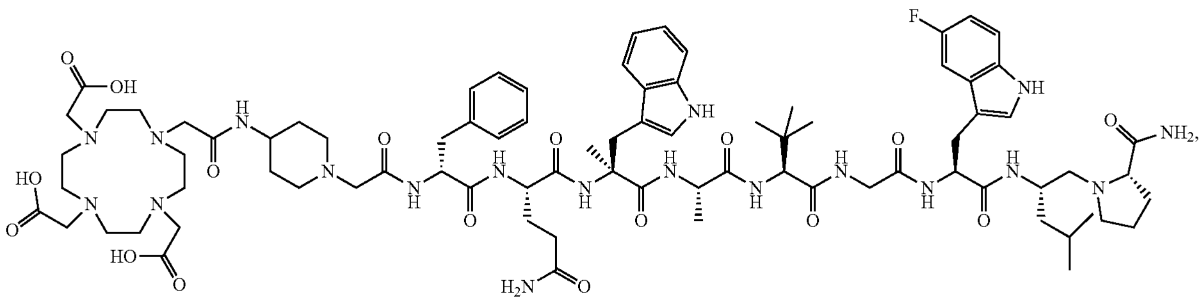

(Compound 10)

wherein the compound is bound by $^{225}$ Ac.

32. A composition comprising a compound of claim 31 and a pharmaceutically acceptable carrier or excipient.

33. A method of treating cancer in a subject comprising, administering to the subject in need thereof a therapeutically effective amount of a compound of claim 31.

34. The method of claim 33, wherein the cancer is prostate cancer, lung cancer, head and neck cancer, colon cancer, kidney cancer, ovarian cancer, liver cancer, pancreatic cancer, breast cancer, glioma or neuroblastoma.

* * * * *

SEQUENCE LISTING

```
Sequence total quantity: 67
SEQ ID NO: 1            moltype = AA  length = 10
FEATURE                 Location/Qualifiers
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    4
                        note = N-methyltryptophan
SITE                    6
                        note = tert-leucine
MOD_RES                 9..10
                        note = linked via peptide or reduced peptide bond
SITE                    10
                        note = thiazoline-4-carboxylic acid
SITE                    10
                        note = C-terminus is amidated
source                  1..10
                        mol_type = protein
                        organism = synthetic construct
SEQUENCE: 1
XFQWAXGHLX                                                    10

SEQ ID NO: 2            moltype = AA  length = 10
FEATURE                 Location/Qualifiers
SITE                    1
                        note = N-terminus linked to a radiometal chelator via
                         4-amino-(1-carboxymethyl)piperidine
                         4-amido-(1-carboxymethyl)piperidine or
                         4-acetamido-(1-carboxymethyl)piperidine
SITE                    1
                        note = D-phenylalanine
SITE                    1
                        note = may be N-methylated
SITE                    2
                        note = may be N-methylated
SITE                    3
                        note = N-methyltryptophan
SITE                    3
                        note = may be N-methylated
SITE                    4
                        note = may be N-methylated
```

```
VARIANT              5
                     note = valine or tert-leucine
SITE                 5
                     note = may be N-methylated
SITE                 6
                     note = may be N-methylated
SITE                 7
                     note = may be N-methylated
VARIANT              8
                     note = statine or leucine
SITE                 8
                     note = may be N-methylated
MOD_RES              8..9
                     note = linked via peptide or reduced peptide bond
VARIANT              9
                     note = amidated or hydroxylamidated proline, amidated or
                      hydroxylamidated leucine or may be absent
SITE                 9
                     note = may be N-methylated
VARIANT              10
                     note = amidated or hydroxylamidated valine, amidated or
                      hydroxylamidated tert-leucine or may be absent
SITE                 10
                     note = may be N-methylated
source               1..10
                     mol_type = protein
                     organism = synthetic construct
SEQUENCE: 2
FQWAXGHXXX                                                         10

SEQ ID NO: 3         moltype = AA  length = 9
FEATURE              Location/Qualifiers
SITE                 1
                     note = D-phenylalanine
SITE                 3
                     note = N-methyltryptophan
SITE                 5
                     note = tert-leucine
MOD_RES              8..9
                     note = linked via reduced peptide bond
SITE                 9
                     note = C-terminus is amidated
source               1..9
                     mol_type = protein
                     organism = synthetic construct
SEQUENCE: 3
FQWAXGHLP                                                          9

SEQ ID NO: 4         moltype = AA  length = 9
FEATURE              Location/Qualifiers
SITE                 1
                     note = D-phenylalanine
SITE                 3
                     note = N-methyltryptophan
SITE                 8
                     note = statine
SITE                 9
                     note = C-terminus is amidated
source               1..9
                     mol_type = protein
                     organism = synthetic construct
SEQUENCE: 4
FQWAVGHXL                                                          9

SEQ ID NO: 5         moltype = AA  length = 9
FEATURE              Location/Qualifiers
SITE                 1
                     note = D-phenylalanine
SITE                 3
                     note = N-methyltryptophan
SITE                 5
                     note = tert-leucine
SITE                 8
                     note = statine
SITE                 9
                     note = C-terminus is amidated
source               1..9
                     mol_type = protein
                     organism = synthetic construct
```

```
SEQUENCE: 5
FQWAXGHXL                                                  9

SEQ ID NO: 6            moltype = AA  length = 9
FEATURE                 Location/Qualifiers
SITE                    1
                        note = D-phenylalanine
SITE                    6
                        note = N-methylated glycine
SITE                    5
                        note = tert-leucine
SITE                    8
                        note = statine
MOD_RES                 8..9
                        note = linked via reduced peptide bond
SITE                    9
                        note = C-terminus is amidated
source                  1..9
                        mol_type = protein
                        organism = synthetic construct
SEQUENCE: 6
FQWAVGWLP                                                  9

SEQ ID NO: 7            moltype = AA  length = 9
FEATURE                 Location/Qualifiers
SITE                    1
                        note = D-phenylalanine
SITE                    3
                        note = N-methyltryptophan
SITE                    5
                        note = tert-leucine
MOD_RES                 8..9
                        note = linked via reduced peptide bond
SITE                    9
                        note = C-terminus is amidated
source                  1..9
                        mol_type = protein
                        organism = synthetic construct
SEQUENCE: 7
FQWAXGWLP                                                  9

SEQ ID NO: 8            moltype = AA  length = 9
FEATURE                 Location/Qualifiers
SITE                    1
                        note = D-phenylalanine
SITE                    3
                        note = N-methyltryptophan
SITE                    5
                        note = tert-leucine
SITE                    7
                        note = 5-fluorotryptophan
MOD_RES                 8..9
                        note = linked via reduced peptide bond
SITE                    9
                        note = C-terminus is amidated
source                  1..9
                        mol_type = protein
                        organism = synthetic construct
SEQUENCE: 8
FQWAXGWLP                                                  9

SEQ ID NO: 9            moltype = AA  length = 9
FEATURE                 Location/Qualifiers
SITE                    1
                        note = D-phenylalanine
SITE                    3
                        note = N-methyltryptophan
SITE                    5
                        note = tert-leucine
SITE                    8
                        note = statine
SITE                    9
                        note = C-terminus is amidated
source                  1..9
                        mol_type = protein
                        organism = synthetic construct
SEQUENCE: 9
FQWAXGWXL                                                  9
```

-continued

```
SEQ ID NO: 10           moltype = AA  length = 9
FEATURE                 Location/Qualifiers
SITE                    1
                        note = D-phenylalanine
SITE                    3
                        note = N-methyltryptophan
SITE                    5
                        note = tert-leucine
SITE                    7
                        note = 5-fluorotryptophan
SITE                    8
                        note = statine
SITE                    9
                        note = C-terminus is amidated
source                  1..9
                        mol_type = protein
                        organism = synthetic construct
SEQUENCE: 10
FQWAXGWXL                                                          9

SEQ ID NO: 11           moltype = AA  length = 9
FEATURE                 Location/Qualifiers
SITE                    1
                        note = D-phenylalanine
SITE                    2
                        note = citrulline
SITE                    3
                        note = N-methyltryptophan
SITE                    5
                        note = tert-leucine
MOD_RES                 8..9
                        note = linked via reduced peptide bond
SITE                    9
                        note = C-terminus is amidated
source                  1..9
                        mol_type = protein
                        organism = synthetic construct
SEQUENCE: 11
FXWAXGHLP                                                          9

SEQ ID NO: 12           moltype = AA  length = 9
FEATURE                 Location/Qualifiers
SITE                    1
                        note = D-phenylalanine
SITE                    3
                        note = N-methyltryptophan
SITE                    5
                        note = tert-leucine
MOD_RES                 8..9
                        note = linked via reduced peptide bond
SITE                    9
                        note = C-terminus is amidated
source                  1..9
                        mol_type = protein
                        organism = synthetic construct
SEQUENCE: 12
FEWAXGHLP                                                          9

SEQ ID NO: 13           moltype = AA  length = 9
FEATURE                 Location/Qualifiers
SITE                    1
                        note = D-phenylalanine
SITE                    2
                        note = 2-amino-4-guanidinobutyric acid
SITE                    3
                        note = N-methyltryptophan
SITE                    5
                        note = tert-leucine
MOD_RES                 8..9
                        note = linked via reduced peptide bond
SITE                    9
                        note = C-terminus is amidated
source                  1..9
                        mol_type = protein
                        organism = synthetic construct
SEQUENCE: 13
FXWAXGHLP                                                          9

SEQ ID NO: 14           moltype = AA  length = 9
```

-continued

```
FEATURE                 Location/Qualifiers
SITE                    1
                        note = D-phenylalanine
SITE                    3
                        note = N-methyltryptophan
SITE                    4
                        note = N-methylated glycine
SITE                    5
                        note = tert-leucine
MOD_RES                 8..9
                        note = linked via reduced peptide bond
SITE                    9
                        note = C-terminus is amidated
source                  1..9
                        mol_type = protein
                        organism = synthetic construct
SEQUENCE: 14
FQWGXGHLP                                                    9

SEQ ID NO: 15           moltype = AA  length = 9
FEATURE                 Location/Qualifiers
SITE                    1
                        note = D-phenylalanine
SITE                    3
                        note = N-methyltryptophan
SITE                    4
                        note = N-methylated glycine
SITE                    5
                        note = tert-leucine
MOD_RES                 8..9
                        note = linked via reduced peptide bond
SITE                    9
                        note = C-terminus is amidated
source                  1..9
                        mol_type = protein
                        organism = synthetic construct
SEQUENCE: 15
FQWGXGWLP                                                    9

SEQ ID NO: 16           moltype = AA  length = 9
FEATURE                 Location/Qualifiers
SITE                    1
                        note = D-phenylalanine
SITE                    6
                        note = N-methylated glycine
MOD_RES                 8..9
                        note = linked via reduced peptide bond
SITE                    9
                        note = C-terminus is amidated
source                  1..9
                        mol_type = protein
                        organism = synthetic construct
SEQUENCE: 16
FQWAVGHLP                                                    9

SEQ ID NO: 17           moltype = AA  length = 10
FEATURE                 Location/Qualifiers
SITE                    1
                        note = D-phenylalanine
SITE                    6
                        note = N-methylated glycine
MOD_RES                 8..9
                        note = linked via reduced peptide bond
SITE                    9
                        note = C-terminus is amidated
source                  1..10
                        mol_type = protein
                        organism = synthetic construct
SEQUENCE: 17
FQWAVGWLPV                                                   10

SEQ ID NO: 18           moltype = AA  length = 10
FEATURE                 Location/Qualifiers
SITE                    1
                        note = D-phenylalanine
SITE                    6
                        note = N-methylated glycine
MOD_RES                 8..9
                        note = linked via reduced peptide bond
```

```
SITE                    9
                        note = C-terminus is amidated
source                  1..10
                        mol_type = protein
                        organism = synthetic construct
SEQUENCE: 18
FQWAVGHLPV                                                    10

SEQ ID NO: 19           moltype = AA  length = 10
FEATURE                 Location/Qualifiers
SITE                    1
                        note = D-phenylalanine
SITE                    3
                        note = N-methyltryptophan
SITE                    5
                        note = tert-leucine
MOD_RES                 8..9
                        note = linked via reduced peptide bond
SITE                    10
                        note = tert-leucine
SITE                    10
                        note = C-terminus is amidated
source                  1..10
                        mol_type = protein
                        organism = synthetic construct
SEQUENCE: 19
FQWAXGWLPX                                                    10

SEQ ID NO: 20           moltype = AA  length = 10
FEATURE                 Location/Qualifiers
SITE                    1
                        note = D-phenylalanine
SITE                    3
                        note = N-methyltryptophan
SITE                    5
                        note = tert-leucine
MOD_RES                 8..9
                        note = linked via reduced peptide bond
SITE                    10
                        note = tert-leucine
SITE                    10
                        note = C-terminus is amidated
source                  1..10
                        mol_type = protein
                        organism = synthetic construct
SEQUENCE: 20
FQWAXGHLPX                                                    10

SEQ ID NO: 21           moltype = AA  length = 10
FEATURE                 Location/Qualifiers
SITE                    1
                        note = piperidine
SITE                    2
                        note = D-phenylalanine
SITE                    4
                        note = 7-fluorotryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
SEQUENCE: 21
XFQWAXGHLP                                                    10

SEQ ID NO: 22           moltype = AA  length = 10
FEATURE                 Location/Qualifiers
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    4
                        note = N-methyltryptophan
SITE                    6
                        note = tert-leucine
```

-continued

```
MOD_RES                9..10
                       note = linked via reduced peptide bond
SITE                   10
                       note = C-terminus is amidated
source                 1..10
                       mol_type = protein
                       organism = synthetic construct
SEQUENCE: 22
XFQWAXGHLP                                                                  10

SEQ ID NO: 23          moltype = AA  length = 10
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
MOD_RES                9..10
                       note = linked via reduced peptide bond
SITE                   10
                       note = C-terminus is amidated
source                 1..10
                       mol_type = protein
                       organism = synthetic construct
SEQUENCE: 23
XFQWAXGHLP                                                                  10

SEQ ID NO: 24          moltype = AA  length = 10
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   9
                       note = statine
SITE                   10
                       note = C-terminus is amidated
source                 1..10
                       mol_type = protein
                       organism = synthetic construct
SEQUENCE: 24
XFQWAVGHXL                                                                  10

SEQ ID NO: 25          moltype = AA  length = 10
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
SITE                   9
                       note = statine
SITE                   10
                       note = C-terminus is amidated
source                 1..10
                       mol_type = protein
                       organism = synthetic construct
SEQUENCE: 25
XFQWAXGHXL                                                                  10

SEQ ID NO: 26          moltype = AA  length = 10
FEATURE                Location/Qualifiers
```

```
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 26
XFQWAVGWLP                                                                10

SEQ ID NO: 27           moltype = AA  length = 10
FEATURE                 Location/Qualifiers
SITE                    1
                        note = 4-amino-1-carboxymethyl-piperidine modified with
                         1,4,7,10-
                         tetrakis(carboxymethyl)-7-acetamide-1,4,10-triazacyclododec
                         ane glutaric acid
SITE                    2
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 27
XFQWAVGWLP                                                                10

SEQ ID NO: 28           moltype = AA  length = 10
FEATURE                 Location/Qualifiers
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    4
                        note = N-methyltryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
SEQUENCE: 28
XFQWAXGWLP                                                                10

SEQ ID NO: 29           moltype = AA  length = 10
FEATURE                 Location/Qualifiers
SITE                    1
                        note = 4-amino-1-carboxymethyl-piperidine modified with
                         1,4,7,10-
                         tetrakis(carboxymethyl)-7-acetamide-1,4,10-triazacyclododec
                         ane glutaric acid
SITE                    2
                        note = D-phenylalanine
SITE                    4
                        note = N-methyltryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
```

-continued

```
SEQUENCE: 29
XFQWAXGWLP                                                   10

SEQ ID NO: 30          moltype = AA  length = 10
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
MOD_RES                9..10
                       note = linked via reduced peptide bond
SITE                   10
                       note = C-terminus is amidated
source                 1..10
                       mol_type = protein
                       organism = synthetic construct
SEQUENCE: 30
XFQWAXGWLP                                                   10

SEQ ID NO: 31          moltype = AA  length = 10
FEATURE                Location/Qualifiers
SITE                   1
                       note = 4-amino-1-carboxymethyl-piperidine modified with
                        2-(7,13,16-tris(carboxymethyl)-
                        1,10-dioxa-4,7,13,16-tetraazacyclooctadecan-4-yl)pentanedio
                        ic acid
SITE                   2
                       note = D-phenylalanine
SITE                   4
                       note = N-methyltryptophan
SITE                   6
                       note = tert-leucine
MOD_RES                9..10
                       note = linked via reduced peptide bond
SITE                   10
                       note = C-terminus is amidated
source                 1..10
                       mol_type = protein
                       organism = synthetic construct
SEQUENCE: 31
XFQWAXGWLP                                                   10

SEQ ID NO: 32          moltype = AA  length = 10
FEATURE                Location/Qualifiers
SITE                   1
                       note = 4-amino-1-carboxymethyl-piperidine modified with
                        1,4,7,10- tetraazacyclododecane-1,4,7,10-tetraacetic acid
SITE                   2
                       note = D-phenylalanine
SITE                   4
                       note = N-methyltryptophan
SITE                   6
                       note = tert-leucine
SITE                   8
                       note = 5-fluorotryptophan
MOD_RES                9..10
                       note = linked via reduced peptide bond
SITE                   10
                       note = C-terminus is amidated
source                 1..10
                       mol_type = protein
                       organism = synthetic construct
SEQUENCE: 32
XFQWAXGWLP                                                   10

SEQ ID NO: 33          moltype = AA  length = 10
FEATURE                Location/Qualifiers
SITE                   1
                       note = 4-amino-1-carboxymethyl-piperidine modified with
                        1,4,7,10-
                        tetrakis(carboxymethyl)-7-acetamide-1,4,10-triazacyclododec
                        ane glutaric acid
```

-continued

```
SITE                    2
                        note = D-phenylalanine
SITE                    4
                        note = N-methyltryptophan
SITE                    6
                        note = tert-leucine
SITE                    8
                        note = 5-fluorotryptophan
MOD_RES                 9..10
                        note = linked via reduced peptide bond
SITE                    10
                        note = C-terminus is amidated
source                  1..10
                        mol_type = protein
                        organism = synthetic construct
SEQUENCE: 33
XFQWAXGWLP                                                                  10

SEQ ID NO: 34           moltype = AA  length = 10
FEATURE                 Location/Qualifiers
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid
SITE                    2
                        note = D-phenylalanine
SITE                    4
                        note = N-methyltryptophan
SITE                    6
                        note = tert-leucine
SITE                    9
                        note = statine
SITE                    10
                        note = C-terminus is amidated
source                  1..10
                        mol_type = protein
                        organism = synthetic construct
SEQUENCE: 34
XFQWAXGWXL                                                                  10

SEQ ID NO: 35           moltype = AA  length = 10
FEATURE                 Location/Qualifiers
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid
SITE                    2
                        note = D-phenylalanine
SITE                    4
                        note = N-methyltryptophan
SITE                    6
                        note = tert-leucine
SITE                    8
                        note = 5-fluorotryptophan
SITE                    9
                        note = statine
SITE                    10
                        note = C-terminus is amidated
source                  1..10
                        mol_type = protein
                        organism = synthetic construct
SEQUENCE: 35
XFQWAXGWXL                                                                  10

SEQ ID NO: 36           moltype = AA  length = 10
FEATURE                 Location/Qualifiers
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid
SITE                    2
                        note = D-phenylalanine
SITE                    3
                        note = citrulline
SITE                    4
                        note = N-methyltryptophan
```

-continued

```
SITE                   6
                       note = tert-leucine
MOD_RES                9..10
                       note = linked via reduced peptide bond
SITE                   10
                       note = C-terminus is amidated
source                 1..10
                       mol_type = protein
                       organism = synthetic construct
SEQUENCE: 36
XFXWAXGHLP                                                          10

SEQ ID NO: 37          moltype = AA  length = 10
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
MOD_RES                9..10
                       note = linked via reduced peptide bond
SITE                   10
                       note = C-terminus is amidated
source                 1..10
                       mol_type = protein
                       organism = synthetic construct
SEQUENCE: 37
XFEWAXGHLP                                                          10

SEQ ID NO: 38          moltype = AA  length = 10
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   3
                       note = 2-amino-4-guanidinobutyric acid
SITE                   4
                       note = N-methyltryptophan
SITE                   6
                       note = tert-leucine
MOD_RES                9..10
                       note = linked via reduced peptide bond
SITE                   10
                       note = C-terminus is amidated
source                 1..10
                       mol_type = protein
                       organism = synthetic construct
SEQUENCE: 38
XFXWAXGHLP                                                          10

SEQ ID NO: 39          moltype = AA  length = 9
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
SITE                   9
                       note = cis-4-cyclohexyloxy-D-proline
SITE                   9
                       note = C-terminus is amidated
source                 1..9
                       mol_type = protein
```

```
                        organism = synthetic construct
SEQUENCE: 39
XFQWAXGWX                                                           9

SEQ ID NO: 40           moltype = AA  length = 9
FEATURE                 Location/Qualifiers
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid
SITE                    2
                        note = D-phenylalanine
SITE                    4
                        note = N-methyltryptophan
SITE                    6
                        note = tert-leucine
SITE                    9
                        note = cis-4-cyclohexylamino-D-proline
SITE                    9
                        note = C-terminus is amidated
source                  1..9
                        mol_type = protein
                        organism = synthetic construct
SEQUENCE: 40
XFQWAXGWX                                                           9

SEQ ID NO: 41           moltype = AA  length = 11
FEATURE                 Location/Qualifiers
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    4
                        note = N-methyltryptophan
SITE                    6
                        note = tert-leucine
SITE                    8
                        note = 5-fluorotryptophan
MOD_RES                 9..10
                        note = linked via reduced peptide bond
SITE                    11
                        note = tert-leucine
SITE                    11
                        note = C-terminus is amidated
source                  1..11
                        mol_type = protein
                        organism = synthetic construct
SEQUENCE: 41
XFQWAXGWLP X                                                        11

SEQ ID NO: 42           moltype = AA  length = 10
FEATURE                 Location/Qualifiers
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    3
                        note = citrulline
SITE                    4
                        note = N-methyltryptophan
SITE                    6
                        note = tert-leucine
SITE                    8
                        note = 3-quinoylalanine
MOD_RES                 9..10
                        note = linked via reduced peptide bond
SITE                    10
                        note = C-terminus is amidated
source                  1..10
                        mol_type = protein
                        organism = synthetic construct
SEQUENCE: 42
XFXWAXGXLP                                                          10

SEQ ID NO: 43           moltype = AA  length = 10
FEATURE                 Location/Qualifiers
```

-continued

```
SITE                  1
                      note = 4-amino-1-carboxymethyl-piperidine modified with
                       1,4,7,10- tetraazacyclododecane-1,4,7,10-tetraacetic acid
SITE                  2
                      note = D-phenylalanine
SITE                  3
                      note = citrulline
SITE                  4
                      note = N-methyltryptophan
SITE                  9
                      note = statine
SITE                  10
                      note = C-terminus is amidated
source                1..10
                      mol_type = protein
                      organism = synthetic construct
SEQUENCE: 43
XFXWAVGHXL                                                                10

SEQ ID NO: 44         moltype = AA  length = 10
FEATURE               Location/Qualifiers
SITE                  1
                      note = 4-amino-1-carboxymethyl-piperidine modified with
                       1,4,7,10- tetraazacyclododecane-1,4,7,10-tetraacetic acid
SITE                  2
                      note = D-phenylalanine
SITE                  3
                      note = citrulline
SITE                  4
                      note = N-methyltryptophan
SITE                  8
                      note = 5-fluorotryptophan
SITE                  9
                      note = statine
SITE                  10
                      note = C-terminus is amidated
source                1..10
                      mol_type = protein
                      organism = synthetic construct
SEQUENCE: 44
XFXWAVGWXL                                                                10

SEQ ID NO: 45         moltype = AA  length = 10
FEATURE               Location/Qualifiers
SITE                  1
                      note = 4-amino-1-carboxymethyl-piperidine modified with
                       1,4,7,10-
                       tetrakis(carbamoylmethyl)-1,4,7,10-tetraazacyclododecane
SITE                  2
                      note = D-phenylalanine
SITE                  7
                      note = N-methylated glycine
MOD_RES               9..10
                      note = linked via reduced peptide bond
SITE                  10
                      note = C-terminus is amidated
source                1..10
                      mol_type = protein
                      organism = synthetic construct
SEQUENCE: 45
XFQWAVGHLP                                                                10

SEQ ID NO: 46         moltype = AA  length = 10
FEATURE               Location/Qualifiers
SITE                  1
                      note = 4-amino-1-carboxymethyl-piperidine modified with
                       1,4,7,10- tetraazacyclododecane-1,4,7,10-tetraacetic acid
SITE                  2
                      note = D-phenylalanine
SITE                  7
                      note = N-methylated glycine
MOD_RES               9..10
                      note = linked via reduced peptide bond
SITE                  10
                      note = C-terminus is amidated
source                1..10
                      mol_type = protein
                      organism = synthetic construct
SEQUENCE: 46
```

-continued

```
XFQWAVGHLP                                                          10

SEQ ID NO: 47          moltype = AA  length = 11
FEATURE                Location/Qualifiers
SITE                   1
                       note = 4-amino-1-carboxymethyl-piperidine modified with
                        1,4,7,10- tetraazacyclododecane-1,4,7,10-tetraacetic acid
SITE                   2
                       note = D-phenylalanine
SITE                   7
                       note = N-methylated glycine
MOD_RES                9..10
                       note = linked via reduced peptide bond
SITE                   11
                       note = C-terminus is amidated
source                 1..11
                       mol_type = protein
                       organism = synthetic construct
SEQUENCE: 47
XFQWAVGWLP V                                                        11

SEQ ID NO: 48          moltype = AA  length = 11
FEATURE                Location/Qualifiers
SITE                   1
                       note = 4-amino-1-carboxymethyl-piperidine modified with
                        1,4,7,10- tetraazacyclododecane-1,4,7,10-tetraacetic acid
SITE                   2
                       note = D-phenylalanine
SITE                   7
                       note = N-methylated glycine
MOD_RES                9..10
                       note = linked via reduced peptide bond
SITE                   11
                       note = C-terminus is amidated
source                 1..11
                       mol_type = protein
                       organism = synthetic construct
SEQUENCE: 48
XFQWAVGHLP V                                                        11

SEQ ID NO: 49          moltype = AA  length = 11
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
MOD_RES                9..10
                       note = linked via reduced peptide bond
SITE                   11
                       note = tert-leucine
SITE                   11
                       note = C-terminus is amidated
source                 1..11
                       mol_type = protein
                       organism = synthetic construct
SEQUENCE: 49
XFQWAXGWLP X                                                        11

SEQ ID NO: 50          moltype = AA  length = 11
FEATURE                Location/Qualifiers
SITE                   1
                       note = 4-amino-1-carboxymethyl-piperidine modified with
                        2,2',2'',2'''-(1,10-
                        dioxa-4,7,13,16-tetraazacyclooctadecane-4,7,13,16-tetrayl)
                        tetraacetic acid
SITE                   2
                       note = D-phenylalanine
SITE                   4
                       note = N-methyltryptophan
SITE                   6
                       note = tert-leucine
MOD_RES                9..10
```

-continued

```
                        note = linked via reduced peptide bond
SITE                    11
                        note = tert-leucine
SITE                    11
                        note = C-terminus is amidated
source                  1..11
                        mol_type = protein
                        organism = synthetic construct
SEQUENCE: 50
XFQWAXGHLP X                                                         11

SEQ ID NO: 51           moltype = AA  length = 11
FEATURE                 Location/Qualifiers
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid
SITE                    2
                        note = D-phenylalanine
SITE                    3
                        note = citrulline
SITE                    4
                        note = N-methyltryptophan
SITE                    6
                        note = tert-leucine
SITE                    8
                        note = 3-quinoylalanine
MOD_RES                 9..10
                        note = linked via reduced peptide bond
SITE                    11
                        note = tert-leucine
SITE                    11
                        note = C-terminus is amidated
source                  1..11
                        mol_type = protein
                        organism = synthetic construct
SEQUENCE: 51
XFXWAXGXLP X                                                         11

SEQ ID NO: 52           moltype = AA  length = 10
FEATURE                 Location/Qualifiers
SITE                    1
                        note = 4-amino-1-carboxymethyl-piperidine modified with
                         1,4,7,10-
                         tetrakis(carboxymethyl)-7-acetamide-1,4,10-triazacyclododec
                         ane glutaric acid
SITE                    2
                        note = D-phenylalanine
SITE                    4
                        note = N-methyltryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
SEQUENCE: 52
XFQWAXGHLP                                                           10

SEQ ID NO: 53           moltype = AA  length = 11
FEATURE                 Location/Qualifiers
SITE                    1
                        note = 4-amino-1-carboxymethyl-piperidine modified with
                         1,4,7,10- tetraazacyclododecane-1,4,7,10-tetraacetic acid
SITE                    2
                        note = D-phenylalanine
SITE                    4
                        note = N-methyltryptophan
SITE                    6
                        note = tert-leucine
MOD_RES                 9..10
                        note = linked via reduced peptide bond
SITE                    11
                        note = tert-leucine
SITE                    11
```

```
                        note = C-terminus is amidated
source                  1..11
                        mol_type = protein
                        organism = synthetic construct
SEQUENCE: 53
XFQWAXGHLP X                                                      11

SEQ ID NO: 54           moltype = AA  length = 10
FEATURE                 Location/Qualifiers
SITE                    1..10
                        note = This sequence is one part of a branched amino acid
                         sequence
SITE                    1
                        note = 4-amino-1-carboxymethyl-piperidine modified with
                         1,4,7,10- tetraazacyclododecane-1,4,7,10-tetraacetic acid
                         glutamate
SITE                    2
                        note = D-phenylalanine
SITE                    4
                        note = 7-fluorotryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
SEQUENCE: 54
XFQWAXGHLP                                                        10

SEQ ID NO: 55           moltype = AA  length = 10
FEATURE                 Location/Qualifiers
SITE                    1..10
                        note = This sequence is one part of a branched amino acid
                         sequence
SITE                    1
                        note = linked to another sequence
SITE                    1
                        note = piperidine
SITE                    2
                        note = D-phenylalanine
SITE                    4
                        note = 7-fluorotryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
SEQUENCE: 55
XFQWAXGHLP                                                        10

SEQ ID NO: 56           moltype = AA  length = 10
FEATURE                 Location/Qualifiers
SITE                    1..10
                        note = This sequence is one part of a branched amino acid
                         sequence
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid- aminoadipic acid-aminoadipic
                         acid-glutamate tripeptide
SITE                    2
                        note = D-phenylalanine
SITE                    4
                        note = N-methyltryptophan
SITE                    6
                        note = tert-leucine
MOD_RES                 9..10
                        note = linked via reduced peptide bond
SITE                    10
                        note = C-terminus is amidated
source                  1..10
```

```
                        mol_type = protein
                        organism = synthetic construct
SEQUENCE: 56
XFQWAXGHLP                                                              10

SEQ ID NO: 57           moltype = AA  length = 10
FEATURE                 Location/Qualifiers
SITE                    1..10
                        note = This sequence is one part of a branched amino acid
                         sequence
SITE                    1
                        note = linked to another sequence
SITE                    1
                        note = piperidine
SITE                    2
                        note = D-phenylalanine
SITE                    4
                        note = N-methyltryptophan
SITE                    6
                        note = tert-leucine
MOD_RES                 9..10
                        note = linked via reduced peptide bond
SITE                    10
                        note = C-terminus is amidated
source                  1..10
                        mol_type = protein
                        organism = synthetic construct
SEQUENCE: 57
XFQWAXGHLP                                                              10

SEQ ID NO: 58           moltype = AA  length = 10
FEATURE                 Location/Qualifiers
SITE                    1
                        note = 4-amino-1-carboxymethyl-piperidine modified with
                         2,2',2'',2'''-(1,10-
                         dioxa-4,7,13,16-tetraazacyclooctadecane-4,7,13,16-tetrayl)
                         tetraacetic acid
SITE                    2
                        note = D-phenylalanine
SITE                    4
                        note = N-methyltryptophan
SITE                    8
                        note = 5-fluorotryptophan
SITE                    9
                        note = statine
SITE                    10
                        note = C-terminus is amidated
source                  1..10
                        mol_type = protein
                        organism = synthetic construct
SEQUENCE: 58
XFQWAVGWXL                                                              10

SEQ ID NO: 59           moltype = AA  length = 10
FEATURE                 Location/Qualifiers
SITE                    1
                        note = 4-amino-1-carboxymethyl-piperidine modified with
                         1,4,7,10-
                         tetrakis(carbamoylmethyl)-1,4,7,10-tetraazacyclododecane
SITE                    2
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 59
XFQWAVGHLP                                                              10

SEQ ID NO: 60           moltype = AA  length = 10
FEATURE                 Location/Qualifiers
SITE                    1
                        note = 4-acetamido-(1-carboxymethyl)piperidine modified
                         with amidated boron trifluoride triazole
SITE                    2
```

-continued

```
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 60
XFQWAVGHLP                                                        10

SEQ ID NO: 61           moltype = AA  length = 10
FEATURE                 Location/Qualifiers
SITE                    1
                        note = 4-amido-(1-carboxymethyl)piperidine modified with
                         trimethylated 2-aminopyridine
SITE                    2
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 61
XFQWAVGHLP                                                        10

SEQ ID NO: 62           moltype = AA  length = 10
FEATURE                 Location/Qualifiers
SITE                    1
                        note = Fluoro-4-amido-(1-carboxymethyl)piperidine
SITE                    2
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 62
XFQWAVGHLP                                                        10

SEQ ID NO: 63           moltype = AA  length = 10
FEATURE                 Location/Qualifiers
SITE                    1
                        note = 18-Fluoro-4-amido-(1-carboxymethyl)piperidine
SITE                    2
                        note = D-phenylalanine
SITE                    7
                        note = N-methylated glycine
MOD_RES                 9..10
                        note = linked via reduced peptide bond
SITE                    10
                        note = C-terminus is amidated
source                  1..10
                        mol_type = protein
                        organism = synthetic construct
SEQUENCE: 63
XFQWAVGHLP                                                        10

SEQ ID NO: 64           moltype = AA  length = 10
FEATURE                 Location/Qualifiers
SITE                    1
                        note = 4-amido-(1-carboxymethyl)piperidine modified with
                         1,4,7,10- tetraazacyclododecane-1,4,7,10-tetraacetic
                         acid-O-methyl pyridine glycine lysine
SITE                    2
                        note = D-phenylalanine
SITE                    4
                        note = N-methyltryptophan
SITE                    6
```

-continued

| | |
|---|---|
| | note = tert-leucine |
| MOD_RES | 9..10 |
| | note = linked via reduced peptide bond |
| SITE | 10 |
| | note = C-terminus is amidated |
| source | 1..10 |
| | mol_type = protein |
| | organism = synthetic construct |
| SEQUENCE: 64 | |
| XFQWAXGHLP | 10 |
| | |
| SEQ ID NO: 65 | moltype = AA length = 10 |
| FEATURE | Location/Qualifiers |
| SITE | 1 |
| | note = 4-amido-(1-carboxymethyl)piperidine modified with 2,2',2'',2'''-(1,10-dioxa-4,7,13,16-tetraazacyclooctadecane-4,7,13,16-tetrayl) tetraacetic acid- O-methyl pyridine glycine lysine |
| SITE | 2 |
| | note = D-phenylalanine |
| SITE | 4 |
| | note = N-methyltryptophan |
| SITE | 6 |
| | note = tert-leucine |
| MOD_RES | 9..10 |
| | note = linked via reduced peptide bond |
| SITE | 10 |
| | note = C-terminus is amidated |
| source | 1..10 |
| | mol_type = protein |
| | organism = synthetic construct |
| SEQUENCE: 65 | |
| XFQWAXGWLP | 10 |
| | |
| SEQ ID NO: 66 | moltype = AA length = 10 |
| FEATURE | Location/Qualifiers |
| SITE | 1 |
| | note = 4-amino-1-carboxymethyl-piperidine modified with 1,4,7,10- tetraazacyclododecane-1,4,7,10-tetraacetic acid |
| SITE | 2 |
| | note = D-phenylalanine |
| SITE | 4 |
| | note = N-methyltryptophan |
| SITE | 9 |
| | note = statine |
| SITE | 10 |
| | note = C-terminus is amidated |
| source | 1..10 |
| | mol_type = protein |
| | organism = synthetic construct |
| SEQUENCE: 66 | |
| XFQWAVGHXL | 10 |
| | |
| SEQ ID NO: 67 | moltype = AA length = 10 |
| FEATURE | Location/Qualifiers |
| SITE | 1 |
| | note = 4-amino-1-carboxymethyl-piperidine modified with 1,4,7,10-tetrakis(carboxymethyl)-7-acetamide-1,4,10-triazacyclododecane glutaric acid |
| SITE | 2 |
| | note = D-phenylalanine |
| SITE | 4 |
| | note = N-methyltryptophan |
| SITE | 9 |
| | note = statine |
| SITE | 10 |
| | note = C-terminus is amidated |
| source | 1..10 |
| | mol_type = protein |
| | organism = synthetic construct |
| SEQUENCE: 67 | |
| XFQWAVGHXL | 10 |